US012765824B2

(12) United States Patent
Connor

(10) Patent No.: US 12,765,824 B2
(45) Date of Patent: Oct. 20, 2026

(54) ELECTROMYOGRAPHIC CLOTHING

(71) Applicant: Robert A. Connor, Wyoming, MN (US)

(72) Inventor: Robert A. Connor, Wyoming, MN (US)

(73) Assignee: Medibotics LLC, Ham Lake, MN (US)

( * ) Notice: Subject to any disclaimer, the term of this patent is extended or adjusted under 35 U.S.C. 154(b) by 0 days.

(21) Appl. No.: 19/025,130

(22) Filed: Jan. 16, 2025

(65) Prior Publication Data

US 2025/0152064 A1 May 15, 2025

Related U.S. Application Data

(63) Continuation-in-part of application No. 18/900,784, filed on Sep. 29, 2024, now abandoned, and a continuation-in-part of application No. 18/369,129, filed on Sep. 15, 2023, said application No. 18/900,784 is a continuation-in-part of application (Continued)

(51) Int. Cl.

| | |
|---|---|
| ***A61B 5/256*** | (2021.01) |
| ***A61B 5/00*** | (2006.01) |
| ***A61B 5/11*** | (2006.01) |
| ***A61B 5/397*** | (2021.01) |

(52) U.S. Cl.

CPC ............ *A61B 5/256* (2021.01); *A61B 5/1121* (2013.01); *A61B 5/1126* (2013.01); *A61B 5/397* (2021.01); *A61B 5/6804* (2013.01); *A61B 2560/0443* (2013.01); *A61B 2560/0468* (2013.01);

(Continued)

(58) Field of Classification Search

CPC ..... A61B 5/256; A61B 5/1121; A61B 5/1126; A61B 5/397; A61B 5/6804; A61B 2560/0443; A61B 2560/0468; A61B 2562/0219; A61B 2562/0261; A61B 5/389; A61B 2503/10; A61B 2505/09; A61B 5/1114; A61B 2562/0266; A61B 2562/046; A61B 2562/12; A61B 5/11; D03D 1/0088; D03D 15/56; G06F 3/016; G06F 3/011; G06F 3/015; G06F 3/014; D10B 2401/061; D10B 2401/18; A41D 1/002; G01B 21/32

See application file for complete search history.

(56) References Cited

U.S. PATENT DOCUMENTS 5,375,610 A 12/1994 LaCourse et al.
5,474,083 A 12/1995 Church et al.

(Continued)

OTHER PUBLICATIONS

Preethichandra et al. (Passive and Active Exoskeleton Solutions: Sensors, Actuators, Applications, and Recent Trends, Sensors (Basel). Nov. 4, 2024;24(21):7095) (Year: 2024).*

*Primary Examiner* — Jacqueline Cheng
*Assistant Examiner* — Tho Q Tran

(57) ABSTRACT

This invention is an article of clothing with electromyographic (EMG) sensors which measures body motion and/or muscle activity. This clothing can be a short-sleeve shirt or a pair of shorts, wherein the electromyographic (EMG) sensors are on the cuffs. The electromyographic (EMG) sensors can be modular; they can be removably attached to different locations in order to create a customized article of electromyographic clothing which optimally measures the muscle activity of a particular person or muscle activity during a particular sport. This clothing can also include bending-based motion sensors.

2 Claims, 33 Drawing Sheets

Related U.S. Application Data

No. 18/369,129, filed on Sep. 15, 2023, which is a continuation-in-part of application No. 17/721,866, filed on Apr. 15, 2022, now Pat. No. 11,892,286, which is a continuation-in-part of application No. 17/356,377, filed on Jun. 23, 2021, now Pat. No. 11,304,628, which is a continuation-in-part of application No. 16/751,245, filed on Jan. 24, 2020, now Pat. No. 11,071,498, which is a continuation-in-part of application No. 16/543,056, filed on Aug. 16, 2019, now Pat. No. 10,839,202, and a continuation-in-part of application No. 16/017,439, filed on Jun. 25, 2018, now Pat. No. 10,921,886, said application No. 16/543,056 is a continuation-in-part of application No. 16/010,448, filed on Jun. 16, 2018, now Pat. No. 10,602,965, said application No. 16/751,245 is a continuation-in-part of application No. 16/010,448, filed on Jun. 16, 2018, now Pat. No. 10,602,965, said application No. 16/017,439 is a continuation-in-part of application No. 16/010,448, filed on Jun. 16, 2018, now Pat. No. 10,602,965, which is a continuation-in-part of application No. 15/702,081, filed on Sep. 12, 2017, now Pat. No. 10,716,510, said application No. 16/751,245 is a continuation-in-part of application No. 15/702,081, filed on Sep. 12, 2017, now Pat. No. 10,716,510, said application No. 16/010,448 is a continuation-in-part of application No. 15/227,254, filed on Aug. 3, 2016, now Pat. No. 10,321,873, said application No. 15/702,081 is a continuation-in-part of application No. 15/227,254, filed on Aug. 3, 2016, now Pat. No. 10,321,873, which is a continuation-in-part of application No. 15/130,995, filed on Apr. 17, 2016, now Pat. No. 9,891,718, and a continuation-in-part of application No. 15/079,447, filed on Mar. 24, 2016, now Pat. No. 10,234,934, said application No. 15/702,081 is a continuation-in-part of application No. 14/795,373, filed on Jul. 9, 2015, now abandoned, said application No. 15/227,254 is a continuation-in-part of application No. 14/736,652, filed on Jun. 11, 2015, now abandoned, said application No. 14/795,373 is a continuation-in-part of application No. 14/736,652, filed on Jun. 11, 2015, now abandoned, said application No. 15/079,447 is a continuation-in-part of application No. 14/664,832, filed on Mar. 21, 2015, now Pat. No. 9,582,072, said application No. 14/736,652 is a continuation-in-part of application No. 14/664,832, filed on Mar. 21, 2015, now Pat. No. 9,582,072, said application No. 15/227,254 is a continuation-in-part of application No. 14/664,832, filed on Mar. 21, 2015, now Pat. No. 9,582,072, which is a continuation-in-part of application No. 14/463,741, filed on Aug. 20, 2014, now Pat. No. 9,588,582, said application No. 15/079,447 is a continuation-in-part of application No. 14/463,741, filed on Aug. 20, 2014, now Pat. No. 9,588,582.

(60) Provisional application No. 62/797,266, filed on Jan. 26, 2019, provisional application No. 62/727,798, filed on Sep. 6, 2018, provisional application No. 62/683,237, filed on Jun. 11, 2018, provisional application No. 62/538,793, filed on Jul. 30, 2017, provisional application No. 62/449,735, filed on Jan. 24, 2017, provisional application No. 62/357,957, filed on Jul. 2, 2016, provisional application No. 62/187,906, filed on Jul. 2, 2015, provisional application No. 62/182,473, filed on Jun. 20, 2015, provisional application No. 62/150,886, filed on Apr. 22, 2015, provisional application No. 62/086,053, filed on Dec. 1, 2014, provisional application No. 62/065,032, filed on Oct. 17, 2014, provisional application No. 62/014,747, filed on Jun. 20, 2014, provisional application No. 61/976,650, filed on Apr. 8, 2014, provisional application No. 61/878,893, filed on Sep. 17, 2013.

(52) U.S. Cl.
CPC ................ *A61B 2562/0219* (2013.01); *A61B 2562/0261* (2013.01)

(56) References Cited

U.S. PATENT DOCUMENTS

| | | | |
|---|---|---|---|
| 5,592,401 | A | 1/1997 | Kramer |
| 5,785,666 | A | 7/1998 | Costello et al. |
| 5,930,741 | A | 7/1999 | Kramer |
| 5,964,719 | A | 10/1999 | Costello et al. |
| 6,050,962 | A | 4/2000 | Kramer et al. |
| 6,148,280 | A | 11/2000 | Kramer |
| 6,428,490 | B1 | 8/2002 | Kramer et al. |
| 6,589,171 | B2 | 7/2003 | Keirsbilck |
| 6,834,436 | B2 | 12/2004 | Townsend et al. |
| 6,944,496 | B2 | 9/2005 | Jeong et al. |
| 6,957,164 | B2 | 10/2005 | Dietz et al. |
| 7,070,571 | B2 | 7/2006 | Kramer et al. |
| 7,152,470 | B2 | 12/2006 | Impio et al. |
| 7,210,240 | B2 | 5/2007 | Townsend et al. |
| 7,365,647 | B2 | 4/2008 | Nativ |
| 7,458,943 | B1 | 12/2008 | Chow et al. |
| 7,559,902 | B2 | 7/2009 | Ting et al. |
| 7,602,301 | B1 | 10/2009 | Stirling et al. |
| 7,698,830 | B2 | 4/2010 | Townsend et al. |
| 7,821,407 | B2 | 10/2010 | Shears et al. |
| 7,825,815 | B2 | 11/2010 | Shears et al. |
| 7,830,249 | B2 | 11/2010 | Dorneich et al. |
| 7,878,030 | B2 | 2/2011 | Burr |
| 7,931,604 | B2 | 4/2011 | Even et al. |
| 7,978,081 | B2 | 7/2011 | Shears et al. |
| 8,033,996 | B2 | 10/2011 | Behar |
| 8,082,762 | B2 | 12/2011 | Burr |
| 8,097,926 | B2 | 1/2012 | De Graff et al. |
| 8,137,270 | B2 | 3/2012 | Keenan et al. |
| 8,139,822 | B2 | 3/2012 | Selner |
| 8,162,857 | B2 | 4/2012 | Lanfermann et al. |
| 8,170,656 | B2 | 5/2012 | Tan et al. |
| 8,185,231 | B2 | 5/2012 | Fernandez |
| 8,209,147 | B2 | 6/2012 | Solinsky |
| 8,277,396 | B2 | 10/2012 | Scott et al. |
| 8,323,190 | B2 | 12/2012 | Vitiello et al. |
| 8,331,097 | B2 | 12/2012 | Yang et al. |
| 8,416,102 | B2 | 4/2013 | Yin |
| 8,435,177 | B2 | 5/2013 | Lanfermann et al. |
| 8,443,634 | B2 | 5/2013 | Scheffler et al. |
| 8,515,532 | B2 | 8/2013 | Yin et al. |
| 8,515,548 | B2 | 8/2013 | Rofougaran et al. |
| 8,536,667 | B2 | 9/2013 | De Graff et al. |
| 8,626,472 | B2 | 1/2014 | Solinsky |
| 8,678,979 | B2 | 3/2014 | Stark et al. |
| 8,768,648 | B2 | 7/2014 | Panther et al. |
| 8,780,540 | B2 | 7/2014 | Whitt et al. |
| 8,780,541 | B2 | 7/2014 | Whitt et al. |
| 8,784,271 | B2 | 7/2014 | Brumback et al. |
| 8,790,255 | B2 | 7/2014 | Behar |
| 8,798,710 | B2 | 8/2014 | Chi |
| 8,821,305 | B2 | 9/2014 | Cusey et al. |
| 8,821,417 | B2 | 9/2014 | McGregor et al. |
| 8,873,227 | B2 | 10/2014 | Whitt et al. |
| 8,886,334 | B2 | 11/2014 | Ghaffari et al. |
| 8,903,517 | B2 | 12/2014 | Perek et al. |
| 8,920,172 | B1 | 12/2014 | Wilmink et al. |
| 8,945,328 | B2 | 2/2015 | Longinotti-Buitoni et al. |

(56) References Cited

U.S. PATENT DOCUMENTS

| | | | |
|---|---|---|---|
| 8,947,353 | B2 | 2/2015 | Boulanger et al. |
| 8,947,864 | B2 | 2/2015 | Whitt et al. |
| 8,948,839 | B1 | 2/2015 | Longinotti-Buitoni et al. |
| 8,979,763 | B2 | 3/2015 | Stivoric et al. |
| 9,026,927 | B2 | 5/2015 | Brumback et al. |
| 9,037,530 | B2 | 5/2015 | Tan et al. |
| 9,039,613 | B2 | 5/2015 | Kuck et al. |
| 9,042,971 | B2 | 5/2015 | Brumback et al. |
| 9,044,150 | B2 | 6/2015 | Brumback et al. |
| 9,049,998 | B2 | 6/2015 | Brumback et al. |
| 2002/0077534 | A1 | 6/2002 | DuRousseau |
| 2003/0083596 | A1 | 5/2003 | Kramer et al. |
| 2005/0054941 | A1 | 3/2005 | Ting et al. |
| 2005/0126026 | A1 | 6/2005 | Townsend et al. |
| 2005/0240087 | A1 | 10/2005 | Keenan et al. |
| 2006/0025666 | A1 | 2/2006 | Getsla et al. |
| 2006/0029198 | A1 | 2/2006 | Dorneich et al. |
| 2006/0058699 | A1 | 3/2006 | Vitiello et al. |
| 2006/0167564 | A1 | 7/2006 | Flaherty et al. |
| 2006/0189899 | A1 | 8/2006 | Flaherty et al. |
| 2007/0050715 | A1 | 3/2007 | Behar |
| 2007/0148624 | A1 | 6/2007 | Nativ |
| 2007/0169364 | A1 | 7/2007 | Townsend et al. |
| 2008/0154113 | A1 | 6/2008 | Zilberman |
| 2008/0171918 | A1 | 7/2008 | Teller et al. |
| 2008/0183051 | A1 | 7/2008 | Teller et al. |
| 2008/0183052 | A1 | 7/2008 | Teller et al. |
| 2008/0191864 | A1 | 8/2008 | Wolfson |
| 2009/0118590 | A1 | 5/2009 | Teller et al. |
| 2009/0229039 | A1 | 9/2009 | Kuck et al. |
| 2009/0240117 | A1 | 9/2009 | Chmiel et al. |
| 2009/0247858 | A1 | 10/2009 | Getsla et al. |
| 2009/0326406 | A1 | 12/2009 | Tan et al. |
| 2010/0036288 | A1 | 2/2010 | Lanfermann et al. |
| 2010/0041974 | A1 | 2/2010 | Ting et al. |
| 2010/0117837 | A1 | 5/2010 | Stirling et al. |
| 2010/0121227 | A1 | 5/2010 | Stirling et al. |
| 2010/0121228 | A1 | 5/2010 | Stirling et al. |
| 2010/0201512 | A1 | 8/2010 | Stirling et al. |
| 2010/0204616 | A1 | 8/2010 | Stirling et al. |
| 2010/0296257 | A1 | 11/2010 | Yang et al. |
| 2011/0052005 | A1 | 3/2011 | Selner |
| 2011/0054271 | A1 | 3/2011 | Derchak et al. |
| 2011/0054272 | A1 | 3/2011 | Derchak |
| 2011/0130643 | A1 | 6/2011 | Derchak et al. |
| 2011/0137200 | A1 | 6/2011 | Yin et al. |
| 2011/0166491 | A1 | 7/2011 | Sankai |
| 2011/0208444 | A1 | 8/2011 | Solinsky |
| 2012/0071771 | A1 | 3/2012 | Behar |
| 2012/0116259 | A1 | 5/2012 | McConnell et al. |
| 2012/0137795 | A1 | 6/2012 | Selner |
| 2012/0143093 | A1 | 6/2012 | Stirling et al. |
| 2012/0150011 | A1 | 6/2012 | Besio |
| 2012/0184826 | A1 | 7/2012 | Keenan et al. |
| 2012/0184871 | A1 | 7/2012 | Jang et al. |
| 2012/0188158 | A1 | 7/2012 | Tan et al. |
| 2012/0223880 | A1 | 9/2012 | Birnbaum et al. |
| 2012/0238845 | A1 | 9/2012 | Yang |
| 2012/0296247 | A1* | 11/2012 | Streeter .................... A61F 5/34 602/5 |
| 2013/0066168 | A1 | 3/2013 | Yang et al. |
| 2013/0068017 | A1 | 3/2013 | Perkins et al. |
| 2013/0073248 | A1 | 3/2013 | Perkins et al. |
| 2013/0102874 | A1 | 4/2013 | Chi |
| 2013/0110011 | A1 | 5/2013 | McGregor et al. |
| 2013/0110415 | A1 | 5/2013 | Davis et al. |
| 2013/0116608 | A1* | 5/2013 | Romcevich ........... A61F 5/0104 602/1 |
| 2013/0123665 | A1 | 5/2013 | Mariani et al. |
| 2013/0211208 | A1 | 8/2013 | Varadan et al. |
| 2013/0253380 | A1 | 9/2013 | Miesel et al. |
| 2013/0317648 | A1 | 11/2013 | Assad |
| 2013/0324888 | A1 | 12/2013 | Solinsky |
| 2014/0053090 | A1 | 2/2014 | Yan et al. |
| 2014/0058476 | A1 | 2/2014 | Crosby et al. |
| 2014/0070957 | A1 | 3/2014 | Longinotti-Buitoni et al. |
| 2014/0125618 | A1 | 5/2014 | Panther et al. |
| 2014/0135593 | A1 | 5/2014 | Jayalth et al. |
| 2014/0135608 | A1 | 5/2014 | Gazzoni et al. |
| 2014/0135631 | A1 | 5/2014 | Brumback et al. |
| 2014/0142403 | A1 | 5/2014 | Brumback et al. |
| 2014/0142459 | A1 | 5/2014 | Jayalth et al. |
| 2014/0171749 | A1 | 6/2014 | Chin et al. |
| 2014/0172310 | A1 | 6/2014 | Chin et al. |
| 2014/0176335 | A1 | 6/2014 | Brumback et al. |
| 2014/0176346 | A1 | 6/2014 | Brumback et al. |
| 2014/0176422 | A1 | 6/2014 | Brumback et al. |
| 2014/0180019 | A1 | 6/2014 | Martinez et al. |
| 2014/0180020 | A1 | 6/2014 | Stivoric et al. |
| 2014/0180021 | A1 | 6/2014 | Stivoric et al. |
| 2014/0180022 | A1 | 6/2014 | Stivoric et al. |
| 2014/0180023 | A1 | 6/2014 | Stivoric et al. |
| 2014/0180137 | A1 | 6/2014 | Stivoric et al. |
| 2014/0180595 | A1 | 6/2014 | Brumback et al. |
| 2014/0198034 | A1 | 7/2014 | Bailey et al. |
| 2014/0198035 | A1 | 7/2014 | Bailey et al. |
| 2014/0210745 | A1 | 7/2014 | Chizeck et al. |
| 2014/0213929 | A1 | 7/2014 | Dunbar |
| 2014/0240103 | A1 | 8/2014 | Lake et al. |
| 2014/0240223 | A1 | 8/2014 | Lake et al. |
| 2014/0247150 | A1 | 9/2014 | Proud |
| 2014/0249397 | A1 | 9/2014 | Lake et al. |
| 2014/0249853 | A1 | 9/2014 | Proud et al. |
| 2014/0267084 | A1 | 9/2014 | Krulce et al. |
| 2014/0277739 | A1 | 9/2014 | Kornbluh et al. |
| 2014/0278139 | A1 | 9/2014 | Hong et al. |
| 2014/0302471 | A1 | 10/2014 | Hanners |
| 2014/0303523 | A1 | 10/2014 | Hong et al. |
| 2014/0316713 | A1 | 10/2014 | Chmiel et al. |
| 2014/0318699 | A1 | 10/2014 | Longinotti-Buitoni et al. |
| 2014/0334083 | A1 | 11/2014 | Bailey |
| 2014/0343392 | A1* | 11/2014 | Yang .................... A61B 5/7221 600/393 |
| 2014/0364701 | A1 | 12/2014 | Masakov |
| 2014/0375465 | A1 | 12/2014 | Fenuccio et al. |
| 2014/0378786 | A1 | 12/2014 | Hong et al. |
| 2014/0378787 | A1 | 12/2014 | Brumback et al. |
| 2014/0378812 | A1 | 12/2014 | Saroka et al. |
| 2014/0378872 | A1 | 12/2014 | Hong et al. |
| 2015/0005608 | A1 | 1/2015 | Evans et al. |
| 2015/0019135 | A1 | 1/2015 | Kacyvenski et al. |
| 2015/0025355 | A1 | 1/2015 | Bailey et al. |
| 2015/0040282 | A1 | 2/2015 | Longinotti-Buitoni et al. |
| 2015/0045699 | A1 | 2/2015 | Mokaya et al. |
| 2015/0051470 | A1 | 2/2015 | Bailey et al. |
| 2015/0057506 | A1 | 2/2015 | Luna et al. |
| 2015/0057770 | A1 | 2/2015 | Bailey et al. |
| 2015/0062844 | A1 | 3/2015 | Bae et al. |
| 2015/0065840 | A1 | 3/2015 | Bailey |
| 2015/0070270 | A1 | 3/2015 | Bailey et al. |
| 2015/0080746 | A1* | 3/2015 | Bleich .................... G16H 20/30 600/479 |
| 2015/0084860 | A1 | 3/2015 | Aleem et al. |
| 2015/0109202 | A1 | 4/2015 | Ataee et al. |
| 2015/0124566 | A1 | 5/2015 | Lake et al. |
| 2015/0141784 | A1 | 5/2015 | Morun et al. |
| 2015/0143601 | A1 | 5/2015 | Longinotti-Buitoni et al. |
| 2015/0145676 | A1 | 5/2015 | Adhikari et al. |
| 2015/0148619 | A1 | 5/2015 | Berg et al. |
| 2015/0148641 | A1 | 5/2015 | Morun et al. |
| 2015/0150122 | A1 | 5/2015 | Son et al. |
| 2015/0169074 | A1 | 6/2015 | Ataee et al. |
| 2017/0246073 | A1* | 8/2017 | Van-De-Velde ........ A61F 13/08 |

* cited by examiner

ELECTROMYOGRAPHIC CLOTHING

CROSS-REFERENCE TO RELATED APPLICATIONS

This application is a continuation in part of patent application Ser. No. 18/900,784 filed on 2024 Sep. 29. This application is a continuation in part of patent application Ser. No. 18/369,129 filed on 2023 Sep. 15. patent application Ser. No. 18/900,784 was a continuation in part of patent application Ser. No. 18/369,129 filed on 2023 Sep. 15.

Patent application Ser. No. 18/369,129 was a continuation in part of patent application Ser. No. 17/721,866 filed on 2022 Apr. 15 which issued as U.S. Pat. No. 11,892,286 on 2024 Feb. 6. patent application Ser. No. 17/721,866 was a continuation in part of patent application Ser. No. 17/356,377 filed on 2021 Jun. 23 which issued as U.S. Pat. No. 11,304,628 on 2022 Apr. 19. patent application Ser. No. 17/721,866 was a continuation in part of patent application Ser. No. 17/356,377 filed on 2021 Jun. 23 which issued as U.S. Pat. No. 11,304,628 on 2022 Apr. 19. patent application Ser. No. 17/356,377 was a continuation in part of patent application Ser. No. 16/751,245 filed on 2020 Jan. 24 which issued as U.S. Pat. No. 11,071,498 on 2021 Jul. 27.

Patent application Ser. No. 16/751,245 was a continuation in part of patent application Ser. No. 16/543,056 filed on 2019 Aug. 16 which issued as U.S. Pat. No. 10,839,202 on 2020 Nov. 17. patent application Ser. No. 16/751,245 claimed the priority benefit of patent provisional application 62/797,266 filed on 2019 Jan. 26. patent application Ser. No. 16/751,245 was a continuation in part of patent application Ser. No. 16/017,439 filed on 2018 Jun. 25 which issued as U.S. Pat. No. 10,921,886 on 2020 Feb. 16. patent application Ser. No. 16/751,245 was a continuation in part of patent application Ser. No. 16/010,448 filed on 2018 Jun. 16 which issued as U.S. Pat. No. 10,602,965 on 2020 Mar. 31. patent application Ser. No. 16/751,245 was a continuation in part of patent application Ser. No. 15/702,081 filed on 2017 Sep. 12 which issued as U.S. Pat. No. 10,716,510 on 2020 Jul. 21.

Patent application Ser. No. 16/543,056 claimed the priority benefit of patent provisional application 62/797,266 filed on 2019 Jan. 26. patent application Ser. No. 16/543,056 claimed the priority benefit of patent provisional application 62/727,798 filed on 2018 Sep. 6. patent application Ser. No. 16/543,056 was a continuation in part of patent application Ser. No. 16/010,448 filed on 2018 Jun. 16 which issued as U.S. Pat. No. 10,602,965 on 2020 Mar. 31. patent application Ser. No. 16/017,439 was a continuation in part of patent application Ser. No. 16/010,448 filed on 2018 Jun. 16 which issued as U.S. Pat. No. 10,602,965 on 2020 Mar. 31. patent application Ser. No. 16/017,439 claimed the priority benefit of patent provisional application 62/683,237 filed on 2018 Jun. 11. patent application Ser. No. 16/017,439 was a continuation in part of patent application Ser. No. 14/795,373 filed on 2015 Jul. 9.

Patent application Ser. No. 16/010,448 claimed the priority benefit of patent provisional application 62/683,237 filed on 2018 Jun. 11. patent application Ser. No. 16/010,448 was a continuation in part of patent application Ser. No. 15/702,081 filed on 2017 Sep. 12 which issued as U.S. Pat. No. 10,716,510 on 2020 Jul. 21. patent application Ser. No. 16/010,448 claimed the priority benefit of patent provisional application 62/538,793 filed on 2017 Jul. 30. patent application Ser. No. 16/010,448 was a continuation in part of patent application Ser. No. 15/227,254 filed on 2016 Aug. 3 which issued as U.S. Pat. No. 10,321,873 on 2019 Jun. 18.

Patent application Ser. No. 15/702,081 claimed the priority benefit of patent provisional application 62/538,793 filed on 2017 Jul. 30. patent application Ser. No. 15/702,081 claimed the priority benefit of patent provisional application 62/449,735 filed on 2017 Jan. 24. patent application Ser. No. 15/702,081 was a continuation in part of patent application Ser. No. 15/227,254 filed on 2016 Aug. 3 which issued as U.S. Pat. No. 10,321,873 on 2019 Jun. 18. patent application Ser. No. 15/702,081 was a continuation in part of patent application Ser. No. 14/795,373 filed on 2015 Jul. 9.

Patent application Ser. No. 15/227,254 claimed the priority benefit of patent provisional application 62/357,957 filed on 2016 Jul. 2. patent application Ser. No. 15/227,254 was a continuation in part of patent application Ser. No. 15/130,995 filed on 2016 Apr. 17 which issued as U.S. Pat. No. 9,891,718 on 2018 Feb. 13. patent application Ser. No. 15/227,254 was a continuation in part of patent application Ser. No. 15/079,447 filed on 2016 Mar. 24 which issued as U.S. Pat. No. 10,234,934 on 2019 Mar. 19. patent application Ser. No. 15/227,254 was a continuation in part of patent application Ser. No. 14/736,652 filed on 2015 Jun. 11. patent application Ser. No. 15/227,254 was a continuation in part of patent application Ser. No. 14/664,832 filed on 2015 Mar. 21 which issued as U.S. Pat. No. 9,582,072 on 2017 Feb. 28.

Patent application Ser. No. 15/130,995 claimed the priority benefit of patent provisional application 62/150,886 filed on 2015 Apr. 22. patent application Ser. No. 15/079,447 claimed the priority benefit of patent provisional application 62/150,886 filed on 2015 Apr. 22. patent application Ser. No. 15/079,447 was a continuation in part of patent application Ser. No. 14/664,832 filed on 2015 Mar. 21 which issued as U.S. Pat. No. 9,582,072 on 2017 Feb. 28. patent application Ser. No. 15/079,447 was a continuation in part of patent application Ser. No. 14/463,741 filed on 2014 Aug. 20 which issued as U.S. Pat. No. 9,588,582 on 2017 Mar. 7.

Patent application Ser. No. 14/795,373 claimed the priority benefit of patent provisional application 62/187,906 filed on 2015 Jul. 2. patent application Ser. No. 14/795,373 claimed the priority benefit of patent provisional application 62/182,473 filed on 2015 Jun. 20. patent application Ser. No. 14/795,373 was a continuation in part of patent application Ser. No. 14/736,652 filed on 2015 Jun. 11. patent application Ser. No. 14/795,373 claimed the priority benefit of patent provisional application 62/086,053 filed on 2014 Dec. 1. patent application Ser. No. 14/795,373 claimed the priority benefit of patent provisional application 62/065,032 filed on 2014 Oct. 17.

Patent application Ser. No. 14/736,652 was a continuation in part of patent application Ser. No. 14/664,832 filed on 2015 Mar. 21 which issued as U.S. Pat. No. 9,582,072 on 2017 Feb. 28. patent application Ser. No. 14/736,652 claimed the priority benefit of patent provisional application 62/014,747 filed on 2014 Jun. 20. patent application Ser. No. 14/664,832 was a continuation in part of patent application Ser. No. 14/463,741 filed on 2014 Aug. 20 which issued as U.S. Pat. No. 9,588,582 on 2017 Mar. 7. patent application Ser. No. 14/664,832 claimed the priority benefit of patent provisional application 61/976,650 filed on 2014 Apr. 8. patent application Ser. No. 14/463,741 claimed the priority benefit of patent provisional application 61/878,893 filed on 2013 Sep. 17.

The entire contents of these applications are incorporated herein by reference.

FEDERALLY SPONSORED RESEARCH: Not Applicable

Sequence Listing or Program

Not Applicable

BACKGROUND—FIELD OF INVENTION: This invention relates to wearable devices and systems for measuring body motion and/or muscle activity.

INTRODUCTION

Electromyographic clothing is clothing which incorporates one or more electromyographic (EMG) sensors in order to measure a person's muscle activity. These electromyographic (EMG) sensors collect electromagnetic energy data concerning the person's muscles and the motor neurons which innervate these muscles. Electromyographic clothing can also include other types of sensors in addition to electromyographic (EMG) sensors. Combined multivariate analysis of data from electromyographic (EMG) sensors and other types of sensors can provide more accurate measurement of muscle activity than data from either type of sensor alone. Electromyographic clothing can be custom designed to optimally measure the muscle activity of a specific person and/or muscle activity during a specific sport. Modular electromyographic clothing can be custom configured to optimally measure the muscle activity of a specific person and/or muscle activity during a specific sport.

There are many potential applications for electromyographic clothing. A prime application is the use of electromyographic clothing for sports and fitness. Electromyographic clothing can be used for sports and fitness applications such as: analyzing patterns of muscle exertion; estimating caloric expenditure and assisting in energy balance management; capturing, measuring, and recognizing full-body motion, posture, and configuration; comparing muscle activity with that of people in a peer group; detecting and correcting muscle group imbalances; enhancing athletic performance; guiding strength training; helping a person to perform a physical activity in a more efficient way; helping to avoid muscle fatigue and over-training; helping to prevent body injury; improving body posture and motion dynamics; improving fitness; monitoring nutritional intake; providing real-time feedback and/or coaching concerning physical activity; recognizing selected plays in athletic events for fan engagement and performance improvement; and recommending using different muscles.

Electromyographic clothing can also be useful for medical diagnostic and/or therapeutic purposes. In various examples, electromyographic clothing can be used for medical and health applications including: analyzing gait and balance; assisting in energy balance management; avoiding injury from repeated motions; collecting and evaluating data concerning muscle activity and evaluating ergonomics; detecting and correcting muscle group imbalances; encouraging proper posture to avoid spinal injury; evaluating range of motion for selected muscles and/or associated body joints; evaluating skeletal muscle tension; guiding physical rehabilitation, occupational therapy, and/or physical therapy; helping a person to perform a physical activity in a safer manner; helping a person to perform a physical activity in a more therapeutic manner; helping to prevent falls and fractures; improving general fitness and health; measuring energy expenditure; monitoring nutritional intake; providing real-time feedback concerning a person's physical activity; recognizing changes in body configuration and posture; and tracking muscle fatigue.

Electromyographic clothing can also be used for artistic and/or entertainment purposes. In various examples, electromyographic clothing can be used for arts and entertainment applications including: capturing, measuring, and recognizing full-body motion in order to animate an avatar or other virtual character in virtual reality, a computer game, an animated motion picture, or performance art; capturing dance moves for instruction or performance applications; and capturing the moves of a musician playing an instrument for instruction or performance applications.

Electromyographic clothing can also be used for remote control of a machine (such as a robot) and/or for telecommunication purposes. In various examples, electromyographic clothing can be used for machine control and communication applications including: controlling a wearable device; controlling a mobile, laptop, or desktop computing device; controlling a prosthetic limb; controlling an appliance and/or security system; remote control of a robot (e.g. telerobotics); enabling teleconferencing and/or telepresence; recognizing body motions; recognizing hand gestures; and translating sign language into words.

Review of the Relevant Art

It can be challenging trying to classify relevant art into discrete categories. However, classification of relevant art into categories, even if imperfect, can be an invaluable tool for reviewing a large body of relevant art. Towards this end, I herein identify nine categories of relevant art and provide examples of relevant art in each category. Some examples of relevant art disclose multiple concepts and thus appear in more than one category.

The nine categories of relevant art which are used for this review are as follows: (1) designs for individual EMG sensors, (2) devices used to position EMG sensors but removed before EMG sensing, (3) devices primarily based on inertial sensors but including EMG sensors, (4) devices with other types of sensors in addition to EMG sensors, (5) devices with selection of a subset of EMG sensors, (6) devices comprising bands or belts with EMG sensors, (7) clothing with EMG sensors, (8) notification management via EMG sensors, and (9) other relevant art concerning EMG sensors.

A first category of relevant art focuses primarily on specific designs for individual electromyographic (EMG) sensors. This art is important for the field of electromyography, but is not among the most relevant for specifying how configurations of multiple sensors can be incorporated into electromyographic clothing. Art in this category includes U.S. Patent Applications: 20130066168 (Yang et al., Mar. 14, 2013, "Method and System for Generating Physiological Signals with Fabric Capacitive Sensors"); 20140135608 (Gazzoni et al., May 15, 2014, "Textile Electrode Device for Acquisition of Electrophysiological Signals from the Skin and Manufacturing Process Thereof"); 20140249397 (Lake et al., Sep. 4, 2014, "Differential Non-Contact Biopotential Sensor"); 20150005608 (Evans et al., Jan. 1, 2015, "Electrode Units for Sensing Physiological Electrical Activity"); 20150141784 (Morun et al., May 21, 2015, "Systems, Articles, and Methods for Capacitive Electromyography Sensors"); and 20150148641 (Morun et al., May 28, 2015, "Systems, Articles, and Methods for Electromyography Sensors").

A second category of relevant art focuses primarily on devices which are used to position electromyographic (EMG) sensors in particular locations with respect to a person's body before sensor use, but these devices are removed before the sensors are used on an ongoing basis. Art in this category does not appear to include electromyographic clothing which is worn during sensor use. Art in this category includes U.S. Pat. No. 6,944,496 (Jeong et al., Sep. 13, 2005, "Apparatus for Positioning and Marking a Location of an EMG Electrode") and U.S. patent application Ser. No. 20/080,154113 (Zilberman, Jun. 26, 2008, "Apparatus and Method for Positioning Electrodes on the Body").

A third category of relevant art focuses primarily on inertial sensors, but includes the possibility of electromyographic (EMG) sensors. Accordingly, art in this category generally does not tackle the challenging aspects of designing electromyographic clothing. Art in this category includes: U.S. Pat. No. 7,602,301 (Stirling et al., Oct. 13, 2009, "Apparatus, Systems, and Methods for Gathering and Processing Biometric and Biomechanical Data"); U.S. Pat. No. 7,821,407 (Shears et al., Oct. 26, 2010, "Apparatus, Systems, and Methods for Gathering and Processing Biometric and Biomechanical Data"); U.S. Pat. No. 7,825,815 (Shears et al., Nov. 2, 2010, "Apparatus, Systems, and Methods for Gathering and Processing Biometric and Biomechanical Data"); and U.S. Pat. No. 8,821,305 (Cusey et al., Sep. 2, 2014, "Apparatus, Systems, and Methods for Gathering and Processing Biometric and Biomechanical Data").

Art in this category also includes: U.S. patent application Ser. No. 20/100,117837 (Stirling et al., May 13, 2010, "Apparatus, Systems, and Methods for Gathering and Processing Biometric and Biomechanical Data"); 20100121227 (Stirling et al., May 13, 2010, "Apparatus, Systems, and Methods for Gathering and Processing Biometric and Biomechanical Data"); 20100121228 (Stirling et al., May 13, 2010, "Apparatus, Systems, and Methods for Gathering and Processing Biometric and Biomechanical Data"); 20100201512 (Stirling et al., Aug. 12, 2010, "Apparatus, Systems, and Methods for Evaluating Body Movements"); 20100204616 (Stirling et al., Aug. 12, 2010, "Apparatus, Systems, and Methods for Gathering and Processing Biometric and Biomechanical Data"); 20120143093 (Stirling et al., Jun. 7, 2012, "Apparatus, Systems, and Methods for Gathering and Processing Biometric and Biomechanical Data"); and 20130123665 (Mariani et al., May 16, 2013, "System and Method for 3D Gait Assessment").

A fourth category of relevant art focuses primarily on the use of other types of sensors (such as inertial motion sensors) in addition to electromyographic (EMG) sensors. In some examples, the use of other types of sensors in addition to EMG sensors is just mentioned tangentially. In other examples, the manner which the operation of other types of sensors can be integrated with the operation of EMG sensors is more fully explored. Art in this category includes: U.S. Pat. No. 5,592,401 (Kramer, Jan. 7, 1997, "Accurate, Rapid, Reliable Position Sensing using Multiple Sensing Technologies"); U.S. Pat. No. 5,930,741 (Kramer, Jul. 27, 1999, "Accurate, Rapid, Reliable Position Sensing using Multiple Sensing Technologies"); U.S. Pat. No. 6,050,962 (Kramer et al., Apr. 18, 2000, "Goniometer-Based Body-Tracking Device and Method"); U.S. Pat. No. 6,148,280 (Kramer, Nov. 14, 2000, "Accurate, Rapid, Reliable Position Sensing using Multiple Sensing Technologies"); U.S. Pat. No. 6,428,490 (Kramer et al., Aug. 6, 2002, "Goniometer-Based Body-Tracking Device and Method"); U.S. Pat. No. 7,070,571 (Kramer et al., Jul. 4, 2006, "Goniometer-Based Body-Tracking Device"); and U.S. Pat. No. 7,830,249 (Dorneich et al., Nov. 9, 2010, "Communications System Based on Real-Time Neurophysiological Characterization").

Art in this category also includes: U.S. Pat. No. 7,878,030 (Burr, Feb. 1, 2011, "Wearable Article with Band Portion Adapted to Include Textile-Based Electrodes and Method of Making Such Article"); U.S. Pat. No. 8,082,762 (Burr, Dec. 27, 2011, "Wearable Article with Band Portion Adapted to Include Textile-Based Electrodes and Method of Making Such Article"); U.S. Pat. No. 8,139,822 (Selner, Mar. 20, 2012, "Designation of a Characteristic of a Physical Capability by Motion Analysis, Systems and Methods"); U.S. Pat. No. 8,162,857 (Lanfermann et al., Apr. 24, 2012, "Limb Movement Monitoring System"); U.S. Pat. No. 8,323,190 (Vitiello et al., Dec. 4, 2012, "Comprehensive Neuromuscular Profiler"); 8945328 (Longinotti-Buitoni et al., Feb. 3, 2015, "Methods of Making Garments Having Stretchable and Conductive Ink"); and 8948839 (Longinotti-Buitoni et al., Feb. 3, 2015, "Compression Garments Having Stretchable and Conductive Ink").

Art in this category also includes: U.S. patent application Ser. No. 20/020,077534 (DuRousseau, Jun. 20, 2002, "Method and System for Initiating Activity Based on Sensed Electrophysiological Data"); 20030083596 (Kramer et al., May 1, 2003, "Goniometer-Based Body-Tracking Device and Method"); 20060029198 (Dorneich et al., Feb. 9, 2006, "Communications System Based on Real-Time Neurophysiological Characterization"); 20060058699 (Vitiello et al., Mar. 16, 2006, "Comprehensive Neuromuscular Profiler"); 20060167564 (Flaherty et al., Jul. 27, 2006, "Limb and Digit Movement System"); 20100036288 (Lanfermann et al., Feb. 11, 2010, "Limb Movement Monitoring System"); 20110052005 (Selner, Mar. 3, 2011, "Designation of a Characteristic of a Physical Capability by Motion Analysis, Systems and Methods"); 20120137795 (Selner, Jun. 7, 2012, "Rating a Physical Capability by Motion Analysis"); 20120184871 (Jang et al., Jul. 19, 2012, "Exercise Monitor and Method for Monitoring Exercise"); 20130317648 (Assad., Nov. 28, 2013, "Biosleeve Human-Machine Interface"); and 20140070957 (Longinotti-Buitoni et al., Mar. 13, 2014, "Wearable Communication Platform").

Art in this category also includes: U.S. patent application Ser. No. 20/140,135593 (Jayalth et al., May 15, 2014, "Wearable Architecture and Methods for Performance Monitoring, Analysis, and Feedback"); 20140142459 (Jayalth et al., May 22, 2014, "Wearable Performance Monitoring, Analysis, and Feedback Systems and Methods"); 20140198034 (Bailey et al., Jul. 17, 2014, "Muscle Interface Device and Method for Interacting with Content Displayed on Wearable Head Mounted Displays"); 20140198035 (Bailey et al., Jul. 17, 2014, "Wearable Muscle Interface Systems, Devices and Methods That Interact with Content Displayed on an Electronic Display"); 20140240103 (Lake et al., Aug. 28, 2014, "Methods and Devices for Combining Muscle Activity Sensor Signals and Inertial Sensor Signals for Gesture-Based Control"); 20140240223 (Lake et al., Aug. 28, 2014, "Method and Apparatus for Analyzing Capacitive EMG and IMU Sensor Signals for Gesture Control"); 20140302471 (Hanners, Oct. 9, 2014, "System and Method for Controlling Gaming Technology, Musical Instruments and Environmental Settings via Detection of Neuromuscular Activity"); 20140318699 (Longinotti-Buitoni et al., Oct. 30, 2014, "Methods of Making Garments Having Stretchable and Conductive Ink"); and 20140334083 (Bailey, Nov. 13, 2014, "Systems, Articles and Methods for Wearable Electronic Devices That Accommodate Different User Forms").

Art in this category also includes: U.S. patent application Ser. No. 20/140,378812 (Saroka et al., Dec. 25, 2014, "Thoracic Garment of Positioning Electromagnetic (EM) Transducers and Methods of Using Such Thoracic Garment"); 20150040282 (Longinotti-Buitoni et al., Feb. 12, 2015, "Compression Garments Having Stretchable and Conductive Ink"); 20150045699 (Mokaya et al., Feb. 12, 2015, "Musculoskeletal Activity Recognition System and Method"); 20150051470 (Bailey et al., Feb. 19, 2015, "Systems, Articles and Methods for Signal Routing in Wearable Electronic Devices"); 20150057770 (Bailey et al., Feb. 26, 2015, "Systems, Articles, and Methods for Human-Electronics Interfaces"); 20150065840 (Bailey, Mar. 5, 2015, "Systems, Articles, and Methods for Stretchable Printed Circuit Boards"); and 20150070270 (Bailey et al., Mar. 12, 2015, "Systems, Articles, and Methods for Electromyography-Based Human-Electronics Interfaces").

Art in this category also includes: U.S. patent application Ser. No. 20/150,084860 (Aleem et al., Mar. 26, 2015, "Systems, Articles, and Methods for Gesture Identification in Wearable Electromyography Devices"); 20150109202 (Atace et al., Apr. 23, 2015, "Systems, Articles, and Methods for Gesture Identification in Wearable Electromyography Devices"); 20150124566 (Lake et al., May 7, 2015, "Systems, Articles and Methods for Wearable Electronic Devices Employing Contact Sensors"); 20150141784 (Morun et al., May 21, 2015, "Systems, Articles, and Methods for Capacitive Electromyography Sensors"); 20150143601 (Longinotti-Buitoni et al., May 28, 2015, "Garments Having Stretchable and Conductive Ink"); 20150148619 (Berg et al., May 28, 2015, "System and Method for Monitoring Biometric Signals"); 20150148641 (Morun et al., May 28, 2015, "Systems, Articles, and Methods for Electromyography Sensors"); and 20150169074 (Ataee et al., Jun. 18, 2015, "Systems, Articles, and Methods for Gesture Identification in Wearable Electromyography Devices").

A fifth category of relevant art focuses on how a subset of EMG sensors from which data is used can be selected from a total number of EMG sensors. Art in this category includes: U.S. Pat. No. 8,170,656 (Tan et al., May 1, 2012, "Wearable Electromyography-Based Controllers for Human-Computer Interface") and U.S. Pat. No. 9,037,530 (Tan et al., May 19, 2015, "Wearable Electromyography-Based Human-Computer Interface"); and U.S. patent application Ser. No. 20/090,326406 (Tan et al., Dec. 31, 2009, "Wearable Electromyography-Based Controllers for Human-Computer Interface"); 20120188158 (Tan et al., Jul. 26, 2012, "Wearable Electromyography-Based Human-Computer Interface"); 20130317648 (Assad., Nov. 28, 2013, "Biosleeve Human-Machine Interface"); 20140135593 (Jayalth et al., May 15, 2014, "Wearable Architecture and Methods for Performance Monitoring, Analysis, and Feedback"); 20140142459 (Jayalth et al., May 22, 2014, "Wearable Performance Monitoring, Analysis, and Feedback Systems and Methods"); and 20150057506 (Luna et al., Feb. 26, 2015, "Arrayed Electrodes in a Wearable Device for Determining Physiological Characteristics").

A sixth category of relevant art focuses on how EMG sensors can be incorporated into bands or belts which are worn on a person's body. Art in this category includes: U.S. Pat. No. 5,474,083 (Church et al., Dec. 12, 1995, "Lifting Monitoring and Exercise Training System"); U.S. Pat. No. 7,559,902 (Ting et al., Jul. 14, 2009, "Physiological Monitoring Garment"); U.S. Pat. No. 7,878,030 (Burr, Feb. 1, 2011, "Wearable Article with Band Portion Adapted to Include Textile-Based Electrodes and Method of Making Such Article"); U.S. Pat. No. 8,082,762 (Burr, Dec. 27, 2011, "Wearable Article with Band Portion Adapted to Include Textile-Based Electrodes and Method of Making Such Article"); U.S. Pat. No. 8,170,656 (Tan et al., May 1, 2012, "Wearable Electromyography-Based Controllers for Human-Computer Interface"); U.S. Pat. No. 9,037,530 (Tan et al., May 19, 2015, "Wearable Electromyography-Based Human-Computer Interface"); and U.S. Pat. No. 9,039,613 (Kuck et al., May 26, 2015, "Belt with Sensors").

Art in this category also includes: U.S. patent application Ser. No. 20/050,054941 (Ting et al., Mar. 10, 2015, "Physiological Monitoring Garment"); 20090229039 (Kuck et al., Sep. 17, 2009, "Belt with Sensors"); 20090326406 (Tan et al., Dec. 31, 2009, "Wearable Electromyography-Based Controllers for Human-Computer Interface"); 20100041974 (Ting et al., Feb. 18, 2010, "Physiological Monitoring Garment"); 20120188158 (Tan et al., Jul. 26, 2012, "Wearable Electromyography-Based Human-Computer Interface"); 20140198034 (Bailey et al., Jul. 17, 2014, "Muscle Interface Device and Method for Interacting with Content Displayed on Wearable Head Mounted Displays"); 20140198035 (Bailey et al., Jul. 17, 2014, "Wearable Muscle Interface Systems, Devices and Methods That Interact with Content Displayed on an Electronic Display"); 20140240103 (Lake et al., Aug. 28, 2014, "Methods and Devices for Combining Muscle Activity Sensor Signals and Inertial Sensor Signals for Gesture-Based Control"); 20140240223 (Lake et al., Aug. 28, 2014, "Method and Apparatus for Analyzing Capacitive EMG and IMU Sensor Signals for Gesture Control"); 20140334083 (Bailey, Nov. 13, 2014, "Systems, Articles and Methods for Wearable Electronic Devices That Accommodate Different User Forms"); 20150025355 (Bailey et al., Jan. 22, 2015, "Systems, Articles and Methods for Strain Mitigation in Wearable Electronic Devices"); and 20150051470 (Bailey et al., Feb. 19, 2015, "Systems, Articles and Methods for Signal Routing in Wearable Electronic Devices").

Art in this category also includes: U.S. patent application Ser. No. 20/150,057506 (Luna et al., Feb. 26, 2015, "Arrayed Electrodes in a Wearable Device for Determining Physiological Characteristics"); 20150057770 (Bailey et al., Feb. 26, 2015, "Systems, Articles, and Methods for Human-Electronics Interfaces"); 20150065840 (Bailey, Mar. 5, 2015, "Systems, Articles, and Methods for Stretchable Printed Circuit Boards"); 20150070270 (Bailey et al., Mar. 12, 2015, "Systems, Articles, and Methods for Electromyography-Based Human-Electronics Interfaces"); 20150084860 (Aleem et al., Mar. 26, 2015, "Systems, Articles, and Methods for Gesture Identification in Wearable Electromyography Devices"); 20150109202 (Ataee et al., Apr. 23, 2015, "Systems, Articles, and Methods for Gesture Identification in Wearable Electromyography Devices"); 20150124566 (Lake et al., May 7, 2015, "Systems, Articles and Methods for Wearable Electronic Devices Employing Contact Sensors"); 20150141784 (Morun et al., May 21, 2015, "Systems, Articles, and Methods for Capacitive Electromyography Sensors"); 20150148641 (Morun et al., May 28, 2015, "Systems, Articles, and Methods for Electromyography Sensors"); and 20150169074 (Ataee et al., Jun. 18, 2015, "Systems, Articles, and Methods for Gesture Identification in Wearable Electromyography Devices").

A seventh category of relevant art focuses on how EMG sensors can be incorporated into articles of clothing which are worn on a person's body. Art in this category includes: U.S. Pat. No. 7,152,470 (Impio et al., Dec. 26, 2006, "Method and Outfit for Measuring of Action of Muscles of Body"); U.S. Pat. No. 7,559,902 (Ting et al., Jul. 14, 2009, "Physiological Monitoring Garment"); U.S. Pat. No. 7,878,030 (Burr, Feb. 1, 2011, "Wearable Article with Band Portion Adapted to Include Textile-Based Electrodes and Method of Making Such Article"); U.S. Pat. No. 8,082,762 (Burr, Dec. 27, 2011, "Wearable Article with Band Portion Adapted to Include Textile-Based Electrodes and Method of Making Such Article"); U.S. Pat. No. 8,162,857 (Lanfermann et al., Apr. 24, 2012, "Limb Movement Monitoring System"); U.S. Pat. No. 8,170,656 (Tan et al., May 1, 2012, "Wearable Electromyography-Based Controllers for Human-Computer Interface"); U.S. Pat. No. 8,185,231 (Fernandez, May 22, 2012, "Reconfigurable Garment Definition and Production Method"); 8945328 (Longinotti-Buitoni et al., Feb. 3, 2015, "Methods of Making Garments Having Stretchable and Conductive Ink"); 8948839 (Longinotti-Buitoni et al., Feb. 3, 2015, "Compression Garments Having Stretchable and Conductive Ink"); and U.S. Pat. No. 9,037,530 (Tan et al., May 19, 2015, "Wearable Electromyography-Based Human-Computer Interface").

Art in this category also includes: U.S. patent application Ser. No. 20/050,054941 (Ting et al., Mar. 10, 2015, "Physiological Monitoring Garment"); 20090326406 (Tan et al., Dec. 31, 2009, "Wearable Electromyography-Based Controllers for Human-Computer Interface"); 20100036288 (Lanfermann et al., Feb. 11, 2010, "Limb Movement Monitoring System"); 20100041974 (Ting et al., Feb. 18, 2010, "Physiological Monitoring Garment"); 20110166491 (Sankai, Jul. 7, 2011, "Biological Signal Measuring Wearing Device and Wearable Motion Assisting Apparatus"); 20120188158 (Tan et al., Jul. 26, 2012, "Wearable Electromyography-Based Human-Computer Interface"); 20130211208 (Varadan et al., Aug. 15, 2013, "Smart Materials, Dry Textile Sensors, and Electronics Integration in Clothing, Bed Sheets, and Pillow Cases for Neurological, Cardiac and/or Pulmonary Monitoring"); and 20130317648 (Assad., Nov. 28, 2013, "Biosleeve Human-Machine Interface").

Art in this category also includes: U.S. patent application Ser. No. 20/140,070957 (Longinotti-Buitoni et al., Mar. 13, 2014, "Wearable Communication Platform"); 20140135593 (Jayalth et al., May 15, 2014, "Wearable Architecture and Methods for Performance Monitoring, Analysis, and Feedback"); 20140142459 (Jayalth et al., May 22, 2014, "Wearable Performance Monitoring, Analysis, and Feedback Systems and Methods"); 20140213929 (Dunbar, Jul. 31, 2014, "Instrumented Sleeve"); 20140318699 (Longinotti-Buitoni et al., Oct. 30, 2014, "Methods of Making Garments Having Stretchable and Conductive Ink"); 20140378812 (Saroka et al., Dec. 25, 2014, "Thoracic Garment of Positioning Electromagnetic (EM) Transducers and Methods of Using Such Thoracic Garment"); 20150040282 (Longinotti-Buitoni et al., Feb. 12, 2015, "Compression Garments Having Stretchable and Conductive Ink"); 20150045699 (Mokaya et al., Feb. 12, 2015, "Musculoskeletal Activity Recognition System and Method"); 20150143601 (Longinotti-Buitoni et al., May 28, 2015, "Garments Having Stretchable and Conductive Ink"); and 20150148619 (Berg et al., May 28, 2015, "System and Method for Monitoring Biometric Signals").

An eighth category of relevant art focuses on how EMG sensors can be used to manage notifications concerning incoming messages. Art in this category includes: U.S. Pat. No. 7,830,249 (Dorneich et al., Nov. 9, 2010, "Communications System Based on Real-Time Neurophysiological Characterization") and U.S. patent application No. 20060029198 (Dorneich et al., Feb. 9, 2006, "Communications System Based on Real-Time Neurophysiological Characterization").

A ninth category of relevant art concerning electromyographic (EMG) sensors which does not fall neatly into one of the above categories, but nonetheless may be relevant to this invention. Art in this category includes: U.S. Pat. No. 8,515,548 (Rofougaran et al., Aug. 20, 2013, "Article of Clothing Including Bio-Medical Units"); and U.S. patent application Ser. No. 20/090,240117 (Chmiel et al., Sep. 24, 2009, "Data Acquisition for Modular Biometric Monitoring System"); 20110054271 (Derchak et al., Mar. 3, 2011, "Noninvasive Method and System for Monitoring Physiological Characteristics"); 20110130643 (Derchak et al., Jun. 2, 2011, "Noninvasive Method and System for Monitoring Physiological Characteristics and Athletic Performance"); 20140058476 (Crosby et al., Feb. 27, 2014, "Apparatus and Methods for Rehabilitating a Muscle and Assessing Progress of Rehabilitation"); and 20140210745 (Chizeck et al., Jul. 31, 2014, "Using Neural Signals to Drive Touch Screen Devices").

SUMMARY OF THE INVENTION

This invention is an article of electromyographic clothing with one or more electromyographic (EMG) sensors which is used to measure body motion and/or muscle activity. This article of electromyographic clothing can comprise: one or more articles of clothing; a plurality of bending-based motion sensors which are attached to and/or integrated into the one or more articles of clothing, wherein these bending-based motion sensors are configured to collect motion data concerning changes in the configurations of a set of body joints; a plurality of electromyographic (EMG) sensors which are attached to and/or integrated into the one or more articles of clothing, wherein these electromyographic (EMG) sensors are configured to collect electromagnetic energy data concerning the neuromuscular activity of a set of muscles, and wherein muscles in the set of muscles move joints in the set of body joints; and a data processing unit which analyzes both data from the bending-based motion sensors and data from the electromyographic (EMG) sensors in order to measure and/or model body motion and/or muscle activity.

Such an article of electromyographic clothing can have advantages over the prior art. Combined, joint, and/or multivariate analysis of both motion data from bending-based motion sensors and electromagnetic energy data from electromyographic (EMG) sensors can enable more accurate measurement and/or modeling of body motion than analysis of data from either type of sensor alone. In an example, this article of electromyographic clothing can further comprise a plurality of inertial motion sensors. Combined, joint, and/or multivariate analysis of motion data from bending-based motion sensors, motion data from inertial motion sensors, and electromagnetic energy data from the electromyographic (EMG) sensors can enable even greater accuracy during various conditions. In an example, electromyographic (EMG) sensors can be modular. In an example, electromyographic (EMG) sensors can be removably-attached to different locations on the article of clothing in order to create a customized article of electromyographic clothing which optimally measures the muscle activity of a particular person or muscle activity during a particular sport.

In an example, an article of electromyographic clothing can have a first set of clothing sections which are configured to have a first average distance from the surface of a person's body and a second set of clothing sections which are configured to have a second average distance from the surface of the person's body. The second average distance is less than the first average distance. Electromyographic (EMG) sensors are attached to and/or integrated into one or more of the clothing sections in the second set. In an example, the second average distance can be manually adjusted by the person wearing the article. In an example, the article of electromyographic clothing can further comprise an actuator which automatically adjusts the second average distance. In an example, the article of electromyographic clothing can be a short-sleeve shirt or a pair of shorts, wherein electromyographic (EMG) sensors are part of the shirt sleeve cuffs and/or pant leg cuffs

BRIEF INTRODUCTION TO THE FIGURES

DETAILED DESCRIPTION OF THE FIGURES

Figure 1:
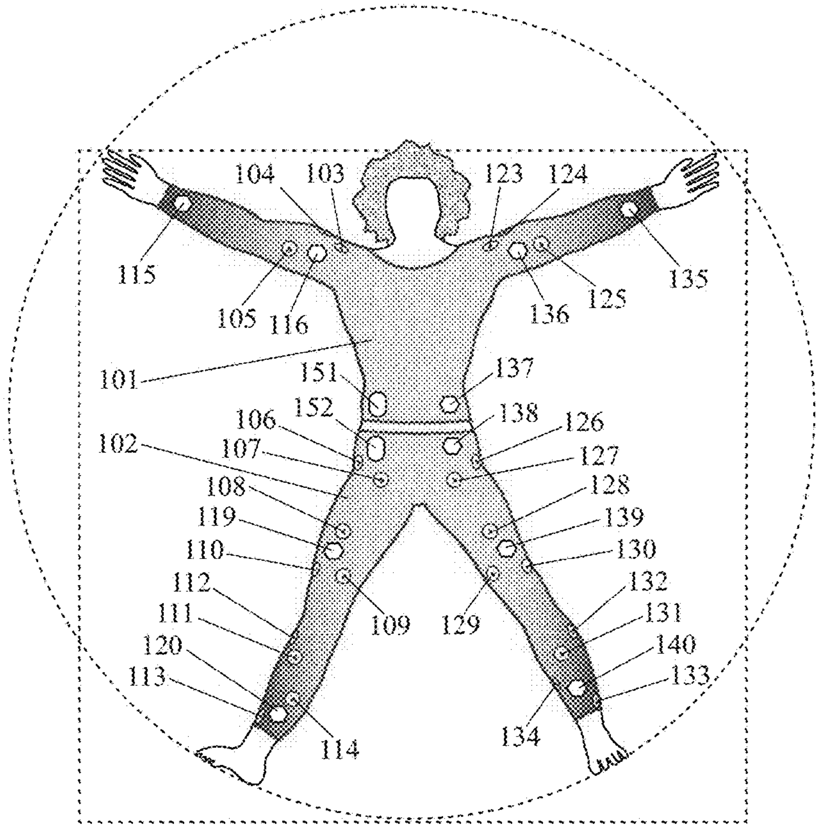
FIGS. 1 and 2 show electromyographic clothing comprising a shirt and pants with a plurality of EMG sensors and inertial motion sensors.

Later in this disclosure, several figures will be provided. These figures show different specific examples of how this invention can be embodied in an article of electromyographic clothing. However, before delving into these specific figures and examples, it is important to provide an introductory discussion concerning electromyographic clothing and electromyographic (EMG) sensors. This introductory discussion explains how electromyographic clothing and sensors can be designed and customized in order to optimally measure the muscle activity of a specific person or muscle activity during a specific type of physical activity. In the process, this discussion introduces the concept of modular electromyographic clothing. The clothing and sensor concepts which are introduced in this discussion can be applied, where relevant, to the specific figures and examples which follow. This eliminates the need to repeat these concepts within each narrative accompanying each specific figure, which would needlessly lengthen this disclosure.

Let us begin this introductory discussion by delving deeper into the basic forms and structural configurations of electromyographic clothing. In an example, an article of electromyographic clothing can have a basic form which is similar to that of an article of conventional (non-electromyographic) clothing. In an example, an article of electromyographic clothing can have a basic form which is selected from the group consisting of: bathrobe, bikini, blouse, boot, bra, briefs, cap, coat, dress, full-body article of clothing, garment with hood, girdle, glove, hat, hoodie, jacket, jeans, jockstrap, jumpsuit, leggings, leotards, long-sleeve shirt, lower-body garment, one-piece garment, overalls, pair of pants, pajamas, panties, pants, shirt, shorts, short-sleeve shirt, skirt, slacks, sock, suit, sweater, sweatpants, sweatshirt, sweat suit, swimsuit, tights, trousers, T-shirt, underpants, undershirt, union suit, upper-body garment, and vest.

In an example, this invention can also be embodied in a wearable device or system which is similar to that of a conventional clothing accessory. In an example, this invention can be embodied in a basic form which is selected from the group consisting of: abdominal brace, adhesive patch, amulet, ankle band, ankle brace, ankle bracelet, ankle strap, arm band, arm bracelet, artificial finger nail, bandage, bangle, beads, belt, bracelet, brooch, button, charm bracelet, chest band, chest strap, collar, contact lens, cuff link, dog tag, ear bud, ear muff, ear plug, ear ring, earphones, elastic band, elbow brace, elbow pad, electronic tattoo, eyeglasses, eyewear, face mask, finger nail attachment, finger ring, finger tube, fitness bracelet, fitness watch, footwear, forearm cuff, goggles, hair band, hair clip, hair pin, headband, headphones, hearing aid, helmet, knee brace, knee pad, leg band, monocle, neck band, neck chain, neck tie, necklace, nose ring, ornamental pin, pantyhose, patch, pendant, pin, pocketbook, poncho, sandal, shoe, shoulder brace, shoulder pad, skin patch, skullcap, sneaker, suspenders, tattoo, tie clip, visor, waist band, watch, wig, and wristband.

In an example, an article of electromyographic clothing can be configured to be worn on one or more portions of a person's body which are selected from the group consisting of: abdomen, ankle, arm, back, ear, elbow, eyes (directly such as via contact lens or indirectly such as via eyewear), finger, foot, forearm, hand, head, hip, jaw, knee, lips, lower arm, lower leg, mouth, neck, nose, palm, pelvis, rib cage, shoulder, spine, teeth, throat, thumb, toe, tongue, torso, upper arm, upper leg, waist, and wrist. In an example, an article of electromyographic clothing can be configured to collect data which is used to estimate the movement, angle, and/or configuration of one or more body joints. In an example, an electromyographic (EMG) sensor can be configured to cover (the mid-section of) a muscle which is proximal or distal from a selected body joint.

In various examples, electromyographic clothing can be used to estimate, measure, and/or model the abduction, extension, flexion, and/or ulnar deviation or radial deviation of a body joint. In various examples, electromyographic clothing can be used to measure one or more joint configurations and/or motions selected from the group consisting of: eversion, extension, flexion, and/or inversion of the ankle; abduction, extension, flexion, lateral bending, and/or rotation of the spine; eversion, extension, flexion, and/or inversion of the elbow; extension and/or flexion of the finger or thumb; pronation, rotation, and/or supination of the forearm; abduction, adduction, extension, flexion, and/or rotation of the hip; extension and/or flexion of the jaw; abduction, adduction, extension, and/or flexion of the knee; eversion and/or inversion of the mid-tarsal; abduction, extension, flexion, and/or rotation of the neck; abduction, adduction, extension, flexion, and/or rotation of the shoulder; extension and/or flexion of the toe; and abduction, extension, flexion, and/or ulnar deviation or radial deviation of the wrist.

An article of electromyographic clothing can be configured to collect data concerning the electromagnetic energy which is emitted by muscles and/or by the nerves which innervate those muscles. In various examples, an article of electromyographic clothing can be configured to collect data concerning electromagnetic energy emitted by the neuromuscular activity of one or more of the following: abductor digiti minimi (*brevis*), abductor hallucis, abductor pollicis (longus), adductor (*brevis*, longus, magnus, minimus), adductor hallucis, adductor pollicis, anconeus, articularis genus, biceps brachii, biceps femoris, *brachialis*, brachioradialis, coracobrachialis, deltoid (anterior, lateral, posterior), deltoideus, extensor carpi radialis (*brevis*, longus), extensor carpi ulnaris, extensor digitorum (*brevis*, longus), extensor hallucis (*brevis*, longus), extensor indicis, extensor pollicis (*brevis*, longus), fibularis tertius, flexor carpi (radialis, ulnaris), flexor digitorum (*brevis*, minimi), flexor digitorum (*profundus*, superficialis), flexor hallucis (*brevis*, longus), flexor pollicis (*brevis*, longus), gastrocnemius (lateralis, *medialis*), gemellus (inferior, superior), gluteus bogus, gluteus maximus, gluteus medius, gluteus minimus, gracilis, iliacus, iliopsoas, infraspinatus, interossei (dorsal, palmer), lateralis of the sastrocnemius, levator scapulae, lumbrical, *medialis* of the gastrocnemius, obturator (externus, internus), opponens digiti minimi, opponens pollicis, palmaris (*brevis*, longus), pectineus, pectoralis (minor, major), peroneus *brevis*, peroneus longus, *piriformis*, plantaris, popliteus, pronator quadratus, pronator *teres*, psoas (major, minor), quadratus femoris, quadratus plantae, quadriceps femoris (rectus femoris, vastus lateralis, vastus medialis), rectus femoris of the quadriceps femoris, rhomboid (minor, major), sartorius, sastrocnemius, semimembranosus, semitendinosus, serratus (anterior), soleus, subclavius, subscapularis, supinator, supraspinatus, tensor fasciae latae, *teres* (minor, major), tibialis anterior, tibialis posterior, trapezius, triceps brachii, triceps surae, vastus *intermedius*, vastus lateralis of the quadriceps femoris, and vastus medialis of the quadriceps femoris.

In an example, one or more electromyographic (EMG) sensors can be created as part of a fabric or textile which is then used to create an article of electromyographic clothing. In an example, one or more electromyographic (EMG) sensors can be created as part of a fabric or textile by weaving, knitting, sewing, embroidering, layering, laminating, adhering, melting, fusing, printing, spraying, painting, cutting, or pressing electroconductive threads, yarns, fibers, strands, layers, inks, or resins. This fabric or textile can then be used to create an article of electromyographic clothing.

In an example, one or more electromyographic (EMG) sensors can be created as part of an article of electromyographic clothing as the clothing is being made. In an example, one or more electromyographic (EMG) sensors can be created by weaving, knitting, sewing, embroidering, layering, laminating, adhering, melting, fusing, printing, spraying, painting, or pressing electroconductive threads, yarns, fibers, strands, layers, inks, or resins as an article of electromyographic clothing is being made.

In an example, one or more electromyographic (EMG) sensors can be permanently attached to (or formed on) an article of clothing after the clothing has been made. In an example, one or more electromyographic (EMG) sensors can be attached to an article of clothing by insertion, hook- and -eye mechanism, sewing, embroidering, adhesion, melting, pressing, printing, snapping, clipping, pinning, or plugging. In an example, one or more modular electromyographic (EMG) sensors can be removably-attached in different configurations to an article of electromyographic clothing by insertion, hook- and -eye mechanism, pressing, snapping, clipping, pinning, or plugging after the clothing has been made. In an example, one or more modular electromyographic (EMG) sensors can be removably-attached in different configurations to an article of electromyographic clothing by insertion, hook- and -eye mechanism, pressing, snapping, clipping, pinning, or plugging by the person who wears the clothing.

In an example, the number, types, locations, orientation, and/or configurations of electromyographic (EMG) sensors which are part of an article of electromyographic clothing can be customized and/or specifically configured to optimally collect data concerning the muscle activity of a specific person. In an example, the number, types, locations, orientation, and/or configurations of electromyographic (EMG) sensors which are part of an article of electromyographic clothing can be customized and/or specifically configured to optimally collect data concerning muscle activity during a specific sport or other specific type of physical activity. In an example, customization of sensor configuration can occur while a fabric or textile is created, wherein this fabric or textile is then used to make an article of clothing. In an example, customization of sensor configuration can occur while an article of clothing is being made. In an example, customization of sensor configuration can occur after an article of clothing has been made.

In an example, customization of sensor configuration can be accomplished with modular components whose configuration is changed by a manufacturer, by a retailer, and/or by the person who wears the clothing. In an example, a manufacturer can combine and/or assemble a set of modular components into an article of electromyographic clothing in order to create an article which optimally measures muscle activity data from a specific person or during a specific type of physical activity. In an example, a clothing seller can combine and/or assemble a set of modular components into an article of electromyographic clothing in order to create an article which optimally measures muscle activity data from a specific person or during a specific type of physical activity. In an example, a clothing wearer can combine and/or assemble a set of modular components into an article of electromyographic clothing in order to create an article which optimally measures muscle activity data from a specific person or during a specific type of physical activity.

In an example, one or more electromyographic (EMG) sensors can be created as part of an electronically-functional fabric or textile from which an article of electromyographic clothing is made. In an example, one or more electromyographic (EMG) sensors can be created as part of an electronically-functional fabric or textile by weaving, knitting, sewing, embroidering, layering, laminating, adhering, melting, fusing, printing, spraying, painting, or pressing electroconductive material into (or onto) a fabric or textile. In an example, electromyographic sensors can be attached to (or created within) a fabric or textile by weaving, knitting, sewing, embroidering, layering, laminating, adhering, melting, fusing, printing, spraying, painting, or pressing. In an example, electroconductive threads, fibers, yarns, strands, filaments, traces, and/or layers within a fabric or textile can be configured near a person's skin in order to receive electromagnetic energy emitted by muscles and nerves below the skin.

In an example, one or more electromyographic (EMG) sensors can be created as part of an article of clothing as that clothing is being made from conventional (non-electronic) fabric or textile. In an example, one or more electromyographic (EMG) sensors can be created as part of an article of clothing by weaving, knitting, sewing, embroidering, layering, laminating, adhering, melting, fusing, printing, spraying, painting, or pressing electroconductive material into (or onto) the clothing while the clothing is being made. In an example, electromyographic sensors can be attached or created by weaving, knitting, sewing, embroidering, layering, laminating, adhering, melting, fusing, printing, spraying, painting, or pressing. In an example, electroconductive threads, fibers, yarns, strands, filaments, traces, and/or layers can be configured near a person's skin in order to receive electromagnetic energy emitted by muscles and nerves below the skin.

In an example, one or more electromyographic (EMG) sensors can be attached to an article of clothing after a conventional article of clothing has been made. In an example, one or more electromyographic (EMG) sensors can be attached to an article of clothing after the clothing has been made using an attachment mechanism selected from the group consisting of: adhesive, band, buckle, button, channel, clasp, clip, electronic connector, flexible channel, hook, hook- and -eye mechanism, magnet, pin, plug, pocket, rivet, sewing, snap, tape, tie, and zipper. In an example, one or more electromyographic (EMG) sensors can be created on an article of clothing after the article of clothing has been made by printing, laminating, adhering, embroidering, melting, and/or sewing electroconductive material onto the clothing after the basic form of the clothing has been made.

In an example, electromyographic clothing can be modular. In an example, modular electromyographic clothing can be constructed and/or adjusted so as to optimally collect data concerning the muscle activity of a specific person or muscle activity during a specific sport (or other type of physical activity). In an example, the number, type, location, orientation, and/or configuration of electromyographic (EMG) sensors on (or within) an article of clothing can be selected, configured, customized, and/or adjusted so as to best collect data concerning the muscle activity of a specific person or muscle activity during a specific type of sport (or other physical activity). In an example, this selection, configuration, customization, and/or adjustment can occur during the creation of a fabric or textile from which the clothing is made, as the article of clothing is being made from a fabric or textile, or after the article of clothing has been made from a fabric or textile.

In an example, the selection, configuration, customization, and/or adjustment of electromyographic (EMG) sensors can be done by a clothing or textile manufacturer, by a clothing retailer, or by a clothing user. In an example, electromyographic clothing can have modular components which are assembled by a manufacturer or retailer in order to create an article of electromyographic clothing which is customized and/or tailor made for a specific person or a specific type of physical activity. In an example, electromyographic clothing can have modular components which are selected, configured, customized, and/or adjusted by the person who wears the clothing in order to optimally measure the muscle activity of that specific person. In an example, electromyographic clothing can have modular components which are selected, configured, customized, and/or adjusted by a person participating in a specific sport (or other type of physical activity) in order to optimally measure the muscle activity during that specific sport (or other type of physical activity).

In an example a customized article of electromagnetic clothing can be created by attaching, clipping, connecting, plugging, inserting, and/or snapping modular electroconductive members onto an article of clothing. In an example, one or more electromyographic (EMG) sensors can be attached (permanently or temporarily) to an article of electromyographic clothing by a mechanism selected from the group consisting of: a buckle, a button, a chain, a clamp, a clasp, a clip, a hook, a hook- and -eye mechanism, a magnet, a pin, a plug, a snap, a strap, a string, a tie, a zipper, an adhesive, an elastic band, an electronic plug, insertion into a channel, insertion into a pocket, insertion into a pouch, and tape.

In an example a customized article of electromagnetic clothing can be created by adhering, gluing, laminating, and/or melting modular electroconductive members onto an article of clothing. In an example a customized article of electromagnetic clothing can be created by weaving, knitting, sewing, embroidering, layering, laminating, adhering, melting, fusing, printing, spraying, painting, or pressing modular electroconductive members onto (or into) an article of clothing. In an example a customized article of electromagnetic clothing can be created by flocking, painting, printing, spraying, and/or screening modular electroconductive material onto an article of clothing. In an example a customized article of electromagnetic clothing can be created by inserting, pressing, rotating, and/or sliding modular electroconductive members onto (or across) the surface an article of clothing.

In an example, a customized modular article of electromyographic clothing can be created by: selecting a module from a first set of EMG sensor modules with the best sensor configuration for measuring muscle activity from a first body location for a specific person or sport; selecting a module from a second set of EMG sensor modules with the best sensor configuration for measuring muscle activity from a second body location for that specific person or sport; selecting a module from a third set of EMG sensor modules with the best sensor configuration for measuring muscle activity from a third body location for that specific person or sport; and combining these three selected modules into a single customized article of clothing. In an example, each module in each set can include at least one electromyographic (EMG) sensor. Alternatively, there can be a set and/or module with no electromyographic (EMG) sensors. A module with no electromyographic (EMG) sensor can serve a variable-size placeholder in a longitudinal series of sets.

In an example, electroconductive threads, fibers, yarns, strands, filaments, traces, layers, inks, and/or resins can be made from one or more materials selected from the group consisting of: aluminum (Al), aluminum alloy, brass (Ms), carbon nanotubes, carbon-based material, ceramic particles, copper (Cu), copper alloy, copper-clad aluminum, fluorine, gold (Au), graphene, magnesium, nickel, niobium (Nb), organic solvent, polyaniline, polymer, rubber, silicone, silver (Ag), silver chloride (AgCl), silver-plated brass (Ms/Ag), silver-plated copper (Cu/Ag), and steel. In an example, naturally non-conductive (or less conductive) electroconductive threads, fibers, yarns, strands, filaments, traces, layers, inks, and/or resins can be made conductive by combining them with material selected from the group consisting of: aluminum (Al), aluminum alloy, brass (Ms), carbon nanotubes, carbon-based material, ceramic particles, copper (Cu), copper alloy, copper-clad aluminum, fluorine rubber, fluorine surfactant, gold (Au), graphene, magnesium, nickel, niobium (Nb), organic solvent, polyaniline, polymer, rubber, silicone, silver (Ag), silver chloride (AgCl), silver-plated brass (Ms/Ag), silver-plated copper (Cu/Ag), and steel. In an example, electroconductive threads, fibers, yarns, strands, filaments, traces, and/or layers can be selected from the group consisting of: conductive core yarn, copper thread coated with polyester, polyester yarn coated with metal, steel fiber yarn, synthetic filament fiber yarn, yarn coated with carbon, yarn coated with copper, and yarn coated with silver.

In an example, an electronically-functional fabric or textile, and/or article of clothing with electromyographic (EMG) sensors can be created by weaving, knitting, sewing, embroidering, layering, laminating, adhering, melting, fusing, printing, spraying, painting, or pressing together electroconductive threads, fibers, yarns, strands, filaments, traces, and/or layers. In an example, the electroconductive threads, yarns, fibers, strands, channels, and/or traces comprising electromyographic (EMG) sensors in clothing can have shapes or configurations which are selected from the group consisting of: circular, elliptical, or other conic section; square, rectangular, hexagon, or other polygon; parallel; perpendicular; crisscrossed; nested; concentric; sinusoidal; undulating; zigzagged; and radial spokes. In an example, an electronically-functional fabric, textile, and/or article of clothing with electromyographic (EMG) sensors can be created by weaving, knitting, sewing, embroidering, layering, laminating, adhering, melting, fusing, printing, spraying, painting, or pressing electroconductive threads, fibers, yarns, strands, filaments, traces, and/or layers together with non-conductive threads, fibers, yarns, filaments, traces, and/or layers.

In an example, an electronically-functional fabric, textile, and/or article of clothing with electromyographic (EMG) sensors can be created by printing, spraying, or otherwise depositing electroconductive ink or resin onto an otherwise non-conductive fabric, textile, and/or article of clothing. In an example, an electronically-functional circuit with electromyographic (EMG) sensors can be created as part of an article of clothing by printing a conductive pattern with electroconductive ink or resin. In an example, an electronically-functional fabric, textile, and/or article of clothing with electromyographic (EMG) sensors can be created by laminating electro-conductive members onto a non-conductive substrate. In an example, an electronically-functional fabric, textile, and/or article of clothing with electromyographic (EMG) sensors can be created by embroidering a generally non-conductive fabric or textile member with electro-conductive members. In an example, an electronically-functional circuit with electromyographic (EMG) sensors can be created for an article of clothing by embroidering a conductive pattern with electroconductive thread.

In an example, an article of electromyographic clothing can be made from one or more elastic, stretchable, and/or tight-fitting materials. In an example, an article of electromyographic clothing or accessory can be made from one or more materials selected from the group consisting of: Acetate, Acrylic, Cotton, Denim, Latex, Linen, Lycra [R], Neoprene, Nylon, Polyester, Rayon, Silk, Spandex, and Wool. In an example, an article of electromyographic clothing can have a uniform elasticity and/or tightness of fit which enables collection of muscle activity data by electromyographic (EMG) sensors on virtually any body surface location covered by the clothing.

In an example, an article of electromyographic clothing can have one or more selected areas with greater elasticity and/or tighter fit which enable collection of muscle activity data by electromyographic (EMG) sensors from these one or more selected areas. In an example, the locations of one or more selected areas with greater elasticity and/or tighter fit can be selected in order to optimally measure muscle activity. In an example, the locations of one or more selected areas with greater elasticity and/or tighter fit can be moved longitudinally or laterally along a body surface in order to optimally measure muscle activity. In an example, the elasticity and/or fit of one or more selected areas of an article of electromyographic clothing can be adjusted and/or changed in order to optimally measure muscle activity.

In an example, the locations of one or more selected areas with greater elasticity and/or tighter fit can be selected in order to optimally measure muscle activity by a specific person or during a specific type of physical activity. In an example, the locations of one or more selected areas with greater elasticity and/or tighter fit can be moved longitudinally or laterally along a body surface in order to optimally measure muscle activity by a specific person or during a specific type of physical activity. In an example, the elasticity and/or fit of one or more selected areas of an article of electromyographic clothing can be adjusted and/or changed in order to optimally measure muscle activity by a specific person or during a specific type of physical activity.

In an example, an article of electromyographic clothing can be close-fitting so that one or more electromyographic (EMG) sensors are in close proximity to a wearer's skin. In an example, an article of electromyographic can be close-fitting so that one or more electromyographic (EMG) sensors do not shift very much with respect to a wearer's skin when the wearer moves. In an example, an article of electromyographic clothing can have generally uniform closeness of fit on a person's body. In an example, an article of electromyographic clothing can have selected portions with a closer and/or tighter fit in order to better measure electromyographic signals from those selected portions. In an example, an article of electromyographic clothing can have a generally loose fit, but also have one or more selected compressive bands which fit more closely or tightly against the wearer's skin. In an example, one or more compressive bands can be integral parts of an article of electromyographic clothing. In an example, or more compressive bands can be modular and adjustably placed at different locations on an article of electromyographic clothing.

In an example, an article can have a first set of portions of electromyographic clothing with a first level of elasticity, closeness of fit, or tightness and can have a second set of portions of electromyographic clothing with a second level of elasticity, closeness of fit, or tightness, wherein the second level is greater than the first level. In an example, selected areas with a greater elasticity, closeness of fit, or tightness can be permanently located at selected locations in an article of electromyographic clothing. In an example, selected clothing components and/or areas with greater elasticity, closeness of fit, or tightness can be modular. In an example, selected components of electromyographic clothing with greater elasticity, closeness of fit, or tightness can be removably-attached and/or moved to different locations on an article of electromyographic clothing.

In an example, an article of electromyographic clothing can comprise: an article of clothing worn by a person which further comprises; a first set of one or more portions of the clothing with a first level of elasticity; a second set of one or more portions of the clothing with a second level of elasticity, wherein the second level is greater than the first level; and a set of electromyographic (EMG) sensors wherein these sensors are configured to collect data concerning electromagnetic energy which is generated by muscle tissue and/or nerves which innervate that muscle tissue, wherein these electromyographic (EMG) sensors are attached to and/or part of the second set of one or more portions of the clothing.

In an example, an article of electromyographic clothing can include one or more circumferential compressive bands with a greater elasticity, closeness of fit, or tightness that the rest of the article, wherein there are one or more electromyographic (EMG) sensors on these bands. In an example, an article of electromyographic clothing can include one or more such compressive bands on portions of the article which span a person's arm and/or leg. In an example, the locations of one or more compressive bands with respect to a person's arm and/or leg can be adjusted by reversibly attaching one or more compressive bands to different locations on an article of electromyographic clothing.

In an example, an article of electromyographic clothing can include one or more helical and/or spiral members with a greater elasticity, closeness of fit, or tightness that the rest of the article, wherein there are one or more electromyographic (EMG) sensors on these bands. In an example, an article of electromyographic clothing can include one or more such helical and/or spiral members on portions of the article which span a person's arm and/or leg. In an example, the locations of one or more helical and/or spiral members with respect to a person's arm and/or leg can be adjusted by reversibly attaching (or sliding or rotating) the one or more helical and/or spiral members to different locations on an article of electromyographic clothing.

Let us continue this introduction by providing some more detail concerning electromyographic (EMG) sensors. The combination of a group of muscle fibers and a motor neuron which innervates that group is called a Motor Unit (MU). Different motor units have different electromagnetic energy signal patterns. An electromyographic (EMG) sensor generally receives an electromagnetic energy signal which is a combination of electromagnetic energy signals from multiple nearby motor units. In an example, electromagnetic current can be created or altered within an electromyographic (EMG) sensor by electromagnetic conduction, induction, and/or capacitance. The electromagnetic energy signal received by an electromyographic (EMG) sensor can be amplified locally before it is transmitted to a data processing unit.

Contracting muscle fibers cause electrical potentials and electromagnetic signals which can be measured from the surface of a person's skin. In an example, an article of electromyographic clothing can incorporate one or more electromyographic (EMG) sensors which do not penetrate a person's skin. In an example, an electromyographic (EMG) sensor can be a surface electromyographic (sEMG) sensor. A surface electromyographic (EMG) sensor measures the combined electromagnetic energy which reaches a person's skin from underlying electrical potentials that travel along one or more nearby contracting muscles. A surface electromyographic (sEMG) sensor will receive stronger EMG signals from muscles and nerves which are closer to the surface of the skin than from deeper muscles and nerves. In an example, an electromyographic (EMG) sensor can be a capacitive electromyographic (cEMG) sensor.

An electromyographic (EMG) sensor which is part of an article of electromyographic clothing can comprise one electrode. In an example, an electromyographic (EMG) sensor can comprise two electrodes. In an example, an electromyographic (EMG) sensor can be a bipolar sensor with a ground electrode and a sensor electrode. In an example, an electromyographic (EMG) sensor can comprise multiple electrodes. In an example, two sensor electrodes can be coupled with an amplifier which increases the voltage difference between them. In an example, the output of an amplifier can be sent to an analog-to-digital converter. In an example, an electromyographic (EMG) sensor can measure changes in electromagnetic energy flow between two electrodes based on one or more parameters selected from the group consisting of: voltage, resistance, impedance, amperage, current, phase, and wave pattern.

In an example, an electromyographic (EMG) sensor which is part of an article of electromyographic clothing can be selected from the group consisting of: bipolar EMG sensor; capacitive-coupling EMG sensor; circular sensor; conductive electrode EMG sensor; conductive yarn EMG sensor; contactless EMG sensor; copper-coated fiber EMG sensor; electromagnetic impedance sensor; monopolar EMG sensor; non-gelled EMG sensor; non-invasive EMG sensor; silver-coated fiber EMG sensor; square EMG sensor; and surface EMG sensor.

With respect to shape, an electromyographic (EMG) sensor which is part of an article of electromyographic clothing can have one or more shapes which are selected from the group consisting of: arcuate, circular, circumferential band, circumferential ring, conic section, egg shape, ellipse, elliptical, half circumferential band, half circumferential ring, hexagonal, octagonal, oval, rectangular, rhomboid, rounded rectangle, rounded square, sinusoidal, square, straight, trapezoidal, and triangular.

With respect to size, an electromyographic (EMG) sensor which is part of an article of electromyographic clothing can cover an area of a person's body which is sufficiently large to record electromagnetic signals from a muscle of interest, but not so large as to have these signals confounded by signals from other muscles. A larger sensor can be more robust for measuring neuromuscular signals from a muscle despite shifts in clothing over a person's skin and despite variation in how clothing fits different people's bodies. In an example, an electromyographic (EMG) sensor can cover an area in the range of 10 mm to 60 mm. With respect to spacing, electromyographic (EMG) sensors can be spaced between 1 mm to 30 mm apart. Bipolar electrodes can be approximately 10 mm to 30 mm apart.

With respect to orientation, an electromyographic (EMG) sensor can be placed on or near a person's skin in an orientation which is substantially perpendicular to the longitudinal axis of a body member on which the sensor is located. In another example, an electromyographic (EMG) sensor can be placed on or near a person's skin in an orientation which is substantially parallel to the longitudinal axis of a body member on which the sensor is located. In an example, an electromyographic (EMG) sensor can be placed on or near a person's skin in an orientation which forms an acute angle with respect to the longitudinal axis of a body member on which the sensor is located.

In an example, an electromyographic (EMG) sensor can be placed on or near a person's skin in an orientation which is aligned with (some or all of) the perimeter and/or circumference of a body member on which the sensor is located. In an example, a series of electromyographic (EMG) sensors can span longitudinally-sequential cross-sectional perimeters of a body member. In an example, the location of a modular electromyographic (EMG) sensor can be adjusted by connecting the sensor to different pairs of connectors on an article of electromyographic clothing. In an example, the radial location of a modular electromyographic (EMG) sensor around the perimeter or circumference of a body member can be adjusted by connecting the sensor to different pairs of connectors.

In an example, an article of electromyographic clothing can comprise an array, grid, mesh, or matrix of multiple electromyographic (EMG) sensors. In an example, one or more EMG sensors in an array can be capacitive, conductive, inductive, and/or impedance sensors. In an example, one or more EMG sensors in an array can be non-invasive, surface, dry, and/or contactless sensors. In an example, an array, grid, mesh, or matrix of electromyographic (EMG) sensors which are part of an article of electromyographic clothing can be arranged along perpendicular axes in a fabric or textile from which an article of clothing is made so that the areas between sensors form squares or rectangles. In an example, sensors can be arranged in an array so that the areas between sensors are triangular or hexagonal in shape. In an example, a plurality of electromyographic (EMG) sensors which are part of an article of electromyographic clothing can form an array, grid, mesh, or matrix comprised of connected circles, ovals, ellipsoids, squares, rhombuses, diamonds, trapezoids, parallelograms, triangles, or hexagons.

In an example, an array, grid, mesh, or matrix of electromyographic (EMG) sensors which are part of an article of electromyographic clothing can be arranged in a series of perimeter and/or circumferential rings, wherein each ring has a different distance from a joint along the longitudinal axis of a body member. In an example, an array, grid, mesh, or matrix of electromyographic (EMG) sensors which are part of an article of clothing can be configured in one or more rings (or partial rings) around cross-sections of an article of clothing (or a body member spanned by the article of clothing). In an example, an array, grid, mesh, or matrix of electromyographic (EMG) sensors on an article of clothing can be configured in one or more columns which are parallel to the longitudinal axis of the article of clothing (or a body member spanned by the article of clothing).

In an example, there can be a first array of electromyographic (EMG) sensors on an article of clothing on the proximal portion of a body member (e.g. upper leg or upper arm) and a second array of electromyographic (EMG) sensors on an article of clothing on the distal portion of a body member (e.g. lower leg or forearm). In an example, there can be a first array of electromyographic (EMG) sensors on an article of clothing on the anterior portion of a body member and a second array of electromyographic (EMG) sensors on an article of clothing on the posterior portion of a body member.

In an example, an array of electromyographic (EMG) sensors can span a percentage of the perimeter or circumference of a cross-section of a body member such as a leg or arm. In an example, this percentage can be within the range of 10% to 25%. In an example, this percentage can be within the range of 25% to 50%. In an example, this percentage can be within the range of 50% to 75%. In an example, this percentage can be within the range of 75% to 100%.

In an example, an array of electromyographic (EMG) sensors can comprise circular sensors which are located in pairs. In an example, an array of electromyographic (EMG) sensors can be pairs of electrodes which are attached to a square or oblong substrate and/or surface. In an example, an array of electromyographic (EMG) sensors can be in pairs which are separated longitudinally along the longitudinal axes of muscles which activate key body joints.

In an example, an array of electromyographic (EMG) sensors can comprise rings or bands which each span the circumference and/or perimeter of a person's arm, wrist, hand, leg, ankle, or foot. In an example, an array of electromyographic (EMG) sensors can comprise half-rings or half-bands which each span half of the circumference a person's arm, wrist, hand, leg, ankle, or foot. In an example, an array of electromyographic (EMG) sensors can comprise quarter-rings or quarter-bands which each span a quarter of the circumference a person's arm, wrist, hand, leg, ankle, or foot. In an example, an array of electromyographic (EMG) sensors can each span a portion of the circumference of a person's arm or leg at substantially the mid-section of one or more muscles which move one or more arm or leg joints. In an example, an array of electromyographic (EMG) sensors can each cross the mid-section of one or more muscles at an acute angle, like a chevron.

In an example, a front half of an array of electromyographic (EMG) sensors can collect data concerning the activity of one or more muscles which move a joint in a first direction and a back half of an array of electromyographic (EMG) sensors can collect data concerning the activity of one or more muscles which move a joint in a second direction. In an example, a front half of an array of electromyographic (EMG) sensors can collect data concerning the activity of one or more muscles which move a joint in extension and a back half of an array of electromyographic (EMG) sensors can collect data concerning the activity of one or more muscles which move a joint in flexion.

In an example, an article of electromyographic clothing can have an available array of electromyographic (EMG) sensors, but only a subset of that array is activated in order to measure the muscle of a specific person or muscle activity during a specific sport (or other type of physical activity). In an example, the entire available array of sensors can be activated to collect data during a calibration or test period and this data can then be used to select the subset of sensors which are activated on an ongoing basis. In an example, a master model of an article of electromyographic clothing can have a large and/or dense array of sensors, but a customized article of electromagnetic clothing can be created for a specific person or sport with only a subset of the sensors in the master model. In an example, data collected when a person is wearing the master model is used to identify the subset of sensors which is to be included in a customized article of clothing for that person. In an example, data from a large array of sensors can be used to identify the smaller subset of sensors which can most efficiently collect muscle activity for a specific person or during a specific sport.

In an example, an article of electromyographic clothing can have other types of sensors in addition to electromyographic (EMG) sensors. In an example, joint multivariate analysis of data from two or more different types of sensors can provide more accurate estimation and/or modeling of muscle activity than data from only one type of sensor. In an example, joint multivariate analysis of data from electromyographic (EMG) sensors and inertial motion sensors can provide more accurate measurement of muscle activity than data from electromyographic (EMG) sensors alone. In an example, an article of electromyographic clothing with multiple types of sensors can provide information for other purposes in addition to measurement of muscle activity.

In an example, an article of electromyographic clothing can further comprise one or more of the following: accelerometer, air pressure sensor, airflow sensor, altimeter, barometer, bend sensor, chewing sensor, compass, electrogoniometer, eye tracking sensor, force sensor, gesture recognition sensor, goniometer, gyroscope, inclinometer, inertial sensor, mechanomyography (MMG) sensor, motion sensor, piezoelectric sensor, piezoresistive sensor, pressure sensor, strain gauge, stretch sensor, tilt sensor, torque sensor, variable impedance sensor, variable resistance sensor, and vibration sensor.

In an example, an article of electromyographic clothing can further comprise one or more of the following: ambient light sensor, camera, chromatography sensor, chromatography sensor, fluorescence sensor, infrared sensor, light intensity sensor, mass spectrometry sensor, near-infrared spectroscopy sensor, optical sensor, optoelectronic sensor, oximeter, oximetry sensor, photochemical sensor, photoelectric sensor, photoplethysmography (PPG) sensor, spectral analysis sensor, spectrometry sensor, spectrophotometric sensor, spectroscopic sensor, and ultraviolet light sensor.

In an example, an article of electromyographic clothing can further comprise one or more of the following: bioimpedance sensor, capacitive sensor, electrocardiogram (ECG) sensor, electrochemical sensor, electroencephalography (EEG) sensor, electrogastrography (EGG) sensor, electromagnetic impedance sensor, electrooculography (EOG) sensor, electroporation sensor, galvanic skin response (GSR) sensor, Hall-effect sensor, humidity sensor, hydration sensor, impedance sensor, magnetic field sensor, magnometer, moisture sensor, skin conductance sensor, skin impedance sensor, skin moisture sensor, and voltmeter. In an example, an article of electromyographic clothing can further comprise one or more of the following: acoustic sensor, ambient sound sensor, audiometer, breathing monitor, microphone, respiration rate monitor, respiratory function monitor, sound sensor, speech recognition sensor, and ultrasound sensor.

In an example, an article of electromyographic clothing can further comprise one or more of the following: ambient temperature sensor, body temperature sensor, skin temperature sensor, temperature sensor, thermal energy sensor, and thermistor. In an example, an article of electromyographic clothing can further comprise one or more of the following: biochemical sensor, blood glucose monitor, blood oximetry sensor, capnography sensor, chemical sensor, chemiresistor sensor, chemoreceptor sensor, cholesterol sensor, glucometer, glucose sensor, osmolality sensor, pH level sensor, pulse oximeter, and tissue oximetry sensor. In an example, an article of electromyographic clothing can further comprise one or more of the following: ambient air monitor, blood flow monitor, blood pressure sensor, body fat sensor, caloric intake monitor, cardiac function sensor, cardiovascular sensor, flow sensor, heart rate sensor, hemoencephalography (HEG) monitor, microbial sensor, microfluidic sensor, pneumography sensor, pulse sensor, spirometry monitor, and swallowing sensor.

In an example, an article of electromyographic clothing can further comprise one or more of the following: actuator, audio speaker, data processor, data processor, global positioning system (GPS) module, micro electromechanical system (MEMS) actuator, piezoelectric actuator, power source, sound-emitting member, speaker, tactile-sensation-creating member, touch-based human-to-computer textile interface, touchpad, wireless data receiver, and wireless data transmitter.

In an example, an article of electromyographic clothing can have multiple electromyographic (EMG) sensors in different locations, with different orientations, of different sizes, and having different configurations which enables combined, joint, and/or multivariate measurement of muscle activity. In an example, having different sets of electromyographic (EMG) sensors spanning the same area of a human body can provide redundant data concerning a selected group of muscles which, in turn, can provide more accurate measurement of their muscle activity than a single set of electromyographic (EMG) sensors.

In an example, having multiple sets of electromyographic (EMG) sensors with different locations, orientations, sizes, and configurations can provide an over-determined system of equations for measuring muscle activity and/or estimating joint angles. In an example, having multiple sets of electromyographic (EMG) sensors with different locations, orientations, sizes, and configurations can reduce measurement variability and error. In an example, having multiple sets of electromyographic (EMG) sensors with different locations, orientations, sizes, and configurations can control for clothing that shifts or slides with respect to a person's body. In an example, having multiple sets of electromyographic (EMG) sensors with different locations, orientations, sizes, and configurations can control for changes in clothing proximity, sensor material fatigue, and malfunction of a subset of sensors.

In an example: a first set of electromyographic (EMG) sensors with a first location, orientation, size, and configuration can provide superior data during a first range of motion, a first number of repeated cycles, a first motion speed, a first clothing location, a first level of clothing elasticity, or a first level of external force or resistance; a second set of electromyographic (EMG) sensors with a second location, orientation, size, and configuration can provide superior data during a second range of motion, a second number of repeated cycles, a second motion speed, a second clothing location, a second level of clothing elasticity, or a second level of external force or resistance; and combined analysis of data from the first set and the second set can provide more accurate measurement of muscle activity than analysis of data from either set alone.

In an example, a first set of electromyographic (EMG) sensors provides better measurement of muscle activity during a first condition; a second set of electromyographic (EMG) sensors provides better measurement of muscle activity during a second condition; combined multivariate analysis of data from both sets of sensors provides more accurate overall measurement of muscle activity than data from either set alone; and an article of clothing includes both sets of sensors.

In an example: a first set of electromyographic (EMG) sensors provides better measurement of muscle activity when an article clothing has a first alignment with a person's body; a second set of electromyographic (EMG) sensors provides better measurement of muscle activity when the article of clothing has a second alignment with the person's body; combined multivariate analysis of data from both sets of sensors provides more accurate overall measurement of muscle activity than data from either set alone; and an article of clothing includes both sets of sensors.

In an example: a first set of electromyographic (EMG) sensors provides better measurement of muscle activity when a joint is within a first angle range; a second set of electromyographic (EMG) sensors provides better measurement of muscle activity when the joint is within a second angle range; combined multivariate analysis of data from both sets of sensors provides more accurate overall measurement of muscle activity than data from either set alone; and an article of clothing includes both sets of sensors.

In an example: a first set of electromyographic (EMG) sensors provides better measurement of muscle activity when clothing has a first closeness of fit; a second set of electromyographic (EMG) sensors provides better measurement of muscle activity when clothing has a second closeness of fit; combined multivariate analysis of data from both sets of sensors provides more accurate overall measurement of muscle activity than data from either set alone; and an article of clothing includes both sets of sensors.

In an example: a first set of electromyographic (EMG) sensors provides better measurement of muscle activity when a joint moves in a first direction; a second set of electromyographic (EMG) sensors provides better measurement of muscle activity when the joint moves in a second direction; combined multivariate analysis of data from both sets of sensors provides more accurate overall measurement of muscle activity than data from either set alone; and an article of clothing includes both sets of sensors.

In an example: a first set of electromyographic (EMG) sensors provides better measurement of muscle activity during a first duration of motion; a second set of electromyographic (EMG) sensors provides better measurement of muscle activity during a second duration of motion; combined multivariate analysis of data from both sets of sensors provides more accurate overall measurement of muscle activity than data from either set alone; and an article of clothing includes both sets of sensors.

In an example: a first set of electromyographic (EMG) sensors provides better measurement of muscle activity during a first exertion level; a second set of electromyographic (EMG) sensors provides better measurement of muscle activity during a second exertion level; combined multivariate analysis of data from both sets of sensors provides more accurate overall measurement of muscle activity than data from either set alone; and an article of clothing includes both sets of sensors.

In an example: a first set of electromyographic (EMG) sensors provides better measurement of muscle activity during a first level of type of environmental interference (such as environmental electromagnetic energy, light, sound, moisture, or movement); a second set of electromyographic (EMG) sensors provides better measurement of muscle activity during a second level of type of environmental interference; combined multivariate analysis of data from both sets of sensors provides more accurate overall measurement of muscle activity than data from either set alone; and an article of clothing includes both sets of sensors.

In an example: a first set of electromyographic (EMG) sensors provides better measurement of muscle activity during a first type or pattern of motion; a second set of electromyographic (EMG) sensors provides better measurement of muscle activity during a second type or pattern of motion; combined multivariate analysis of data from both sets of sensors provides more accurate overall measurement of muscle activity than data from either set alone; and an article of clothing includes both sets of sensors.

In an example: a first set of electromyographic (EMG) sensors provides better measurement of muscle activity during a first range of motion; a second set of electromyographic (EMG) sensors provides better measurement of muscle activity during a second range of motion; combined multivariate analysis of data from both sets of sensors provides more accurate overall measurement of muscle activity than data from either set alone; and an article of clothing includes both sets of sensors.

In an example: a first set of electromyographic (EMG) sensors provides better measurement of muscle activity during a first number of repeated motions; a second set of electromyographic (EMG) sensors provides better measurement of muscle activity during a second number of repeated motions; combined multivariate analysis of data from both sets of sensors provides more accurate overall measurement of muscle activity than data from either set alone; and an article of clothing includes both sets of sensors.

In an example: a first set of electromyographic (EMG) sensors provides better measurement of muscle activity at a first muscle movement speed; a second set of electromyographic (EMG) sensors provides better measurement of muscle activity at a second muscle movement speed; combined multivariate analysis of data from both sets of sensors provides more accurate overall measurement of muscle activity than data from either set alone; and an article of clothing includes both sets of sensors.

In an example, an article of electromyographic clothing can have a second set of wearable sensors in addition to a first set of electromyographic (EMG) sensors. In an example, the second set of wearable sensors can be inertial motion sensors, such as accelerometers. In an example, the second set of wearable sensors can be bending motion sensors, such as electrogoniometers. In an example, sensors in the second set can be selected from the group consisting of: accelerometer, air pressure sensor, airflow sensor, altimeter, barometer, bend sensor, chewing sensor, compass, electrogoniometer, eye tracking sensor, force sensor, gesture recognition sensor, goniometer, gyroscope, inclinometer, inertial sensor, mechanomyography (MMG) sensor, motion sensor, piezoelectric sensor, piezoresistive sensor, pressure sensor, strain gauge, stretch sensor, tilt sensor, torque sensor, variable impedance sensor, variable resistance sensor, and vibration sensor.

In an example, sensors in the second set can be selected from the group consisting of: ambient light sensor, camera, chromatography sensor, chromatography sensor, fluorescence sensor, infrared sensor, light intensity sensor, mass spectrometry sensor, near-infrared spectroscopy sensor, optical sensor, optoelectronic sensor, oximeter, oximetry sensor, photochemical sensor, photoelectric sensor, photoplethysmography (PPG) sensor, spectral analysis sensor, spectrometry sensor, spectrophotometric sensor, spectroscopic sensor, and ultraviolet light sensor.

In an example, sensors in the second set can be selected from the group consisting of: bioimpedance sensor, electrocardiogram (ECG) sensor, electrochemical sensor, electroencephalography (EEG) sensor, electrogastrography (EGG) sensor, electromagnetic impedance sensor, electrooculography (EOG) sensor, electroporation sensor, galvanic skin response (GSR) sensor, Hall-effect sensor, humidity sensor, hydration sensor, impedance sensor, magnetic field sensor, magnometer, moisture sensor, skin conductance sensor, skin impedance sensor, skin moisture sensor, and voltmeter. In an example, sensors in the second set can be selected from the group consisting of: acoustic sensor, ambient sound sensor, audiometer, breathing monitor, microphone, respiration rate monitor, respiratory function monitor, sound sensor, speech recognition sensor, and ultrasound sensor.

In an example, sensors in the second set can be selected from the group consisting of: ambient temperature sensor, body temperature sensor, skin temperature sensor, temperature sensor, thermal energy sensor, and thermistor. In an example, sensors in the second set can be selected from the group consisting of: biochemical sensor, blood glucose monitor, blood oximetry sensor, capnography sensor, chemical sensor, chemiresistor sensor, chemoreceptor sensor, cholesterol sensor, glucometer, glucose sensor, osmolality sensor, pH level sensor, pulse oximeter, and tissue oximetry sensor. In an example, sensors in the second set can be selected from the group consisting of: ambient air monitor, blood flow monitor, blood pressure sensor, body fat sensor, caloric intake monitor, cardiac function sensor, cardiovascular sensor, flow sensor, heart rate sensor, hemoencephalography (HEG) monitor, microbial sensor, microfluidic sensor, pneumography sensor, pulse sensor, spirometry monitor, and swallowing sensor.

In an example, electromyographic clothing which includes a second set of a different type of wearable sensors (other than electromyographic sensors) can provide redundant data concerning the activity of a selected group of muscles—enabling more accurate measurement of this muscle activity than clothing which uses electromyographic (EMG) sensors alone. In an example, having two or more sets of different types of sensors can provide: an over-determined system of equations for joint angle estimation; reduced measurement error; reduced measurement variability; a means to control for shifting or sliding of the sensors with respect to a person's body; a means to control for changes in clothing proximity to the body; and a means to control for material fatigue and sensor malfunction.

In an example: a first set of electromyographic (EMG) sensors can provide superior data during a first range of motion, a first number of repeated cycles, a first motion speed, a first clothing location, a first level of clothing elasticity, or a first level of external force or resistance; a second set of another type of wearable sensors can provide superior data during a second range of motion, a second number of repeated cycles, a second motion speed, a second clothing location, a second level of clothing elasticity, or a second level of external force or resistance; and combined analysis of data from the first set of electromyographic (EMG) sensors and data from the second set of the other type of sensors can provide more accurate measurement of muscle activity than analysis of data from either type of sensor alone.

In an example, a first set of sensors (comprised of EMG sensors) provides better measurement of muscle activity during a first condition; a second set of sensors (comprised of another type of wearable sensors which are not EMG sensors) provides better measurement of muscle activity during a second condition; combined multivariate analysis of data from both sets of sensors provides more accurate overall measurement of muscle activity than data from either set alone; and an article of clothing includes both sets of sensors.

In an example: a first set of sensors (comprised of EMG sensors) provides better measurement of muscle activity when an article clothing has a first alignment with a person's body; a second set of sensors (comprised of another type of wearable sensors which are not EMG sensors) provides better measurement of muscle activity when the article of clothing has a second alignment with the person's body; combined multivariate analysis of data from both sets of sensors provides more accurate overall measurement of muscle activity than data from either set alone; and an article of clothing includes both sets of sensors.

In an example: a first set of sensors (comprised of EMG sensors) provides better measurement of muscle activity when a joint is within a first angle range; a second set of sensors (comprised of another type of wearable sensors which are not EMG sensors) provides better measurement of muscle activity when the joint is within a second angle range; combined multivariate analysis of data from both sets of sensors provides more accurate overall measurement of muscle activity than data from either set alone; and an article of clothing includes both sets of sensors.

In an example: a first set of sensors (comprised of EMG sensors) provides better measurement of muscle activity when clothing has a first closeness of fit; a second set of sensors (comprised of another type of wearable sensors which are not EMG sensors) provides better measurement of muscle activity when clothing has a second closeness of fit; combined multivariate analysis of data from both sets of sensors provides more accurate overall measurement of muscle activity than data from either set alone; and an article of clothing includes both sets of sensors.

In an example: a first set of sensors (comprised of EMG sensors) provides better measurement of muscle activity when a joint moves in a first direction; a second set of sensors (comprised of another type of wearable sensors which are not EMG sensors) provides better measurement of muscle activity when the joint moves in a second direction; combined multivariate analysis of data from both sets of sensors provides more accurate overall measurement of muscle activity than data from either set alone; and an article of clothing includes both sets of sensors.

In an example: a first set of sensors (comprised of EMG sensors) provides better measurement of muscle activity during a first duration of motion; a second set of sensors (comprised of another type of wearable sensors which are not EMG sensors) provides better measurement of muscle activity during a second duration of motion; combined multivariate analysis of data from both sets of sensors provides more accurate overall measurement of muscle activity than data from either set alone; and an article of clothing includes both sets of sensors.

In an example: a first set of sensors (comprised of EMG sensors) provides better measurement of muscle activity during a first exertion level; a second set of sensors (comprised of another type of wearable sensors which are not EMG sensors) provides better measurement of muscle activity during a second exertion level; combined multivariate analysis of data from both sets of sensors provides more accurate overall measurement of muscle activity than data from either set alone; and an article of clothing includes both sets of sensors.

In an example: a first set of sensors (comprised of EMG sensors) provides better measurement of muscle activity during a first level of type of environmental interference (such as environmental electromagnetic energy, light, sound, moisture, or movement); a second set of sensors (comprised of another type of wearable sensors which are not EMG sensors) provides better measurement of muscle activity during a second level of type of environmental interference; combined multivariate analysis of data from both sets of sensors provides more accurate overall measurement of muscle activity than data from either set alone; and an article of clothing includes both sets of sensors.

In an example: a first set of sensors (comprised of EMG sensors) provides better measurement of muscle activity during a first type or pattern of motion; a second set of sensors (comprised of another type of wearable sensors which are not EMG sensors) provides better measurement of muscle activity during a second type or pattern of motion; combined multivariate analysis of data from both sets of sensors provides more accurate overall measurement of muscle activity than data from either set alone; and an article of clothing includes both sets of sensors.

In an example: a first set of sensors (comprised of EMG sensors) provides better measurement of muscle activity during a first range of motion; a second set of sensors (comprised of another type of wearable sensors which are not EMG sensors) provides better measurement of muscle activity during a second range of motion; combined multivariate analysis of data from both sets of sensors provides more accurate overall measurement of muscle activity than data from either set alone; and an article of clothing includes both sets of sensors.

In an example: a first set of sensors (comprised of EMG sensors) provides better measurement of muscle activity during a first number of repeated motions; a second set of sensors (comprised of another type of wearable sensors which are not EMG sensors) provides better measurement of muscle activity during a second number of repeated motions; combined multivariate analysis of data from both sets of sensors provides more accurate overall measurement of muscle activity than data from either set alone; and an article of clothing includes both sets of sensors.

In an example: a first set of sensors (comprised of EMG sensors) provides better measurement of muscle activity at a first muscle movement speed; a second set of sensors (comprised of another type of wearable sensors which are not EMG sensors) provides better measurement of muscle activity at a second muscle movement speed; combined multivariate analysis of data from both sets of sensors provides more accurate overall measurement of muscle activity than data from either set alone; and an article of clothing includes both sets of sensors.

In an example, multivariate analysis of muscle activity data collected by multiple sets wearable sensors can take into account (control for) conditions which affect data collection. These conditions can be selected from the group consisting of: amount of skin perspiration, skin temperature, environmental moisture and/or humidity level, ambient temperature, altitude and/or atmospheric pressure, amount of body hair in proximity to a sensor, amount of body fat, wearer age, muscle length, electrode motion and shifting, duration and/or intensity of exercise duration, exercise history, and level of external force and/or resistance.

In an example, an article of electromyographic clothing can be made from an electromagnetically-functional fabric or textile. In an example, an electromagnetically-function fabric or textile can be creating using a plain weave, rib weave, basket weave, twill weave, satin weave, or leno weave. In an example, an electromagnetically-functional fabric or textile can be made by weaving, knitting, braiding, sewing, embroidering, fusing, layering, laminating, printing, or pressing together an array of electroconductive fibers, cables, filaments, strands, threads, traces, wires, or yarns. In an example, electroconductive fibers, cables, filaments, strands, threads, traces, wires, or yarns can be woven, knitted, braided, sewn, embroidered, fused, layered, laminated, printed, or pressed together with non-electroconductive fibers, cables, strands, threads, traces, wires, or yarns. In an example, electroconductive fibers, cables, filaments, strands, threads, traces, wires, or yarns can be embroidered, fused, layered, laminated, printed, pressed, or sprayed onto a layer of non-electroconductive fabric, textile, or other flexible material.

In an example, an electroconductive fiber, cable, filament, strand, thread, trace, wire, or yarn can be created by coating, impregnating, or mixing a non-conductive (or less conductive) material with a conductive (or more conductive) material. In an example, an electroconductive fiber, cable, filament, strand, thread, trace, wire, or yarn can be created using one or more materials selected from the group consisting of: acetate, acrylic, ceramic particles, cotton, denim, elastane, flax, fluorine, latex, linen, Lycra [TM], neoprene, nylon, organic solvent, polyamide, polyaniline, polyester, polymer, polypyrrole, polyurethane, rayon, rubber, silicon, silicone, silk, spandex, wool, aluminum, aluminum alloy, brass, carbon, carbon nanotubes, copper, copper alloy, gold, graphene, Kevlar [TM], magnesium, Mylar [TM], nickel, niobium (Nb), silver, silver alloy, silver epoxy, and steel.

In an example, an electroconductive fiber, cable, filament, strand, thread, trace, wire, or yarn can be substantially straight within an electromagnetically-functional fabric or textile. In an example, an electroconductive fiber, cable, filament, strand, thread, trace, wire, or yarn can have a wave pattern within an electromagnetically-functional fabric or textile. In an example, an electroconductive fiber, cable, filament, strand, thread, trace, wire, or yarn can have a sinusoidal shape. In an example, an electroconductive fiber, cable, filament, strand, thread, trace, wire, or yarn can span a portion of the perimeter or circumference of a body member. In an example, two sets of electroconductive fibers, cables, filaments, strands, threads, traces, wires, or yarns can overlap and/or intersect in a substantially perpendicular manner within an electromagnetically-functional fabric or textile. In an example, a first set of electroconductive fibers, cables, filaments, strands, threads, traces, wires, or yarns and a second set of electroconductive fibers, cables, filaments, strands, threads, traces, wires, or yarns can overlap and/or intersect in a substantially perpendicular manner within an electromagnetically-functional fabric or textile.

In an example, an electronically-functional fabric or textile can be created by printing, silk-screening, spraying, flocking, fusing, adhering, gluing, painting, pressing, or laminating electroconductive ink, resin, fluid, gel, or particles onto a non-conductive (or less conductive) material. In an example, an electromagnetically-functional fabric or textile can be created by printing (two-dimensional or three-dimensional), adhering, depositing, flocking, fusing, gluing, laminating, painting, silk-screening, or spraying fluid, gel, ink, resin, or particles comprising aluminum, aluminum alloy, brass, carbon, carbon nanotubes, copper, copper alloy, gold, graphene, Kevlar [TM], magnesium, Mylar [TM], nickel, niobium, silver, silver alloy, silver epoxy, or steel.

In an example, an electronically-functional fabric or textile can be created by etching or cutting an electroconductive layer in a fabric or textile. In an example, an electronically-functional fabric or textile can be created by etching or cutting a non-electroconductive layer between two electroconductive layers in a fabric or textile. In an example, an electronically-functional fabric or textile can be created by etching or cutting using a laser.

In an example, an article of electromyographic clothing can be created using a plain weave, rib weave, basket weave, twill weave, satin weave, or leno weave. In an example, an article of electromyographic clothing can be made by weaving, knitting, braiding, sewing, embroidering, fusing, layering, laminating, printing, or pressing together an array of electroconductive fibers, cables, filaments, strands, threads, traces, wires, or yarns.

In an example, an electroconductive fiber, cable, filament, strand, thread, trace, wire, or yarn can be substantially straight within an article of electromyographic clothing. In an example, an electroconductive fiber, cable, filament, strand, thread, trace, wire, or yarn can have a wave pattern within an article of electromyographic clothing. In an example, an electroconductive fiber, cable, filament, strand, thread, trace, wire, or yarn can have a sinusoidal shape. In an example, an electroconductive fiber, cable, filament, strand, thread, trace, wire, or yarn can span a portion of the perimeter or circumference of a body member. In an example, two sets of electroconductive fibers, cables, filaments, strands, threads, traces, wires, or yarns can overlap and/or intersect in a substantially perpendicular manner within an electromagnetically-functional fabric or textile. In an example, a first set of electroconductive fibers, cables, filaments, strands, threads, traces, wires, or yarns and a second set of electroconductive fibers, cables, filaments, strands, threads, traces, wires, or yarns can overlap and/or intersect in a substantially perpendicular manner within an electromagnetically-functional fabric or textile.

In an example, an article of electromyographic clothing can be created by printing, silk-screening, spraying, flocking, fusing, adhering, gluing, painting, pressing, or laminating electroconductive ink, resin, fluid, gel, or particles onto a non-conductive (or less conductive) material. In an example, an article of electromyographic clothing can be created by printing (two-dimensional or three-dimensional), adhering, depositing, flocking, fusing, gluing, laminating, painting, silk-screening, or spraying fluid, gel, ink, resin, or particles comprising aluminum, aluminum alloy, brass, carbon, carbon nanotubes, copper, copper alloy, gold, graphene, Kevlar [TM], magnesium, Mylar [TM], nickel, niobium, silver, silver alloy, silver epoxy, or steel.

In an example, an article of electromyographic clothing can be created by adhering one or more electromyographic (EMG) sensors to the clothing after the basic form of the clothing has been made. In an example, an article of electromyographic clothing can be created by etching or cutting an electroconductive layer in a fabric or textile. In an example, an article of electromyographic clothing can be created by etching or cutting a non-electroconductive layer between two electroconductive layers in a fabric or textile. In an example, an article of electromyographic clothing can be created by etching or cutting using a laser.

In an example, an article of electromyographic clothing and/or the fabric or textile from which the article is made can be elastic, close-fitting, and/or stretchable so as to bring one or more electromyographic (EMG) sensors into close proximity with a person's skin. In an example, an article of electromyographic clothing can be made with one or more elastic, close-fitting, and/or stretchable fabrics or textiles selected from the group consisting of: Acetate, Acrylic, Cotton, Denim, Latex, Linen, Lycra [R], Neoprene, Nylon, Polyester, Rayon, Silk, Spandex, and Wool.

In an example, an article of electromyographic clothing can have uniform elasticity, closeness-of-fit, and/or stretchability. In an example, an article of electromyographic can further comprise a first portion with a first level of elasticity, closeness-of-fit, and/or stretchability and a second portion with a second level of elasticity, closeness-of-fit, and/or stretchability. In an example, the second level can be greater than the first level. In an example, electromyographic (EMG) sensors can be selectively located in (or on) the second portion. In an example, a second portion can be located so as to span a central portion of a selected muscle or muscle group. In an example, a second portion can be located so as to span a central portion of a bone segment between two joints.

In an example, an article of electromyographic clothing can comprise a first portion with a first level of elasticity, closeness-of-fit, and/or stretchability and a second portion with a second level of elasticity, closeness-of-fit, and/or stretchability, wherein the second portion further comprises one or more electromyographic (EMG) sensors and wherein the location of the second portion can be moved with respect to the first portion. In an example, the second portion can overlap the first portion. In an example, the second portion can fit around the first portion. In an example, the second portion can be reversibly-attached to the first portion. In an example, the location at which the second portion is reversibly attached to the first portion can be moved so as to optimally collect data concerning muscle activity by a specific person or muscle activity during a specific type of physical activity. In an example, the second portion can be attached to the first portion by one or more attachment mechanisms selected from the group consisting of: hook-and -eye (e.g. Velcro [TM]), snap, clip, hook, pin, zipper, insertion into a channel, button, clasp, plug, cord, and tie.

In an example, an article of electromyographic clothing can comprise a first portion with a first level of elasticity, closeness-of-fit, and/or stretchability and a second portion with a second level of elasticity, closeness-of-fit, and/or stretchability, wherein the second portion further comprises one or more electromyographic (EMG) sensors, and wherein the second portion is closer to a person's skin than the first portion. In an example, the second portion can be interior to the first portion. In an example, the first and second portions can be concentric, with the second portion being inside the first portion. In an example, the first and second portions can be nested, with the second portion being inside the first portion.

In an example, an article of electromyographic clothing can comprise a shirt with a first portion with a first level of elasticity, closeness-of-fit, and/or stretchability and a second portion with a second level of elasticity, closeness-of-fit, and/or stretchability, wherein the second level is greater than the first level, and wherein the second portion can further comprises one or more electromyographic (EMG) sensors. In an example, the second portion can be located inside the first portion. In an example, the second portion can be located within the sleeve of the first portion. In an example, the second portion can comprise a compressive band which is located within the sleeve of the first portion. In an example, the second portion can be located outside the first portion. In an example, the second portion can be located outside the sleeve of the first portion. In an example, the second portion can comprise a compressive band which is located outside the sleeve of the first portion. In an example, the location of the second portion can be shifted, slide, or otherwise moved with respect to the first portion in order to better collect data concerning muscle activity. In an example, the first and second portions can be in electromagnetic communication with each other.

In an example, an article of electromyographic clothing can comprise a pair of pants or shorts with a first portion with a first level of elasticity, closeness-of-fit, and/or stretchability and a second portion with a second level of elasticity, closeness-of-fit, and/or stretchability, wherein the second level is greater than the first level, and wherein the second portion can further comprises one or more electromyographic (EMG) sensors. In an example, the second portion can be located inside the first portion. In an example, the second portion can be located within the leg of the first portion. In an example, the second portion can comprise a compressive band which is located within the leg of the first portion. In an example, the second portion can be located outside the first portion. In an example, the second portion can be located outside the leg of the first portion. In an example, the second portion can comprise a compressive band which is located outside the leg of the first portion. In an example, the location of the second portion can be shifted, slide, or otherwise moved with respect to the first portion in order to better collect data concerning muscle activity. In an example, the first and second portions can be in electromagnetic communication with each other.

In an example, an article of electromyographic clothing can comprise a shirt with electromyographic (EMG) sensors, wherein this shirt has a first configuration with a first level of elasticity, closeness-of-fit, and/or stretchability and a second configuration with a second level of elasticity, closeness-of-fit, and/or stretchability, wherein the second level is greater than the first level. In an example, the shirt can be manually adjusted and/or changed from the first configuration to the second configuration in order to better collect data concerning muscle activity. In an example, the shirt can be automatically adjusted and/or changed from the first configuration to the second configuration in order to better collect data concerning muscle activity.

In an example, an article of electromyographic clothing can comprise a pair of pants or shorts with electromyographic (EMG) sensors, wherein this pair of pants or shorts has a first configuration with a first level of elasticity, closeness-of-fit, and/or stretchability and a second configuration with a second level of elasticity, closeness-of-fit, and/or stretchability, wherein the second level is greater than the first level. In an example, the shirt can be manually adjusted and/or changed from the first configuration to the second configuration in order to better collect data concerning muscle activity. In an example, the shirt can be automatically adjusted and/or changed from the first configuration to the second configuration in order to better collect data concerning muscle activity.

In an example, adjustment of the elasticity, closeness-of-fit, and/or stretchability of an article of electromyographic clothing (such as a shirt or pair of pants) can be based on analysis of data from electromyographic (EMG) sensors. In an example, adjustment of the elasticity, closeness-of-fit, and/or stretchability of an article of electromyographic clothing can be based on data from one or more wearable sensors selected from the group consisting of: pressure sensor, strain sensor, and optical sensor. In an example, this adjustment of elasticity, closeness-of-fit, and/or stretchability can be done in an iterative manner. In an example, this adjustment of elasticity, closeness-of-fit, and/or stretchability can be done by inflating a channel or pocket within an article of clothing. In an example, this adjustment of elasticity, closeness-of-fit, and/or stretchability can be done by adjusting a cord, band, or tie on the article of clothing. In an example, this adjustment of elasticity, closeness-of-fit, and/or stretchability can be done automatically by an electromagnetic actuator on (or within) an article of clothing.

In an example, this invention can be embodied in an article of electromyographic clothing whose elasticity, stretchability, closeness-of-fit, and/or compressive pressure can be manually adjusted as it is worn. In an example, this invention can be embodied in an article of electromyographic clothing whose elasticity, stretchability, closeness-of-fit, and/or compressive pressure can be automatically adjusted as it is worn. In an example, the elasticity, stretchability, closeness-of-fit, and/or compress pressure of selected portions of an article of electromyographic clothing can be adjusted by one or more mechanisms selected from the group consisting of: adjusting the position of a hook- and -eye attachment mechanism; inflating of an inflatable member which is part of the article of clothing; rotating a member around which fabric of the article of clothing is wound; shrinking or expanding piezoelectric fibers or strands which are integrated into clothing fabric; and sliding an attachment mechanism along a partially circumferential track which is part of the article of clothing. In an example, this invention can be embodied in an article of clothing made with elastic, stretchable, close-fitting, and/or compressive material with a textile bias which moves electromyographic (EMG) sensors into close proximity to the surface of a person's body.

In an example, electromagnetic signals from muscles which are received by electromyographic (EMG) sensors on an article of electromyographic clothing can be monitored. If these electromagnetic signals become weak or inaccurate because the electromyographic (EMG) sensors are not sufficiently close to a person's body, then one or more circumferential actuators can be contracted so that the article of clothing (and, thus, the sensors) fits closer. In an example, the fit of an article of electromyographic clothing can be adjusted in real time based on data from electromyographic (EMG) sensors. In an example, an article of electromyographic clothing (or a clothing accessory) can be loose when data collection is not needed, but can be automatically tightened (using one or more actuators) when data collection is needed.

In an example, this invention can be embodied in an article of electromyographic clothing comprising: (a) at least one adjustable circumferential portion of an article of clothing, wherein this portion is configured to span at least 25% of the circumference of the person's arm or leg, wherein this adjustable circumferential portion has a first configuration with a first distance from or first pressure exerted onto the surface of the person's arm or leg, wherein this adjustable circumferential portion has a second configuration with a second distance from or second pressure exerted onto the surface of the person's arm or leg, and wherein the person can change the adjustable circumferential portion from the first configuration to the second configuration while wearing the article of clothing; and (b) at least one electromyographic (EMG) sensor, wherein this electromyographic (EMG) sensor is configured to collect data concerning electromagnetic energy from muscle activity of the person's arm or leg, and wherein the distance of this energy sensor from the surface of the person's arm or leg and/or pressure exerted by this energy sensor onto the surface of the person's arm or leg is changed when the adjustable circumferential portion is changed from the first configuration to the second configuration.

In an example, an article of electromyographic clothing can include a mechanism to ensure that the article is worn in a desired position and/or configuration with respect to a person's body and selected muscles therein. In an example, a design or mark on an article of clothing can be configured so that the article of clothing is in a desired position or configuration when the design or mark is aligned with a specific body joint (e.g. aligned with a knee cap or elbow). In an example, an article of electromyographic clothing can be used in combination with an image-analyzing application. In an example, an image of the article being worn by a person can be analyzed in order to determine whether a design or mark on the clothing is in the proper position.

In an example, a hole or opening in an article of clothing can be configured so that the article of clothing is in a desired position or configuration when the hole or opening is over a specific body joint (e.g. over a knee cap or elbow). In an example, a hole or opening in an article of clothing can be configured so that the article of clothing is in a desired position or configuration when a finger or toe, respectively, extends through a hole or opening. In an example, an area on an article of clothing with greater or lesser elasticity can be configured so that the article of clothing is in a desired position or configuration when this area is aligned with a specific body joint.

In an example, an article of electromyographic clothing can be used to adjust the mode and/or energy level of communication via a computer-to-human interface. In an example, this interface can be based on light, sound, or touch. In an example, when data from an electromagnetic muscle activity sensor indicates that a person is very active, then a device can change the mode of a user interface from a touch-based or light-based interface to a sound-based interface that is less likely to be confounded by active motion. In an example, when an electromagnetic muscle activity sensor indicates that a person is very active, then this system can increase the energy level of computer-to-human communication. For example, the system can increase the volume of sound-based communication, increase the brightness of light-based communication, and/or increase the strength of tactile-based communication. In an example, a person can change the mode of a user interface by making a specific hand gesture which is detected by an electromagnetic muscle activity sensor. In an example, a person can increase or decrease the energy level of a user interface by making a first hand gesture or a second hand gesture, respectively, which is detected by an electromagnetic muscle activity sensor.

In an example, an article of electromyographic clothing can be used to modify the filtration of incoming electronic communications and/or notifications in a computer-to-human interface. In an example, communication filtering and/or notification can be modified based on a person's overall level of body motion. In an example, when data from an electromyographic (EMG) sensor indicates that a person is very active (e.g. probably exercising), then a device can impose more selective criteria which must be met by an electronic communication in order for the person to be immediately notified of that electronic communication. In an example, when data from an electromyographic (EMG) sensor indicates that a person is very inactive (e.g. probably sleeping), then the system can impose more selective criteria which must be met by an electronic communication in order for the person to be immediately notified of that electronic communication.

In an example, filtering and/or notification functions for incoming electronic communications can be modified based on identification of a particular type or configuration of body motion. In an example, when a person moves their arms or hand into a particular configuration or gesture, then this is identified by the electromagnetic muscle activity sensor and modifies the filtering and/or notification of incoming electronic messages. In an example, when movements of a person's arms indicate that they are probably driving, then this can increase the filtration and/or reduce the notification of incoming electronic communications to automatically improve driving safety. More generally, an article of electromyographic clothing can be part of a physiologically-aware communication notification system wherein the filtration of incoming electronic communications is modified based on a person's body motion, configuration, posture, and/or gestures.

In an example, an article of electromyographic clothing can be used to control the operation of a home appliance or environmental control system. In an example, an article of electromyographic clothing can remotely control the operation of a Heating Ventilation and Air Conditioning (HVAC) system. In an example, an article of electromyographic clothing can remotely control the operation of one or more home appliances and/or devices selected from the group consisting of: air conditioner, ceiling light, coffee maker, dehumidifier, dish washer, door lock, door opener, dryer, fan, freezer, furnace, heat pump, home entertainment center, home robot, hot tub, humidifier, microwave, music player, oven, swimming pool, refrigerator, security camera, robotic guard chicken, sprinkler system, stand -alone lights, television, wall light, washing machine, water heater, water purifier, water softener, window lock, window opener, and wireless network.

In an example, an article of electromyographic clothing can comprise one or more elastic and/or compressive bands holding electromyographic (EMG) sensors, wherein each band fits snugly around the cross-sectional perimeter of a body member which is covered by the article of clothing. In an example, one or more elastic and/or compressive bands can be an integral part of the primary layer of an article of electromyographic clothing. In an example, one or more elastic and/or compressive bands can be located inside the primary layer of an article of electromyographic clothing. In an example, one or more elastic and/or compressive bands can be located outside the primary layer of an article of electromyographic clothing. In an example, one or more elastic bands with electromyographic (EMG) sensors can be permanently attached to one or more locations, respectively, on an article of clothing. In an example, the locations of one or more elastic and/or compressive bands can be moved to different locations on an article of clothing.

In an example, this invention can be embodied in an article of electromyographic clothing comprising: (a) an article of clothing worn by a person, wherein this article of clothing further comprises a plurality of attachment mechanisms at different locations on the article of clothing; (b) at least one compressive circumferential member; wherein this compressive circumferential member has a first configuration in which it is removably attached to first attachment mechanism at a first location on the article of clothing, is configured to circumferentially span at least a portion the circumference of a portion of the person's body, and is configured to press the article of clothing toward the surface of this portion of the person's body; wherein this compressive circumferential member has a second configuration in which it is attached to second attachment mechanism at a second location on the article of clothing, is configured to circumferentially span at least a portion the circumference of a portion of the person's body, and is configured to press the article of clothing toward the surface of this portion of the person's body; and (c) at least one electromyographic (EMG) sensor, wherein this electromyographic (EMG) sensor is configured to collect data concerning muscle activity from a first location when the at least one compressive circumferential member is in the first configuration and this electromyographic (EMG) sensor is configured to collected data concerning muscle activity from a second location when the at least one compressive circumferential member is in the second location.

In an example, an article of electromyographic clothing can have one or more holes or openings. In an example, one or more holes on an article of electromyographic clothing can allow an attachable electromyographic (EMG) sensor to have direct contact with a person's skin when the sensor is attached over the hole. In an example, one or more holes on an article of electromyographic clothing can allow an attachable electromyographic (EMG) sensor to have direct contact with a person's skin when a compressive band or path containing such a sensor is attached over the hole.

In an example, an article of electromyographic clothing can comprise one or more fabric channels, pockets, or pouches into which one or more electromyographic (EMG) sensors can be reversibly inserted. In an example, not only can an electromyographic (EMG) sensor be reversibly inserted into, or removed from, such a fabric channel, pocket, or pouch, but the location of an electromyographic (EMG) sensor can be further refined by sliding or otherwise moving the sensor within a fabric channel, pocket, or pouch. In an example, a fabric channel can encircle (or partially encircle) an arm or leg and the precise location of an electromagnetic (EMG) sensor around the perimeter of that arm or leg can be adjusted by sliding it to a particular location within the fabric channel. In an example, a fabric channel can longitudinally span (or partially span) an arm or leg and the precise location of an electromagnetic (EMG) sensor along the length of that arm or leg can be adjusted by sliding it to a particular location along the fabric channel.

In an example, placing an electromyographic (EMG) sensor in a first flexible channel or pathway can provide optimal collection of data concerning muscle activity for a first person with a first body size and/or shape and placing an electromyographic (EMG) sensor in a second flexible channel or pathway can provide optimal collection of data concerning muscle activity for a second person with a second body size and/or shape. Accordingly, creating an article of clothing with multiple flexible channels or pathways into which one or more electromyographic (EMG) sensors can be removably inserted can enable optimized and/or customized EMG data collection for a specific person. This can enable more accurate data concerning muscle activity for a specific person. In an example, more-proximal EMG sensor locations can be optimal for a first person and more-distal EMG sensor locations can be optimal for a second person.

In an example, an electromyographic sensor can be inserted into a fabric channel, pocket, or pouch via a hole. In an example, this hole can be closed after an electromyographic (EMG) sensor has been inserted in order to prevent the sensor from slipping out unintentionally during physical activity. In an example, a hole in a fabric channel can be closed by one or more means selected from the group consisting of: hook- and -eye mechanism, snap, button, zipper, clip, pin, plug, and clasp. In an example, an electromyographic (EMG) sensor can be attached to a particular location along the longitudinal axis of a fabric channel.

In an example, a fabric channel, pocket, or pouch can be created as part of an article of electromyographic clothing by weaving, knitting, sewing, embroidering, layering, laminating, adhering, melting, fusing, printing, spraying, painting, or pressing. In an example, a fabric channel can be created on (or attached to) the interior surface of an article of clothing which faces toward the wearer's body. In an example, a fabric channel can be created on (or attached to) the exterior surface of an article of clothing which faces away from the wearer's body. In an example, there can be one or more openings, holes, or discontinuities in the interior surface of a fabric channel which enable a sensor within the channel to be in direct contact with the wearer's skin at one or more selected locations. In an example, a user can customize the number, locations, and/or sizes of holes or openings in order to customize an article of clothing for the user and/or for a particular type of physical activity.

In an example, a fabric channel can span the entire perimeter or circumference of a cross-section of a body member spanned by the article of clothing. In an example, a fabric channel can be circular or spiral in shape. In an example, a fabric channel can span a portion of the perimeter or circumference of a cross-section of a body member spanned by the article of clothing. In an example, a fabric channel can be shaped like a section of a circle or other conic section. In an example, a fabric channel can span the anterior portion of the perimeter or circumference of a cross-section of a body member. In an example, a fabric channel can span the posterior portion of the perimeter or circumference of a cross-section of a body member. In an example, a fabric channel can span a lateral portion of the perimeter or circumference of a cross-section of a body member. In an example, a fabric channel can span from 10% to 25%, from 25% to 50%, or from 50% to 75%, or from 75% to 100% of the circumference of a body member.

In an example, an article of electromyographic clothing can comprise: an article of clothing which is configured to span a body member, wherein this article of clothing further comprises a first flexible channel with a longitudinal axis which spans (a portion of) a first cross-sectional perimeter or circumference of the body member and a second flexible channel with a longitudinal axis which spans (a portion of) a second cross-sectional perimeter or circumference of the body member; and an electromyographic (EMG) sensor for collecting data concerning electromagnetic energy from muscle activity, wherein this sensor is removably inserted into either the first flexible channel or into the second flexible channel depending on whether the first flexible channel or the second flexible channel enables more accurate data collection concerning the muscle activity of a specific person and/or the muscle activity of a specific type of activity.

In an example, an article of electromyographic clothing can comprise one or more (electroconductive) tracks along which one or more electromyographic (EMG) sensors can be slid in order to find the best measurement locations for collecting data concerning muscle activity. In an example, a track can be circumferential and allow an electromyographic (EMG) sensor to be slid circumferentially around (a portion of) a person's arm, leg, or torso. In an example, a track can be longitudinal and allow an electromyographic (EMG) sensor to be slid longitudinally along (a portion of) a person's arm, leg, or torso.

In an example, an article of electromyographic clothing can have an array of electrodes which are integrated into the article of clothing, but only a sub-set of them are activated for use as electromyographic (EMG) sensors through the use of modular electrical connectors. In an example, a plurality of modular electrical connectors can be removably-attached to electrodes on an article of clothing and only those electrodes which are connected are used to collect muscle activity data. In an example, a modular electrical connector can create an electromagnetic pathway between an electrode in an article of electromyographic clothing and a control unit. In an example, a control unit can further comprise a power source, an amplifier, a data processor, a memory, a data transmitter, a data receiver, and a display screen. In an example, an article of electromyographic clothing can comprise a plurality, array, and/or grid of electromyographic (EMG) sensors. In an example, not all of these electromyographic (EMG) sensors collect data concerning muscle activity at a given time—only those which are connected to a control unit by the attachment of a removably-attachable electrical connectors or a series of removably-attachable electrical connectors.

In an example, this invention can be embodied in a method for creating customized electromyographic clothing comprising: creating an image of a specific person's body; using this image to create a virtual kinematic model of this specific person's skeleton, tendons, muscles, and/or nerves; and using this virtual kinematic model to create an article of customized electromyographic clothing for the person, wherein this article of customized electromyographic clothing further comprises one or more electromyographic (EMG) sensors which collect data the person's neuromuscular activity, and wherein the size, shape, elasticity, and/or electromagnetic sensor configuration of this article of customized electromyographic clothing is customized for this specific person based on the virtual kinematic model.

In an example, an image of a person's body which is used to create a virtual kinematic model can be a moving image, a motion picture, and/or a video. In an example, an image of a person's body which is used to create a virtual kinematic model can be an exterior image of the exterior of a person's clothes and/or the person's skin. In an example, an image of a person's body which is used to create a virtual kinematic model can be an interior image of the person's bones, tendons, muscles, nerves, or other body tissue. In an example, an interior image can be obtained using one of more imaging techniques selected from the group consisting of: x-rays; computerized tomography; magnetic resonance; fluoroscopy; nuclear medicine; and positron emission. In an example, a virtual kinematic model of a specific person's body can include one or more components selected from the group consisting of: bones; joints; tendons; muscles; and efferent nerves.

In an example, one or more characteristics of an article of customized electromyographic clothing can be customized for a specific person based on a virtual kinematic model of that person, wherein these characteristics as selected from the group consisting of: clothing size; clothing shape; clothing elasticity; configuration of electromyographic (EMG) sensors; configuration of inertial measurement sensors; and configuration of bend sensors. In an example, the position, location, and/or orientation of electromyographic sensors on an article of electromyographic clothing can be customized to optimally collect data concerning muscle activity based on the virtual kinematic model of that person. In an example, the number, proportion, location, size, shape, and orientation of electromyographic sensors and inertial motion sensors on an article of electromyographic clothing can be customized to optimally collect data concerning muscle activity based on the virtual kinematic model of that person.

In an example, this invention can be embodied in a method for creating customized electromyographic clothing comprising: creating images of one or more people playing a selected sport; using these images to create virtual kinematic models of these people's skeletons, tendons, muscles, and/or nerves while playing this selected sport; and using these virtual kinematic models to create at least one article of customized electromyographic clothing for people to wear playing that sport, wherein this article of customized electromyographic clothing further comprises one or more electromyographic (EMG) sensors which collect data the person's neuromuscular activity, and wherein the size, shape, elasticity, and/or electromagnetic sensor configuration of this article of customized electromyographic clothing is customized for this selected sport based on these virtual kinematic models.

In an example, images of people playing this sport which are used to create virtual kinematic models can be a moving images, motion pictures, and/or videos. In an example, images of people playing this sport which are used to create virtual kinematic models can be exterior images of the exteriors of these people's clothes and/or skin. In an example, images of people's bodies which are used to create a virtual kinematic models can be an interior images of their bones, tendons, muscles, nerves, or other body tissue. In an example, interior images can be obtained using one of more imaging techniques selected from the group consisting of: x-rays; computerized tomography; magnetic resonance; fluoroscopy; nuclear medicine; and positron emission. In an example, virtual kinematic models of people's bodies can include one or more components selected from the group consisting of: bones; joints; tendons; muscles; and efferent nerves.

In an example, one or more characteristics of an article of customized electromyographic clothing can be customized for a selected sport based on virtual kinematic models of people playing that sport, wherein these characteristics as selected from the group consisting of: clothing size; clothing shape; clothing elasticity; configuration of electromyographic (EMG) sensors; configuration of inertial measurement sensors; and configuration of bend sensors. In an example, the position, location, and/or orientation of electromyographic sensors on an article of electromyographic clothing can be customized to optimally collect data concerning muscle activity based on the virtual kinematic model of that person. In an example, the number, proportion, location, size, shape, and orientation of electromyographic sensors and inertial motion sensors on an article of electromyographic clothing can be customized to optimally collect data concerning muscle activity based on virtual kinematic models of people playing a selected sport.

In an example, this invention can be embodied in a modular system for creating customized electromyographic clothing comprising: (a) a first set of alternative modules for an article of clothing, wherein each module in this first set is configured to be worn on a first portion of a person's body, wherein at least one module in this first set includes at least one electromyographic (EMG) sensor, and wherein there is variation in the location, orientation, size, shape, number, and/or configuration of electromyographic (EMG) sensors between different modules in this first set; and (b) a second set of alternative modules for an article of clothing, wherein each module in this second set is configured to be worn on a second portion of a person's body, wherein at least one module in this second set includes at least one electromyographic (EMG) sensor, wherein there is variation in the location, orientation, size, shape, number, and/or configuration of electromyographic (EMG) sensors between different modules in this second set, and wherein a first module is selected from the first set, a second module is selected from the second set, and the selected first and second modules are combined to form part (or all) of a single customized article of clothing for collecting data concerning electromagnetic energy from neuromuscular activity by a specific person or during a specific type of physical activity.

In an example, the orientations of electromyographic (EMG) sensors can vary across different modules within a set. In an example, the number of electromyographic (EMG) sensors can vary across different modules within a set. In an example, the size or shape of electromyographic (EMG) sensors can vary across different modules within a set. In an example, the location of electromyographic (EMG) sensors can vary across different modules within a set. In an example, the type or fit of fabric or textile can vary across different modules within a set. In an example, some modules can be larger in size and other modules can be smaller in size in order to customize an article of clothing for variation in a specific person's body shape. In an example, modules can vary in elasticity and/or stretchability in order to achieve the right fit on a specific person's body shape.

In an example, a system of modular electromyographic clothing can include a removably-attachable electromyographic patch, wherein this electromyographic patch includes one or more electromyographic (EMG) sensors. In an example, a removably-attachable electromyographic patch can be attached to (and removed from) one or more different locations on an article of electromyographic clothing in order to enable collection of muscle activity data from different locations on a person's body. In an example, a system of modular electromyographic clothing can allow a person to test attachment of a removably-attachable electromyographic patch with electromyographic sensors to different locations in order to find the location from which it optimally measures muscle activity for a particular person or a particular sport. In an example, a removably-attachable electromyographic patch can be attached to electromyographic clothing by one or more mechanisms selected from the group consisting of: hook- and -eye material, insertion into a fabric channel or pocket, snap, clip, clasp, hook, plug, loop, and elastic band.

In an example, the shape of a removably-attachable electromyographic patch can be selected from the group consisting of: square, rectangular, saddle, circular, oval, oblong, rounded square, rounded rectangle, and hexagonal. In an example, a removably-attachable electromyographic patch can be attached to the inside surface of an article of electromyographic clothing. In an example, a removably-attachable electromyographic patch can be attached to the outside surface of an article of electromyographic clothing. In an example, a removably-attachable electromyographic patch can be attached to the outside of an article of electromyographic clothing at a location wherein the clothing has a hole so that the electromyographic patch can nonetheless be in direct contact with a person's skin.

In an example, a removably-attachable electromyographic patch can span a selected percentage of the perimeter of a body member such as an arm or leg. In an example, this percentage can be in the range of 25% to 75%. In an example, an electromyographic patch can be slid along the surface of a body member in order to adjust its location with respect to underlying muscles. In an example, an electromyographic patch can be rotated on the surface of a body member in order to adjust its location with respect to underlying muscles.

In an example, an article of electromyographic clothing can have a total array of electromyographic (EMG) sensors or electrodes, but only a subset of that array of electromyographic (EMG) sensors or electrodes is activated at a given time. In an example, this subset of electromyographic (EMG) sensors can be selected so as to most efficiency collect data concerning muscle activity of a specific person or during a specific type of physical activity. In an example, only activating and using a subset of electromyographic (EMG) sensors can conserve energy.

In an example, a total array of electromyographic (EMG) sensors can be activated and used during a calibration and/or testing period. Data from the calibration and/or testing period can be analyzed to determine an efficient subset of sensors to activate on an ongoing basis. In an example, a reduction in the number of activated sensors (from total to subset) can be done automatically by a data processing system. In an example, a reduction in the number of activated sensors (from total to subset) can be done manually by manually disconnecting some sensors from activation. In an example, the number of sensors in an activated subset can be at least 25% less than the number of total sensors. In an example, the number of sensors in an activated subset can be at least 50% less than the number of total sensors.

In an example, a master article of electromyographic clothing can have a first (large) array of electromyographic (EMG) sensors or electrodes. In an example, a person can wear the master article of electromyographic clothing during a calibration and/or testing period in order to determine a subset array of sensors or electrodes which most efficiently collects data concerning muscle activity of that person (with a desired minimum level of accuracy). In an example, data from this calibration and/or testing period is used to identify this efficient subset array of electromyographic (EMG) sensors and a customized article of electromyographic clothing with that subset array is created for this person. In an example, the customized article of electromyographic clothing can be created from modular components. In an example, the person only wears the master article during a calibration period and the person wears the customized article with the subset array on an ongoing basis. This can help to achieve a desired level of accuracy of muscle activity measurement while containing cost and conserving energy use. In an example, the number of sensors in the customized article can be at least 25% less than number of sensors in the master article. In an example, the number of sensors in the customized article can be at least 50% less than number of sensors in the master article.

In an example, this invention can be embodied in a method for creating a customized article of electromyographic clothing comprising: creating a master model of an article of clothing with a first plurality of electromyographic (EMG) sensors which collect data concerning muscle activity; having a person wear this master model while the person performs muscle activity; analyzing data from the master model while the person performs muscle activity in order to identify a second plurality of electromyographic (EMG) sensors on the master model which are most useful for collecting data concerning the muscle activity of this specific person or muscle activity during a specific type of physical activity, wherein the second plurality is a subset of the first plurality; and creating a customized article of clothing to measure muscle activity with the second plurality of electromyographic (EMG) sensors to collect data concerning muscle activity of this specific person or muscle activity during the specific type of physical activity. In an example, the number of sensors in the second plurality can be less than 50% of the number of sensors in the first plurality. In an example, the number of sensors in the second plurality can be less than 25% of the number of sensors in the first plurality.

In an example, one or more geometric parameters of electromyographic (EMG) sensors can be adjusted by a person wearing an article of electromyographic clothing. In an example, these adjustable geometric parameters can be selected from the group consisting of: their distance from the surface of the person's body; the pressure which they exert against the surface of the person's body; their flexibility or elasticity; the angle at which they span the longitudinal axis of a muscle; the longitudinal location at which span the longitudinal axis of a muscle; their longitudinal shape; and their cross-sectional shape.

In an example, an article of electromyographic clothing can further comprise one or more components selected from the group consisting of: amplifier, analog-to-digital converter, battery, bioidentification sensor, camera, central processing unit, chemical sensor, computer-to-human interface, control module, data communication component, data control unit, data processor, data receiver, data transmitter, electric motor, electromagnetic actuator, energy-harvesting power source, eyewear, gesture recognition interface, graphic display, keypad, kinetic energy transducer, memory, microprocessor, myostimulator, optical sensor, piezoelectric actuator, power source, signal amplifier, speaker, spectroscopic sensor, speech recognition component, stepper motor, tactile-sensation-creating member, thermal energy transducer, touch screen, visual display, voice producing interface, voice recognition interface, wireless data receiver, and wireless data transmitter.

In an example, an article of electromyographic clothing can enable payment and commerce functionality in situations wherein conventional payment mechanisms are infeasible or inconvenient. In an example, in a zero-gravity situation (such as that encountered by astronauts) where monetary exchange would be difficult, an article of electromyographic clothing can enable commercial exchanges and banking functions. In an example, an article of electromyographic clothing can comprise an astro teller. In an example, a first payment mechanism can be part of an upper arm device and a second payment mechanism can be part of a lower leg device. In an example, the value of a specific transaction could be correlated to the number of payment mechanisms engaged. In an example, some transactions could cost an arm and a leg.

In an example, an article of electromyographic clothing can further comprise a computer-human interface selected from the group consisting of: alarm, animated display, augmented reality display, button, buzzer or alarm, comparing progress toward meeting muscle activity goals with other people, display screen, display showing which muscles a person is using and/or should use, electrical stimulation of the skin, electronically-functional textile, energy balance display, eye gaze tracker, gesture recognition interface, haptic feedback, image projector, infrared light emitter, keypad, light, light display array or matrix, light emitting diode (LED) array or matrix, liquid crystal display (LCD), MEMS actuator, message filtering and/or notification, microphone, myostimulator, neurostimulator, phone call, playing a tone, playing music, real-time coaching advice, ring tone, sharing data with friends, social network interface, speaker or other sound-emitting member, spectroscopic sensor, speech or voice recognition interface, text message, thermometer, touch pad or screen, vibration, and voice message.

FIGS. 1 through 44 show examples of how this invention can be embodied in a device and system for measuring body motion and/or muscle activity comprising: (a) one or more articles of clothing or clothing accessories; (b) a plurality of motion sensors which are attached to and/or integrated into the one or more articles of clothing or clothing accessories, wherein these motion sensors are configured to collect motion data concerning changes in the configurations of a set of body joints; (c) a plurality of electromyographic (EMG) sensors which are attached to and/or integrated into the one or more articles of clothing or clothing accessories, wherein these EMG sensors are configured to collect electromagnetic energy data concerning the neuromuscular activity of a set of muscles, and wherein muscles in the set of muscles move joints in the set of body joints; and (d) a data processing unit which analyzes both motion data from both the motion sensors and electromagnetic energy data from the EMG sensors to measure and/or model body motion and/or body muscle activity.

These figures also show examples of how this invention can be embodied in a device and system for measuring body motion and/or muscle activity comprising: (a) one or more articles of clothing or clothing accessories; (b) a plurality of motion sensors which are attached to and/or integrated into the one or more articles of clothing or clothing accessories, wherein these motion sensors are configured to collect motion data concerning changes in the configurations of a set of body joints; (c) a plurality of electromyographic (EMG) sensors which are attached to and/or integrated into the one or more articles of clothing or clothing accessories, wherein these EMG sensors are configured to collect electromagnetic energy data concerning the neuromuscular activity of a set of muscles, and wherein muscles in the set of muscles move joints in the set of body joints; and (d) a data transmitting unit which transmits both motion data from the motion sensors and electromagnetic energy data from the EMG sensors to a remote data processing unit which analyzes both motion data from the motion sensors and electromagnetic energy data from the EMG sensors to measure and/or model body motion and/or body muscle activity.

FIGS. 1 through 44 show examples of this invention wherein one or more articles of clothing comprise an upper body garment and a lower body garment. These figures show examples of this invention wherein a set of body joints comprises one or more body joints selected from the group consisting of: shoulder; elbow; hip; and knee. These figures show examples of this invention wherein a set of body joints comprises both of a person's shoulders, both of a person's elbows, both of a person's hips, and both of a person's knees. These figures show examples of this invention wherein a set of body muscles comprises one or more muscles selected from the group consisting of: biceps brachii muscle; biceps femoris muscle; deltoideus muscle; gastrocnemius muscle; gluteus medius muscle; quadriceps femoris muscle; sastrocnemius muscle; semitendinosus muscle; tensor fasciae latae muscle; and triceps brachii muscle.

FIGS. 1 through 44 show examples of this invention wherein the one or more articles of clothing include an upper body garment (such as a shirt). These figures show examples of this invention wherein the set of body joints spanned by an upper body garment comprises one or more body joints selected from the group consisting of: shoulder; and elbow. These figures show examples of this invention wherein the set of body joints spanned by an upper body garment comprises both of a person's shoulders and both of a person's elbows. These figures show examples of this invention wherein the set of body muscles spanned by an upper body garment comprises one or more muscles selected from the group consisting of: biceps brachii muscle; deltoideus muscle; and triceps brachii muscle.

FIGS. 1 through 44 show examples of this invention wherein the one or more articles of clothing include a lower body garment (such as a pair of pants). These figures show examples of this invention wherein the set of body joints spanned by a lower body garment comprises one or more body joints selected from the group consisting of: hip; and knee. These figures show examples of this invention wherein the set of body joints spanned by a lower body garment comprises both of a person's hips and both of a person's knees. These figures show examples of this invention wherein the set of body muscles spanned by a lower body garment comprises one or more muscles selected from the group consisting of: biceps femoris muscle; gastrocnemius muscle; gluteus medius muscle; quadriceps femoris muscle; sastrocnemius muscle; semitendinosus muscle; and tensor fasciae latae muscle.

In an example, one or more motion sensors in a plurality of motion sensors can be selected from the group consisting of: accelerometer; conductive fiber motion sensor; electrogoniometer; fluid pressure sensor; gyroscope; inclinometer; inductive transducer; inertial sensor; longitudinal pressure sensor; magnometer; optical bend sensor; piezoelectric fiber; piezoelectric sensor; piezoresistive fiber; piezoresistive sensor; strain gauge, and ultrasonic motion sensor.

In an example, one or more EMG sensors in a plurality of EMG sensors can be selected from the group consisting of: bipolar EMG sensor; capacitive-coupling EMG sensor; circular sensor; conductive electrode EMG sensor; conductive yarn EMG sensor; contactless EMG sensor; copper-coated fiber EMG sensor; electromagnetic impedance sensor; monopolar EMG sensor; non-gelled EMG sensor; non-invasive EMG sensor; silver-coated fiber EMG sensor; square EMG sensor; and surface EMG sensor.

In an example, each EMG sensor can be configured to collect electromagnetic muscle activity from a location selected from the group consisting of: the anterior portion of the deltoideus muscle; the deltoideus medius muscle; the gluteus maximus muscle; the gluteus medius muscle; the lateral head of the triceps brachii muscle; the lateralis of the sastrocnemius muscle; the long head and short head of the biceps femoris muscle; the long head of the triceps brachii muscle; the *medialis* of the gastrocnemius muscle; the peroneus *brevis* muscle; the peroneus longus muscle; the posterior portion of the deltoideus muscle; the rectus femoris of the quadriceps femoris muscle; the semitendinosus muscle; the short head and/or long head of the biceps brachii muscle; the soleus muscle; the tensor fasciae latae muscle; the tibialis anterior muscle; the vastus lateralis of the quadriceps femoris muscle; and the vastus medialis of the quadriceps femoris muscle.

In an example, one or more EMG sensors can be configured to collect electromagnetic muscle activity from a plurality of locations selected from the group consisting of: the anterior portion of the deltoideus muscle; the deltoideus medius muscle; the gluteus maximus muscle; the gluteus medius muscle; the lateral head of the triceps brachii muscle; the lateralis of the sastrocnemius muscle; the long head and short head of the biceps femoris muscle; the long head of the triceps brachii muscle; the *medialis* of the gastrocnemius muscle; the peroneus *brevis* muscle; the peroneus longus muscle; the posterior portion of the deltoideus muscle; the rectus femoris of the quadriceps femoris muscle; the semitendinosus muscle; the short head and/or long head of the biceps brachii muscle; the soleus muscle; the tensor fasciae latae muscle; the tibialis anterior muscle; the vastus lateralis of the quadriceps femoris muscle; and the vastus medialis of the quadriceps femoris muscle.

In an example, a set of body joints whose motions are tracked can be selected from the group consisting of: knee, elbow, hip, pelvis, shoulder, ankle, foot, toe, wrist, palm, finger, torso, rib cage, spine, neck, and jaw. In an example, an article of clothing can be selected from the group consisting of: shirt, blouse, jacket, pants, dress, shorts, glove, sock, shoe, underwear, belt, and union suit. In an example, an article of clothing can be selected from the group consisting of: shirt, T-shirt, blouse, sweatshirt, sweater, neck tie, collar, cuff, jacket, vest, other upper-body garment, pants, shorts, jeans, slacks, sweatpants, briefs, skirt, other lower-body garment, underwear, underpants, panties, pantyhose, jockstrap, undershirt, bra, brassier, girdle, bathrobe, pajamas, hat, cap, skullcap, headband, hoodie, poncho, other garment with hood, sock, shoe, sneaker, sandal, other footwear, suit, coat, dress, jump suit, one-piece garment, union suit, swimsuit, bikini, other full-body garment, and glove.

In an example, an article of clothing can be made from one or more materials selected from the group consisting of: Acetate, Acrylic, Cotton, Denim, Latex, Linen, Lycra®, Neoprene, Nylon, Polyester, Rayon, Silk, Spandex, and Wool. In an example, an article of clothing can be made from fabric and/or constructed in such a manner that it does not shift with respect to the person's skin when a person moves a body joint. In an example, an article of clothing can be close-fitting so that it does not shift with respect to a person's skin when the person moves a body joint. In an example, an article of clothing can cling to a person's skin so that it does not shift with respect to the person's skin when the person moves a body joint.

In an example, a clothing accessory can be selected from the group consisting of: a flexible adhesive member that is attached to the skin spanning a knee; a flexible adhesive member that is attached to the skin spanning an elbow; a flexible adhesive member that is attached to the skin spanning a shoulder; a flexible adhesive member that is attached to the skin spanning a hip; a flexible adhesive member that is attached to the skin spanning an ankle; and a flexible adhesive member that is attached to the skin spanning the torso and/or waist.

In an example, a clothing accessory can be selected from the group consisting of: a flexible bandage that is attached to the skin spanning a knee; an flexible bandage that is attached to the skin spanning an elbow; a flexible bandage that is attached to the skin spanning a shoulder; a flexible bandage that is attached to the skin spanning a hip; a flexible bandage that is attached to the skin spanning an ankle; and a flexible bandage that is attached to the skin spanning the torso and/or waist.

In an example, a clothing accessory can be selected from the group consisting of: an electronic tattoo that is attached to the skin spanning a knee; an electronic tattoo that is attached to the skin spanning an elbow; an electronic tattoo that is attached to the skin spanning a shoulder; an electronic tattoo that is attached to the skin spanning a hip; an electronic tattoo that is attached to the skin spanning an ankle; and an electronic tattoo that is attached to the skin spanning the torso and/or waist.

In other examples, a clothing accessory can be selected from the group consisting of: wrist band, wrist watch, smart watch, bracelet, bangle, strap, other wrist-worn band, eyewear, eyeglasses, contact lens, virtual reality glasses or visor, augmented reality glasses or visor, monocle, goggles, sunglasses, eye mask, visor, electronically-functional eyewear, necklace, neck chain, neck band, collar, dog tags, pendant, beads, medallion, brooch, pin, button, cuff link, tie clasp, finger ring, artificial finger nail, finger nail attachment, finger tube, head band, hair band, wig, headphones, helmet, ear ring, ear plug, ear bud, hearing aid, ear muff, other ear attachment, respiratory mask, face mask, nasal mask, nose ring, nasal pillow, arm bracelet, bangle, amulet, strap, or band, ankle bracelet, bangle, amulet, strap, or band, artificial tooth, dental implant, dental appliance, dentures, dental bridge, braces, upper palate attachment or insert, tongue ring, band, chain, electronic tattoo, adhesive patch, bandage, belt, waist band, suspenders, chest band, abdominal brace, elbow brace, knee brace, shoulder brace, shoulder pad, ankle brace, pocketbook, purse, key chain, and wallet.

In an example, combined and/or multivariate analysis of both (a) motion data from the motion sensors and (b) electromagnetic energy data from the EMG sensors can enable more accurate measurement and/or modeling of body motion than analysis of data from motion sensors alone. In an example, combined and/or multivariate analysis of both (a) motion data from the motion sensors and (b) electromagnetic energy data from the EMG sensors can enable more accurate measurement and/or modeling of body motion than analysis of electromagnetic energy data from the EMG sensors alone. In an example, combined and/or multivariate analysis of both (a) motion data from the motion sensors and (b) electromagnetic energy data from the EMG sensors can enable more accurate measurement and/or modeling of muscle activity than analysis of data from motion sensors alone. In an example, combined, joint, and/or multivariate analysis of both (a) motion data from the motion sensors and (b) electromagnetic energy data from the EMG sensors can enable more accurate measurement and/or modeling of muscle activity than analysis of electromagnetic energy data from the EMG sensors alone.

In an example, data from EMG sensors can supplement data from motion sensors for more accurate measurement of body motion during key portions of joint range of motion wherein data from motion sensors alone is less accurate. In an example, this can be at extreme positions in the range of motion. In an example, data from EMG sensors can supplement data from motion sensors for more accurate measurement of body motion at key times in joint motion wherein data from motion sensors alone is less accurate. In an example, this can be at the beginning or end of a series of repeated actions. In an example, this can be at the beginning or end of a time of especially-strenuous physical activity. In an example, data from EMG sensors can supplement data from motion sensors for more accurate measurement of body motion during isometric activity wherein pressure is being applied against a motion-resisting external object. In an example, data from EMG sensors can supplement data from motion sensors for more accurate measurement of body motion when the person is being moved by an external device such as a car, elevator, escalator, airplane, etc. In an example, data from EMG sensors can supplement data from motion sensors for more accurate measurement of body motion when an article of clothing fits relatively loosely and/or shifts over the surface of the person's skin when the person moves.

In an example, data from motion sensors can supplement data from EMG sensors for more accurate measurement of muscle activity during key portions of joint range of motion wherein data from EMG sensors alone is less accurate. In an example, this can be at extreme positions in the range of motion. In an example, data from motion sensors can supplement data from EMG sensors for more accurate measurement of muscle activity at key times in joint motion wherein data from EMG sensors alone is less accurate. In an example, this can be at the beginning or end of a series of repeated actions. In an example, this can be at the beginning or end of a time of especially-strenuous physical activity. In an example, data from motion sensors can supplement data from EMG sensors for more accurate measurement of muscle activity during isometric activity wherein pressure is being applied against a motion-resisting external object. In an example, data from motion sensors can supplement data from EMG sensors for more accurate measurement of muscle activity when the person is being moved by an external device such as a car, elevator, escalator, airplane, etc. In an example, data from motion sensors can supplement data from EMG sensors for more accurate measurement of muscle activity when an article of clothing fits relatively loosely and/or shifts over the surface of the person's skin when the person moves.

In an example, a device and system for measuring body motion and/or muscle activity with both EMG sensors and motion sensors can be used to measure, estimate, and/or model changes in body configuration and posture. In an example, a device and system for measuring body motion and/or muscle activity with both EMG sensors and motion sensors can be used for motion capture instead of (or in addition to) a camera-based motion capture system. In an example, a device and system for measuring body motion and/or muscle activity with both EMG sensors and motion sensors can be used as a human-to-computer interface for virtual reality or other applications. In an example, a device and system for measuring body motion and/or muscle activity with both EMG sensors and motion sensors can be used for measuring and improving muscle activity and/or athletic performance. In an example, a device and system for measuring body motion and/or muscle activity with both EMG sensors and motion sensors can be used for injury prevention or rehabilitation. In an example, a device and system for measuring body motion and/or muscle activity with both EMG sensors and motion sensors can be used to measure energy expenditure.

In an example, data from motion sensors and data from EMG sensors can be jointly analyzed using one or more statistical methods selected from the group consisting of: Analysis of Variance (ANOVA), Artificial Neural Network (ANN), Auto Regression, Bayesian filter or other Bayesian statistical method, centroid analysis, Chi-Squared analysis, cluster analysis, covariance analysis, decision tree analysis, Eigenvalue Decomposition, Factor Analysis, Fast Fourier Transform (FFT) or other Fourier transformation, Hidden Markov model or other Markov modeling, Kalman Filter, kinematic modeling, Least Squares Estimation (LSE), Discriminant Analysis (DA), linear regression, linear transform, logarithmic function analysis, logistic regression, logit analysis, machine learning, mean or median analysis, Multivariate Linear Regression (MLR), Logit analysis, multivariate parametric classifiers, Neural Network, Non-Linear Programming (NLP), normalization, orthogonal transformation, pattern recognition, Power Spectral Density (PSD) analysis, power spectrum analysis, Principal Components analysis, probit analysis, Random Forest Gump (RFG) analysis, spectral analysis, spectroscopic analysis, spline function, survival analysis, three-dimensional modeling, time series analysis, variance, and wavelet analysis.

In an example, a device and system for measuring body motion and/or muscle activity can (further) comprise one or more sensors selected from the group consisting of: EMG sensor; bending-based motion sensor; accelerometer; gyroscope; inclinometer; vibration sensor; gesture-recognition interface; goniometer; strain gauge; stretch sensor; pressure sensor; flow sensor; air pressure sensor; altimeter; blood flow monitor; blood pressure monitor; global positioning system (GPS) module; compass; skin conductance sensor; impedance sensor; Hall-effect sensor; electrochemical sensor; electrocardiogramansor; electroencephalography (EEG) sensor; electrogastrography (EGG) sensor; electromyography (EMG) sensor; electrooculography (EOG); cardiac function monitor; heart rate monitor; pulmonary function and/or respiratory function monitor; light energy sensor; ambient light sensor; infrared sensor; optical sensor; ultraviolet light sensor; photoplethysmography (PPG) sensor; camera; video recorder; spectroscopic sensor; light-spectrum-analyzing sensor; near-infrared, infrared, ultraviolet, or white light spectroscopy sensor; mass spectrometry sensor; Raman spectroscopy sensor; sound sensor; microphone; speech and/or voice recognition interface; chewing and/or swallowing monitor; ultrasound sensor; thermal energy sensor; skin temperature sensor; blood glucose monitor; blood oximeter; body fat sensor; caloric expenditure monitor; caloric intake monitor; glucose monitor; humidity sensor; and pH level sensor.

In an example, data from multiple types of sensors can be jointly analyzed using one or more statistical methods selected from the group consisting of: Analysis of Variance (ANOVA), Artificial Neural Network (ANN), Auto Regression, Bayesian filter or other Bayesian statistical method, centroid analysis, Chi-Squared analysis, cluster analysis, covariance analysis, decision tree analysis, Eigenvalue Decomposition, Factor Analysis, Fast Fourier Transform (FFT) or other Fourier transformation, Hidden Markov model or other Markov modeling, Kalman Filter, kinematic modeling, Least Squares Estimation (LSE), Discriminant Analysis (DA), linear regression, linear transform, logarithmic function analysis, logistic regression, logit analysis, machine learning, mean or median analysis, Multivariate Linear Regression (MLR), Logit analysis, multivariate parametric classifiers, Neural Network, Non-Linear Programming (NLP), normalization, orthogonal transformation, pattern recognition, Power Spectral Density (PSD) analysis, power spectrum analysis, Principal Components analysis, probit analysis, Random Forest Gump (RFG) analysis, spectral analysis, spectroscopic analysis, spline function, survival analysis, three-dimensional modeling, time series analysis, variance, and wavelet analysis.

In an example, a device and system for measuring body motion and/or muscle activity can (further) comprise a human-to-computer interface. This human-to-computer interface can comprise one or more members selected from the group consisting of: buttons, knobs, dials, or keys; display screen; gesture-recognition interface; microphone; physical keypad or keyboard; virtual keypad or keyboard; speech or voice recognition interface; touch screen; EMG-recognition interface; and EEG-recognition interface.

In an example, a device and system for measuring body motion and/or muscle activity can (further) comprise a computer-to-human interface. In an example, this computer-to-human interface can provide feedback to the person concerning their body motion and/or muscle activity. This computer-to-human interface can comprise one or more members selected from the group consisting of: a display screen; a speaker or other sound-emitting member; a myostimulating member; a neurostimulating member; a speech or voice recognition interface; a synthesized voice; a vibrating or other tactile sensation creating member; MEMS actuator; an electromagnetic energy emitter; an infrared light projector; an LED or LED array; and an image projector.

In an example, a wearable clothing accessory or device can comprise: a band which is configured to be worn around a person's wrist or arm; electromyography sensors on the band; and a data processor on the band, wherein data from the electromyographic sensors is analyzed to identify hand gestures and/or function as a human-to-computer interface.

In an example, the wearable clothing accessory or device can further comprise one or more inertial-based motion sensors, and wherein data from the electromyographic sensors and data from the inertial-based motion sensors are jointly-analyzed to identify hand gestures and/or function as a human-to-computer interface. In an example, the wearable clothing accessory or device can further comprise one or more inertial-based motion sensors and one or more bending-based motion sensors; and wherein data from the electromyographic sensors, data from the inertial-based motion sensors, and data from the bending-based motion sensors are jointly-analyzed to identify hand gestures and/or function as a human-to-computer interface. In an example, the wearable clothing accessory or device can further comprise one or more actuators which automatically contract the band to make the electromyographic sensors fit more closely to a person's body.

In an example, the number, types, locations, orientation, and/or configurations of the electromyographic sensors can be customized and/or specifically-configured to optimally collect data concerning muscle activity during a specific sport or other specific type of physical activity, and wherein the electromyographic sensors can be removably attached to different locations on the wearable clothing accessory or device by a mechanism selected from the group consisting of: a buckle, a button, a chain, a clamp, a clasp, a clip, a hook, a hook- and -eye mechanism, a magnet, a pin, a plug, a snap, a strap, a string, a tie, a zipper, an adhesive, an elastic band, an electronic plug, insertion into a channel, insertion into a pocket, insertion into a pouch, and tape. In an example, the band can have an elliptical shape. In an example, the electromyographic sensors collectively can span a percentage of the perimeter or circumference of a cross-section of an arm and wherein this percentage is within the range of 25% to 50%.

In an example, analysis of data from the electromyographic sensors can enable the person to control or more devices selected from the group consisting of: air conditioner; ceiling, wall, table, or floor light; clock; coffee maker; computer tablet; different wearable device; dish washer; door lock or opener; dryer; fan; furnace or heater; home appliance; home appliance; home entertainment center; home robot; home security system; microwave; mobile, laptop, or desktop computing device; music player; oven; phone; prosthetic limb; refrigerator; robot; security camera; smart bed; sprinkler system; animatronic chicken; teleconferencing equipment; television; vehicle; washing machine; and wireless network.

In an example, analysis of data from the electromyographic sensors can enable the person to: change notification settings for incoming electronic communications; change the brightness of a light-based computer-to-human interface; change the energy level of a computer-to-human interface; change the mode of a computer-to-human interface; change the tactile level of a tactile-based computer-to-human interface; change the volume of a sound-based computer-to-human interface; filter incoming electronic communications; modify a light-based computer-to-human interface; modify a sound-based computer-to-human interface; modify a tactile-based computer-to-human interface; or translate sign language into words.

In an example, an article of smart clothing or clothing accessory can comprise: an article of clothing or clothing accessory configured to be worn by a person; an energy-transducing member; and an attachment mechanism. In an example, the article of clothing or clothing accessory can be a wrist band, the energy-transducing member can comprise one or more electromyography sensors on the wrist band, the attachment mechanism can be the wrist band, the article of clothing or clothing accessory can further comprise a data processor, and data from the electromyographic sensors can be analyzed to identify hand gestures and/or function as a human-to-computer interface.

The following figures also show examples of how this invention can be embodied in a system of smart clothing or wearable accessories for measuring full-body motion and motion-related physiology comprising: at least four wearable body motion sensors, wherein these body motion sensors are configured to be part of a set of clothing or wearable accessories which are worn by a person, and wherein these four wearable body motion sensors collectively collect data concerning changes in the angles of at least four major body joints; at least four wearable electromyographic (EMG) sensors, wherein these EMG sensors are configured to be part of a set of clothing or wearable accessories which are worn by the person, and wherein these four wearable EMG sensors collectively collect data concerning muscle activity associated with the at least four major body joints; and a combined data analysis component, wherein this combined data analysis component receives and jointly analyzes data from the body motion sensors and the EMG sensors in order to derive more accurate and/or useful information about the person's activity and/or physiology than is possible with analysis of either body motion data or EMG data alone, and wherein data from body motion sensors and EMG sensors associated with at least four major body joints provides more accurate and/or useful information about the person's full-body activity and/or physiology than is possible with data from a single body location.

Figure 2:
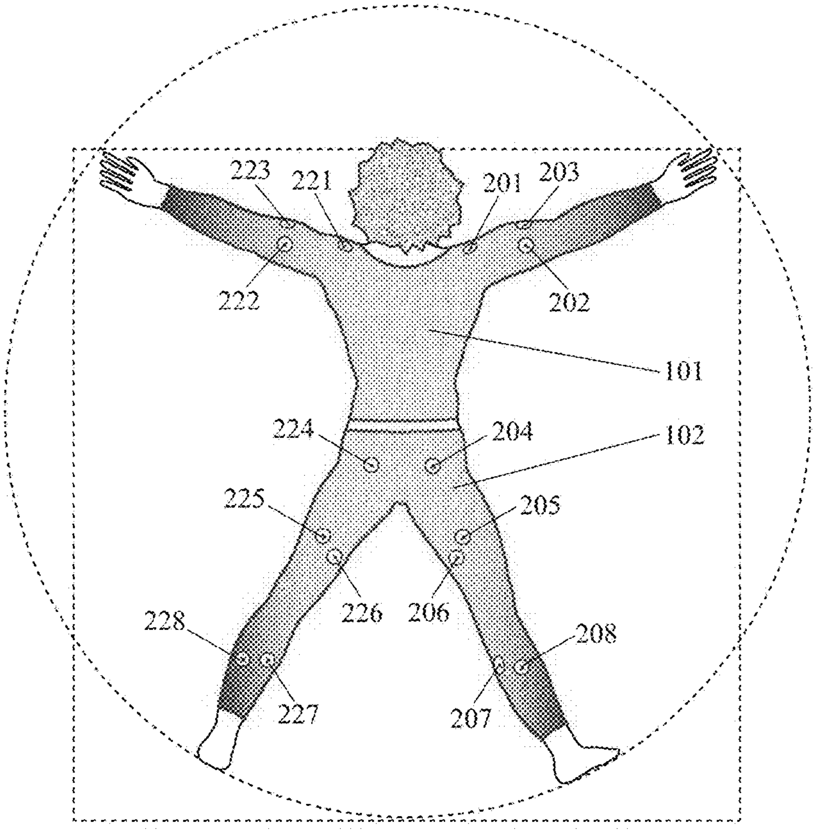

FIGS. 1 and 2 show an example of how this invention can be embodied in a device and system for measuring body motion and/or muscle activity comprising: one or more articles of clothing or clothing accessories; a plurality of motion sensors which are attached to and/or integrated into the one or more articles of clothing or clothing accessories, wherein these motion sensors are configured to collect motion data concerning changes in the configurations of a set of body joints; a plurality of electromyographic (EMG) sensors which are attached to and/or integrated into the one or more articles of clothing or clothing accessories, wherein these EMG sensors are configured to collect electromagnetic energy data concerning the neuromuscular activity of a set of muscles, and wherein muscles in the set of muscles move joints in the set of body joints; and a data processing unit which analyzes both motion data from the motion sensors and electromagnetic energy data from the EMG sensors in order to measure and/or model body motion and/or muscle activity.

FIG. 1 shows a front view of this device and system for measuring body motion and/or muscle activity. FIG. 2 shows a rear view of this same device and system for measuring body motion and/or muscle activity. The dotted-line circle and square are not part of the invention, but rather are included as a "shout out" to Leonardo and his Vitruvian Man drawing which inspired the body configuration shown in these figures. In this example, the system comprises separate upper and lower body garments (such as a shirt and a pair of pants). In another example, this system can comprise a one-piece full-body garment (such as a union suit, jump suit, or overalls).

In this example, both the upper and lower body garments are relatively elastic and close-fitting garments. In an example, one or more articles of clothing or wearable accessories can be made from a close-fitting, elastic, and/or stretchable fabric. In an example, an article of clothing or wearable accessory can be made from one or more materials selected from the group consisting of: Acetate, Acrylic, Cotton, Denim, Latex, Linen, Lycra®, Neoprene, Nylon, Polyester, Rayon, Silk, Spandex, and Wool.

In the example shown in FIGS. 1 and 2, the upper body garment is a long-sleeve shirt. In other examples, an upper body garment can be a short-sleeve shirt or a vest. In this example, the upper body garment spans a set of joints which comprises both of a person's shoulders and both of a person's elbows. In this example, the upper body garment comprises a plurality of motion sensors which collect data concerning movement of both of the person's shoulders and both of the person's elbows. In this example, the upper body garment further comprises a plurality of electromyographic (EMG) sensors which collect electromagnetic energy data concerning muscles selected from the group consisting of: biceps brachii muscle; deltoideus muscle; and triceps brachii muscle.

In the example shown in FIGS. 1 and 2, the lower body garment is a pair of pants. In other examples, a lower body garment can be a pair of shorts. In this example, the lower body garment spans a set of joints which comprises both of a person's hips and both of a person's knees. In this example, a plurality of motion sensors collects data concerning movement of both hips and knees. In this example, the lower body garment further comprises a plurality of EMG sensors which collect electromagnetic energy data concerning muscles selected from the group consisting of: biceps femoris muscle; gastrocnemius muscle; gluteus medius muscle; quadriceps femoris muscle; sastrocnemius muscle; semitendinosus muscle; and tensor fasciae latae muscle.

In this example, the motion sensors are accelerometers. In other examples, motion sensors can be selected from the group consisting of: accelerometer; conductive fiber motion sensor; electrogoniometer; fluid pressure sensor; gyroscope; inclinometer; inductive transducer; inertial sensor; longitudinal pressure sensor; magnometer; optical bend sensor; piezoelectric fiber; piezoelectric sensor; piezoresistive fiber; piezoresistive sensor; RFID-based motion sensor; strain gauge; and ultrasonic-based motion sensor. In this example, the EMG sensors are bipolar EMG sensors. In other examples, EMG sensors can be selected from the group consisting of: bipolar EMG sensor; capacitive-coupling EMG sensor; circular sensor; conductive electrode EMG sensor; conductive yarn EMG sensor; contactless EMG sensor; copper-coated fiber EMG sensor;

electromagnetic impedance sensor; monopolar EMG sensor; non-gelled EMG sensor; non-invasive EMG sensor; silver-coated fiber EMG sensor; square EMG sensor; and surface EMG sensor.

We now discuss the specific components and numeric labels in the example that is shown in FIGS. 1 and 2. The example shown in FIGS. 1 and 2 shows a separate upper body garment 101 and lower body garment 102. In this example, upper body garment 101 is a shirt and lower body garment 102 is a pair of pants. In this example, a plurality of EMG sensors is integrated into upper body garment 101 and lower body garment 102. In this example, a plurality of motion sensors is also integrated into upper body garment 101 and lower body garment 102.

As shown in FIG. 1, on the right side (from the person's perspective) of upper body garment 101, EMG sensor 103 is configured to collect data concerning electromagnetic neuromuscular activity of the anterior portion of the right deltoideus muscle. EMG sensor 104 is configured to collect data concerning electromagnetic neuromuscular activity of the right deltoideus medius muscle. EMG sensor 105 is configured to collect data concerning electromagnetic neuromuscular activity of the short head and/or long head of the right biceps brachii muscle.

As shown in FIG. 1, on the left side (from the person's perspective) of upper body garment 101, EMG sensor 123 is configured to collect data concerning electromagnetic neuromuscular activity of the anterior portion of the left deltoideus muscle. EMG sensor 124 is configured to collect data concerning electromagnetic neuromuscular activity of the left deltoideus medius muscle. EMG sensor 125 is configured to collect data concerning electromagnetic neuromuscular activity of the short head and/or long head of the left biceps brachii muscle.

As shown in FIG. 1, on the right side (from the person's perspective) of lower body garment 102, EMG sensor 106 is configured to collect data concerning electromagnetic neuromuscular activity of the right gluteus medius muscle. EMG sensor 107 is configured to collect data concerning electromagnetic neuromuscular activity of the right tensor fasciae latae muscle. EMG sensor 108 is configured to collect data concerning electromagnetic neuromuscular activity of the rectus femoris of the right quadriceps femoris muscle. EMG sensor 109 is configured to collect data concerning electromagnetic neuromuscular activity of the vastus medialis of the right quadriceps femoris muscle. EMG sensor 110 is configured to collect data concerning electromagnetic neuromuscular activity of the vastus lateralis of the right quadriceps femoris muscle. EMG sensor 111 is configured to collect data concerning electromagnetic neuromuscular activity of the right tibialis anterior muscle. EMG sensor 112 is configured to collect data concerning electromagnetic neuromuscular activity of the right peroneus longus muscle. EMG sensor 113 is configured to collect data concerning electromagnetic neuromuscular activity of the right peroneus *brevis* muscle. EMG sensor 114 is configured to collect data concerning electromagnetic neuromuscular activity of the right soleus muscle.

As shown in FIG. 1, on the left side (from the person's perspective) of lower body garment 102, EMG sensor 126 is configured to collect data concerning electromagnetic neuromuscular activity of the left gluteus medius muscle. EMG sensor 127 is configured to collect data concerning electromagnetic neuromuscular activity of the left tensor fasciae latae muscle. EMG sensor 128 is configured to collect data concerning electromagnetic neuromuscular activity of the rectus femoris of the left quadriceps femoris muscle. EMG sensor 129 is configured to collect data concerning electromagnetic neuromuscular activity of the vastus medialis of the left quadriceps femoris muscle. EMG sensor 130 is configured to collect data concerning electromagnetic neuromuscular activity of the vastus lateralis of the left quadriceps femoris muscle. EMG sensor 131 is configured to collect data concerning electromagnetic neuromuscular activity of the left tibialis anterior muscle. EMG sensor 132 is configured to collect data concerning electromagnetic neuromuscular activity of the left peroneus longus muscle. EMG sensor 133 is configured to collect data concerning electromagnetic neuromuscular activity of the left peroneus *brevis* muscle. EMG sensor 134 is configured to collect data concerning electromagnetic neuromuscular activity of the left soleus muscle.

In the example that is shown in FIGS. 1 and 2, the upper and lower body garments also comprise a plurality of motion sensors. In this example, these motion sensors are integrated into the garments. In another example, these motions sensors can be removably attached to the garments. In an example, the motion sensors can be modular. In this example, the motion sensors are accelerometers. In other examples, motion sensors can be selected from the group consisting of: accelerometer; conductive fiber motion sensor; electrogoniometer; fluid pressure sensor; gyroscope; inclinometer; inductive transducer; inertial sensor; longitudinal pressure sensor; magnometer; optical bend sensor; piezoelectric fiber; piezoelectric sensor; piezoresistive fiber; piezoresistive sensor; RFID-based motion sensor; strain gauge; and ultrasonic-based motion sensor. In this example, the EMG sensors are bipolar EMG sensors.

In the example shown in FIG. 1, motion sensor 115 is configured to collect data concerning movement of the lower right arm. In this example, motion sensor 116 is configured to collect data concerning movement of the upper right arm. Motion sensor 135 is configured to collect data concerning movement of the lower left arm. Motion sensor 136 is configured to collect data concerning movement of the upper left arm. Motion sensor 137 is configured to collect data concerning movement of the upper trunk. Motion sensor 138 is configured to collect data concerning movement of the lower truck. Motion sensor 119 is configured to collect data concerning movement of the upper right leg. Motion sensor 120 is configured to collect data concerning movement of the lower right leg. Motion sensor 139 is configured to collect data concerning movement of the upper left leg.

Motion sensor 140 is configured to collect data concerning movement of the lower left leg.

The example shown in FIGS. 1 and 2 also includes a data processing unit 151 for the upper body garment and a separate data processing unit 152 for the lower body garment. In an example, this system can be embodied in a one-piece full-body article of clothing which spans both the upper and lower body (such as a union suit, jumpsuit, or overalls). In an example, with a one-piece full-body article of clothing spanning both the upper and lower body, a single data processing unit can be sufficient. In this example, the data processing unit is in wireless electromagnetic communication with the EMG sensors and motion sensors. In an example, a data processing unit can be in direct (e.g. non-wireless) electromagnetic communication with the EMG sensors and motion sensors. In an example, this direct electromagnetic communication can be through electromagnetic wires and/or electromagnetically-conductive pathways in the clothing textile.

In an example, combined, joint, and/or multivariate analysis of both (a) motion data from the motion sensors and (b) electromagnetic energy data from the EMG sensors can enable more accurate measurement and/or modeling of body motion than analysis of data from motion sensors alone. In an example, combined, joint, and/or multivariate analysis of both (a) motion data from the motion sensors and (b) electromagnetic energy data from the EMG sensors can enable more accurate measurement and/or modeling of body motion than analysis of electromagnetic energy data from the EMG sensors alone. In an example, combined, joint, and/or multivariate analysis of both (a) motion data from the motion sensors and (b) electromagnetic energy data from the EMG sensors can enable more accurate measurement and/or modeling of muscle activity than analysis of data from motion sensors alone. In an example, combined, joint, and/or multivariate analysis of both (a) motion data from the motion sensors and (b) electromagnetic energy data from the EMG sensors can enable more accurate measurement and/or modeling of muscle activity than analysis of electromagnetic energy data from the EMG sensors alone.

In an example, data from EMG sensors can supplement data from motion sensors for more accurate measurement of body motion during key portions of joint range of motion wherein data from motion sensors alone is less accurate. In an example, this can be at extreme positions in the range of motion. In an example, data from EMG sensors can supplement data from motion sensors for more accurate measurement of body motion at key times in joint motion wherein data from motion sensors alone is less accurate. In an example, this can be at the beginning or end of a series of repeated actions. In an example, this can be at the beginning or end of a time of especially-strenuous physical activity. In an example, data from EMG sensors can supplement data from motion sensors for more accurate measurement of body motion during isometric activity wherein pressure is being applied against a motion-resisting external object. In an example, data from EMG sensors can supplement data from motion sensors for more accurate measurement of body motion when the person is being moved by an external device such as a car, elevator, escalator, airplane, etc. In an example, data from EMG sensors can supplement data from motion sensors for more accurate measurement of body motion when an article of clothing fits relatively loosely and/or shifts over the surface of the person's skin when the person moves.

In an example, data from motion sensors can supplement data from EMG sensors for more accurate measurement of muscle activity during key portions of joint range of motion wherein data from EMG sensors alone is less accurate. In an example, this can be at extreme positions in the range of motion. In an example, data from motion sensors can supplement data from EMG sensors for more accurate measurement of muscle activity at key times in joint motion wherein data from EMG sensors alone is less accurate. In an example, this can be at the beginning or end of a series of repeated actions. In an example, this can be at the beginning or end of a time of especially-strenuous physical activity. In an example, data from motion sensors can supplement data from EMG sensors for more accurate measurement of muscle activity during isometric activity wherein pressure is being applied against a motion-resisting external object. In an example, data from motion sensors can supplement data from EMG sensors for more accurate measurement of muscle activity when the person is being moved by an external device such as a car, elevator, escalator, airplane, etc. In an example, data from motion sensors can supplement data from EMG sensors for more accurate measurement of muscle activity when an article of clothing fits relatively loosely and/or shifts over the surface of the person's skin when the person moves.

In an example, data from motion sensors and data from EMG sensors can be jointly analyzed using one or more statistical methods selected from the group consisting of: Analysis of Variance (ANOVA), Artificial Neural Network (ANN), Auto Regression, Bayesian filter or other Bayesian statistical method, centroid analysis, Chi-Squared analysis, cluster analysis, covariance analysis, decision tree analysis, Eigenvalue Decomposition, Factor Analysis, Fast Fourier Transform (FFT) or other Fourier transformation, Hidden Markov model or other Markov modeling, Kalman Filter, kinematic modeling, Least Squares Estimation (LSE), Discriminant Analysis (DA), linear regression, linear transform, logarithmic function analysis, logistic regression, logit analysis, machine learning, mean or median analysis, Multivariate Linear Regression (MLR), Logit analysis, multivariate parametric classifiers, Neural Network, Non-Linear Programming (NLP), normalization, orthogonal transformation, pattern recognition, Power Spectral Density (PSD) analysis, power spectrum analysis, Principal Components analysis, probit analysis, Random Forest Gump (RFG) analysis, spectral analysis, spectroscopic analysis, spline function, survival analysis, three-dimensional modeling, time series analysis, variance, and wavelet analysis.

In an example analysis of data from the motion sensors and the EMG sensors can occur entirely within the wearable data processing units (151 and 152). In another example, the wearable data processing units (151 and 152) can wirelessly transmit data from the motion sensors and EMG sensors to a remote computing device and analysis of this data to measure and/or model body motion and/or muscle activity can occur partially or entirely within that remote computer device. In an example, a data processing unit can further comprise one or more components selected from the group consisting of: battery; other power source; kinetic energy transducer; thermal energy transducer; wireless data transmitter; wireless data receiver; microphone; speaker; camera; spectroscopic sensor or other optical sensor; touch screen; keypad; buttons; gesture recognition interface; display screen; and tactile-sensation-creating member.

FIG. 2 shows the same example that was shown in FIG. 1, but from a rear perspective. In FIG. 2, on the right side (from the person's perspective) of upper body garment 101, EMG sensor 201 is configured to collect data concerning electromagnetic neuromuscular activity of the posterior portion of the right deltoideus muscle. EMG sensor 202 is configured to collect data concerning electromagnetic neuromuscular activity of the long head of the right triceps brachii muscle. EMG sensor 203 is configured to collect data concerning electromagnetic neuromuscular activity of the lateral head of the right triceps brachii muscle.

In FIG. 2, on the left side (from the person's perspective) of upper body garment 101, EMG sensor 221 is configured to collect data concerning electromagnetic neuromuscular activity of the posterior portion of the left deltoideus muscle. EMG sensor 222 is configured to collect data concerning electromagnetic neuromuscular activity of the long head of the left triceps brachii muscle. EMG sensor 223 is configured to collect data concerning electromagnetic neuromuscular activity of the lateral head of the left triceps brachii muscle.

In FIG. 2, on the right side (from the person's perspective) of the lower body garment 102, EMG sensor 204 is configured to collect data concerning electromagnetic neuromuscular activity of the right gluteus maximus muscle. EMG sensor 205 is configured to collect data concerning electromagnetic neuromuscular activity of the long head and short head of the right biceps femoris muscle. EMG sensor 206 is configured to collect data concerning electromagnetic neuromuscular activity of the right semitendinosus muscle. EMG sensor 207 is configured to collect data concerning electromagnetic neuromuscular activity of the right *medialis* of the gastrocnemius muscle. EMG sensor 208 is configured to collect data concerning electromagnetic neuromuscular activity of the right lateralis of the sastrocnemius muscle.

In FIG. 2, on the left side (from the person's perspective) of the lower body garment 102, EMG sensor 224 is configured to collect data concerning electromagnetic neuromuscular activity of the left gluteus maximus muscle. EMG sensor 225 is configured to collect data concerning electromagnetic neuromuscular activity of the long head and short head of the left biceps femoris muscle. EMG sensor 226 is configured to collect data concerning electromagnetic neuromuscular activity of the left semitendinosus muscle. EMG sensor 227 is configured to collect data concerning electromagnetic neuromuscular activity of the left *medialis* of the gastrocnemius muscle. EMG sensor 228 is configured to collect data concerning electromagnetic neuromuscular activity of the left lateralis of the sastrocnemius muscle.

In the example shown in FIGS. 1 and 2, there are motion sensors only on the front sides of the garments. In another example, there could be motion sensors only on the rear sides of the garments. In another example, there could be motion sensors on both the front and rear sides of the garments. In the example shown in FIGS. 1 and 2, there are data processing units only on the front sides of the garments. In another example, there could be data processing units only on the rear sides of the garments. In another example, there could be data processing units on both the front and rear sides of the garments.

In an example, the device and system for measuring body motion and/or muscle activity that is shown in FIGS. 1 and 2 can further comprise one or more articles of clothing or clothing accessories selected from the group consisting of: glove, finger ring, watch, wrist band, bracelet, armband, tubular elbow band, hat, headband, earphones, ear bud, hearing aid, partially ear-encircling device, collar, necklace, pendant, pin, glasses or other eyewear, vest, chest band or strap, bra, belt, pair shorts, swim suit, tubular knee band, ankle band, sock, and shoe.

In an example, the device and system for measuring body motion and/or muscle activity shown in FIGS. 1 and 2 can include a human-to-computer interface. In an example, this human-to-computer interface can be incorporated into one of the data processing units shown in FIGS. 1 and 2. In an example a human-to-computer interface can comprise one or more members selected from the group consisting of: buttons, knobs, dials, or keys; display screen; gesture-recognition interface; microphone; physical keypad or keyboard; virtual keypad or keyboard; speech or voice recognition interface; touch screen; EMG-recognition interface; and EEG-recognition interface.

In an example, the device and system for measuring body motion and/or muscle activity shown in FIGS. 1 and 2 can include a computer-to-human interface. In an example, this computer-to-human interface can be incorporated into one of the data processing units shown in FIGS. 1 and 2. In an example, a computer-to-human interface can provide feedback to the person concerning their body motion and/or muscle activity. In an example, a computer-to-human interface can comprise one or more members selected from the group consisting of: a display screen; a speaker or other sound-emitting member; a myostimulating member; a neurostimulating member; a speech or voice recognition interface; a synthesized voice; a vibrating or other tactile sensation creating member; MEMS actuator; an electromagnetic energy emitter; an infrared light projector; an LED or LED array; and an image projector. Relevant variations discussed elsewhere in this disclosure or in priority-linked disclosures can also be applied to this example.

Figure 3:
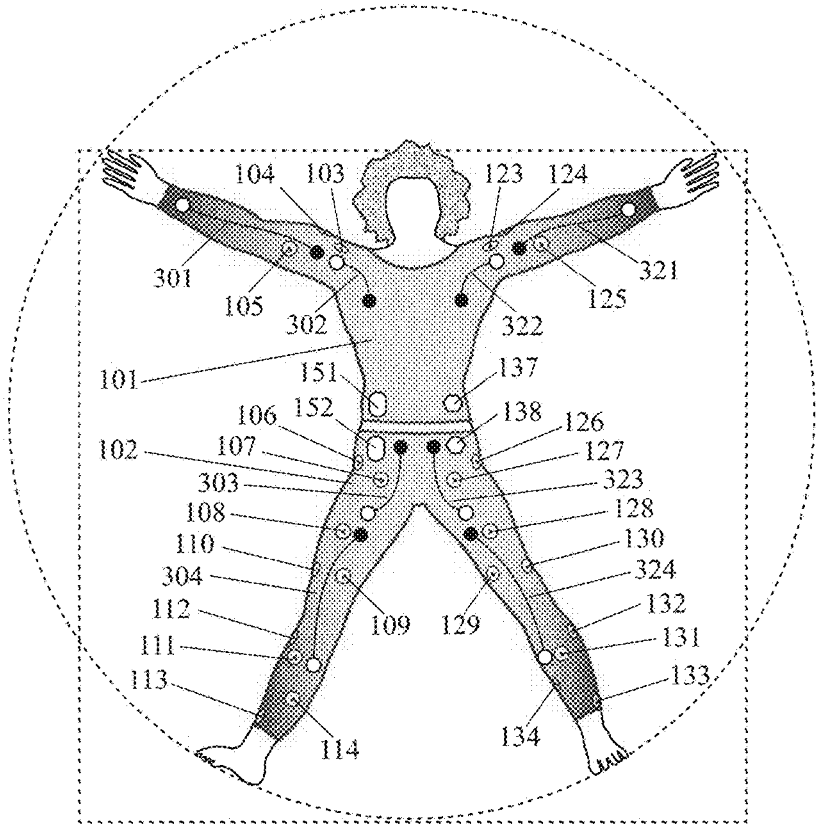
FIGS. 3 and 4 show electromyographic clothing comprising a shirt and pants with a plurality of EMG sensors and bending motion sensors.
Figure 4:
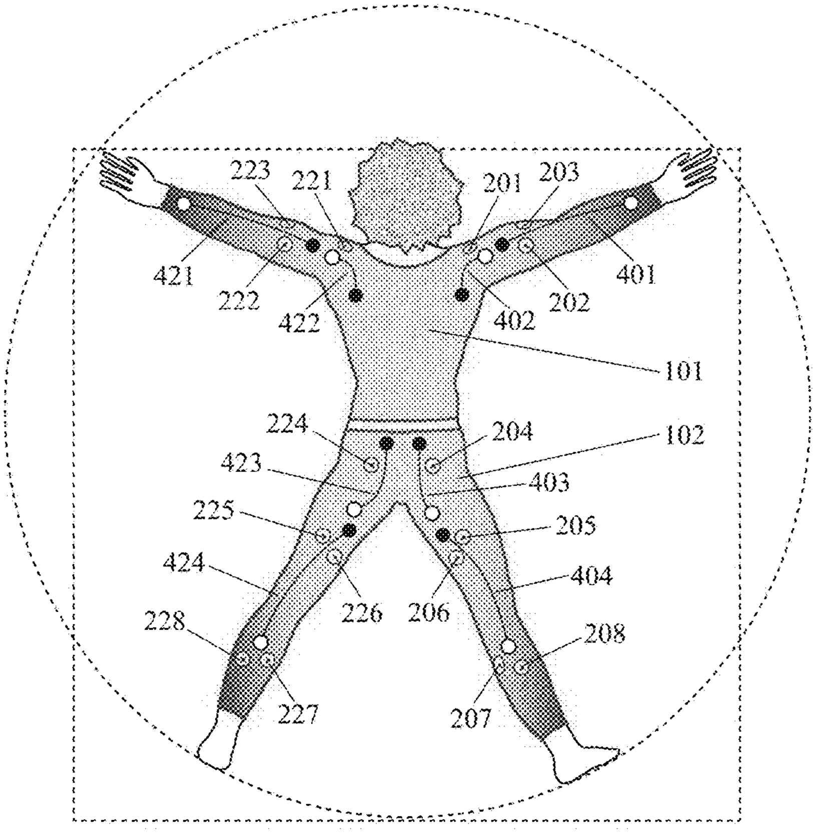

FIGS. 3 and 4 show another example of how this invention can be embodied in a device and system for measuring body motion and/or muscle activity comprising: one or more articles of clothing or clothing accessories; a plurality of motion sensors which are attached to and/or integrated into the one or more articles of clothing or clothing accessories, wherein these motion sensors are configured to collect motion data concerning changes in the configurations of a set of body joints; a plurality of electromyographic (EMG) sensors which are attached to and/or integrated into the one or more articles of clothing or clothing accessories, wherein these EMG sensors are configured to collect electromagnetic energy data concerning the neuromuscular activity of a set of muscles, and wherein muscles in the set of muscles move joints in the set of body joints; and a data processing unit which analyzes both motion data from the motion sensors and electromagnetic energy data from the EMG sensors in order to measure and/or model body motion and/or muscle activity.

The example shown in FIGS. 3 and 4 is like the example shown in FIGS. 1 and 2 except that the motion sensors are bending-based motion sensors which longitudinally span joints (instead of accelerometers). In this example, the bending-based motion sensors are fluid-filled or gas-filled pressure sensors which longitudinally span joints, wherein pressures within the sensors change as joint angles change. In other examples, bending-based motion sensors can be selected from the group consisting of: conductive fiber motion sensor; electrogoniometer; optical bend sensor; piezoelectric fiber; piezoelectric sensor; piezoresistive fiber; piezoresistive sensor; strain gauge; and ultrasonic-based motion sensor.

In this example, the EMG sensors are bipolar EMG sensors. In other examples, EMG sensors can be selected from the group consisting of: bipolar EMG sensor; capacitive-coupling EMG sensor; circular sensor; conductive electrode EMG sensor; conductive yarn EMG sensor; contactless EMG sensor; copper-coated fiber EMG sensor; electromagnetic impedance sensor; monopolar EMG sensor;

non-gelled EMG sensor; non-invasive EMG sensor; silver-coated fiber EMG sensor; square EMG sensor; and surface EMG sensor.

FIG. 3 shows a front view of this device and system for measuring body motion and/or muscle activity. FIG. 4 shows a rear view of this same device and system for measuring body motion and/or muscle activity. In this example, both the upper and lower body garments are relatively elastic and close-fitting garments. In an example, one or more articles of clothing or wearable accessories can be made from a close-fitting, elastic, and/or stretchable fabric. In an example, an article of clothing or wearable accessory can be made from one or more materials selected from the group consisting of: Acetate, Acrylic, Cotton, Denim, Latex, Linen, Lycra®, Neoprene, Nylon, Polyester, Rayon, Silk, Spandex, and Wool.

In the example shown in FIGS. 3 and 4, the upper body garment is a long-sleeve shirt. In other examples, an upper body garment can be a short-sleeve shirt or a vest. In this example, the upper body garment spans a set of joints which comprises both of a person's shoulders and both of a person's elbows. In this example, the upper body garment comprises a plurality of motion sensors which collect data concerning movement of both of the person's shoulders and both of the person's elbows. In this example, the upper body garment further comprises a plurality of electromyographic (EMG) sensors which collect electromagnetic energy data concerning muscles selected from the group consisting of: biceps brachii muscle; deltoideus muscle; and triceps brachii muscle.

In the example shown in FIGS. 3 and 4, the lower body garment is a pair of pants. In other examples, a lower body garment can be a pair of shorts. In this example, the lower body garment spans a set of joints which comprises both of a person's hips and both of a person's knees. In this example, a plurality of motion sensors collects data concerning movement of both hips and knees. In this example, the lower body garment further comprises a plurality of EMG sensors which collect electromagnetic energy data concerning muscles selected from the group consisting of: biceps femoris muscle; gastrocnemius muscle; gluteus medius muscle; quadriceps femoris muscle; sastrocnemius muscle; semitendinosus muscle; and tensor fasciae latae muscle.

As shown in FIG. 3, on the right side (from the person's perspective) of upper body garment 101, EMG sensor 103 is configured to collect data concerning electromagnetic neuromuscular activity of the anterior portion of the right deltoideus muscle. EMG sensor 104 is configured to collect data concerning electromagnetic neuromuscular activity of the right deltoideus medius muscle. EMG sensor 105 is configured to collect data concerning electromagnetic neuromuscular activity of the short head and/or long head of the right biceps brachii muscle.

As shown in FIG. 3, on the left side (from the person's perspective) of upper body garment 101, EMG sensor 123 is configured to collect data concerning electromagnetic neuromuscular activity of the anterior portion of the left deltoideus muscle. EMG sensor 124 is configured to collect data concerning electromagnetic neuromuscular activity of the left deltoideus medius muscle. EMG sensor 125 is configured to collect data concerning electromagnetic neuromuscular activity of the short head and/or long head of the left biceps brachii muscle.

As shown in FIG. 3, on the right side (from the person's perspective) of lower body garment 102, EMG sensor 106 is configured to collect data concerning electromagnetic neuromuscular activity of the right gluteus medius muscle. EMG sensor 107 is configured to collect data concerning electromagnetic neuromuscular activity of the right tensor fasciae latae muscle. EMG sensor 108 is configured to collect data concerning electromagnetic neuromuscular activity of the rectus femoris of the right quadriceps femoris muscle. EMG sensor 109 is configured to collect data concerning electromagnetic neuromuscular activity of the vastus medialis of the right quadriceps femoris muscle. EMG sensor 110 is configured to collect data concerning electromagnetic neuromuscular activity of the vastus lateralis of the right quadriceps femoris muscle. EMG sensor 111 is configured to collect data concerning electromagnetic neuromuscular activity of the right tibialis anterior muscle. EMG sensor 112 is configured to collect data concerning electromagnetic neuromuscular activity of the right peroneus longus muscle. EMG sensor 113 is configured to collect data concerning electromagnetic neuromuscular activity of the right peroneus *brevis* muscle. EMG sensor 114 is configured to collect data concerning electromagnetic neuromuscular activity of the right soleus muscle.

As shown in FIG. 3, on the left side (from the person's perspective) of lower body garment 102, EMG sensor 126 is configured to collect data concerning electromagnetic neuromuscular activity of the left gluteus medius muscle. EMG sensor 127 is configured to collect data concerning electromagnetic neuromuscular activity of the left tensor fasciae latae muscle. EMG sensor 128 is configured to collect data concerning electromagnetic neuromuscular activity of the rectus femoris of the left quadriceps femoris muscle. EMG sensor 129 is configured to collect data concerning electromagnetic neuromuscular activity of the vastus medialis of the left quadriceps femoris muscle. EMG sensor 130 is configured to collect data concerning electromagnetic neuromuscular activity of the vastus lateralis of the left quadriceps femoris muscle. EMG sensor 131 is configured to collect data concerning electromagnetic neuromuscular activity of the left tibialis anterior muscle. EMG sensor 132 is configured to collect data concerning electromagnetic neuromuscular activity of the left peroneus longus muscle. EMG sensor 133 is configured to collect data concerning electromagnetic neuromuscular activity of the left peroneus *brevis* muscle. EMG sensor 134 is configured to collect data concerning electromagnetic neuromuscular activity of the left soleus muscle.

As shown in FIG. 3, the upper and lower body garments also comprise a plurality of bending-based motion sensors which longitudinally span body joints. In this example, bending-based motion sensors are integrated into the garments. In this example, bending-based motion sensor 301 longitudinally spans the person's right elbow and bending-based motion sensor 302 longitudinally spans the person's right shoulder. Bending-based motion sensor 303 longitudinally spans the person's right hip and bending-based motion sensor 304 longitudinally spans the person's right knee. In this example, bending-based motion sensor 321 longitudinally spans the person's left elbow and bending-based motion sensor 322 longitudinally spans the person's left shoulder. Bending-based motion sensor 323 longitudinally spans the person's left hip and bending-based motion sensor 324 longitudinally spans the person's left knee.

As also shown in FIG. 3, this example also includes a data processing unit 151 for the upper body garment and a separate data processing unit 152 for the lower body garment. In an example, this system can be embodied in a one-piece full-body article of clothing which spans both the upper and lower body (such as a union suit, jumpsuit, or overalls). In an example, with a one-piece full-body article of clothing spanning both the upper and lower body, a single data processing unit can be sufficient. In this example, the data processing unit is in wireless electromagnetic communication with the EMG sensors and motion sensors. In an example, a data processing unit can be in direct (e.g. non-wireless) electromagnetic communication with the EMG sensors and motion sensors. In an example, this direct electromagnetic communication can be through electromagnetic wires and/or electromagnetically-conductive pathways in the clothing textile.

In an example, combined, joint, and/or multivariate analysis of both (a) motion data from the motion sensors and (b) electromagnetic energy data from the EMG sensors can enable more accurate measurement and/or modeling of body motion than analysis of data from motion sensors alone. In an example, combined, joint, and/or multivariate analysis of both (a) motion data from the motion sensors and (b) electromagnetic energy data from the EMG sensors can enable more accurate measurement and/or modeling of body motion than analysis of electromagnetic energy data from the EMG sensors alone. In an example, combined, joint, and/or multivariate analysis of both (a) motion data from the motion sensors and (b) electromagnetic energy data from the EMG sensors can enable more accurate measurement and/or modeling of muscle activity than analysis of data from motion sensors alone. In an example, combined, joint, and/or multivariate analysis of both (a) motion data from the motion sensors and (b) electromagnetic energy data from the EMG sensors can enable more accurate measurement and/or modeling of muscle activity than analysis of electromagnetic energy data from the EMG sensors alone.

In an example, data from EMG sensors can supplement data from motion sensors for more accurate measurement of body motion during key portions of joint range of motion wherein data from motion sensors alone is less accurate. In an example, this can be at extreme positions in the range of motion. In an example, data from EMG sensors can supplement data from motion sensors for more accurate measurement of body motion at key times in joint motion wherein data from motion sensors alone is less accurate. In an example, this can be at the beginning or end of a series of repeated actions. In an example, this can be at the beginning or end of a time of especially-strenuous physical activity. In an example, data from EMG sensors can supplement data from motion sensors for more accurate measurement of body motion during isometric activity wherein pressure is being applied against a motion-resisting external object. In an example, data from EMG sensors can supplement data from motion sensors for more accurate measurement of body motion when the person is being moved by an external device such as a car, elevator, escalator, airplane, etc. In an example, data from EMG sensors can supplement data from motion sensors for more accurate measurement of body motion when an article of clothing fits relatively loosely and/or shifts over the surface of the person's skin when the person moves.

In an example, data from motion sensors can supplement data from EMG sensors for more accurate measurement of muscle activity during key portions of joint range of motion wherein data from EMG sensors alone is less accurate. In an example, this can be at extreme positions in the range of motion. In an example, data from motion sensors can supplement data from EMG sensors for more accurate measurement of muscle activity at key times in joint motion wherein data from EMG sensors alone is less accurate. In an example, this can be at the beginning or end of a series of repeated actions. In an example, this can be at the beginning or end of a time of especially-strenuous physical activity. In an example, data from motion sensors can supplement data from EMG sensors for more accurate measurement of muscle activity during isometric activity wherein pressure is being applied against a motion-resisting external object. In an example, data from motion sensors can supplement data from EMG sensors for more accurate measurement of muscle activity when the person is being moved by an external device such as a car, elevator, escalator, airplane, etc. In an example, data from motion sensors can supplement data from EMG sensors for more accurate measurement of muscle activity when an article of clothing fits relatively loosely and/or shifts over the surface of the person's skin when the person moves.

In an example, data from motion sensors and data from EMG sensors can be jointly analyzed using one or more statistical methods selected from the group consisting of: Analysis of Variance (ANOVA), Artificial Neural Network (ANN), Auto Regression, Bayesian filter or other Bayesian statistical method, centroid analysis, Chi-Squared analysis, cluster analysis, covariance analysis, decision tree analysis, Eigenvalue Decomposition, Factor Analysis, Fast Fourier Transform (FFT) or other Fourier transformation, Hidden Markov model or other Markov modeling, Kalman Filter, kinematic modeling, Least Squares Estimation (LSE), Discriminant Analysis (DA), linear regression, linear transform, logarithmic function analysis, logistic regression, logit analysis, machine learning, mean or median analysis, Multivariate Linear Regression (MLR), Logit analysis, multivariate parametric classifiers, Neural Network, Non-Linear Programming (NLP), normalization, orthogonal transformation, pattern recognition, Power Spectral Density (PSD) analysis, power spectrum analysis, Principal Components analysis, probit analysis, Random Forest Gump (RFG) analysis, spectral analysis, spectroscopic analysis, spline function, survival analysis, three-dimensional modeling, time series analysis, variance, and wavelet analysis.

In an example analysis of data from the motion sensors and the EMG sensors can occur entirely within the wearable data processing units (151 and 152). In another example, the wearable data processing units (151 and 152) can wirelessly transmit data from the motion sensors and EMG sensors to a remote computing device and analysis of this data to measure and/or model body motion and/or muscle activity can occur partially or entirely within that remote computer device. In an example, a data processing unit can further comprise one or more components selected from the group consisting of: battery; other power source; kinetic energy transducer; thermal energy transducer; wireless data transmitter; wireless data receiver; microphone; speaker; camera; spectroscopic sensor or other optical sensor; touch screen; keypad; buttons; gesture recognition interface; display screen; and tactile-sensation-creating member.

FIG. 4 shows the same example that was shown in FIG. 3, but from a rear perspective. In FIG. 4, on the right side (from the person's perspective) of upper body garment 101, EMG sensor 201 is configured to collect data concerning electromagnetic neuromuscular activity of the posterior portion of the right deltoideus muscle. EMG sensor 202 is configured to collect data concerning electromagnetic neuromuscular activity of the long head of the right triceps brachii muscle. EMG sensor 203 is configured to collect data concerning electromagnetic neuromuscular activity of the lateral head of the right triceps brachii muscle.

In FIG. 4, on the left side (from the person's perspective) of upper body garment 101, EMG sensor 221 is configured to collect data concerning electromagnetic neuromuscular activity of the posterior portion of the left deltoideus muscle. EMG sensor 222 is configured to collect data concerning electromagnetic neuromuscular activity of the long head of the left triceps brachii muscle. EMG sensor 223 is configured to collect data concerning electromagnetic neuromuscular activity of the lateral head of the left triceps brachii muscle.

In FIG. 4, on the right side (from the person's perspective) of the lower body garment 102, EMG sensor 204 is configured to collect data concerning electromagnetic neuromuscular activity of the right gluteus maximus muscle. EMG sensor 205 is configured to collect data concerning electromagnetic neuromuscular activity of the long head and short head of the right biceps femoris muscle. EMG sensor 206 is configured to collect data concerning electromagnetic neuromuscular activity of the right semitendinosus muscle. EMG sensor 207 is configured to collect data concerning electromagnetic neuromuscular activity of the right *medialis* of the gastrocnemius muscle. EMG sensor 208 is configured to collect data concerning electromagnetic neuromuscular activity of the right lateralis of the sastrocnemius muscle.

In FIG. 4, on the left side (from the person's perspective) of the lower body garment 102, EMG sensor 224 is configured to collect data concerning electromagnetic neuromuscular activity of the left gluteus maximus muscle. EMG sensor 225 is configured to collect data concerning electromagnetic neuromuscular activity of the long head and short head of the left biceps femoris muscle. EMG sensor 226 is configured to collect data concerning electromagnetic neuromuscular activity of the left semitendinosus muscle. EMG sensor 227 is configured to collect data concerning electromagnetic neuromuscular activity of the left *medialis* of the gastrocnemius muscle. EMG sensor 228 is configured to collect data concerning electromagnetic neuromuscular activity of the left lateralis of the sastrocnemius muscle.

In the example shown in FIGS. 3 and 4, there are bending-based motion sensors on the rear sides as well as on the front sides of the garments. Analysis of data from two bending-based sensors, one which longitudinally spans the anterior surface of a joint and one which longitudinally spans the posterior surface of the joint, can provide more accurate measurement of joint angle than data from either an anterior surface sensor or a posterior surface sensor alone. As shown in FIG. 4, bending-based motion sensor 401 longitudinally spans the posterior surface of the person's right elbow and bending-based motion sensor 402 longitudinally spans the posterior surface of the person's right shoulder. Bending-based motion sensor 403 longitudinally spans the posterior surface of the person's right hip and bending-based motion sensor 404 longitudinally spans the posterior surface of the person's right knee. In this example, bending-based motion sensor 421 longitudinally spans the posterior surface of the person's left elbow and bending-based motion sensor 422 longitudinally spans the posterior surface of the person's left shoulder. Bending-based motion sensor 423 longitudinally spans the posterior surface of the person's left hip and bending-based motion sensor 424 longitudinally spans the posterior surface of the person's left knee.

In an example, the device and system for measuring body motion and/or muscle activity that is shown in FIGS. 3 and 4 can further comprise one or more articles of clothing or clothing accessories selected from the group consisting of: glove, finger ring, watch, wrist band, bracelet, armband, tubular elbow band, hat, headband, earphones, ear bud, hearing aid, partially ear-encircling device, collar, necklace, pendant, pin, glasses or other eyewear, vest, chest band or strap, bra, belt, pair shorts, swim suit, tubular knee band, ankle band, sock, and shoe.

In an example, the device and system for measuring body motion and/or muscle activity shown in FIGS. 3 and 4 can include a human-to-computer interface. In an example, this human-to-computer interface can be incorporated into one of the data processing units shown in FIGS. 3 and 4. In an example a human-to-computer interface can comprise one or more members selected from the group consisting of: buttons, knobs, dials, or keys; display screen; gesture-recognition interface; microphone; physical keypad or keyboard; virtual keypad or keyboard; speech or voice recognition interface; touch screen; EMG-recognition interface; and EEG-recognition interface.

In an example, the device and system for measuring body motion and/or muscle activity shown in FIGS. 3 and 4 can include a computer-to-human interface. In an example, this computer-to-human interface can be incorporated into one of the data processing units shown in FIGS. 3 and 4. In an example, a computer-to-human interface can provide feedback to the person concerning their body motion and/or muscle activity. In an example, a computer-to-human interface can comprise one or more members selected from the group consisting of: a display screen; a speaker or other sound-emitting member; a myostimulating member; a neurostimulating member; a speech or voice recognition interface; a synthesized voice; a vibrating or other tactile sensation creating member; MEMS actuator; an electromagnetic energy emitter; an infrared light projector; an LED or LED array; and an image projector. Relevant variations discussed elsewhere in this disclosure or in priority-linked disclosures can also be applied to this example.

Figure 5:
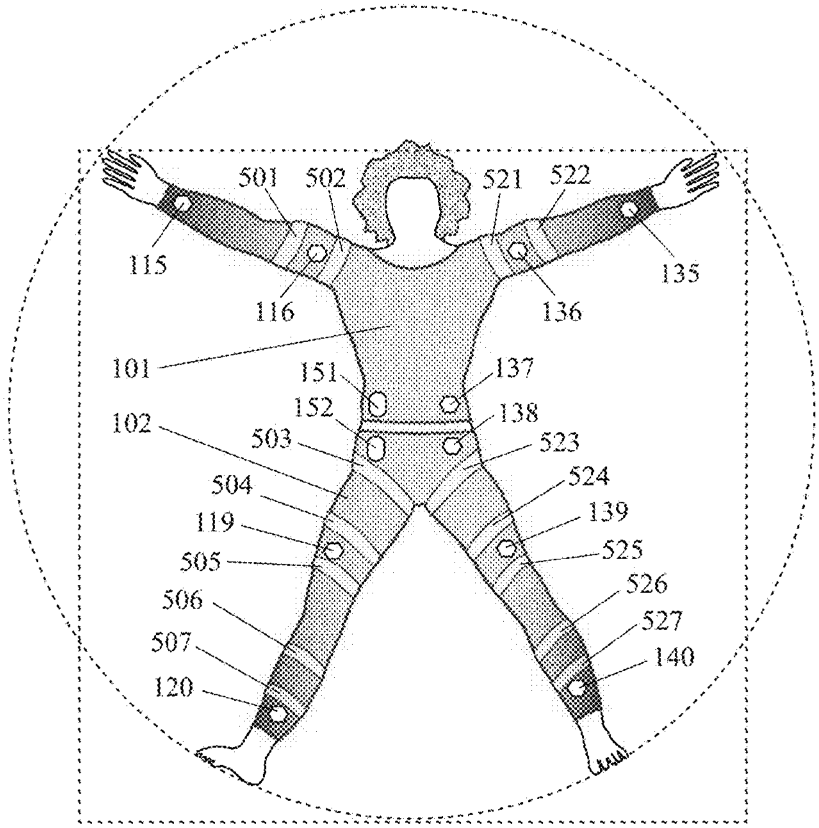
FIGS. 5 and 6 show electromyographic clothing comprising a shirt and pants with a plurality of band-shaped EMG sensors and inertial motion sensors.
Figure 6:
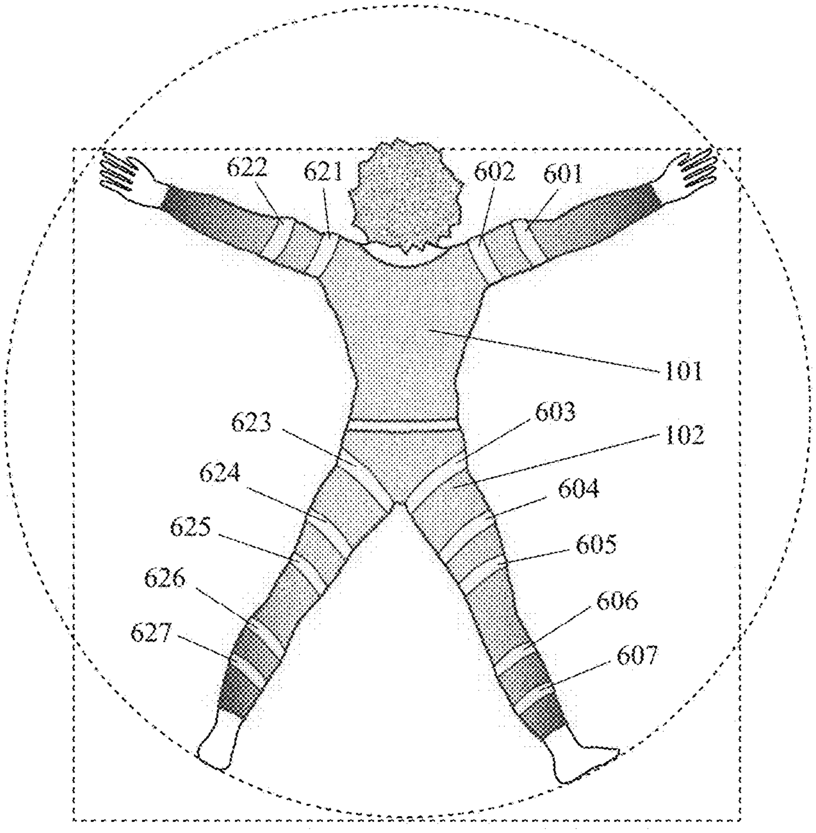

FIGS. 5 and 6 show another example of how this invention can be embodied in a device and system for measuring body motion and/or muscle activity comprising: one or more articles of clothing or clothing accessories; a plurality of motion sensors which are attached to and/or integrated into the one or more articles of clothing or clothing accessories, wherein these motion sensors are configured to collect motion data concerning changes in the configurations of a set of body joints; a plurality of electromyographic (EMG) sensors which are attached to and/or integrated into the one or more articles of clothing or clothing accessories, wherein these EMG sensors are configured to collect electromagnetic energy data concerning the neuromuscular activity of a set of muscles, and wherein muscles in the set of muscles move joints in the set of body joints; and a data processing unit which analyzes both motion data from the motion sensors and electromagnetic energy data from the EMG sensors in order to measure and/or model body motion and/or muscle activity.

The example shown in FIGS. 5 and 6 is like the example shown in FIGS. 1 and 2, except that each EMG sensor is a (partially) circumferential ring or band which at least partially spans the circumference of a limb. In this example, some of the (partially) circumferential ring or band shaped EMG sensors cover more than one of the locations specified by smaller, individual EMG sensors in FIGS. 1 and 2. A potential disadvantage of using such (partial) circumferential ring or band shaped EMG sensors is that they may measure mixed neuromuscular electromagnetic signals from multiple muscles. However, a potential advantage of using such (partial) circumferential ring or band shaped EMG sensors is that fewer EMG sensors are required and such EMG sensors can be more robust concerning measurement accuracy with variation in location on a person's body relative to underlying muscles. The question of which is better—individual small EMG sensors (such as those in FIGS. 1 and 2) or partial-circumferential ring or band shaped EMG sensors (such as those in FIGS. 5 and 6)—can depend on the type of clothing and application.

In the example shown in FIGS. 5 and 6, the (partially) circumferential ring or band shaped EMG sensors are partially circumferential. In particular, the EMG sensors are half rings or half bands. They are in pairs. A first half-ring or half-band EMG sensor spans the anterior surface of a limb at a given longitudinal location on the limb. A second half-ring or half-band EMG sensor spans the posterior surface of the limb at the same longitudinal location on the limb. This is why EMG sensors at similar longitudinal locations on a limb have different numbers in the front view (FIG. 5) vs. the rear view (FIG. 6). This can be more accurate for measuring electromagnetic energy from different muscles than having each EMG sensor be a complete ring or band which spans the full circumference of a limb. Nonetheless, in an alternative example, a device or system can have EMG sensors which are each a complete ring or band which fully spans the circumference of a limb.

Again, the terms "right" and "left" are from the perspective of the person wearing the clothing. In the front perspective of this example which is shown in FIG. 5, half-ring sensor 501 is configured to collect data concerning electromagnetic neuromuscular activity of the short head and/or long head of the right biceps brachii muscle. Half-ring sensor 502 is configured to collect data concerning electromagnetic neuromuscular activity of the anterior portion of the right deltoideus muscle and the right deltoideus medius muscle. Half-ring sensor 503 is configured to collect data concerning electromagnetic neuromuscular activity of the right gluteus medius muscle and the right tensor fasciae latae muscle. Half-ring sensor 504 is configured to collect data concerning electromagnetic neuromuscular activity of the rectus femoris of the right quadriceps femoris muscle. Half-ring sensor 505 is configured to collect data concerning electromagnetic neuromuscular activity of the vastus medialis of the right quadriceps femoris muscle and the vastus lateralis of the right quadriceps femoris muscle. Half-ring sensor 506 is configured to collect data concerning electromagnetic neuromuscular activity of the right tibialis anterior muscle and the right peroneus longus muscle. Half-ring sensor 507 is configured to collect data concerning electromagnetic neuromuscular activity of the right peroneus *brevis* muscle and the right soleus muscle.

In the example shown in FIG. 5, half-ring sensor 521 is configured to collect data concerning electromagnetic neuromuscular activity of the short head and/or long head of the left biceps brachii muscle. Half-ring sensor 522 is configured to collect data concerning electromagnetic neuromuscular activity of the anterior portion of the left deltoideus muscle and the left deltoideus medius muscle. Half-ring sensor 523 is configured to collect data concerning electromagnetic neuromuscular activity of the left gluteus medius muscle and the left tensor fasciae latae muscle. Half-ring sensor 524 is configured to collect data concerning electromagnetic neuromuscular activity of the rectus femoris of the left quadriceps femoris muscle. Half-ring sensor 525 is configured to collect data concerning electromagnetic neuromuscular activity of the vastus medialis of the left quadriceps femoris muscle and the vastus lateralis of the left quadriceps femoris muscle. Half-ring sensor 526 is configured to collect data concerning electromagnetic neuromuscular activity of the left tibialis anterior muscle and the left peroneus longus muscle. Half-ring sensor 527 is configured to collect data concerning electromagnetic neuromuscular activity of the left peroneus *brevis* muscle and the left soleus muscle.

In the rear perspective of this example which is shown in FIG. 6, half-ring sensor 601 is configured to collect data concerning electromagnetic neuromuscular activity of the long head of the right triceps brachii muscle and the lateral head of the right triceps brachii muscle. Half-ring sensor 602 is configured to collect data concerning electromagnetic neuromuscular activity of the posterior portion of the right deltoideus muscle. Half-ring sensor 603 is configured to collect data concerning electromagnetic neuromuscular activity of the right gluteus maximus muscle. Half-ring sensor 604 is configured to collect data concerning electromagnetic neuromuscular activity of the long head and short head of the right biceps femoris muscle and the right semitendinosus muscle. Half-ring sensor 606 is configured to collect data concerning electromagnetic neuromuscular activity of the *medialis* of the right gastrocnemius muscle and the lateralis of the right sastrocnemius muscle. In this example, half-ring 605 and half-ring 607 on the rear side are for support only and have no EMG sensor.

In the example in FIG. 6, half-ring sensor 621 is configured to collect data concerning electromagnetic neuromuscular activity of the long head of the left triceps brachii muscle and the lateral head of the left triceps brachii muscle. Half-ring sensor 622 is configured to collect data concerning electromagnetic neuromuscular activity of the posterior portion of the left deltoideus muscle. Half-ring sensor 623 is configured to collect data concerning electromagnetic neuromuscular activity of the left gluteus maximus muscle. Half-ring sensor 624 is configured to collect data concerning electromagnetic neuromuscular activity of the long head and short head of the left biceps femoris muscle and the left semitendinosus muscle. Half-ring sensor 626 is configured to collect data concerning electromagnetic neuromuscular activity of the *medialis* of the left gastrocnemius muscle and the lateralis of the left sastrocnemius muscle. In this example, half-ring 625 and half-ring 627 on the rear side are for support only and have no EMG sensor.

The example that is shown in FIGS. 5 and 6 also comprises a plurality of motion sensors. In this example, these motion sensors are integrated into the garments. In another example, these motions sensors can be removably attached to the garments. In an example, the motion sensors can be modular. In this example, the motion sensors are accelerometers. In other examples, motion sensors can be selected from the group consisting of: accelerometer; conductive fiber motion sensor; electrogoniometer; fluid pressure sensor; gyroscope; inclinometer; inductive transducer; inertial sensor; longitudinal pressure sensor; magnometer; optical bend sensor; piezoelectric fiber; piezoelectric sensor; piezoresistive fiber; piezoresistive sensor; RFID-based motion sensor; strain gauge; and ultrasonic-based motion sensor.

As shown in FIG. 5, motion sensor 115 is configured to collect data concerning movement of the lower right arm. In this example, motion sensor 116 is configured to collect data concerning movement of the upper right arm. Motion sensor 135 is configured to collect data concerning movement of the lower left arm. Motion sensor 136 is configured to collect data concerning movement of the upper left arm. Motion sensor 137 is configured to collect data concerning movement of the upper trunk. Motion sensor 138 is configured to collect data concerning movement of the lower truck. Motion sensor 119 is configured to collect data concerning movement of the upper right leg. Motion sensor 120 is configured to collect data concerning movement of the lower right leg. Motion sensor 139 is configured to collect data concerning movement of the upper left leg. Motion sensor 140 is configured to collect data concerning movement of the lower left leg.

The example shown in FIGS. 5 and 6 also includes a data processing unit 151 for the upper body garment and a separate data processing unit 152 for the lower body garment. In an example, this system can be embodied in a one-piece full-body article of clothing which spans both the upper and lower body (such as a union suit, jumpsuit, or overalls). In an example, with a one-piece full-body article of clothing spanning both the upper and lower body, a single data processing unit can be sufficient. In this example, the data processing unit is in wireless electromagnetic communication with the EMG sensors and motion sensors. In an example, a data processing unit can be in direct (e.g. non-wireless) electromagnetic communication with the EMG sensors and motion sensors. In an example, this direct electromagnetic communication can be through electromagnetic wires and/or electromagnetically-conductive pathways in the clothing textile. In an example, one or more articles of clothing or wearable accessories can be made from a close-fitting, elastic, and/or stretchable fabric. In an example, an article of clothing or wearable accessory can be made from one or more materials selected from the group consisting of: Acetate, Acrylic, Cotton, Denim, Latex, Linen, Lycra®, Neoprene, Nylon, Polyester, Rayon, Silk, Spandex, and Wool.

In the example shown in FIGS. 5 and 6, there are motion sensors only on the front sides of the garments. In another example, there could be motion sensors only on the rear sides of the garments. In another example, there could be motion sensors on both the front and rear sides of the garments. In the example shown in FIGS. 5 and 6, there are data processing units only on the front sides of the garments. In another example, there could be data processing units only on the rear sides of the garments. In another example, there could be data processing units on both the front and rear sides of the garments.

In an example, the device and system for measuring body motion and/or muscle activity that is shown in FIGS. 5 and 6 can further comprise one or more articles of clothing or clothing accessories selected from the group consisting of: glove, finger ring, watch, wrist band, bracelet, armband, tubular elbow band, hat, headband, earphones, ear bud, hearing aid, partially ear-encircling device, collar, necklace, pendant, pin, glasses or other eyewear, vest, chest band or strap, bra, belt, pair shorts, swim suit, tubular knee band, ankle band, sock, and shoe.

In an example, the device and system for measuring body motion and/or muscle activity shown in FIGS. 5 and 6 can include a human-to-computer interface. In an example, this human-to-computer interface can be incorporated into one of the data processing units shown in FIGS. 5 and 6. In an example a human-to-computer interface can comprise one or more members selected from the group consisting of: buttons, knobs, dials, or keys; display screen; gesture-recognition interface; microphone; physical keypad or keyboard; virtual keypad or keyboard; speech or voice recognition interface; touch screen; EMG-recognition interface; and EEG-recognition interface.

In an example, the device and system for measuring body motion and/or muscle activity shown in FIGS. 5 and 6 can include a computer-to-human interface. In an example, this computer-to-human interface can be incorporated into one of the data processing units shown in FIGS. 5 and 6. In an example, a computer-to-human interface can provide feedback to the person concerning their body motion and/or muscle activity. In an example, a computer-to-human interface can comprise one or more members selected from the group consisting of: a display screen; a speaker or other sound-emitting member; a myostimulating member; a neurostimulating member; a speech or voice recognition interface; a synthesized voice; a vibrating or other tactile sensation creating member; MEMS actuator; an electromagnetic energy emitter; an infrared light projector; an LED or LED array; and an image projector.

In an example, combined, joint, and/or multivariate analysis of both (a) motion data from the motion sensors and (b) electromagnetic energy data from the EMG sensors can enable more accurate measurement and/or modeling of body motion than analysis of data from motion sensors alone. In an example, combined, joint, and/or multivariate analysis of both (a) motion data from the motion sensors and (b) electromagnetic energy data from the EMG sensors can enable more accurate measurement and/or modeling of body motion than analysis of electromagnetic energy data from the EMG sensors alone. In an example, combined, joint, and/or multivariate analysis of both (a) motion data from the motion sensors and (b) electromagnetic energy data from the EMG sensors can enable more accurate measurement and/or modeling of muscle activity than analysis of data from motion sensors alone. In an example, combined, joint, and/or multivariate analysis of both (a) motion data from the motion sensors and (b) electromagnetic energy data from the EMG sensors can enable more accurate measurement and/or modeling of muscle activity than analysis of electromagnetic energy data from the EMG sensors alone.

In an example, data from EMG sensors can supplement data from motion sensors for more accurate measurement of body motion during key portions of joint range of motion wherein data from motion sensors alone is less accurate. In an example, this can be at extreme positions in the range of motion. In an example, data from EMG sensors can supplement data from motion sensors for more accurate measurement of body motion at key times in joint motion wherein data from motion sensors alone is less accurate. In an example, this can be at the beginning or end of a series of repeated actions. In an example, this can be at the beginning or end of a time of especially-strenuous physical activity. In an example, data from EMG sensors can supplement data from motion sensors for more accurate measurement of body motion during isometric activity wherein pressure is being applied against a motion-resisting external object. In an example, data from EMG sensors can supplement data from motion sensors for more accurate measurement of body motion when the person is being moved by an external device such as a car, elevator, escalator, airplane, etc. In an example, data from EMG sensors can supplement data from motion sensors for more accurate measurement of body motion when an article of clothing fits relatively loosely and/or shifts over the surface of the person's skin when the person moves.

In an example, data from motion sensors can supplement data from EMG sensors for more accurate measurement of muscle activity during key portions of joint range of motion wherein data from EMG sensors alone is less accurate. In an example, this can be at extreme positions in the range of motion. In an example, data from motion sensors can supplement data from EMG sensors for more accurate measurement of muscle activity at key times in joint motion wherein data from EMG sensors alone is less accurate. In an example, this can be at the beginning or end of a series of repeated actions. In an example, this can be at the beginning or end of a time of especially-strenuous physical activity. In an example, data from motion sensors can supplement data from EMG sensors for more accurate measurement of muscle activity during isometric activity wherein pressure is being applied against a motion-resisting external object. In an example, data from motion sensors can supplement data from EMG sensors for more accurate measurement of muscle activity when the person is being moved by an external device such as a car, elevator, escalator, airplane, etc. In an example, data from motion sensors can supplement data from EMG sensors for more accurate measurement of muscle activity when an article of clothing fits relatively loosely and/or shifts over the surface of the person's skin when the person moves.

In an example, data from motion sensors and data from EMG sensors can be jointly analyzed using one or more statistical methods selected from the group consisting of: Analysis of Variance (ANOVA), Artificial Neural Network (ANN), Auto Regression, Bayesian filter or other Bayesian statistical method, centroid analysis, Chi-Squared analysis, cluster analysis, covariance analysis, decision tree analysis, Eigenvalue Decomposition, Factor Analysis, Fast Fourier Transform (FFT) or other Fourier transformation, Hidden Markov model or other Markov modeling, Kalman Filter, kinematic modeling, Least Squares Estimation (LSE), Discriminant Analysis (DA), linear regression, linear transform, logarithmic function analysis, logistic regression, logit analysis, machine learning, mean or median analysis, Multivariate Linear Regression (MLR), Logit analysis, multivariate parametric classifiers, Neural Network, Non-Linear Programming (NLP), normalization, orthogonal transformation, pattern recognition, Power Spectral Density (PSD) analysis, power spectrum analysis, Principal Components analysis, probit analysis, Random Forest Gump (RFG) analysis, spectral analysis, spectroscopic analysis, spline function, survival analysis, three-dimensional modeling, time series analysis, variance, and wavelet analysis. Relevant variations discussed elsewhere in this disclosure or in priority-linked disclosures can also be applied to this example.

Figure 7:
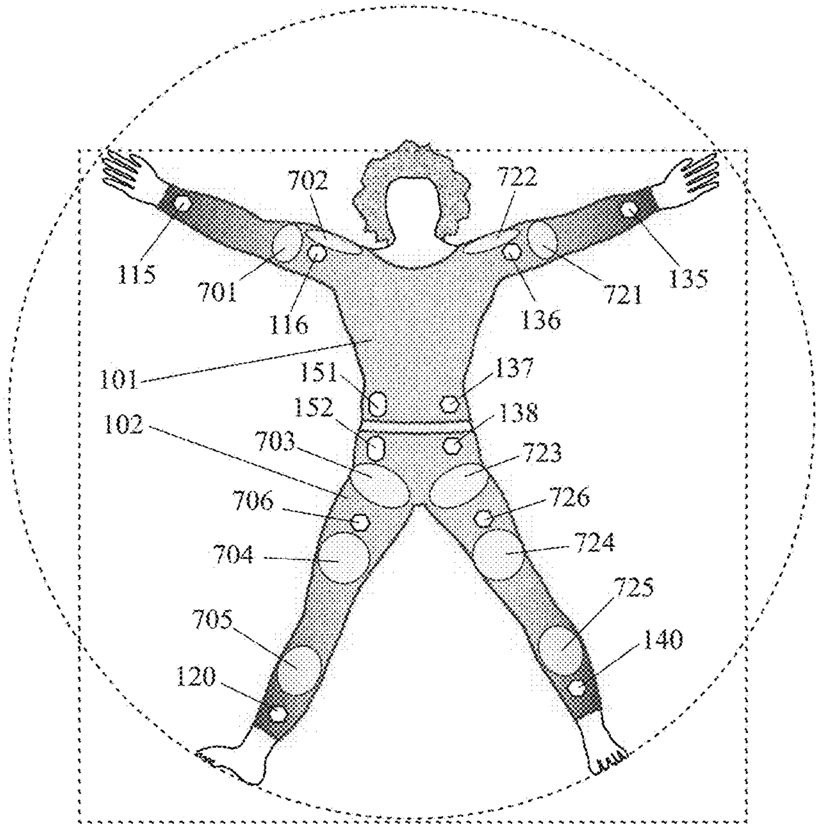
FIGS. 7 and 8 show electromyographic clothing comprising a shirt and pants with a plurality of saddle-shaped EMG sensors and inertial motion sensors.
Figure 8:
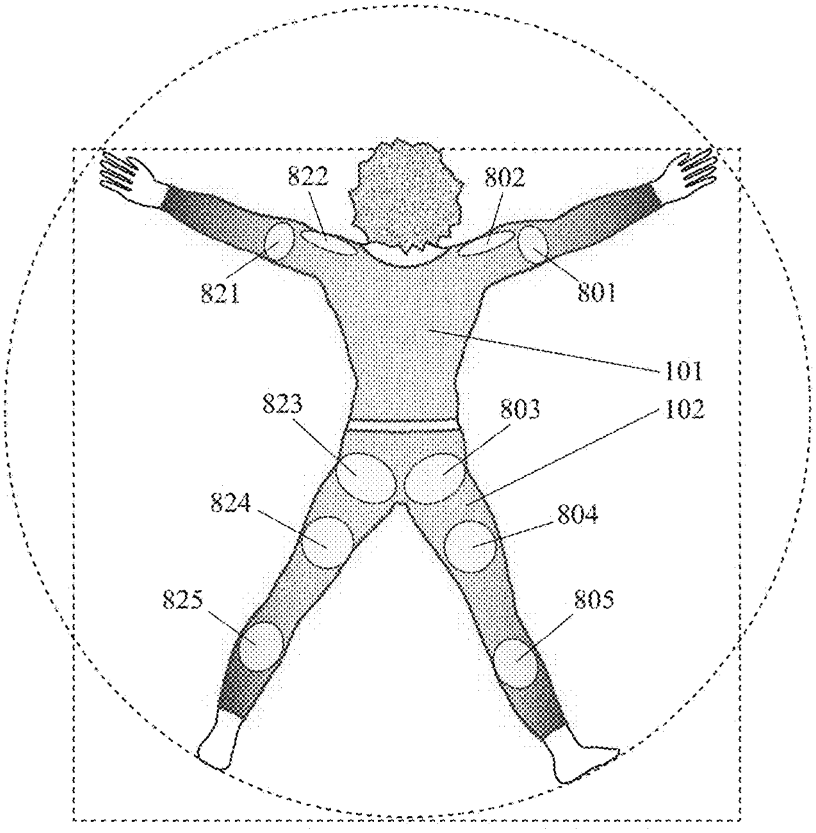

FIGS. 7 and 8 show another example of how this invention can be embodied in a device and system for measuring body motion and/or muscle activity comprising: one or more articles of clothing or clothing accessories; a plurality of motion sensors which are attached to and/or integrated into the one or more articles of clothing or clothing accessories, wherein these motion sensors are configured to collect motion data concerning changes in the configurations of a set of body joints; a plurality of electromyographic (EMG) sensors which are attached to and/or integrated into the one or more articles of clothing or clothing accessories, wherein these EMG sensors are configured to collect electromagnetic energy data concerning the neuromuscular activity of a set of muscles, and wherein muscles in the set of muscles move joints in the set of body joints; and a data processing unit which analyzes both motion data from the motion sensors and electromagnetic energy data from the EMG sensors in order to measure and/or model body motion and/or muscle activity.

The example shown in FIGS. 7 and 8 is like the example shown in FIGS. 5 and 6, except that each EMG sensor is a shaped like a conic section (such as a circle or ellipse) which has been curved around the arcuate three-dimensional surface of a limb like a saddle. Accordingly, we refer to the EMG sensors in FIGS. 7 and 8 as "saddle shaped." In a variation on this example, an EMG sensor could be shaped like a polygon (such as a square or rectangle) which is curved around the arcuate three-dimensional surface of a limb like a saddle.

The example shown in FIGS. 7 and 8 is also like the example shown in FIGS. 1 and 2, except that the EMG sensors are larger than those in FIGS. 1 and 2. In an example, the EMG sensors in FIGS. 7 and 8 can each have an area in the range of 4 to 30 square inches. Some of the EMG sensors in FIGS. 7 and 8 are sufficiently large to cover two or more of the signal measuring locations that are individually covered by the smaller EMG sensors in FIGS. 1 and 2.

A potential disadvantage of the larger size of the saddle-shaped EMG sensors in FIGS. 7 and 8 is that they may receive mixed neuromuscular electromagnetic signals from multiple muscles, making it difficult to differentiate between the activities of individual muscles. Potential advantages of the larger size of the saddle-shaped EMG sensors in FIGS. 7 and 8 are that: fewer sensors are needed to span the entire body; and the larger sensors can be more robust for measuring neuromuscular signals from a muscle despite shifts in clothing over a person's skin and despite variation in how clothing fits different people's bodies. The answer to the question of whether it is better to have larger EMG sensors (such as those in FIGS. 7 and 8) or smaller EMG sensors (such as those in FIGS. 1 and 2) can depend on the elasticity of the clothing and the type application.

Again, as in previous examples, the terms "right" and "left" are used from the perspective of the person wearing the clothing. As shown in FIG. 7, saddle-shaped sensor 701 is configured to collect data concerning electromagnetic neuromuscular activity of the short head and/or long head of the right biceps brachii muscle. Saddle-shaped sensor 702 is configured to collect data concerning electromagnetic neuromuscular activity of the anterior portion of the right deltoideus muscle and the right deltoideus medius muscle. Saddle-shaped sensor 703 is configured to collect data concerning electromagnetic neuromuscular activity of the gluteus medius muscle and the right tensor fasciae latae muscle. Saddle-shaped sensor 704 is configured to collect data concerning electromagnetic neuromuscular activity of the rectus femoris of the right quadriceps femoris muscle, the vastus medialis of the right quadriceps femoris muscle, and the vastus lateralis of the right quadriceps femoris muscle. Saddle-shaped sensor 705 is configured to collect data concerning electromagnetic neuromuscular activity of the right tibialis anterior muscle, the right peroneus longus muscle, the right peroneus *brevis* muscle, and the right soleus muscle.

As shown in FIG. 7, saddle-shaped sensor 721 is configured to collect data concerning electromagnetic neuromuscular activity of the short head and/or long head of the left biceps brachii muscle. Saddle-shaped sensor 722 is configured to collect data concerning electromagnetic neuromuscular activity of the anterior portion of the left deltoideus muscle and the left deltoideus medius muscle. Saddle-shaped sensor 723 is configured to collect data concerning electromagnetic neuromuscular activity of the gluteus medius muscle and the left tensor fasciae latae muscle. Saddle-shaped sensor 724 is configured to collect data concerning electromagnetic neuromuscular activity of the rectus femoris of the left quadriceps femoris muscle, the vastus medialis of the left quadriceps femoris muscle, and the vastus lateralis of the left quadriceps femoris muscle. Saddle-shaped sensor 725 is configured to collect data concerning electromagnetic neuromuscular activity of the left tibialis anterior muscle, the left peroneus longus muscle, the left peroneus *brevis* muscle, and the left soleus muscle.

As shown in FIG. 8, saddle-shaped sensor 801 is configured to collect data concerning electromagnetic neuromuscular activity of the long head of the right triceps brachii muscle and the lateral head of the right triceps brachii muscle. Saddle-shaped sensor 802 is configured to collect data concerning electromagnetic neuromuscular activity of the posterior portion of the right deltoideus muscle. Saddle-shaped sensor 803 is configured to collect data concerning electromagnetic neuromuscular activity of the right gluteus maximus muscle. Saddle-shaped sensor 804 is configured to collect data concerning electromagnetic neuromuscular activity of the long head and short head of the right biceps femoris muscle and the right semitendinosus muscle. Saddle-shaped sensor 805 is configured to collect data concerning electromagnetic neuromuscular activity of the *medialis* of the right gastrocnemius muscle and the lateralis of the right sastrocnemius muscle.

As shown in FIG. 8, saddle-shaped sensor 821 is configured to collect data concerning electromagnetic neuromuscular activity of the long head of the left triceps brachii muscle and the lateral head of the left triceps brachii muscle. Saddle-shaped sensor 822 is configured to collect data concerning electromagnetic neuromuscular activity of the posterior portion of the left deltoideus muscle. Saddle-shaped sensor 823 is configured to collect data concerning electromagnetic neuromuscular activity of the left gluteus maximus muscle. Saddle-shaped sensor 824 is configured to collect data concerning electromagnetic neuromuscular activity of the long head and short head of the left biceps femoris muscle and the left semitendinosus muscle. Saddle-shaped sensor 825 is configured to collect data concerning electromagnetic neuromuscular activity of the *medialis* of the left gastrocnemius muscle and the lateralis of the left sastrocnemius muscle.

The motion sensors, data processing units, and potential statistical analysis methods for FIGS. 7 and 8 are the same as those which were discussed previously for FIGS. 5 and 6. Relevant variations discussed elsewhere in this disclosure or in priority-linked disclosures can also be applied to this example.

Figure 9:
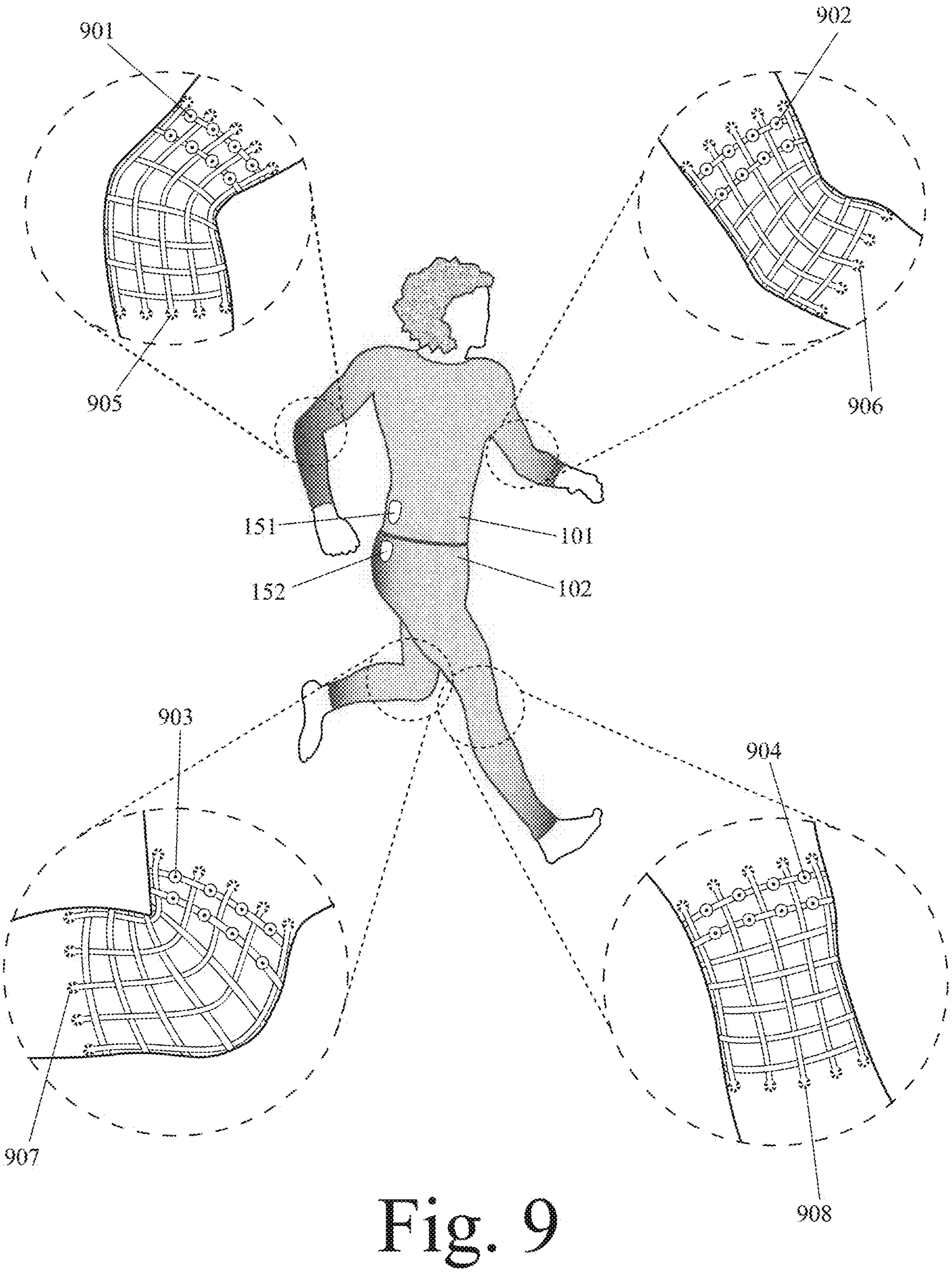
FIGS. 9 and 10 show two examples of electromyographic clothing wherein EMG sensors and bending motion sensors are woven together.

FIG. 9 shows another example of how this invention can be embodied in a device and system for measuring body motion and/or muscle activity comprising: one or more articles of clothing or clothing accessories; a plurality of motion sensors which are attached to and/or integrated into the one or more articles of clothing or clothing accessories, wherein these motion sensors are configured to collect motion data concerning changes in the configurations of a set of body joints; a plurality of electromyographic (EMG) sensors which are attached to and/or integrated into the one or more articles of clothing or clothing accessories, wherein these EMG sensors are configured to collect electromagnetic energy data concerning the neuromuscular activity of a set of muscles, and wherein muscles in the set of muscles move joints in the set of body joints; and a data processing unit which analyzes both motion data from the motion sensors and electromagnetic energy data from the EMG sensors in order to measure and/or model body motion and/or muscle activity.

FIG. 9 shows an example of how both the EMG sensors and the motion sensors can be woven or otherwise integrated into the textile (or fabric) of the clothing. In FIG. 9, both the EMG sensors and the motion sensors are woven into the textile of upper body garment 101 (such as a shirt) and a lower body garment 102 (such as a pair of pants). In this example, EMG sensors comprise electrodes (including 901, 902, 903, and 904) which are in electromagnetic communication with electromagnetically-conductive fibers, threads, strands, and/or channels which are woven into the textile of the clothing. In this example, the fibers, threads, strands, and/or channels associated with the EMG sensors are generally perpendicular to the longitudinal axes of the muscles which move the selected set of body joints. In an example, pairs of EMG electrodes can be located at different locations along the longitudinal axis of a muscle. In an example, pairs of EMG electrodes can be separated by 1 to 5 centimeters. In an example, a pair of EMG electrodes can be located near the mid-section of a muscle.

In FIG. 9, the motion sensors (including 905, 906, 907, and 908) comprise bend-sensing fibers, threads, strands, tubes, and/or channels which are woven into the textile of the clothing. In this example, the fibers, threads, strands, tubes, and/or channels associated with the motion sensors are generally parallel to the longitudinal axes of the bones which comprise the selected set of body joints. In this example, the motion sensors are bending-based motion sensors which each spans the longitudinal axis of a selected body joint. In this example, the end-points of the bending-based motion sensors are located proximally and distally from the selected body joints. In this example, bending-based motion sensors measure changes in the angles of selected body joints by measuring changes in the conductivity, resistance, and/or impendence of electromagnetic energy flowing through the bending-based motion sensors. In an example, a bending-based motion sensor can be a piezoelectric sensor.

In an alternative example, bending-based motion sensors can be optically functional instead of electromagnetically functional. In an example, bending-based motion sensors can measure changes in the angles of body joints by measuring changes in the intensity, spectrum, phase, or polarity of light energy flowing through the bending-based motion sensors. In an example, bending-based motion sensors can be pressure functional instead of electromagnetically functional. In an example, bending-based motion sensors can measure changes in the pressure or flow rate of gas or fluid in the bending-based motion sensors. In an example, the bending-based motion sensors can be sonically functional instead of electromagnetically functional. In an example, bending-based motion sensors can measure changes in the amplitude or waveform of sonic energy flowing through the bending-based motion sensors.

The central portion of FIG. 9 shows a running person who is wearing an upper body garment 101 and a lower body garment 102. The four corners of FIG. 9 show four semi-transparent close-up views (within four dotted-line circles) of the areas of the upper body garment 101 and lower body garment 102 which span the person's elbows and knees. These four semi-transparent close-up views (within four dotted-line circles) show how EMG sensors and motion sensors can be woven into the textile of the clothing.

In particular, the four semi-transparent close-up views in FIG. 9 show how: the fibers, threads, strands, and/or channels associated with the EMG sensors (including 901, 902, 903, and 904) are generally perpendicular to the longitudinal axes of the muscles which move the selected set of body joints; and the fibers, threads, strands, tubes, and/or channels associated with the motion sensors (including 905, 906, 907, and 908) are generally parallel to the longitudinal axes of the bones which comprise the selected set of body joints. Although FIG. 9 does not show semi-transparent close-up views of the areas of the upper and lower body garments which span other joints (such as shoulders and hips), there can be EMG sensors and motion sensors woven into these other areas as well.

In an example, an article of clothing for measuring body motion and/or muscle activity can be made with a substantively-uniform electronically-functional textile, but EMG sensors and motion sensors can be integrated with (or attached to) the weave so as to span only selected body muscles and body joints. In an example, only those areas of an article of clothing which span selected body muscles and body joints may be made with electronically-functional textile and the EMG sensors and motion sensors can be integrated with (or attached to) those areas. In an example, the electrodes, fibers, threads, channels, and/or tubes of EMG sensors and bending-based motion sensors can be integrated with (or attached to) a textile by one or more methods selected from the group consisting of: weaving, knitting, braiding, sewing, adhesion, gluing, laminating, melting, layering, printing, painting, and sandwiching. In an example, EMG sensors and motion sensors can overlap. In an example, EMG sensors and motion sensors can be woven or braided together.

In an example, one or more EMG sensors can be placed over (the mid-section of) a muscle which is proximal or distal from a selected body joint. In an example, an EMG sensor can be configured in an orientation which is generally perpendicular to the muscle when the joint is extended. In an example, one or more bending-based motion sensors can be placed so as to span the surface of a selected body joint in proximal-to-distal (or distal-to-proximal) manner. In an example, a bending-based motion sensor can span the body joint in an orientation which is generally parallel to that joint when the joint is extended. In an example, the EMG sensors and motion sensors can be woven or otherwise integrated in orientations which are substantially perpendicular to each other (when viewed as projected onto a flat two-dimensional surface). In the example in FIG. 9, both the EMG sensors and the motion sensors are integrated into the textile of the clothing. In an alternative example, the EMG sensors can be integrated into the textile and the motion sensors can be externally attached to the clothing. In an alternative example, the motion sensors can be integrated into the textile and the EMG sensors can be externally attached to the clothing.

In this example, the fibers, strands, threads, channels, and/or tubes associated with EMG sensors and/or motion sensors which are integrated into a textile follow generally-straight lines when the textile is laid flat. In an example, the fibers, strands, threads, channels, and/or tubes associated with EMG sensors and/or motion sensors which are integrated into a textile can be arcuate even when the textile is laid flat. In an example, the fibers, strands, threads, channels, and/or tubes associated with EMG sensors and/or motion sensors can have shapes or configurations which are selected from the group consisting of: circular, elliptical, or other conic section; square, rectangular, hexagon, or other polygon; parallel; perpendicular; crisscrossed; nested; concentric; sinusoidal; undulating; zigzagged; and radial spokes.

FIG. 9 also shows two data processing units (151 and 152) which are similar to those in previous examples. In an example, EMG sensors and motion sensors can be in electromagnetic communication with a data processing unit by wires or other direct electromagnetic conductance. In an example, EMG sensors and motion sensors can be in wireless electromagnetic communication with a data processing unit. Relevant variations discussed elsewhere in this disclosure or in priority-linked disclosures can also be applied to this example.

Figure 10:
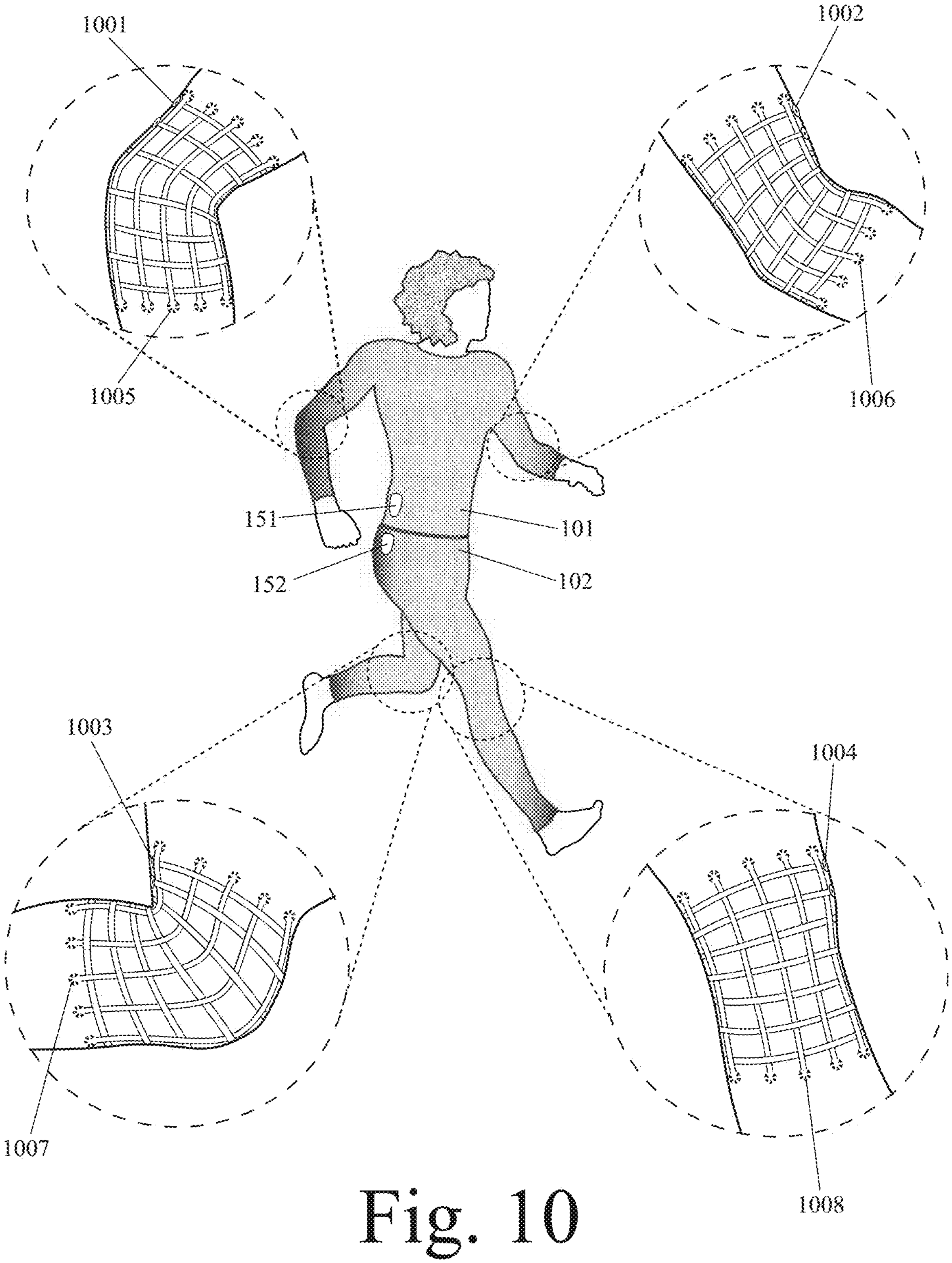

FIG. 10 shows another example of how this invention can be embodied in a device and system for measuring body motion and/or muscle activity comprising: one or more articles of clothing or clothing accessories; a plurality of motion sensors which are attached to and/or integrated into the one or more articles of clothing or clothing accessories, wherein these motion sensors are configured to collect motion data concerning changes in the configurations of a set of body joints; a plurality of electromyographic (EMG) sensors which are attached to and/or integrated into the one or more articles of clothing or clothing accessories, wherein these EMG sensors are configured to collect electromagnetic energy data concerning the neuromuscular activity of a set of muscles, and wherein muscles in the set of muscles move joints in the set of body joints; and a data processing unit which analyzes both motion data from the motion sensors and electromagnetic energy data from the EMG sensors in order to measure and/or model body motion and/or muscle activity.

The example shown in FIG. 10 is like the example shown in FIG. 9 except that there is only one EMG sensor (e.g. 1001, 1002, 1003, or 1004) in electromagnetic communication with an electromagnetically-conductive fiber, thread, strand, and/or channel at a particular location along the longitudinal axis of the muscle whose activity is being measured. The motion sensors (e.g. 1005, 1006, 1007, and 1008) and data processing units (151 and 152) in the example shown in FIG. 10 are like those in the example shown in FIG. 9. Relevant variations discussed elsewhere in this disclosure or in priority-linked disclosures can also be applied to this example.

Figure 11:
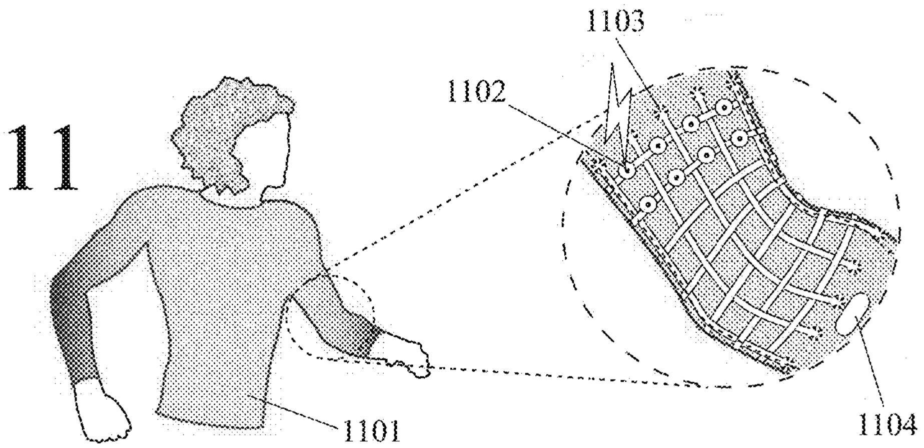
FIGS. 11 through 13 show electromyographic clothing with EMG sensors, bending-based motion sensors, and inertial motion sensors operating with different types of fit: close fit, moderate fit, and loose fit.
Figure 12:
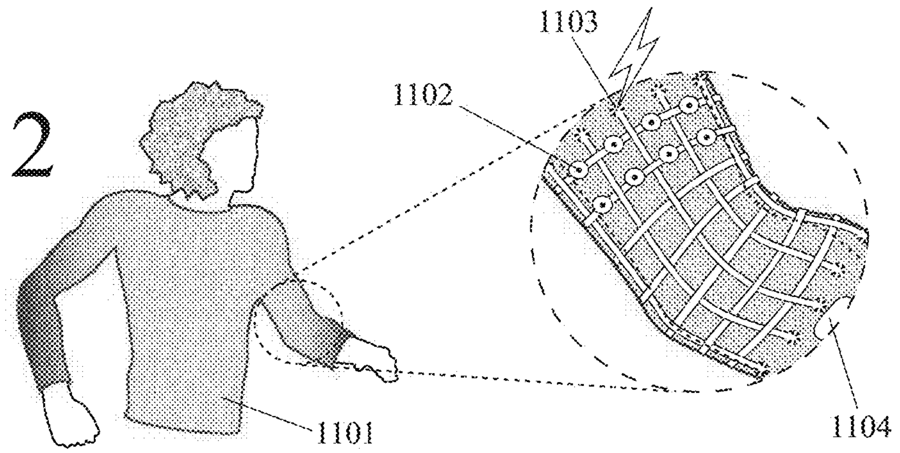
Figure 13:
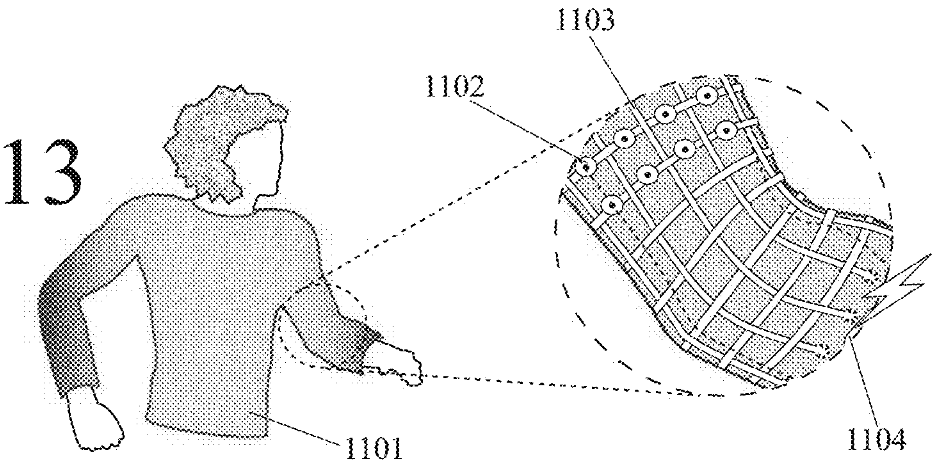

FIGS. 11 through 13 show another example of how this invention can be embodied in a device and system for measuring body motion and/or muscle activity comprising: one or more articles of clothing or clothing accessories; a plurality of motion sensors which are attached to and/or integrated into the one or more articles of clothing or clothing accessories, wherein these motion sensors are configured to collect motion data concerning changes in the configurations of a set of body joints; a plurality of electromyographic (EMG) sensors which are attached to and/or integrated into the one or more articles of clothing or clothing accessories, wherein these EMG sensors are configured to collect electromagnetic energy data concerning the neuromuscular activity of a set of muscles, and wherein muscles in the set of muscles move joints in the set of body joints; and a data processing unit which analyzes both motion data from the motion sensors and electromagnetic energy data from the EMG sensors in order to measure and/or model body motion and/or muscle activity.

The left side of each of FIGS. 11 through 13 shows the upper body of a running person wearing an upper body garment 1101. The right side of each of FIGS. 11 through 13 shows a close-up, semi-transparent view (in a dashed-line circle) of the portion of upper body garment 1101 which covers a person's left elbow. Although each of these figures only shows a close-up, semi-transparent view (in a dashed-line circle) of one body joint (the left elbow), upper body garment 1101 can have similar (body motion and muscle energy measuring) portions which cover other upper body joints (such as a person's right elbow and both shoulders).

In the close-up, semi-transparent views which are shown in the dashed-line circles, the underlying perimeter of a person's body (under the garment) is shown by dotted lines.

FIG. 11 shows an example wherein upper body garment 1104 fits relatively tightly over the under perimeter of a person's elbow. FIG. 12 shows an example wherein upper body garment 1104 fits in a moderate manner (neither very tight nor very loose) over the underlying perimeter of a person's elbow. FIG. 13 shows an example wherein upper body garment 1104 fits loosely over the underlying perimeter of a person's elbow.

FIGS. 11 through 13 show an example of how a device and system for measuring body motion and/or muscle activity with different types of sensors can provide more accurate measurement of body motion and/or muscle activity than a device and system with only one type of sensor, especially when there is variability in how clothing fits. Some types of clothing fit tightly; other types of clothing fit loosely. Some types of clothing are relatively elastic; other types of clothing are relatively inelastic. Some types of clothing shift over a person's skin as the person moves; other types of clothing do not shift very much. Some types of clothing exert significant pressure against a person's skin; other types of clothing do not exert much pressure against a person's skin. A device and system with different types of sensors can have the data collection flexibility to accurately measure body motion and muscle activity across this spectrum of clothing types.

In an example, some types of sensors can be better for measuring body motion and/or muscle activity with relatively-tight clothing and other types of sensors can be better with relatively-loose clothing. In an example, some types of sensors can be better for measuring body motion and/or muscle activity with relatively elastic clothing and other types of sensors can be better with relatively inelastic clothing. In an example, some types of sensors can be better for measuring body motion and/or muscle activity with clothing that shifts over a person's skin and other types of sensors can be better with clothing that does not shift. In an example, some types of sensors can be better for measuring body motion and/or muscle activity with clothing that exerts significant pressure against a person's skin and other types of sensors can be better with clothing that does not exert much pressure against a person's skin.

In an example, an EMG sensor can work well for measuring muscle activity as part of relatively-tight clothing or clothing that exerts pressure against a person's skin. In an example, a bending-based motion sensor can work well for measuring body motion as part of relatively-tight clothing or clothing that exerts pressure against a person's skin. In an example, an accelerometer-based motion sensor can work well for measuring body motion as part of relatively-loose clothing or clothing that does not exert pressure against a person's skin. In an example, an article of clothing with three different kinds of sensors (such as EMG sensors, bending-based motion sensors, and accelerometer-based motion sensors) can measure body motion and/or muscle activity more accurately over a wider range of clothing types and fits than an article of clothing with just one type of sensor.

In an example, an article of clothing can fit differently on different people. In an example, an article of clothing with different types of sensors can combine data from these different sensors in different proportions when the clothing is worn by different people, depending on how the clothing fits on those different people. In an example, an article of clothing can rely more heavily on data concerning body motion and/or muscle activity from a first type of sensor when worn by a person for whom the clothing fits tightly, but the article of clothing can rely more heavily on data from a second type of sensor when worn by a person for whom the clothing fits loosely.

In an example, an article of clothing can fit different people differently, depending on their overall body shape and size. In an example, an article of clothing can have three different types of sensors (e.g. EMG sensors, bending-based motion sensors, and accelerometer-based motion sensors) and give more weight to data from one of the three different types of sensors, depending on how loosely or tightly the clothing fits on a particular person.

In an example, an article of clothing can fit the same person differently at different locations on their body, depending on their body proportions. In an example, an article of clothing can have three different types of sensors (e.g. EMG sensors, bending-based motion sensors, and accelerometer-based motion sensors) and give more weight to data from one of the three different types of sensors in different body locations, depending on how loosely or tightly the clothing fits at a particular body location.

In an example, an article of clothing can fit the same person differently at different times, especially if the person gains or loses weight. In an example, an article of clothing can have three different types of sensors (e.g. EMG sensors, bending-based motion sensors, and accelerometer-based motion sensors) and give more weight to data from one of the three different types of sensors, depending on how loosely or tightly the clothing fits the person at a particular time.

FIG. 11 shows an example of how an article of clothing with multiple sensors can work when the clothing fits tightly. In FIG. 11, the underlying perimeter of the person's elbow is shown by dotted lines within the semi-transparent view (in the dashed-line circle) of the area of the upper body garment which spans the elbow. In FIG. 11 the dotted lines showing the underlying perimeter of the person's elbow are very close to the perimeter of the garment, indicating a very close fit.

FIG. 12 shows an example of how an article of clothing with multiple sensors can work when the clothing fits in a moderate (neither very tight nor very loose) manner. In FIG. 12, the underlying perimeter of the person's elbow is shown by dotted lines within the semi-transparent view (in the dashed-line circle) of the area of the upper body garment which spans the elbow. In FIG. 12 the dotted lines showing the underlying perimeter of the person's elbow are at a moderate distance from the perimeter of the garment, indicating a moderate fit.

FIG. 13 shows an example of how an article of clothing with multiple sensors can work when the clothing fits loosely. In FIG. 13, the underlying perimeter of the person's elbow is shown by dotted lines within the semi-transparent view (in the dashed-line circle) of the area of the upper body garment which spans the elbow. In FIG. 13 the dotted lines showing the underlying perimeter of the person's elbow are far from the perimeter of the garment, indicating a loose fit.

The article of clothing (upper body garment 1101) shown in FIGS. 11 through 13 comprises EMG sensors (including 1102), bending-based motion sensors (including 1103), and accelerometer-based motion sensor (1104). In the example in FIG. 11 wherein the clothing fits relatively tightly against the person's body, the EMG sensors provide the best measurement of body motion and/or muscle activity. This is figuratively represented by the lightning symbol (representing data signals) coming from EMG sensor 1102 in FIG. 11.

In the example in FIG. 12 wherein the clothing fits in a moderate manner (neither very tight nor very loose), the bending-based motion sensors provide the best measurement of body motion and/or muscle activity. This is figuratively represented by the lightning symbol (representing data signals) coming from bending-based motion sensor 1103 in FIG. 12.

In the example in FIG. 13 wherein the clothing fits relatively loosely, accelerometer-based motion sensor 1104 provides the best measurement of body motion and/or muscle activity. This is figuratively represented by the lightning symbol (representing data signals) coming from accelerometer-based motion sensor 1104 in FIG. 13. In another example, the order of which type of sensor provides better measurement for which level of clothing fit can be different. In another example, data from all three types of sensors can be used for all three levels of clothing fit, but the relative weight which is given to data from each type of sensor can vary with the level of clothing fit.

In an example, the manner in which an article of clothing fits (on a particular person, on a particular location on a person, and/or at a particular time) can be determined by analysis of data from one or more EMG sensors or motion sensors. In an example, particular patterns of data can be associated with clothing that is more or less tight, more or less elastic, and/or exerting higher or lower pressure on skin. In an alternative example, an article of clothing can have additional sensors which are used to separately determine how an article of clothing fits. In an example, an article of clothing can have additional pressure sensors, strain sensors, or optical sensors which independently determine whether an article of clothing fits in a manner which is tight vs. loose, elastic vs. inelastic, or high pressure vs. low pressure. In an example, data from one or more additional sensors can be used to inform which type of EMG sensor or motion sensor is given greatest weight when measuring body motion and/or muscle activity.

In an example, data from one or more EMG sensors, motion sensors, or other types of sensors can be jointly analyzed using one or more statistical methods selected from the group consisting of: Analysis of Variance (ANOVA), Artificial Neural Network (ANN), Auto Regression, Bayesian filter or other Bayesian statistical method, centroid analysis, Chi-Squared analysis, cluster analysis, covariance analysis, decision tree analysis, Eigenvalue Decomposition, Factor Analysis, Fast Fourier Transform (FFT) or other Fourier transformation, Hidden Markov model or other Markov modeling, Kalman Filter, kinematic modeling, Least Squares Estimation (LSE), Discriminant Analysis (DA), linear regression, linear transform, logarithmic function analysis, logistic regression, logit analysis, machine learning, mean or median analysis, Multivariate Linear Regression (MLR), Logit analysis, multivariate parametric classifiers, Neural Network, Non-Linear Programming (NLP), normalization, orthogonal transformation, pattern recognition, Power Spectral Density (PSD) analysis, power spectrum analysis, Principal Components analysis, probit analysis, Random Forest Gump (RFG) analysis, spectral analysis, spectroscopic analysis, spline function, survival analysis, three-dimensional modeling, time series analysis, variance, and wavelet analysis. Relevant variations discussed elsewhere in this disclosure or in priority-linked disclosures can also be applied to this example.

Figure 14:
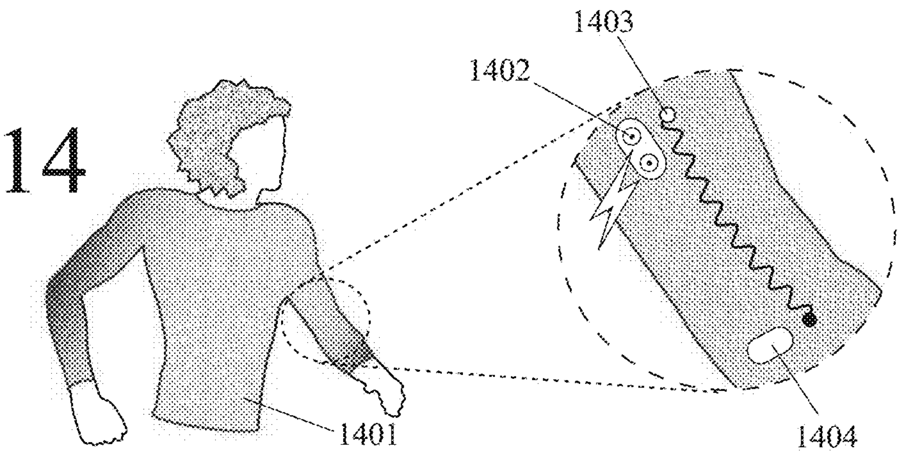
FIGS. 14 through 16 show electromyographic clothing with EMG sensors, bending-based motion sensors, and inertial motion sensors at different joint angles: full extension, moderate contraction, and strong contraction.
Figure 15:
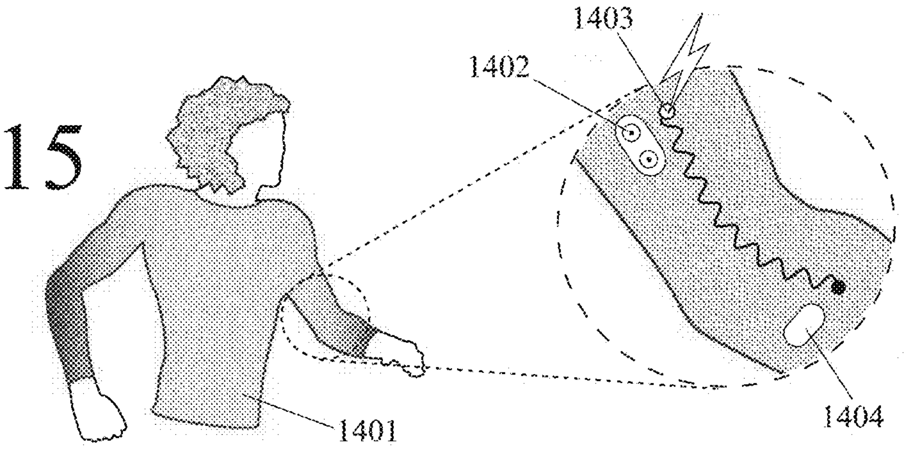
Figure 16:
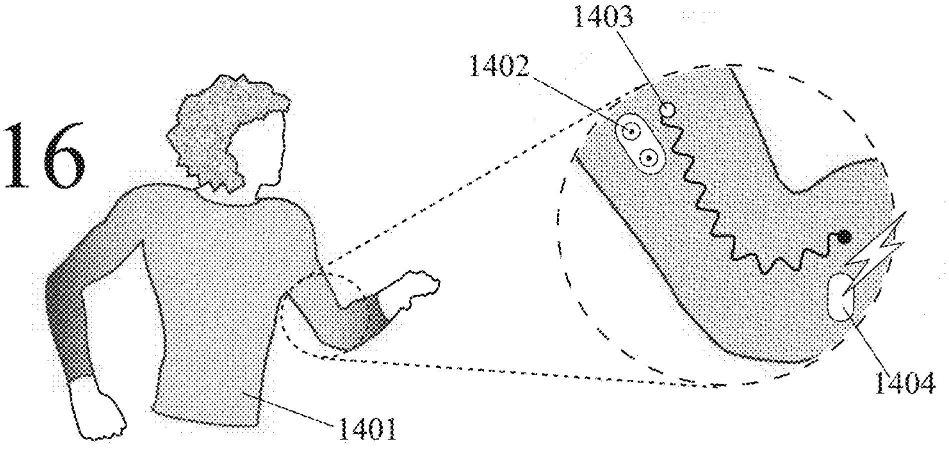

FIGS. 14 through 16 show another example of how this invention can be embodied in a device and system for measuring body motion and/or muscle activity comprising: one or more articles of clothing or clothing accessories; a plurality of motion sensors which are attached to and/or integrated into the one or more articles of clothing or clothing accessories, wherein these motion sensors are configured to collect motion data concerning changes in the configurations of a set of body joints; a plurality of electromyographic (EMG) sensors which are attached to and/or integrated into the one or more articles of clothing or clothing accessories, wherein these EMG sensors are configured to collect electromagnetic energy data concerning the neuromuscular activity of a set of muscles, and wherein muscles in the set of muscles move joints in the set of body joints; and a data processing unit which analyzes both motion data from the motion sensors and electromagnetic energy data from the EMG sensors in order to measure and/or model body motion and/or muscle activity.

FIGS. 14 through 16 show three sequential views of a running person wearing upper body garment 1401. In these three sequential views, the person's left elbow is moving and is bending at different angles within its range of motion during the three views. The left side of each of FIGS. 14 through 16 shows the upper body of the running person at three sequential times. The right side of each of FIGS. 14 through 16 shows a corresponding close-up view (in a dashed-line circle) of the portion of upper body garment 1401 which covers the person's left elbow at each of these three sequential times. Although each figure only shows a close-up view of one body joint (e.g. the left elbow), upper body garment 1401 can have similar (body motion and muscle energy measuring) portions and sensors which cover other upper body joints (such as the person's right elbow and both shoulders).

FIG. 14 shows upper body garment 1401 at a first point in time when the person's left elbow is almost entirely extended (at an angle of approximately 170 degrees). FIG. 15 shows upper body garment 1401 at a second point in time when the person's left elbow is moderately contracted (at an angle of approximately 140 degrees). FIG. 16 shows the upper body garment 1401 at a third point in time when the person's left elbow is more contracted (at an angle of approximately 90 degrees). FIGS. 14 through 16 also shown that upper body garment 1401 includes EMG sensor 1402, bending-based motion sensor 1403, and accelerometer-based motion sensor 1404.

FIGS. 14 through 16 show an example of how a device and system for measuring body motion and/or muscle activity with different types of sensors can provide more accurate measurement of body motion and/or muscle activity than a device and system with only one type of sensor, especially over different portions of the range of joint motion for a body joint. In an example, a first type of sensor can be better for measuring body motion and/or muscle activity when there are only small-scale joint movements and/or small joint contraction angles. In an example, a second type of sensor can be better for measuring body motion and/or muscle activity when there are large-scale joint movements and/or large joint contraction angles. In an example, a first type of sensor can provide the most accurate measurement of joint movement and/or muscle activity at very small or very large angles at the endpoints of the range of motion for a joint. In an example, a second type of sensor can provide the most accurate measurement of joint movement and/or muscle activity within the mid-range of the range of motion for a joint. In an example, each of three different types of sensors can have a portion of a joint's range of motion for which it is the optimal type of measurement sensor.

In FIG. 14 wherein the elbow is almost-fully extended, EMG sensor 1402 provides the best measurement of body motion and/or muscle activity. This is figuratively represented by the lightning symbol (representing data signals)

coming from EMG sensor 1402 in FIG. 14. In FIG. 15 wherein the elbow is moderately contracted, bending-based motion sensor 1403 provides the best measurement of body motion and/or muscle activity. This is figuratively represented by the lightning symbol (representing data signals) coming from bending-based motion sensor 1403 in FIG. 15. In FIG. 16 wherein the elbow is more contracted, accelerometer-based motion sensor 1404 provides the best measurement of body motion and/or muscle activity. This is figuratively represented by the lightning symbol (representing data signals) coming from accelerometer-based motion sensor 1404 in FIG. 16. In another example, the order of which type of sensor provides better measurement over which portion of the elbow range of motion can be different. In another example, data from all three types of sensors can be used throughout the entire range of motion, but the relative weight which is given to data from each type of sensor can vary with joint angle.

In an example, data from one or more EMG sensors and one or more motion sensors can be jointly analyzed using one or more statistical methods selected from the group consisting of: Analysis of Variance (ANOVA), Artificial Neural Network (ANN), Auto Regression, Bayesian filter or other Bayesian statistical method, centroid analysis, Chi-Squared analysis, cluster analysis, covariance analysis, decision tree analysis, Eigenvalue Decomposition, Factor Analysis, Fast Fourier Transform (FFT) or other Fourier transformation, Hidden Markov model or other Markov modeling, Kalman Filter, kinematic modeling, Least Squares Estimation (LSE), Discriminant Analysis (DA), linear regression, linear transform, logarithmic function analysis, logistic regression, logit analysis, machine learning, mean or median analysis, Multivariate Linear Regression (MLR), Logit analysis, multivariate parametric classifiers, Neural Network, Non-Linear Programming (NLP), normalization, orthogonal transformation, pattern recognition, Power Spectral Density (PSD) analysis, power spectrum analysis, Principal Components analysis, probit analysis, Random Forest Gump (RFG) analysis, spectral analysis, spectroscopic analysis, spline function, survival analysis, three-dimensional modeling, time series analysis, variance, and wavelet analysis. Relevant variations discussed elsewhere in this disclosure or in priority-linked disclosures can also be applied to this example.

Figure 17:
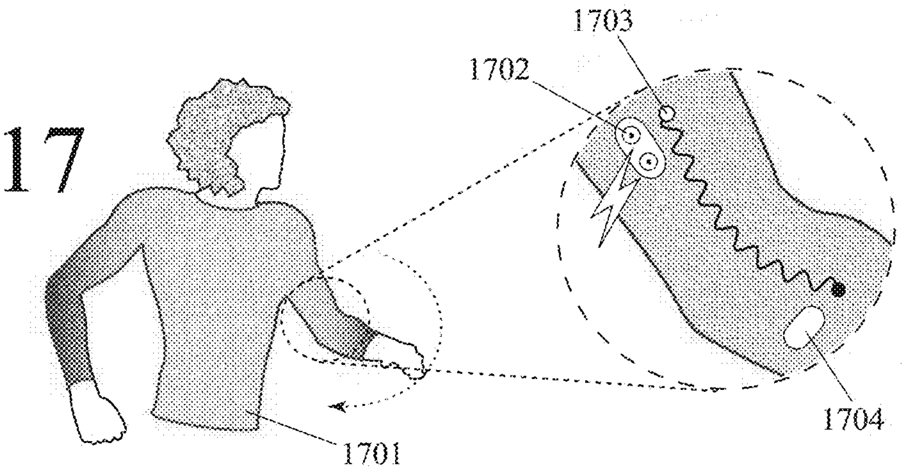
FIGS. 17 through 19 show electromyographic clothing with EMG sensors, bending-based motion sensors, and inertial motion sensors during cumulative movement repetitions.
Figure 18:
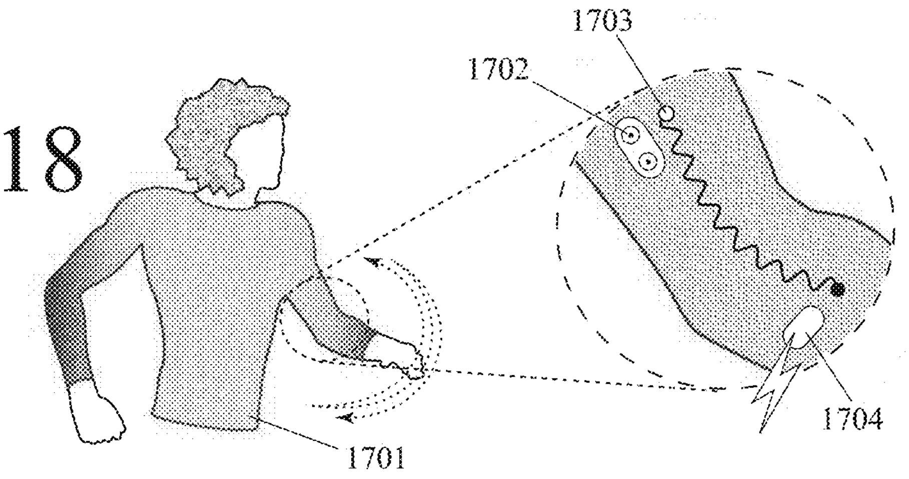
Figure 19:
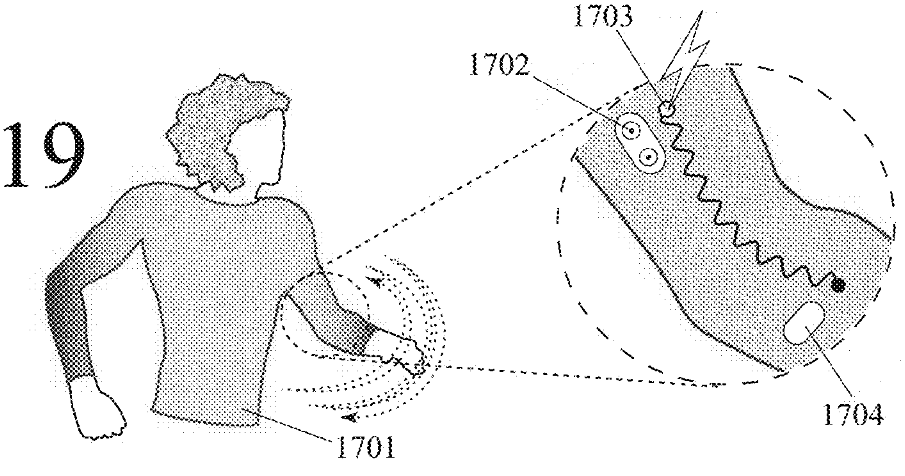

FIGS. 17 through 19 show another example of how this invention can be embodied in a device and system for measuring body motion and/or muscle activity comprising: one or more articles of clothing or clothing accessories; a plurality of motion sensors which are attached to and/or integrated into the one or more articles of clothing or clothing accessories, wherein these motion sensors are configured to collect motion data concerning changes in the configurations of a set of body joints; a plurality of electromyographic (EMG) sensors which are attached to and/or integrated into the one or more articles of clothing or clothing accessories, wherein these EMG sensors are configured to collect electromagnetic energy data concerning the neuromuscular activity of a set of muscles, and wherein muscles in the set of muscles move joints in the set of body joints; and a data processing unit which analyzes both motion data from the motion sensors and electromagnetic energy data from the EMG sensors in order to measure and/or model body motion and/or muscle activity.

FIGS. 17 through 19 show a running person wearing upper body garment 1701 at three different times. During these three times, the person is moving their left elbow in a repeated back- and -forth motion. The left side of each figure shows the upper body of the running person. The right side of each of figure shows a corresponding close-up view (in a dashed-line circle) of the portion of upper body garment 1701 which covers the person's left elbow at each of these three times. Although each figure only shows a close-up view of one body joint (e.g. the left elbow), upper body garment 1701 can have similar (body motion and muscle energy measuring) portions and sensors which cover other upper body joints (such as the person's right elbow and both shoulders).

FIG. 17 shows a first situation in which the person is moving their left elbow at a first speed and/or with a first number of movement repetitions. FIG. 18 shows a second situation in which the person is moving their left elbow at a second speed (which is greater than the first speed) and/or with a second number of movement repetitions (which is greater than the first number of movement repetitions). FIG. 19 shows a third situation in which the person is moving their left elbow at a third speed (which is greater than the second speed) and/or with a third number of movement repetitions (which is greater than the second number of movement repetitions.

FIGS. 17 through 19 show an example of how a device and system for measuring body motion and/or muscle activity with different types of sensors can provide more accurate measurement of body motion and/or muscle activity than a device and system with only one type of sensor, especially with variation in movement speed and/or variation in the number of movement repetitions. In an example, a first type of sensor can be better for measuring body motion and/or muscle activity with low speed and/or minimally repeated movements. In an example, a second type of sensor can be better for measuring body motion and/or muscle activity with moderate speed and/or moderately repeated movements. In an example, a third type of sensor can be better for measuring body motion and/or muscle activity with high speed and/or highly repeated movements.

In FIG. 17 wherein the person is moving their elbow at a low speed and/or with little movement repetition, EMG sensor 1702 provides the best measurement of body motion and/or muscle activity. This is figuratively represented by the lightning symbol (representing data signals) coming from EMG sensor 1702 in FIG. 17. In FIG. 18 wherein the person is moving their elbow at a moderate speed and/or with a moderate number of repetitions, accelerometer-based motion sensor 1704 provides the best measurement of body motion and/or muscle activity. This is figuratively represented by the lightning symbol (representing data signals) coming from accelerometer-based motion sensor 1704 in FIG. 18. In FIG. 19 wherein the person is moving their elbow at a high speed and/or elbow with a high number of repetitions, bending-based motion sensor 1703 provides the best measurement of body motion and/or muscle activity. This is figuratively represented by the lightning symbol (representing data signals) coming from bending-based motion sensor 1703 in FIG. 19. In another example, the order of which type of sensor provides better measurement over which movement speeds or numbers of movement repetitions can be different. In another example, data from all three types of sensors can be used for all movement speeds and/or movement repetitions, but the relative weight which is given to data from each type of sensor can vary with speed and/or number of repetitions.

In an example, data from one or more EMG sensors and one or more motion sensors can be jointly analyzed using one or more statistical methods selected from the group consisting of: Analysis of Variance (ANOVA), Artificial Neural Network (ANN), Auto Regression, Bayesian filter or other Bayesian statistical method, centroid analysis, Chi-Squared analysis, cluster analysis, covariance analysis, decision tree analysis, Eigenvalue Decomposition, Factor Analysis, Fast Fourier Transform (FFT) or other Fourier transformation, Hidden Markov model or other Markov modeling, Kalman Filter, kinematic modeling, Least Squares Estimation (LSE), Discriminant Analysis (DA), linear regression, linear transform, logarithmic function analysis, logistic regression, logit analysis, machine learning, mean or median analysis, Multivariate Linear Regression (MLR), Logit analysis, multivariate parametric classifiers, Neural Network, Non-Linear Programming (NLP), normalization, orthogonal transformation, pattern recognition, Power Spectral Density (PSD) analysis, power spectrum analysis, Principal Components analysis, probit analysis, Random Forest Gump (RFG) analysis, spectral analysis, spectroscopic analysis, spline function, survival analysis, three-dimensional modeling, time series analysis, variance, and wavelet analysis. Relevant variations discussed elsewhere in this disclosure or in priority-linked disclosures can also be applied to this example.

Figure 20:
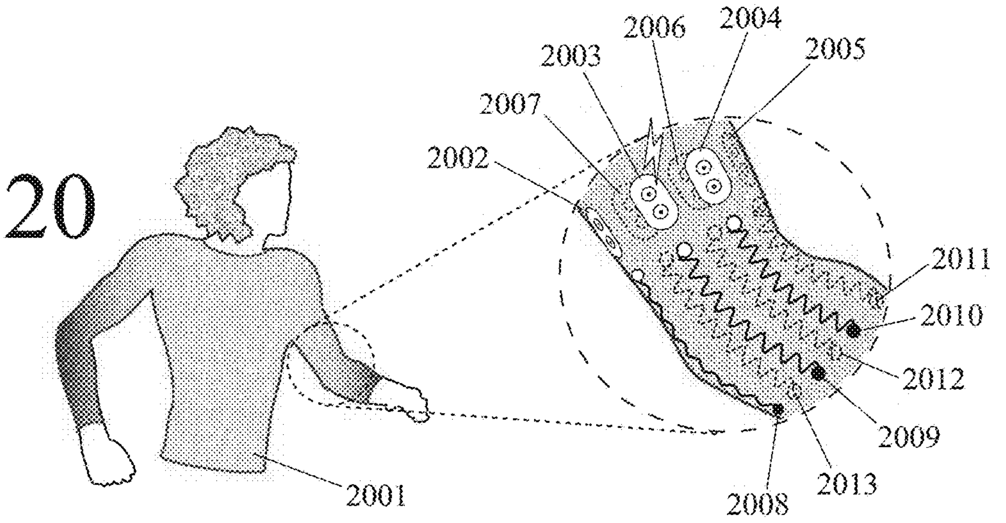
FIGS. 20 through 22 show electromyographic clothing with EMG sensors and bending-based motion sensors as clothing shifts on a body.
Figure 21:
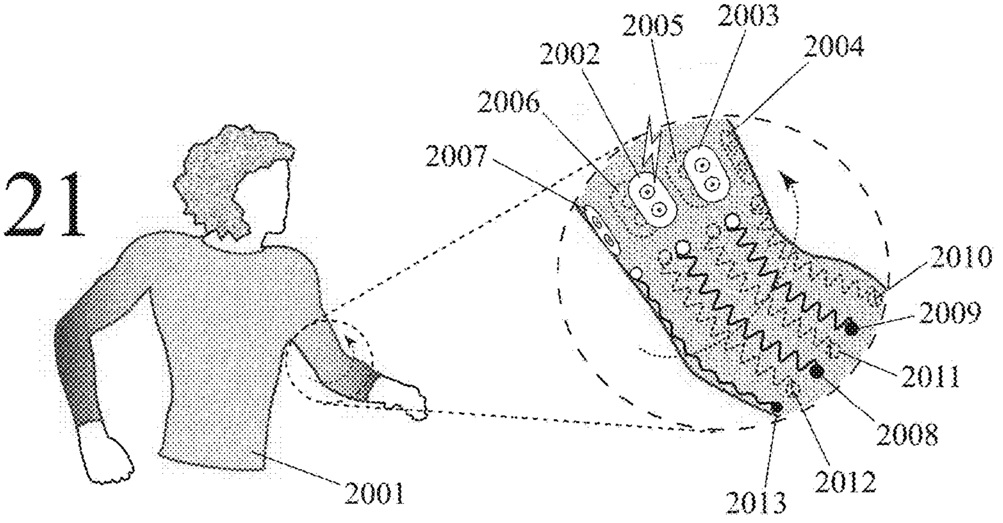
Figure 22:
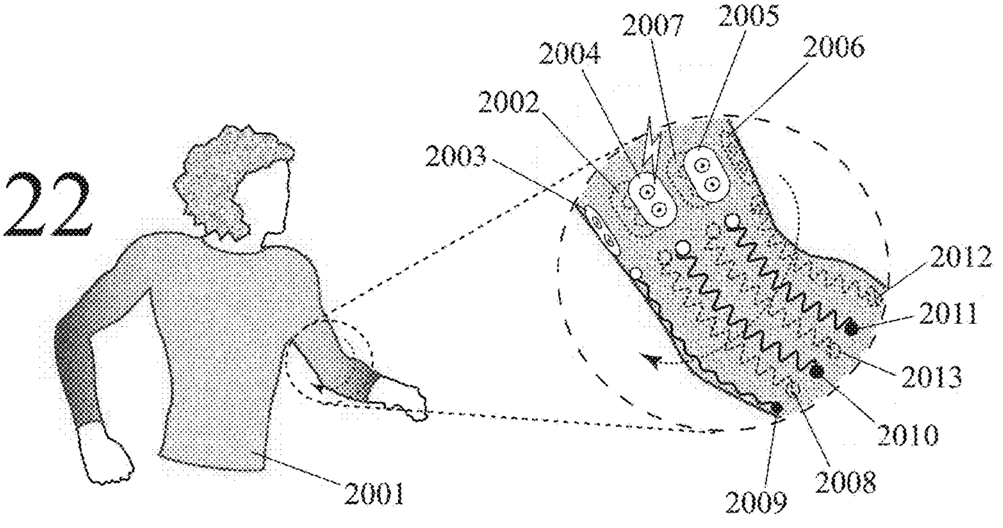

FIGS. 20 through 22 show another example of how this invention can be embodied in a device and system for measuring body motion and/or muscle activity comprising: one or more articles of clothing or clothing accessories; a plurality of motion sensors which are attached to and/or integrated into the one or more articles of clothing or clothing accessories, wherein these motion sensors are configured to collect motion data concerning changes in the configurations of a set of body joints; a plurality of electromyographic (EMG) sensors which are attached to and/or integrated into the one or more articles of clothing or clothing accessories, wherein these EMG sensors are configured to collect electromagnetic energy data concerning the neuromuscular activity of a set of muscles, and wherein muscles in the set of muscles move joints in the set of body joints; and a data processing unit which analyzes both motion data from the motion sensors and electromagnetic energy data from the EMG sensors in order to measure and/or model body motion and/or muscle activity.

FIGS. 20 through 22 show a running person wearing upper body garment 2001 at three different times. The left side of each figure shows the upper body of the running person. The right side of each of figure shows a corresponding close-up view (in a dashed-line circle) of the portion of upper body garment 2001 which covers the person's left elbow. The close-up views show that upper body garment 2001 includes: a plurality of EMG sensors (2002, 2003, 2004, 2005, 2006, and 2007) which encircle the person's arm above the person's elbow at different polar coordinate locations around the circumference of the person's arm; and a plurality of bending-based motion sensors (2008, 2009, 2010, 2011, 2012, and 2013) which longitudinally cross the person's elbow at different polar-coordinate locations around the circumference of the person's elbow. In an example, these polar-coordinate locations can be evenly spaced around the 360-degree circumference. Although each figure only shows a close-up view of one body joint (e.g. the left elbow), upper body garment 2001 can have similar (body motion and muscle energy measuring) portions and sensors which cover other upper body joints (such as the person's right elbow and both shoulders).

FIG. 20 shows a first situation in which the portion of upper body garment 2001 which covers the person's elbow does so in a first configuration such that: the EMG sensors encircle the person's arm at a first set of polar coordinates; and the motion sensors cross the person's elbow at a first set of polar coordinates.

FIG. 21 shows a second situation in which the portion of upper body garment 2001 which covers the person's elbow has shifted (partially) circumferentially and counter-clockwise around the person's arm and elbow. In an example, this shifting can be caused by the person moving their arm during an activity. As a result, in FIG. 21: the EMG sensors now encircle the person's arm at a second set of polar coordinates; and the motion sensors cross the person's elbow at a second set of polar coordinates. In this example, the second set of polar coordinates are shifted by approximately 60 degrees relative to the first set of polar coordinates. In an example, a second set of polar coordinates can be shifted by a number of degrees in a range of 10 to 90 degrees.

FIG. 22 shows a third situation in which the portion of upper body garment 2001 which covers the person's elbow has shifted (partially) circumferentially and clockwise around the person's arm and elbow. In an example, this shifting can be caused by the person moving their arm during an activity. As a result, in FIG. 22: the EMG sensors now encircle the person's arm at a third set of polar coordinates; and the motion sensors cross the person's elbow at a third set of polar coordinates. In this example, the second set of polar coordinates are shifted by approximately-60 degrees relative to the first set of polar coordinates. In an example, a third set of polar coordinates can be shifted by a number of degrees in a range of −10 to −90 degrees.

In an example, a device and system for measuring body motion and/or muscle activity can analyze changes in patterns of data from the plurality of EMG sensors and/or the plurality of motion sensors as a person moves. In an example, pattern recognition can be used to identify which EMG sensors and/or which motion sensors are at which polar coordinates around the person's arm and/or elbow. In this manner, the device and system can identify when the upper body garment has shifted (partially) circumferentially around the person's arm and/or elbow and can virtually correct for such shifts.

In an example, a device and system can identify which EMG sensor and/or which motion sensor is at which location relative to specific muscles and/or joints. In an example, a device and system can assign different sensing roles to different EMG and/or motion sensors around the circumference of the person's arm and/or elbow to correct for physical shifting of these EMG and/or motion sensors around the person's arm and/or elbow due to shifting clothing.

For example, in FIG. 20, EMG sensor 2003 serves the role of measuring neuromuscular signals from the anterior of the person's arm. This is figuratively represented by a lightning symbol coming from EMG sensor 2003 in FIG. 20. However, in FIG. 21, EMG sensor 2003 has been physically (circumferentially) shifted by clothing movement to a different location. In FIG. 21, EMG sensor 2002 is now in the location where EMG sensor 2003 was in FIG. 20. In this example, the device and system recognizes that this physical shift has occurred by analyzing the patterns of electromagnetic data coming from these sensors as the person moves their arm. Accordingly, in FIG. 21, the device and system assigns the role of measuring neuromuscular signals from the anterior of the person's arm to EMG sensor 2002 (instead of EMG sensor 2003). As another example of such shift compensation, in FIG. 22, EMG sensor 2003 has been circumferentially shifted in the other direction. Accordingly, the device and system assigns the role of measuring neuromuscular signals from the anterior of the person's arm to EMG sensor 2004. As shown by these examples, a device and system can virtually correct for circumferential clothing shifting by using data analysis to identify clothing shifts and changing its interpretation of data from different sensors.

In an example, data from one or more EMG sensors and one or more motion sensors can be jointly analyzed using one or more statistical methods selected from the group consisting of: Analysis of Variance (ANOVA), Artificial Neural Network (ANN), Auto Regression, Bayesian filter or other Bayesian statistical method, centroid analysis, Chi-Squared analysis, cluster analysis, covariance analysis, decision tree analysis, Eigenvalue Decomposition, Factor Analysis, Fast Fourier Transform (FFT) or other Fourier transformation, Hidden Markov model or other Markov modeling, Kalman Filter, kinematic modeling, Least Squares Estimation (LSE), Discriminant Analysis (DA), linear regression, linear transform, logarithmic function analysis, logistic regression, logit analysis, machine learning, mean or median analysis, Multivariate Linear Regression (MLR), Logit analysis, multivariate parametric classifiers, Neural Network, Non-Linear Programming (NLP), normalization, orthogonal transformation, pattern recognition, Power Spectral Density (PSD) analysis, power spectrum analysis, Principal Components analysis, probit analysis, Random Forest Gump (RFG) analysis, spectral analysis, spectroscopic analysis, spline function, survival analysis, three-dimensional modeling, time series analysis, variance, and wavelet analysis. Relevant variations discussed elsewhere in this disclosure or in priority-linked disclosures can also be applied to this example.

FIGS. 23 through 26 show two examples of a device and system for measuring muscle activity comprising: one or more articles of clothing or clothing accessories which are worn by a person; one or more electromyographic (EMG) sensors which are attached to and/or integrated into the one or more articles of clothing or clothing accessories in order to collect electromagnetic energy data concerning the neuromuscular activity of a selected set of muscles; and one or more actuators which automatically adjust the fit of the one or more articles of clothing or clothing accessories so that the one or more electromyographic (EMG) sensors more accurately measure the neuromuscular activity of the selected set of muscles.

In an example, one or more actuators can be circumferential actuators which are attached to and/or integrated into a portion of an article of clothing (or clothing accessory) which spans (at least part of) the circumference of a body member. In an example, one or more circumferential actuators can span (at least part of) the circumference of a person's arm, elbow, shoulder, torso, hip, or leg. In an example, one or more circumferential actuators can be piezoelectric members which contract or expand in response to the application of electric current. In an example, one or more circumferential actuators can be Micro Electro Mechanical Systems (MEMS) which contract or expand when activated.

In an example, contraction or expansion of one or more circumferential actuators which are integrated into an article of clothing (or clothing accessory) can change how tightly or loosely the article of clothing (or clothing accessory) fits around a portion of a person's body. In an example, contraction or expansion of one or more circumferential actuators which are integrated into an article of clothing (or clothing accessory) can change how tightly or loosely an article of clothing (or clothing accessory) fits around a person's arm, elbow, shoulder, torso, hip, or leg.

In an example, a device and system for measuring muscle activity can monitor electromagnetic energy signals received from one or more EMG sensors which are attached to or integrated into an article of clothing (or clothing accessory). When these electromagnetic energy signals are weak or inaccurate because the EMG sensors are not sufficiently close to the person's body, then the device and system can contract one or more circumferential actuators so that the clothing fits closer to the person's body and thus the EMG sensors are closer to the person's body as well. In an example, a device and system for measuring muscle activity can adjust the fit of clothing in real time, based on analysis of data from EMG sensors, to adjust how close the EMG sensors are to the person's body. In an example, such a device and system can allow an article of clothing (or a clothing accessory) to be relatively loose when EMG sensors do not need to be very close to a person's body, but can activate one or more circumferential actuators to make the article of clothing (or clothing accessory) fit tighter when the EMG sensors must be closer to the person's body for accurate muscle activity measurement.

Figure 23:
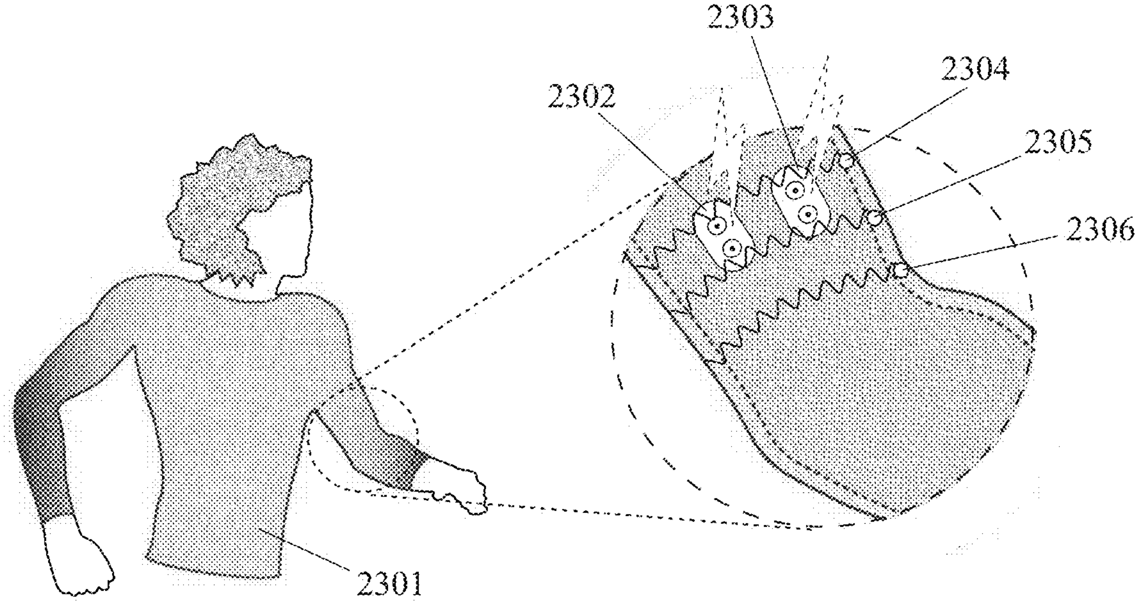
FIGS. 23 and 24 show electromyographic clothing with EMG sensors and circumferential actuators to adjust fit.

FIG. 23 shows an example of such a device and system for measuring muscle activity when upper body garment 2301 is too loose around a person's left elbow. In FIG. 23, the underlying perimeter of the surface of the person's body is shown by dotted lines in the close-up semi-transparent view within the dashed-line circle on the right side of FIG. 23. In FIG. 23, EMG sensors 2302 and 2303 measure weak and/or inaccurate electromagnetic signals from an underlying set of muscles in the person's arm because the clothing fits too loosely and the EMG sensors are too far away from the surface of the person's arm. These weak and/or inaccurate electromagnetic signals are figuratively represented by the dotted-line lightning bolt symbols associated with EMG sensors 2302 and 2303 in FIG. 23.

Figure 24:
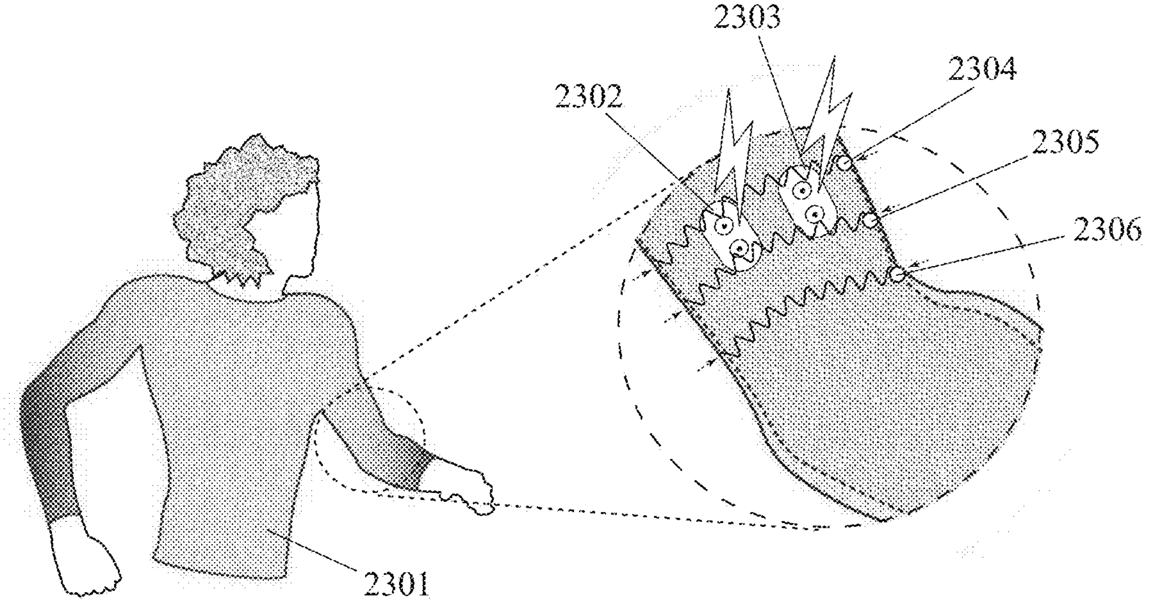

In FIG. 24, the device and system has analyzed data from EMG sensors 2302 and 2303 and identified that these signals were weak and/or inaccurate because EMG sensors 2302 and 2303 were too far away from the surface of the person's arm. In FIG. 24, the device and system has contracted circumferential actuators 2304, 2305, and 2306; which has made upper body garment 2301 fit more tightly around the person's arm; which has brought EMG sensors 2302 and 2303 closer to the surface of the person's arm; which has improved the strength and/or accuracy of electromagnetic signals received by the EMG sensors from a selected set of muscles in the person's arm. These strong and/or accurate electromagnetic signals are figuratively represented by the solid-line lightning bolt symbols associated with EMG sensors 2302 and 2303 in FIG. 24. In other words—"If the fit ain't great, you must actuate."

FIGS. 23 and 24 only show close-up, semi-transparent views (in dashed-line circles) of the person's left elbow, but upper body garment 2301 can have similar EMG sensors and circumferential actuators in other portions of the upper body garment which cover other body joints (such as the other elbow, shoulders, torso, etc.). In an example, a device and system for measuring muscle activity can also comprise a lower body garment with similar EMG sensors and circumferential actuators covering other body joints (such as hips, knees, and ankles). Relevant variations discussed elsewhere in this disclosure or in priority-linked disclosures can also be applied to this example.

Figure 25:
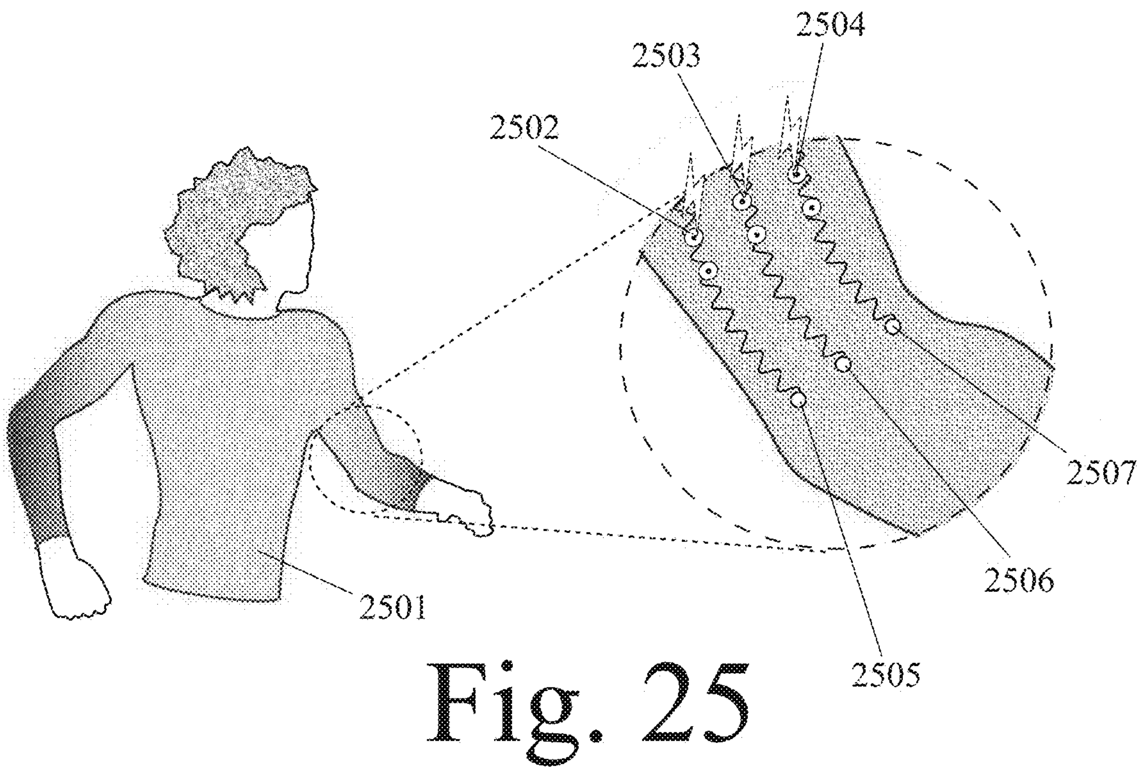
FIGS. 25 and 26 show electromyographic clothing with EMG sensors and longitudinal actuators to adjust fit.
Figure 26:
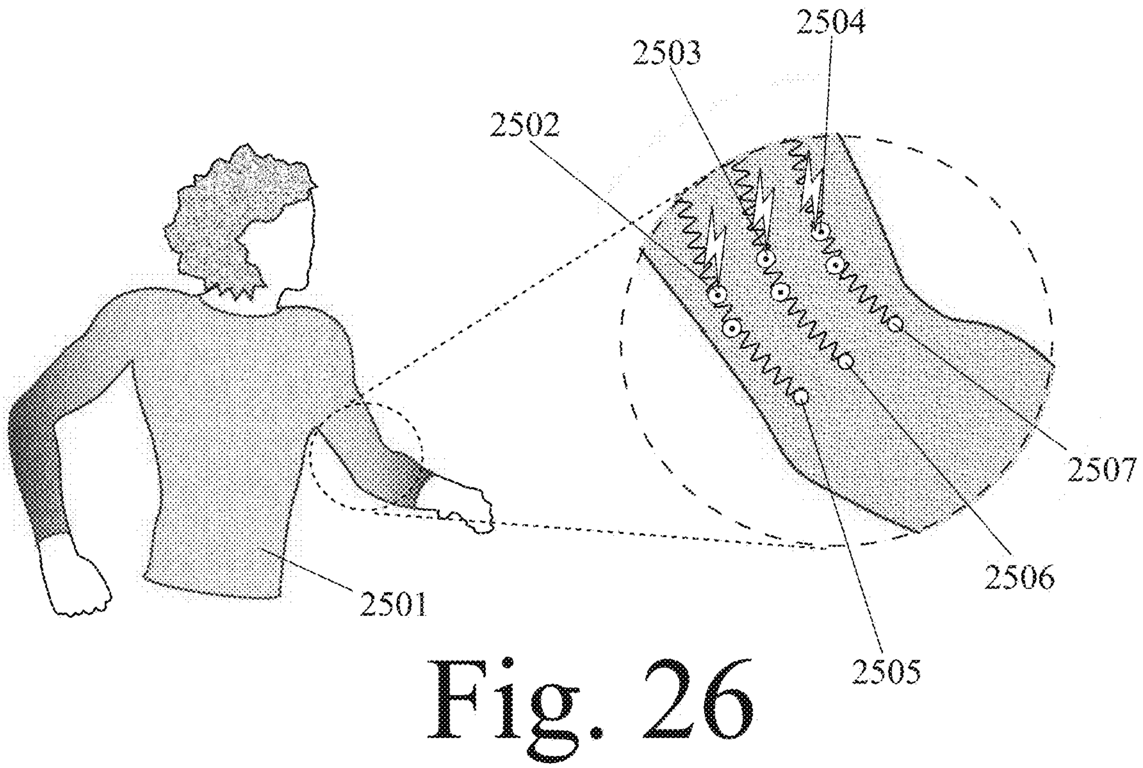

FIGS. 25 and 26 show another example of a device and system for measuring muscle activity comprising: one or more articles of clothing or clothing accessories which are worn by a person; one or more electromyographic (EMG) sensors which are attached to and/or integrated into the one or more articles of clothing or clothing accessories in order to collect electromagnetic energy data concerning the neuromuscular activity of a selected set of muscles; and one or more actuators which automatically adjust the fit of the one or more articles of clothing or clothing accessories so that the one or more electromyographic (EMG) sensors more accurately measure the neuromuscular activity of the selected set of muscles.

In an example, one or more actuators can be longitudinal actuators which are attached to and/or integrated into a portion of an article of clothing (or clothing accessory) which spans (at least part of) the longitudinal surface of a body member. In an example, one or more longitudinal actuators can span (at least part of) the length of a person's arm, elbow, shoulder, torso, hip, or leg. In an example, one or more longitudinal actuators can be piezoelectric members which contract or expand in response to the application of electric current. In an example, one or more longitudinal actuators can be Micro Electro Mechanical Systems (MEMS) which contract or expand when activated.

In an example, contraction or expansion of one or more longitudinal actuators which are integrated into an article of clothing (or clothing accessory) can change how tightly or loosely the article of clothing (or clothing accessory) fits along a portion of a person's body. In an example, contraction or expansion of one or more longitudinal actuators which are integrated into an article of clothing (or clothing accessory) can change how tightly or loosely an article of clothing (or clothing accessory) fits along a person's arm, elbow, shoulder, torso, hip, or leg.

In an example, a device and system for measuring muscle activity can monitor electromagnetic energy signals received from one or more EMG sensors which are attached to or integrated into an article of clothing (or clothing accessory). When these electromagnetic energy signals are weak or inaccurate because the EMG sensors are not sufficiently close to the person's body, then the device and system can contract one or more longitudinal actuators so that the clothing fits closer to the person's body and thus the EMG sensors are closer to the person's body as well. In an example, a device and system for measuring muscle activity can adjust the fit of clothing in real time, based on analysis of data from EMG sensors, to adjust how close the EMG sensors are to the person's body. In an example, such a device and system can allow an article of clothing (or a clothing accessory) to be relatively loose when EMG sensors do not need to be very close to a person's body, but can activate one or more longitudinal actuators to make the article of clothing (or clothing accessory) fit tighter when the EMG sensors must be closer to the person's body for accurate muscle activity measurement.

FIG. 25 shows an example of such a device and system for measuring muscle activity when upper body garment 2501 is too loose along a person's left elbow. In FIG. 25, EMG sensors 2502, 2503, and 2504 measure weak and/or inaccurate electromagnetic signals from an underlying set of muscles in the person's arm because the clothing fits too loosely and the EMG sensors are too far away from the surface of the person's arm. These weak and/or inaccurate electromagnetic signals are figuratively represented by the dotted-line lightning bolt symbols associated with EMG sensors 2502, 2503, and 2504 in FIG. 25.

In FIG. 26, the device and system has analyzed data from EMG sensors 2502, 2503, and 2504 and identified that these signals were weak and/or inaccurate because EMG sensors 2502, 2503, and 2504 were too far away from the surface of the person's arm. In FIG. 26, the device and system has contracted longitudinal actuators 2505, 2506, and 2507; which has made upper body garment 2501 fit more tightly along the person's arm; which has brought EMG sensors 2502, 2503, and 2504 closer to the surface of the person's arm; which has improved the strength and/or accuracy of electromagnetic signals received by the EMG sensors from a selected set of muscles in the person's arm. These strong and/or accurate electromagnetic signals are figuratively represented by the solid-line lightning bolt symbols associated with EMG sensors 2502, 2503, and 2504 in FIG. 26.

FIGS. 25 and 26 only show close-up, semi-transparent views (in dashed-line circles) of the person's left elbow, but upper body garment 2501 can have similar EMG sensors and longitudinal actuators in other portions of the upper body garment which cover other body joints (such as the other elbow, shoulders, torso, etc.). In an example, a device and system for measuring muscle activity can also comprise a lower body garment with similar EMG sensors and longitudinal actuators covering other body joints (such as hips, knees, and ankles). Relevant variations discussed elsewhere in this disclosure or in priority-linked disclosures can also be applied to this example.

FIGS. 27 through 30 show two examples of an article of clothing for measuring muscle activity comprising: an article of clothing worn by a person, wherein this article of clothing has a first set of clothing sections with a first average distance from the surface of the person's body and a second set of clothing sections with a second average distance from the surface of the person's body, and wherein the second average distance is less than the first average distance; and one or more electromyographic (EMG) sensors which are attached to and/or integrated into one or more of the clothing sections in the second set. In an example, the second average distance from the person's body can be less than half of the first average distance from the person's body. In an example, the second average distance can be 10% to 75% of the first average distance.

FIGS. 27 through 30 also show two examples of an article of clothing for measuring muscle activity comprising: an article of clothing worn by a person, wherein this article of clothing has an overall first level of closeness of fit with respect to the person's body, wherein this article of clothing has selected tighter areas with a second level of closeness of fit with respect to the person's body, and wherein the second level is at least 10% closer than the first level; and one or more electromyographic (EMG) sensors which are attached to and/or integrated into one or more of the selected tighter areas.

In an example, a clothing section in the second set can at span a portion of the person's body in a circumferential manner. In an example, a clothing section in the second set can encircle a portion of the person's body. In an example, a clothing section in the second set can encircle a person's shoulder, elbow, arm, torso, hip, knee, or leg. In an example, a clothing section in the second set can be shaped like a ring, band, and/or conic section which spans at least a portion of the circumference of a portion of the person's body. In an example, a clothing section in the second set can be shaped like a ring, band, and/or conic section which encircles a portion of the person's body. In an example, a clothing section in the second set can be shaped like a ring, band, and/or conic section which encircles a person's shoulder, elbow, arm, torso, hip, knee, or leg.

In an example, an article of clothing for measuring muscle activity can include multiple rings and/or bands which fit more tightly than the overall article of clothing, wherein these multiple rings and/or bands each include one or more electromyographic (EMG) sensors. In an example, clothing sections in the second set can comprise two or more close-fitting rings or bands around each of the person's arms and three or more close-fitting rings or bands around each of the person's legs. In an example, each of the clothing sections in the second set can further comprise one or more EMG sensors.

In an example, the exterior diameter (or perimeter) of an article of clothing can be narrower (or smaller) for the second sections than for the first sections of the article of clothing, externally reflecting the fact that the second sections fit tighter (closer to the surface of the person's body) than the first sections. In an alternative example, the exterior diameter (or perimeter) of the article of clothing need not be narrower (or smaller) when there are gaps, pouches, or compartments between an interior surface (layer) of the clothing and an external surface (layer) of the clothing.

Figure 27:
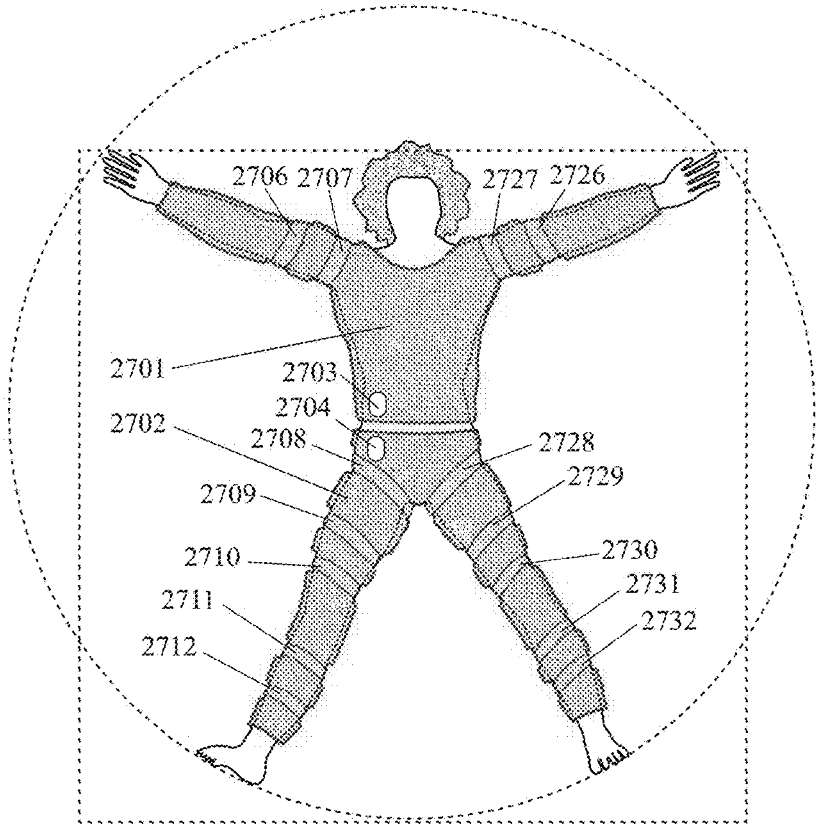
FIGS. 27 through 30 show two examples of electromyographic clothing with EMG sensors on selected close-fitting bands.
Figure 28:
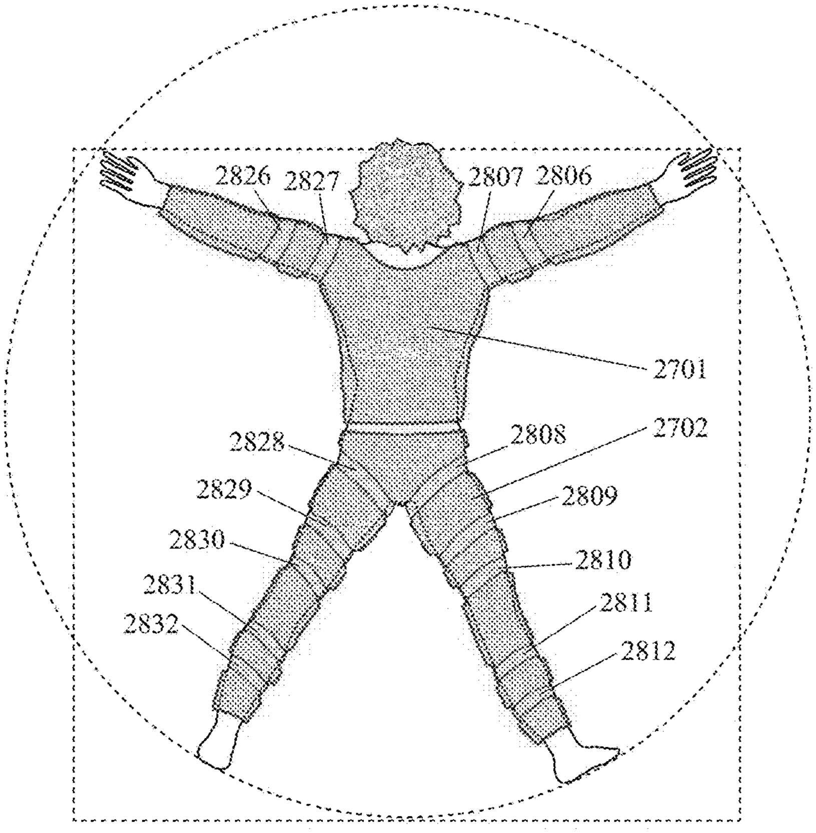

FIGS. 27 and 28 show an example of an article of clothing for measuring muscle activity comprising: an article of clothing worn by a person, wherein this article of clothing has a first set of clothing sections with a first average distance from the surface of the person's body and a second set of clothing sections with a second average distance from the surface of the person's body, and wherein the second average distance is less than the first average distance; and one or more electromyographic (EMG) sensors which are attached to and/or integrated into one or more of the clothing sections in the second set. In this example, the exterior diameter (or perimeter) of the article of clothing is narrower (or smaller) for the second clothing sections than for the first clothing sections, externally reflecting the fact that the second sections fit tighter (closer to the surface of the person's body) than the first sections.

Looking at FIGS. 27 and 28 in detail, they show upper body garment 2701 and lower body garment 2702. These figures also show an upper body data processing unit 2703 and a lower body data processing unit 2704. FIG. 27 shows a second set of clothing sections which fit more closely than the overall garments. In the front view of this example shown in FIG. 27, the second set of clothing sections comprises 2706, 2707, 2708, 2709, 2710, 2711, 2712, 2726, 2727, 2728, 2729, 2730, 2731, and 2732. Each of these sections further comprises one or more EMG sensors which are not shown in this view. In the rear view of this example shown in FIG. 28, the second set of clothing sections comprises 2806, 2807, 2808, 2809, 2810, 2811, 2812, 2826, 2827, 2828, 2829, 2830, 2831, and 2832. In this example, the second set of clothing sections are half rings or half bands which each span a portion of the circumference of the person's shoulder, arm, hip, or leg. In another example, a second set of clothing sections can be full rings or full bands which each spans the full circumference of a person's shoulder, arm, hip, or leg. Relevant variations discussed elsewhere in this disclosure or in priority-linked disclosures can also be applied to this example.

Figure 29:
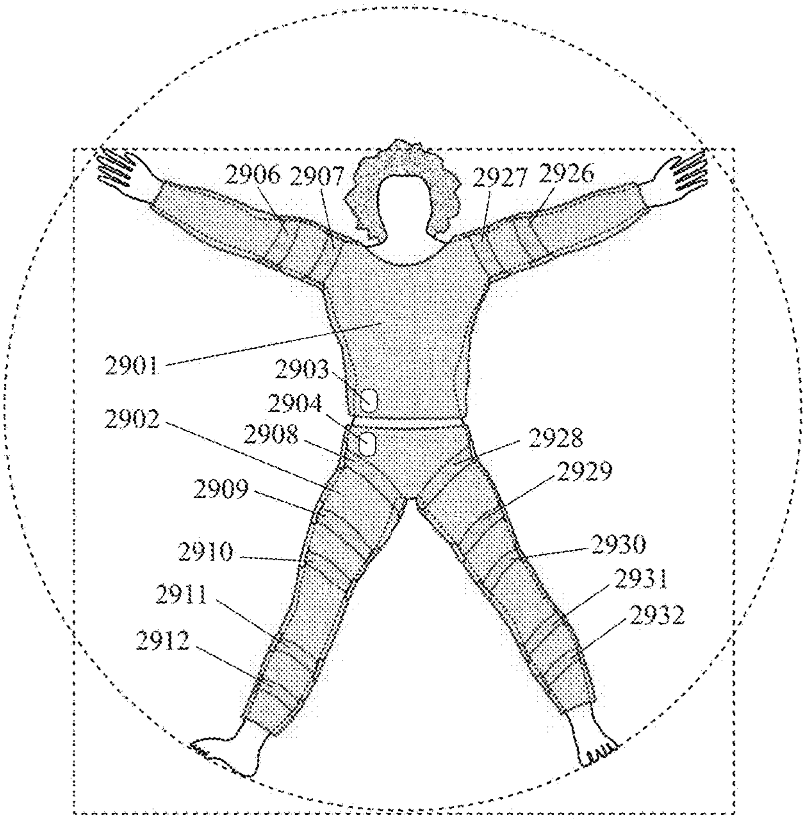
Figure 30:
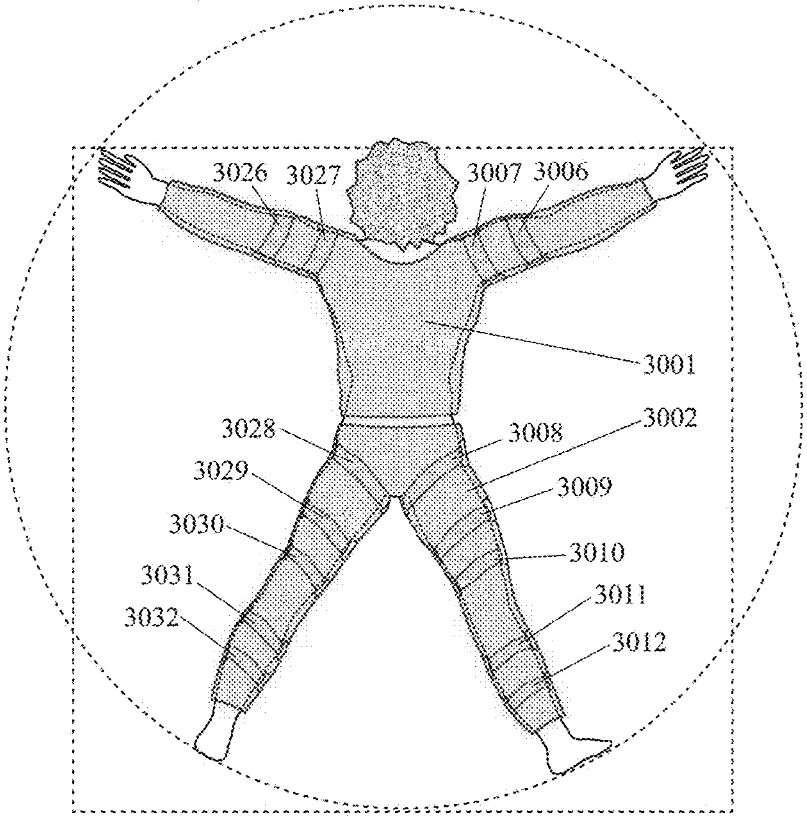

FIGS. 29 and 30 show another example of an article of clothing for measuring muscle activity comprising: an article of clothing worn by a person, wherein this article of clothing has a first set of clothing sections with a first average distance from the surface of the person's body and a second set of clothing sections with a second average distance from the surface of the person's body, and wherein the second average distance is less than the first average distance; and one or more electromyographic (EMG) sensors which are attached to and/or integrated into one or more of the clothing sections in the second set. This example is like the one in FIGS. 27 and 28, except that the exterior diameter (or perimeter) of the article of clothing is not narrower (or smaller) for the second sections because there are gaps, pouches, or compartments between an interior surface (layer) of the clothing and an external surface (layer) of the clothing—especially for the second sections.

Looking at FIGS. 29 and 30 in detail, they show upper body garment 2901 and lower body garment 2902. These figures also show an upper body data processing unit 2903 and a lower body data processing unit 2904. FIG. 29 shows a second set of clothing sections which fit more closely than the overall garments. In the front view of this example shown in FIG. 29, the second set of clothing sections comprises 2906, 2907, 2908, 2909, 2910, 2911, 2912, 2926, 2927, 2928, 2929, 2930, 2931, and 2932. Each of these sections further comprises one or more EMG sensors which are not shown in this view. In the rear view of this example shown in FIG. 30, the second set of clothing sections comprises 3006, 3007, 3008, 3009, 3010, 3011, 3012, 3026, 3027, 3028, 3029, 3030, 3031, and 3032. In this example, the second set of clothing sections are half rings or half bands which each span a portion of the circumference of the person's shoulder, arm, hip, or leg. In another example, a second set of clothing sections can be full rings or full bands which each spans the full circumference of a person's shoulder, arm, hip, or leg. Relevant variations discussed elsewhere in this disclosure or in priority-linked disclosures can also be applied to this example.

Figure 31:
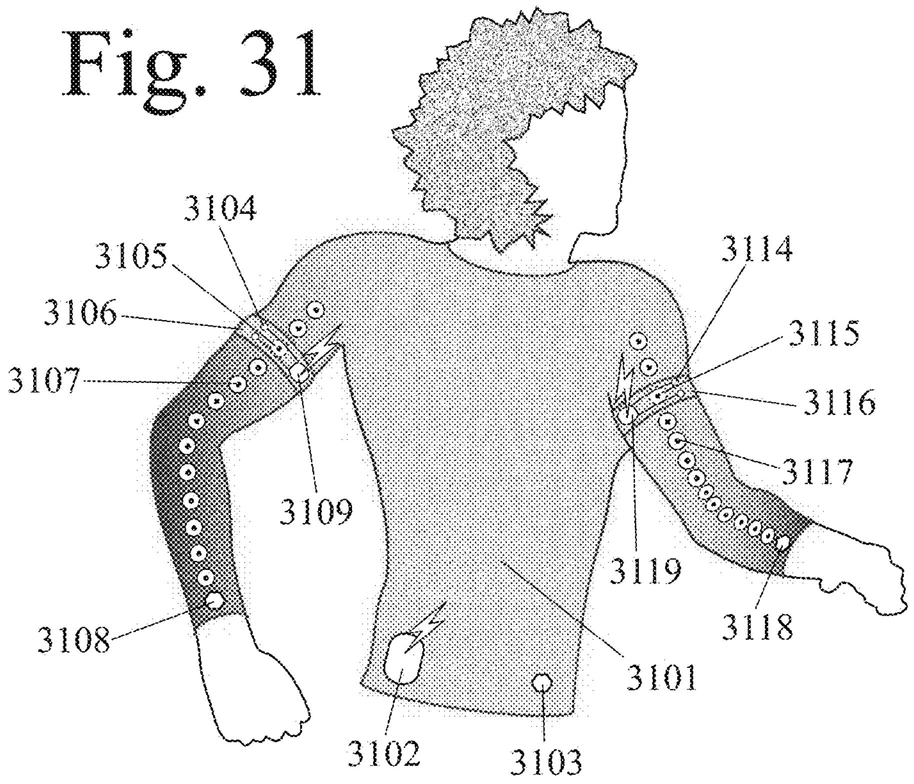
FIGS. 31 and 32 show electromyographic clothing with a longitudinal plurality of attachment mechanisms for EMG sensors.
Figure 32:
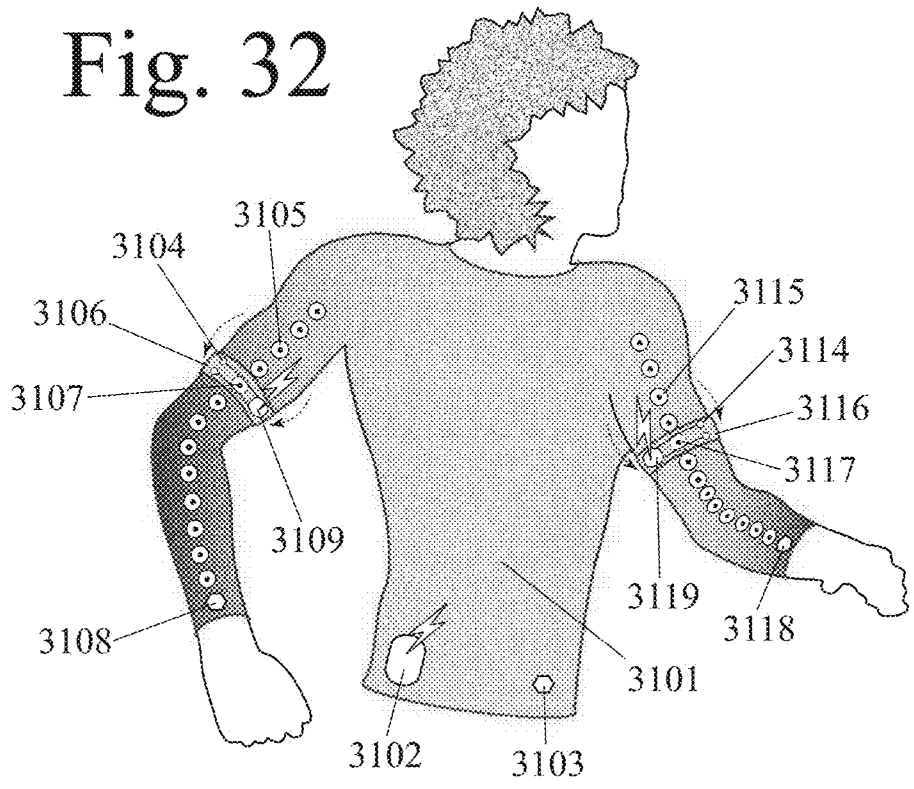

FIGS. 31 and 32 show an example of an article of clothing for measuring muscle activity comprising: an article of clothing worn by a person, wherein this article of clothing further comprises a plurality of attachment mechanisms which are distributed longitudinally along the person's arm or leg; and one or more modular electromyographic (EMG) sensors which can be removably attached by the person to one or more of the attachment mechanisms. This article of clothing allows a person to selectively attach one or more modular electromyographic (EMG) sensors to selected locations on the article of clothing so as to most effectively measure electromagnetic signals from a selected muscle or set of muscles. In an example, a device or system including this article of clothing can analyze data from the EMG signals as they are removably attached to different locations and can give the person feedback concerning which attachment locations are optimal.

Specifically, FIGS. 31 and 32 show: upper body garment 3101; data processing unit 3102; motion sensors 3103, 3108, and 3118; attachment mechanisms (including 3105, 3107, 3115, and 3117); movable bands 3106 and 3116; EMG sensors 3104 and 3114; and wireless data transmitters 3109 and 3119. FIG. 31 shows this article of clothing when movable bands 3106 and 3116 (and EMG sensors 3104 and 3114 on these bands) are attached to attachment mechanisms 3105 and 3115. FIG. 32 shows this same article of clothing after moveable bands 3106 and 3116 (and EMG sensors 3104 and 3114 on these bands) have been moved down the person's arms to attachment mechanisms 3107 and 3117. In an example, an attachment mechanism can be selected from the group consisting of: snap, button, clip, clasp, hook- and -eye connection, pin, plug, and zipper.

In an example, movement of the bands and EMG sensors from FIG. 31 to FIG. 32 can enable more accurate measurement of electromagnetic energy from a selected muscle or set of muscles. In an example, movement of the bands and EMG sensors from FIG. 31 to FIG. 32 can enable measurement of electromagnetic energy from a different selected muscle or set of muscles. In an example, a device or system including this article of clothing can provide real-time audio, visual, or tactile feedback to the person in order to guide the person to attach the bands (and EMG sensors) to the best attachment locations for optimally measuring electromagnetic signals from a selected muscle or set of muscles. Relevant variations discussed elsewhere in this disclosure or in priority-linked disclosures can also be applied to this example.

FIGS. 33 through 36 show two examples of a device and system for measuring body motion and/or muscle activity comprising: at least one electromyographic (EMG) sensor; and at least one article of clothing (or clothing accessory), wherein the article of clothing (or clothing accessory) has a track or pathway to which the electromyographic (EMG) sensor is attached, and wherein the electromyographic (EMG) sensor can be moved relative to the article of clothing (or clothing accessory) by moving the electromyographic (EMG) sensor along the track or pathway.

In an example, an EMG sensor can be moved along a track or pathway by sliding the EMG sensor along the track or pathway. In an example, an EMG sensor can be moved circumferentially around (a portion of) a person's shoulder, arm, torso, hip, or leg by moving the EMG sensor along a circumferential track or pathway. In an example, a circumferential track or pathway can span some (or all) of the circumference of a person's shoulder, arm, torso, hip, or leg. In an example, an EMG sensor can be moved longitudinally along (a portion of) the length of a person's shoulder, arm, torso, hip, or leg by moving the EMG sensor along a longitudinal track or pathway. In an example, a longitudinal track or pathway can span some or all of the length of a person's shoulder, arm, torso, hip, or leg.

In an example, the ability to move an EMG sensor along a circumferential track or pathway on an article of clothing (or clothing accessory) can enable more accurate measurement of electromagnetic signals from a selected muscle or set of muscles. In an example, the ability to move an EMG sensor along a longitudinal track or pathway on an article of clothing (or clothing accessory) can enable more accurate measurement of electromagnetic signals from a selected muscle or set of muscles.

In an example, a person wearing this article of clothing (or clothing accessory) can manually move one or more EMG sensors along a track or pathway. In an example, an article of clothing can be part of a device and system which provides the person with feedback to guide the person to move an EMG sensor to the best location along a track or pathway for optimal measurement of electromagnetic signals from a selected muscle or set of muscles. In an example, an article of clothing can further comprise one or more actuators which automatically move one or more EMG sensors to the best locations for optimal measurement of electromagnetic signals from one or more selected muscles or sets of muscles.

Figure 33:
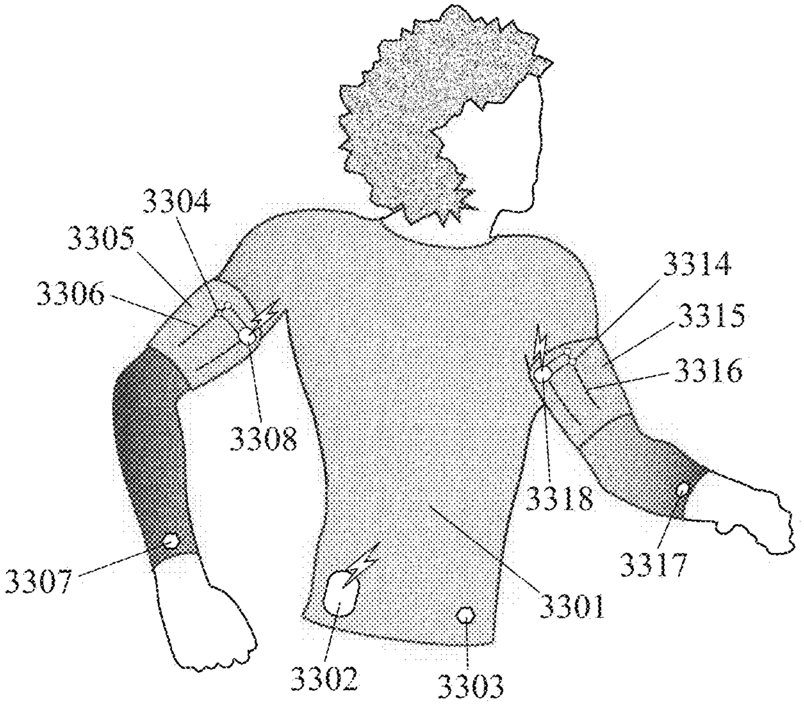
FIGS. 33 through 36 show two examples of electromyographic clothing with sliding tracks for EMG sensors.
Figure 34:
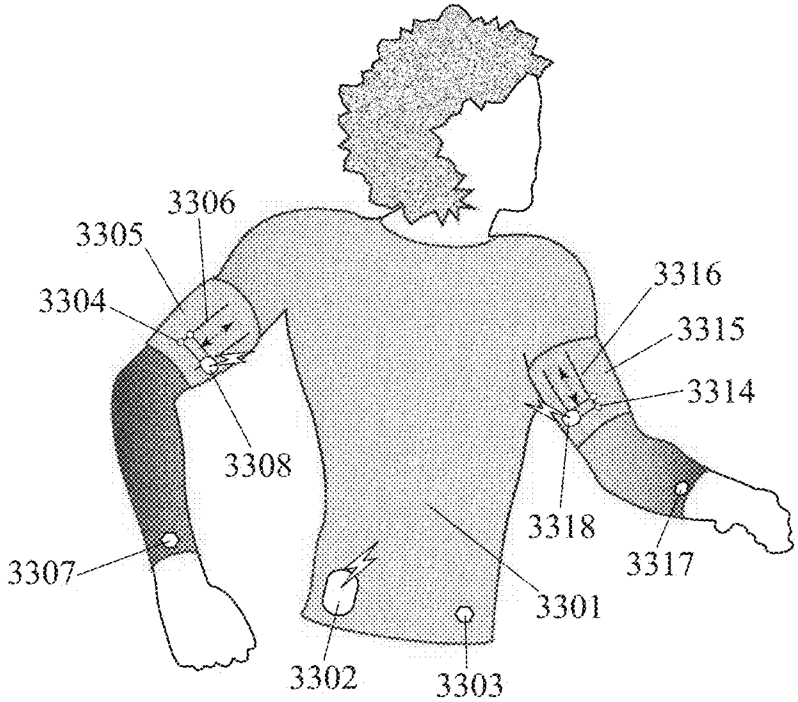

FIGS. 33 and 34 show: upper body garment 3301; data processing unit 3302; motion sensors 3303, 3307, and 3317; arm bands 3305 and 3315; longitudinal tracks or pathways 3306 and 3316; EMG sensors 3304 and 3314; and wireless data transmitters 3308 and 3318. FIG. 33 shows this example in a first configuration wherein EMG sensors 3304 and 3314 are at upper locations along tracks or pathways 3306 and 3316. FIG. 34 shows this example in a second configuration after EMG sensors 3304 and 3314 have been slid longitudinally along tracks or pathways 3306 and 3316 to lower locations. In an example, EMG sensors 3304 and 3314 can better measure electromagnetic energy from a selected muscle or set of muscles from the lower locations. In an example, EMG sensors 3304 and 3314 can measure electromagnetic energy from a different set of selected muscles or group of muscles from the lower locations. Relevant variations discussed elsewhere in this disclosure or in priority-linked disclosures can also be applied to this example.

Figure 35:
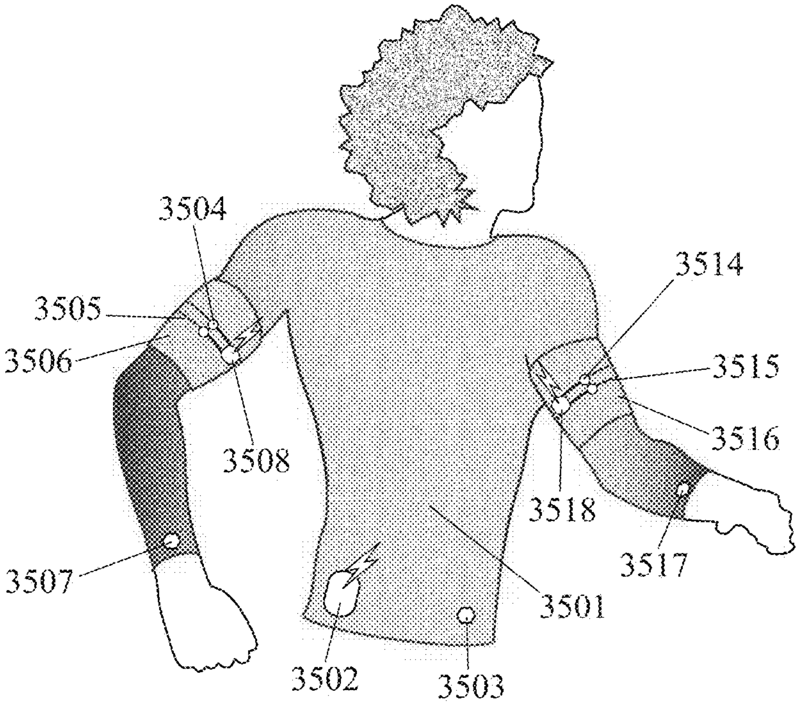
Figure 36:
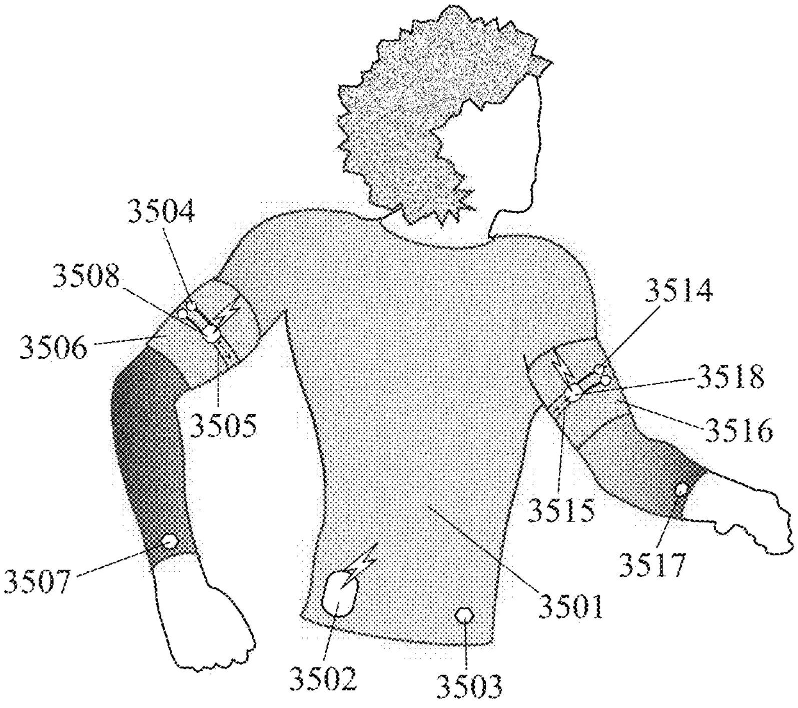

FIGS. 35 and 36 show: upper body garment 3501; data processing unit 3502; motion sensors 3503, 3507, and 3517; arm bands 3506 and 3516; circumferential tracks or pathways 3505 and 3515; EMG sensors 3504 and 3514; and wireless data transmitters 3508 and 3518. FIG. 35 shows this example in a first configuration wherein EMG sensors 3504 and 3514 are at first radial locations along tracks or pathways 3505 and 3515. FIG. 36 shows this example in a second configuration after EMG sensors 3504 and 3514 have been slid circumferentially along tracks or pathways 3505 and 3515 to second radial locations. In an example, EMG sensors 3504 and 3514 can better measure electromagnetic energy from a selected muscle or set of muscles from the second radial locations. In an example, EMG sensors 3504 and 3514 can measure electromagnetic energy from a different set of selected muscles or group of muscles from the second radial locations.

FIGS. 37 through 40 show two examples of an article of clothing for measuring body motion and/or muscle activity comprising: an article of clothing worn by a person, wherein this article of clothing has a first set of clothing sections with a first average distance from the surface of the person's body and a second set of clothing sections with a second average distance from the surface of the person's body, and wherein the second average distance can be manually decreased by the person while the person is wearing the article of clothing; and one or more electromyographic (EMG) sensors which are attached to and/or integrated into one or more of the clothing sections in the second set. In an example, the second average distance from the person's body can be manually decreased to less than half of the first average distance from the person's body. In an example, the second average distance can be manually decreased to between 10% and 90% of the first average distance.

In an example, a clothing section in the second set can span a portion of the person's body in a circumferential manner. In an example, a clothing section in the second set can encircle a portion of the person's body. In an example, a clothing section in the second set can encircle a person's shoulder, elbow, arm, torso, hip, knee, or leg. In an example, a clothing section in the second set can be shaped like a ring, band, and/or conic section which spans at least a portion of the circumference of a portion of the person's body. In an example, a clothing section in the second set can be shaped like a ring, band, and/or conic section which encircles a portion of the person's body. In an example, a clothing section in the second set can be shaped like a ring, band, and/or conic section which encircles a person's shoulder, elbow, arm, torso, hip, knee, or leg.

In an example, an article of clothing for measuring body motion and/or muscle activity can include multiple rings and/or bands whose level of tightness can be manually increased by the person wearing the article of clothing, wherein these multiple rings and/or bands each include one or more electromyographic (EMG) sensors. In an example, an article of clothing can comprise two or more adjustable-fit rings or bands around each of the person's arms and three or more adjustable-fit rings or bands around each of the person's legs. In an example, each of these rings or bands can further comprise one or more EMG sensors.

In an example, the fit of a second set of clothing sections (such as rings or bands) in an article of clothing for measuring body motion and/or muscle activity can be adjusted by means of hook- and -eye connections. In an example, a person can unfasten a hook- and -eye connection of a clothing section (such as a ring or band) and refasten the clothing section with a smaller diameter around a shoulder, arm, elbow, torso, hip, knee, or leg. In an example, the fit of a second set of clothing sections (such as rings or bands) in an article of clothing for measuring body motion and/or muscle activity can be adjusted by means of a rotating knob which spools a tensile member. In an example, a person can turn a rotating member, which in turn spools a tensile member and tightens the clothing section (such as a ring or band) around a shoulder, arm, elbow, torso, hip, knee, or leg. Relevant variations discussed elsewhere in this disclosure or in priority-linked disclosures can also be applied to this example.

Figure 37:
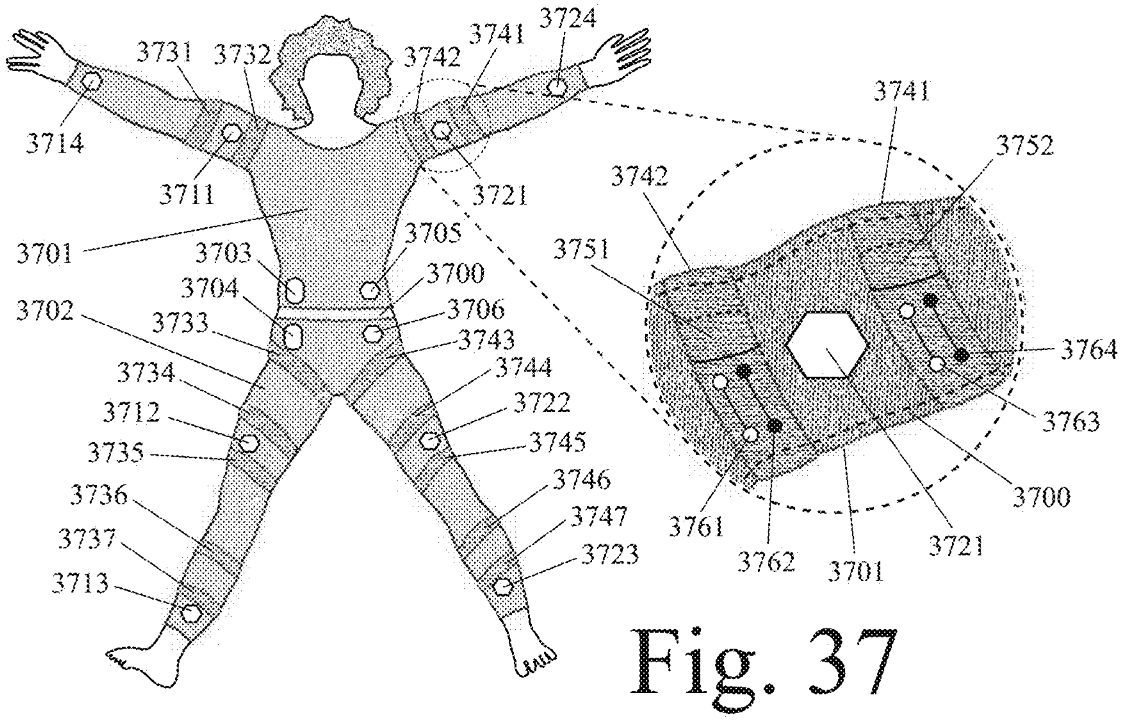
FIGS. 37 through 40 show two examples of electromyographic clothing with adjustable-fit bands for EMG sensors.
Figure 38:
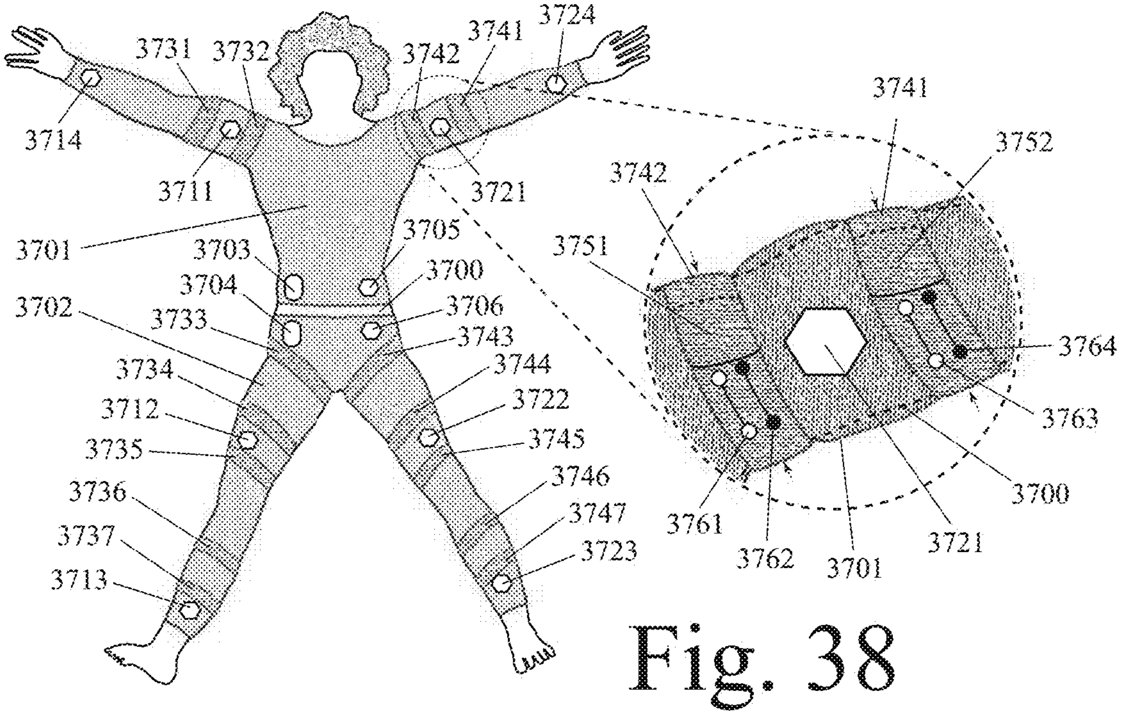

FIGS. 37 and 38 show: upper body garment 3701 and lower body garment 3702 worn by person 3700; upper body data processing unit 3703 and lower body data processing unit 3704; motion sensors 3705, 3706, 3711, 3712, 3713, 3714, 3721, 3722, 3723, and 3724; a second set of clothing sections comprising 3731, 3732, 3733, 3734, 3735, 3736, 3737, 3741, 3742, 3743, 3744, 3745, 3746, and 3747; and EMG sensors (including 3761, 3762, 3763, and 3764). FIGS. 37 and 38 only show EMG sensors in the close-up, semi-transparent views (in dashed-line circles) of clothing sections on the person's left arm, but other clothing sections of the upper and lower body garments are assumed to include similar EMG sensors as well.

FIG. 37 shows this example in a first configuration wherein the second set of clothing sections have a fit (level of tightness) which is similar to that of the rest of the article of clothing. FIG. 38 shows this example in a second configuration after the hook- and -eye attachments of the second set of clothing sections have been refastened so as to selectively make the second set of clothing sections tighter. In an example, the EMG sensors which are attached to (or integrated into) the second set of clothing sections can more accurately measure electromagnetic signals from muscles when the article of clothing is in the second configuration. Relevant variations discussed elsewhere in this disclosure or in priority-linked disclosures can also be applied to this example.

Figure 39:
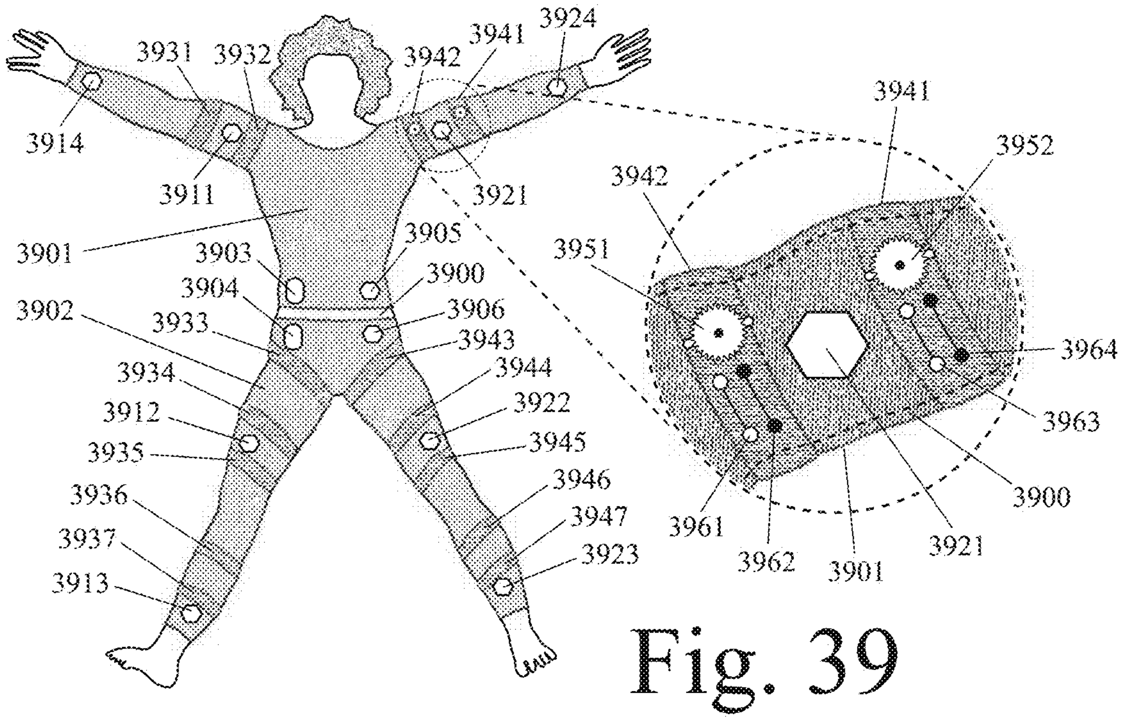
Figure 40:
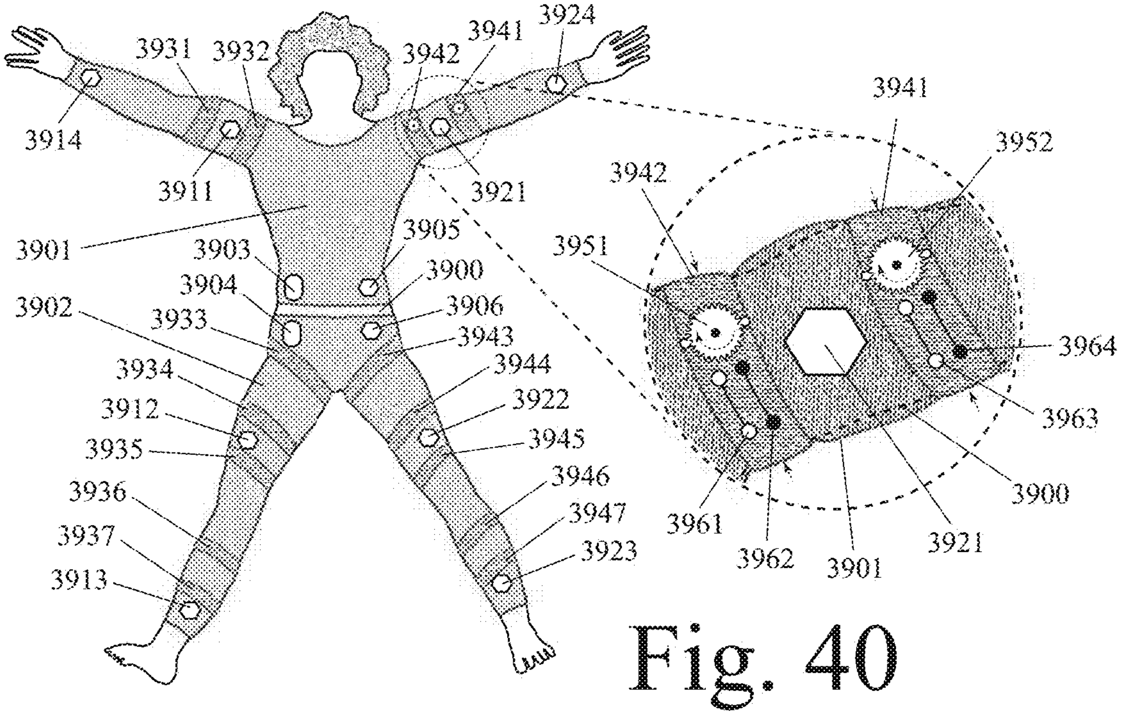

The example that is shown in FIGS. 39 and 40 is similar to the example in FIGS. 37 and 38, except that the fit of the second set of clothing sections are adjusted by turning knobs (such as 3951 and 3952) instead of refastening a hook- and -eye attachment mechanism. FIGS. 39 and 40 show: upper body garment 3901 and lower body garment 3902 worn by person 3900; upper body data processing unit 3903 and lower body data processing unit 3904; motion sensors 3905, 3906, 3911, 3912, 3913, 3914, 3921, 3922, 3923, and 3924; a second set of clothing sections comprising 3931, 3932, 3933, 3934, 3935, 3936, 3937, 3941, 3942, 3943, 3944, 3945, 3946, and 3947; and EMG sensors (including 3961, 3962, 3963, and 3964). FIGS. 39 and 40 only show EMG sensors in the close-up, semi-transparent views (in dashed-line circles) of clothing sections on the person's left arm, but other clothing sections of the upper and lower body garments are assumed to include similar EMG sensors as well. Relevant variations discussed elsewhere in this disclosure or in priority-linked disclosures can also be applied to this example.

Figure 41:
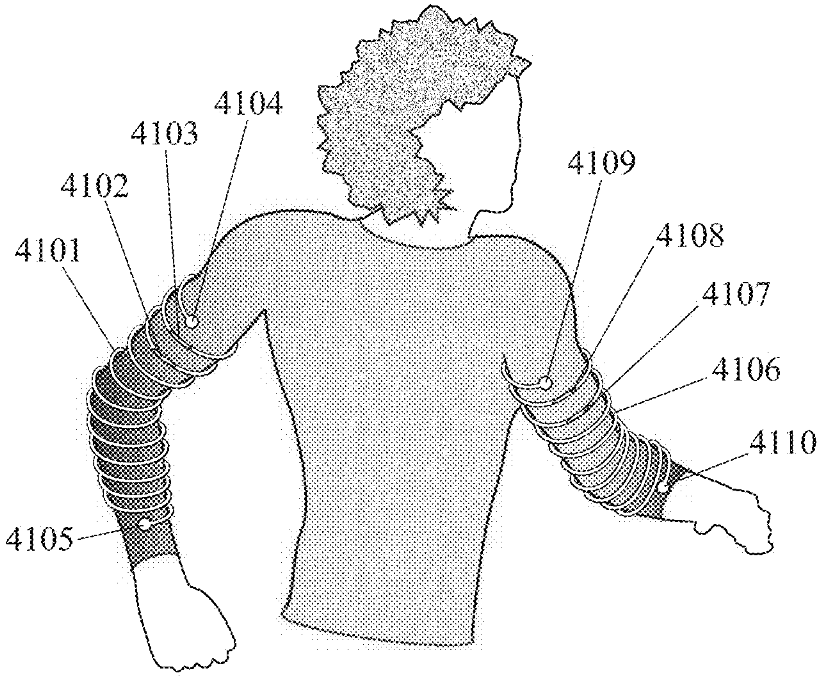
FIGS. 41 and 42 show two examples of electromyographic clothing comprising wearable helical members with EMG sensors.

FIG. 41 shows an example of how this invention can be embodied in a device and system for measuring body motion and/or muscle activity comprising: one or more helical members (4101 and 4106) which are each worn around an arm or leg; one or more EMG sensors (4102, 4103, 4107, and 4108) which are attached to and/or incorporated into the one or more helical members; and one or more motion sensors (4104, 4105, 4109, and 4110) which are attached to and/or incorporated into the one or more helical members.

Figure 42:
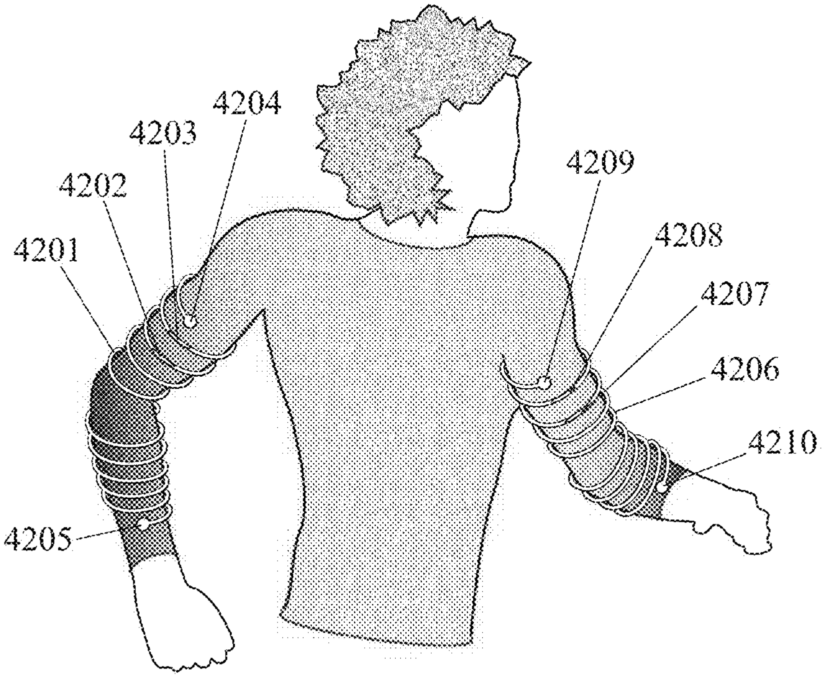

The example shown in FIG. 42 is like the one in FIG. 41 except that the helical members have a wider gap between spirals as they span body joints (e.g. elbow or knee). The example in FIG. 42 comprises: one or more helical members (4201 and 4206) which are each worn around an arm or leg; one or more EMG sensors (4202, 4203, 4207, and 4208) which are attached to and/or incorporated into the one or more helical members; and one or more motion sensors (4204, 4205, 4209, and 4210) which are attached to and/or incorporated into the one or more helical members. Relevant variations discussed elsewhere in this disclosure or in priority-linked disclosures can also be applied to this example.

Figure 43:
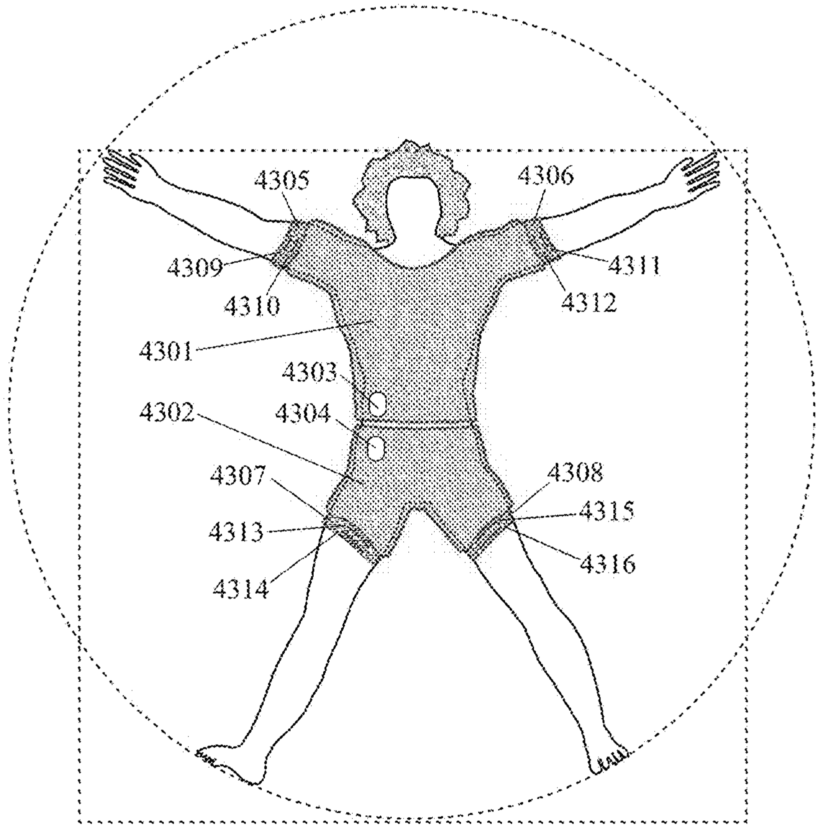
FIGS. 43 and 44 show electromyographic clothing comprising a short-sleeve shirt and a pair of shorts wherein EMG sensors are in the cuffs of the shirt sleeves and the shorts legs.
Figure 44:
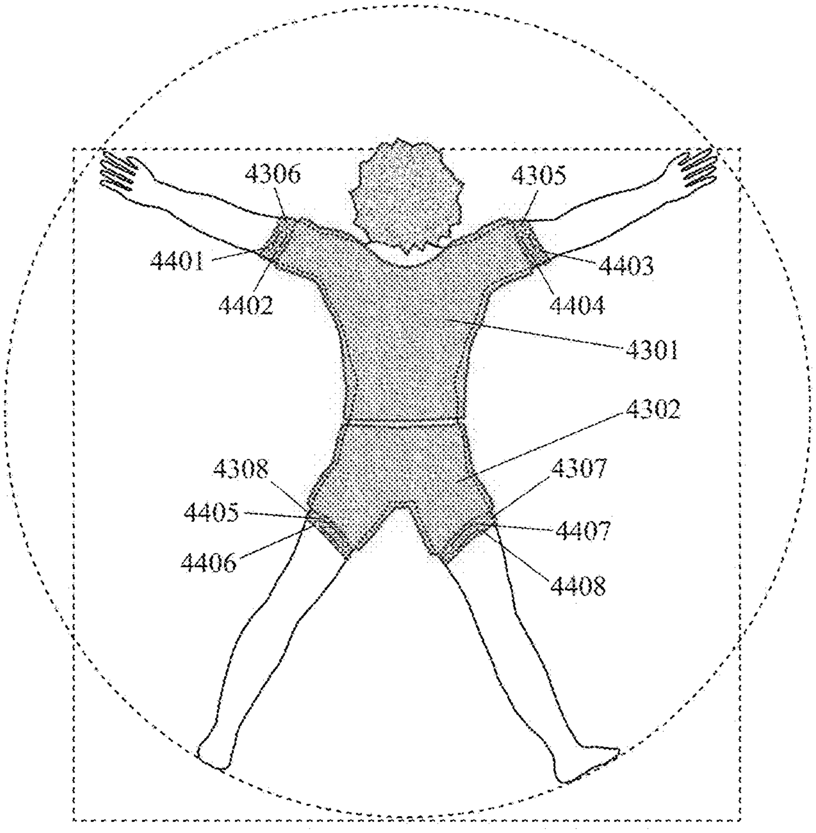

FIGS. 43 through 44 show an article of clothing for measuring body motion and/or muscle activity comprising: one or more articles of clothing worn by a person, wherein these articles of clothing each have a first set of clothing sections with a first average distance from the surface of the person's body and a second set of clothing sections with a second average distance from the surface of the person's body, and wherein the second average distance is less than the first average distance; and one or more electromyographic (EMG) sensors which are attached to and/or integrated into one or more of the clothing sections in the second set. FIG. 43 shows a front view of this example and FIG. 44 shows a rear view of this example.

In this example, an upper body garment (4301) is a short-sleeve shirt and a lower body garment (4302) is a pair of shorts. In this example, the clothing sections in the second set are rings or bands which are positioned at the ends of the sleeves of the short-sleeve shirt and at the ends of the pant legs of the shorts. The front view of this example in FIG. 43 shows: upper body garment 4301 and lower body garment 4302; upper body data processing unit 4303 and lower body data processing unit 4304; rings or bands 4305, 4306, 4307, and 4308); and EMG sensors 4309, 4310, 4311, 4311, 4313, 4314, 4315, and 4316. The rear view of this example in FIG. 44 shows: upper body garment 4301 and lower body garment 4302; rings or bands 4305, 4306, 4306, and 4307); and EMG sensors 4401, 4402, 4403, 4404, 4405, 4406, 4407, and 4408.

In an example, this invention can be embodied in an article of clothing for measuring muscle activity comprising: an article of clothing which is configured to span a body member, wherein this article of clothing further comprises a first flexible channel with a longitudinal axis which spans (a portion of) a first cross-sectional perimeter or circumference of the body member and a second flexible channel with a longitudinal axis which spans (a portion of) a second cross-sectional perimeter or circumference of the body member; and an electromyographic (EMG) sensor for collecting data concerning electromagnetic energy from muscle activity, wherein this sensor is removably inserted into either the first flexible channel or into the second flexible channel depending on whether the first flexible channel or the second flexible channel enables more accurate data collection concerning the muscle activity of a specific person and/or the muscle activity of a specific type of activity. Relevant variations discussed elsewhere in this disclosure or in priority-linked disclosures can also be applied to this example.

Figure 45:
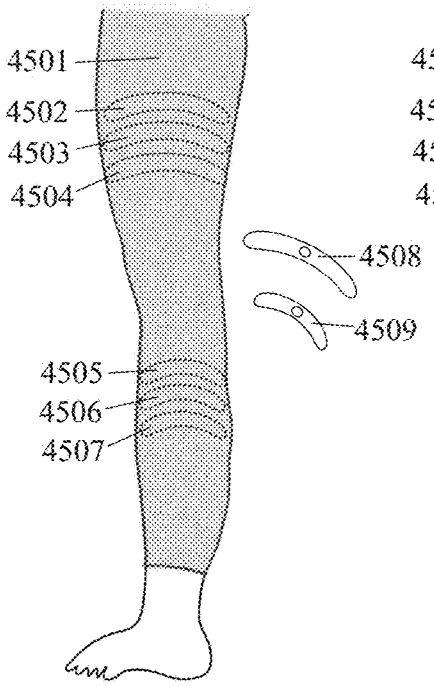
FIGS. 45 through 50 show two examples of electromyographic clothing with flexible channels into which EMG sensors can be adjustably slid.
Figure 46:
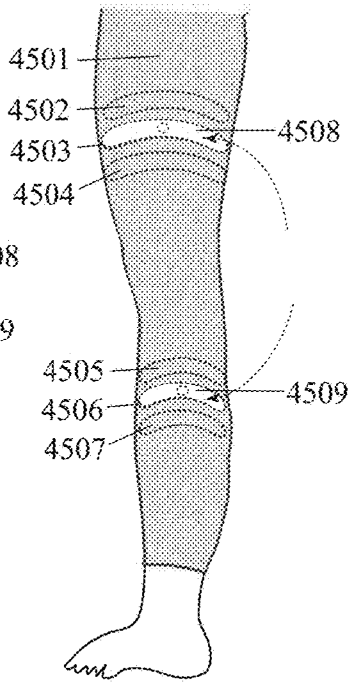
Figure 47:
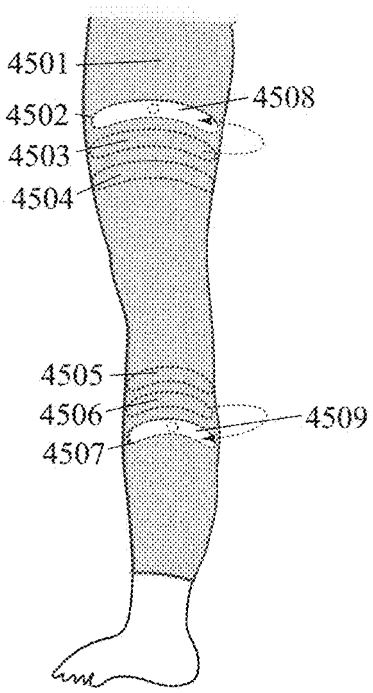

FIGS. 45 through 47 show an example of how this invention can be embodied in an article of clothing for measuring muscle activity comprising: an article of clothing 4501 which is configured to span a body member, wherein this article of clothing further comprises a first flexible channel 4503 with a longitudinal axis which spans (a portion of) a first cross-sectional perimeter or circumference of the body member and a second flexible channel 4502 with a longitudinal axis which spans (a portion of) a second cross-sectional perimeter or circumference of the body member; and an electromyographic (EMG) sensor 4508 for collecting data concerning electromagnetic energy from muscle activity, wherein this sensor is removably inserted into either the first flexible channel or into the second flexible channel depending on whether the first flexible channel or the second flexible channel enables more accurate data collection concerning the muscle activity of a specific person and/or the muscle activity of a specific type of activity. In the example shown in FIGS. 45 through 47, there is also a third flexible channel 4504 into which the electromyographic (EMG) sensor 4508 can be removably inserted. In this example, there is also a second electromyographic (EMG) sensor 4509 which can be removably inserted into one of three other flexible channels, 4505, 4506, and 4507.

FIGS. 45 through 47 show three sequential views of the same example. FIG. 45 shows this example at a first time before electromyographic (EMG) sensor 4508 has been inserted into any flexible channel. FIG. 46 shows this example at a second time when electromyographic (EMG) sensor 4508 has been removably inserted into first flexible channel 4503. FIG. 46 shows this example at a third time when electromyographic (EMG) sensor 4508 has been removed from first flexible channel 4503 and inserted into second flexible channel 4502. In this example, electromyographic (EMG) sensor is left in second flexible channel 4502 because it better collects data concerning muscle activity for a specific person or for a specific type of activity when located within this channel.

In an example, electromyographic (EMG) sensor 4508 can be inserted into (or removed from) a flexible channel by horizontal sliding. In an example, an electromyographic (EMG) sensor can be connected (or disconnected) within a flexible channel via an attachment member. In an example, an attachment member can be selected from the group consisting of: hook- and -eye connection, clip, clasp, buckle, hook, plug, pin, snap, zipper, and button.

In this example, article of clothing 4501 is a pair of pants of which only one leg is shown in these figures. In another example, an article of clothing can be a different type of lower-body garment. In an example, an article of clothing can be a pair of shorts, underpants, a knee pad or tube, a leg band, a skirt, a sock, or a shoe. In an example, a body member which is spanned by an article of clothing can be a leg, a knee, an ankle, a foot, a hip, or a torso. In an example, an article of clothing can be an upper-body garment. In an example, an article of clothing can be a shirt, an undershirt, a sweatshirt, a jacket, an elbow pad or tube, a wrist band, or an arm band. In an example, a body member which is spanned by the article of clothing can be an arm, a hand, a finger, a neck, or a torso. In an example, an article of clothing can be made with an elastic and/or stretchable fabric or textile. In an example, an article of clothing can be close-fitting. In an example, the elasticity of an article of clothing can be customized for a particular person when the article of clothing is created. In an example, the elasticity of an article of clothing can be adjusted after an article of clothing is created.

In an example, a flexible channel or pathway can be a channel or pathway in (or through) an article of clothing. In an example, a flexible channel or pathway can be formed in an article of clothing as the article of clothing is made. In an example, a flexible channel or pathway can be attached to an article of clothing after the article of clothing is made. In an example, a flexible channel or pathway can be comprised of a fabric, textile, and/or cloth. In an example, a flexible channel or pathway can be made from two or more layers of fabric, textile, and/or cloth which are sewn, woven, knitted, melted, or adhered together. In an example, a flexible channel or pathway can be made from a tube of fabric, textile, and/or cloth whose ends are sewn, woven, melted, knitted, or adhered together. In an example, a flexible channel or pathway can be created in (or on) an article of clothing by sewing, weaving, knitting, adhering, melting, pressing, melting, or printing. In an example, a flexible channel or pathway can be created in (or on) an article of clothing by one or more attachment mechanisms selected from the group consisting of: hook- and -eye mechanism, zipper, snap, hook, clip, clasp, buckle, button, plug, and pin.

In an example, a flexible channel or pathway can be created on the interior surface of an article of clothing, wherein the interior surface faces the body of the person who wears the clothing. In an example, a flexible channel or pathway can be in direct contact with a person's skin. In an example, a flexible channel or pathway can have one or more openings, holes, or discontinuities which enable a sensor inserted into the channel or pathway to have direct contact with the person's skin. In an example, a flexible channel or pathway can be created on the exterior surface of an article of clothing, wherein the exterior surface faces away from the body of the person who wears the clothing.

In an example, a flexible channel or pathway can have a longitudinal axis and have openings at one or both ends of this longitudinal axis. In an example, an electromyographic (EMG) sensor can be inserted into one or both of these ends. In an example, there can also be a closure mechanism which reversibly closes one or both ends of a channel or pathway in order to prevent an electromyographic (EMG) sensor from slipping out by mistake. In an example, this closure mechanism can be selected from the group consisting of: hook- and -eye mechanism, zipper, snap, hook, clip, clasp, buckle, button, plug, and pin.

In an example, a flexible channel or pathway can span the entire perimeter or circumference of a cross-section of a body member spanned by the article of clothing. In an example, a flexible channel or pathway can be circular or spiral in shape. In an example, a flexible channel or pathway can span a portion of the perimeter or circumference of a cross-section of a body member spanned by the article of clothing. In an example, a flexible channel or pathway can be shaped like a section of a circle or other conic section. In an example, a flexible channel or pathway can span the anterior portion of the perimeter or circumference of a cross-section of a body member. In an example, a flexible channel or pathway can span the posterior portion of the perimeter or circumference of a cross-section of a body member. In an example, a flexible channel or pathway can span a lateral portion of the perimeter or circumference of a cross-section of a body member. In an example, a flexible channel or pathway can span from 10% to 25% of the perimeter or circumference of a cross-section of a body member. In an example, a flexible channel or pathway can span from 25% to 50% of the perimeter or circumference of a cross-section of a body member. In an example, this span percentage can be from 50% to 75%. In an example, this span percentage can be from 75% to 100%.

In an example, a flexible channel or pathway can span the perimeter or circumference of a cross-section of a body member in a manner which is substantially perpendicular to the proximal-to-distal longitudinal axis of that body member. In an example, a flexible channel or pathway can span the perimeter or circumference of a cross-section of a body member in a manner which intersects the proximal-to-distal longitudinal axis of that body member at an acute angle. In an example, a flexible channel or pathway can be arcuate and intersect with the proximal-to-distal longitudinal axis of a body member at different angles. In an example, a flexible channel or pathway can have a constant width. In an example, a constant width can be in the range of ⅛" to ½". In an example, a constant width can be in the range of ½" to 3". In an example, a flexible channel or pathway can have a width which varies along the longitudinal axis of the flexible channel or pathway.

In an example, a first flexible channel or pathway and a second flexible channel or pathway can be parallel to each other. In an example, a first flexible channel or pathway and a second flexible channel or pathway can be contiguous to each other. In an example, a first flexible channel or pathway and a second flexible channel or pathway can be separated by a constant distance. In an example, a first flexible channel or pathway and a second flexible channel or pathway can separated by a distance in the range of ⅛" to ½". In an example, a first flexible channel or pathway and a second flexible channel or pathway can separated by a distance in the range of ½" to 3".

In an example, a first flexible channel or pathway can be more proximal to a person's torso (or heart) and a second flexible channel or pathway can be more distal from the person's torso (or heart). In an example, there can be a proximal-to-distal sequence of multiple flexible channels or pathways on a body member. In an example, there can be a sequence of multiple flexible channels or pathways which is distal to a joint on a body member and a sequence of multiple flexible channels or pathways which is proximal to a joint on a body member. In an example, there can be a proximal-to-distal sequence of multiple arcuate flexible channels or pathways on a body member which collectively form a "rainbow" configuration. In an example, there can be a proximal-to-distal sequence of multiple arcuate flexible channels or pathways on a body member which collectively form a "sergeant stripes" configuration. In an example, there can be a proximal-to-distal sequence of multiple arcuate flexible channels or pathways on a body member which collectively form a "Michelin man" (TM) configuration.

In an example, an electromyographic (EMG) sensor can comprise one electrode. In an example, an electromyographic (EMG) sensor can comprise two electrodes. In an example, an electromyographic (EMG) sensor can comprise multiple electrodes. In an example, an electromyographic (EMG) sensor can be formed in a fabric or textile member by weaving. In an example, an electromyographic (EMG) sensor can be formed in a fabric or textile member by weaving electroconductive threads, fibers, yarns, and/or traces within a fabric or textile member. In an example, an electromyographic (EMG) sensor can be formed on a fabric or textile member by printing. In an example, an electromyographic (EMG) sensor can be formed on a fabric or textile member by printing a on a fabric or textile member with electroconductive ink and/or resin. In an example, an electromyographic (EMG) sensor can be formed on a fabric or textile member by embroidery. In an example, an electromyographic (EMG) sensor can be formed on a fabric or textile member by embroidering a fabric or textile member with electroconductive threads, fibers, and/or yarns. In an example, an electromyographic (EMG) sensor can be formed on a fabric or textile member by adhesion. In an example, an electromyographic (EMG) sensor can be formed on a fabric or textile member by adhering electroconductive members to a fabric or textile member.

In an example, an electromyographic (EMG) sensor can further comprise one or more components selected from the group consisting of: a power source, an amplifier, a data processor, a data transmitter, and a data receiver. In an example, an electromyographic (EMG) sensor can have members which form an electromagnetic connection to electromagnetic pathways in the article of clothing when the sensor is inserted into a flexible channel or pathway. In an example, this electromagnetic connection is disconnected when the sensor is removed from the flexible channel or pathway. In an example, an article of clothing can further comprise one or more components selected from the group consisting of: a power source, an amplifier, a data processor, a data transmitter, a data receiver, and a display or other computer-to-human interface. In an example, an electromyographic (EMG) sensor can be removed from a flexible channel or pathway before an article of clothing is washed. Other relevant example configuration variations which are discussed elsewhere in this disclosure can also be applied to the example shown here in FIGS. 45 through 47.

In an example, a first set of data concerning electromagnetic energy from muscle activity can be collected by an electromyographic (EMG) sensor when the sensor is inserted into a first flexible channel. In an example, a second set of data concerning electromagnetic energy from muscle activity can be collected by an electromyographic (EMG) sensor when the sensor is inserted into a second flexible channel. In an example, the first and second sets of data can be analyzed by a data processor during a testing and/or calibration period in order to determine which channel is the best location from which to collect data in order to measure muscle activity of a particular person or to measure muscle activity during a particular type of physical activity. In an example, a sensor can be placed sequentially in two or more channels during a testing and/or calibration period in order to determine the best channel location and then left in the best channel location as long as the clothing is worn by the same person or as long as the person is engaged in the same type of activity wearing that clothing.

In an example, having multiple flexible channels or pathways into which an electromyographic (EMG) sensor can be placed can enable the creation of a customized article of clothing which is optimized for measuring the muscle activity of a specific person or muscle activity during a specific type of physical activity. For example, an electromyographic (EMG) sensor might be optimally inserted into flexible channel 4502 in order to measure the muscle activity of a person with long legs and optimally inserted into flexible 4504 in order to measure the muscle activity of a person with short legs. For example, an electromyographic (EMG) sensor might be optimally inserted into flexible channel 4502 in order to measure the muscle activity of a person with wide legs and optimally inserted into flexible 4504 in order to measure the muscle activity of a person with skinny legs. For example, an electromyographic (EMG) sensor might be optimally inserted into flexible channel 4502 in order to measure the muscle activity of a person playing basketball and optimally inserted into flexible 4504 in order to measure the muscle activity of a person playing golf.

In an example, data processing to determine the optimal channel location for a sensor for a particular person or activity can be performed in a data processor which is part of the removable sensor, within a data processor which is part of the article of clothing (and in electromagnetic communication with the removable sensor), or within a remote data processor (such as a data processor in a hand -held device) which is in wireless communication with the sensor and/or article of clothing.

In an example, placing an electromyographic (EMG) sensor in a first flexible channel or pathway can provide optimal collection of data concerning muscle activity for a first person with a first body size and/or shape and placing an electromyographic (EMG) sensor in a second flexible channel or pathway can provide optimal collection of data concerning muscle activity for a second person with a second body size and/or shape. Accordingly, creating an article of clothing with multiple flexible channels or pathways into which one or more electromyographic (EMG) sensors can be removably inserted can enable optimized and/or customized EMG data collection for a specific person. This can enable more accurate data concerning muscle activity for a specific person. In an example, more-proximal EMG sensor locations can be optimal for a first person and more-distal EMG sensor locations can be optimal for a second person.

In an example, placing an electromyographic (EMG) sensor in a first flexible channel or pathway can provide optimal collection of data concerning muscle activity for a first type of physical activity and placing an electromyographic (EMG) sensor in a second flexible channel or pathway can provide optimal collection of data concerning muscle activity for a second type of physical activity. Accordingly, creating an article of clothing with multiple flexible channels or pathways into which one or more electromyographic (EMG) sensors can be removably inserted can enable optimized and/or customized EMG data collection for a specific type of physical activity. This can enable more accurate data concerning muscle activity for a specific type of physical activity. In an example, more-proximal EMG sensor locations can be optimal for a first sport and more-distal EMG sensor locations can be optimal for a second sport. Relevant variations discussed elsewhere in this disclosure or in priority-linked disclosures can also be applied to this example.

Figure 48:
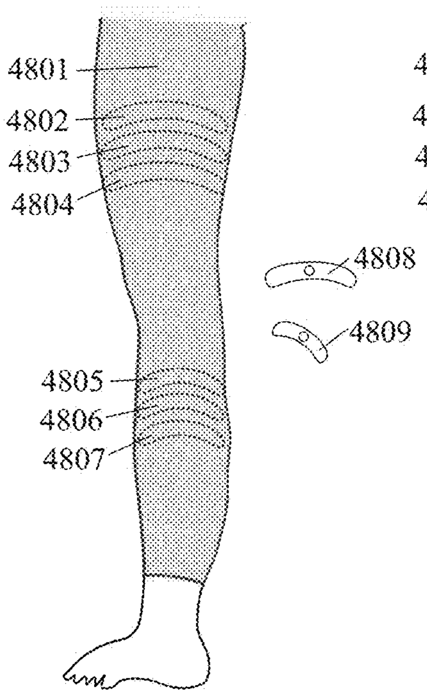
Figure 49:
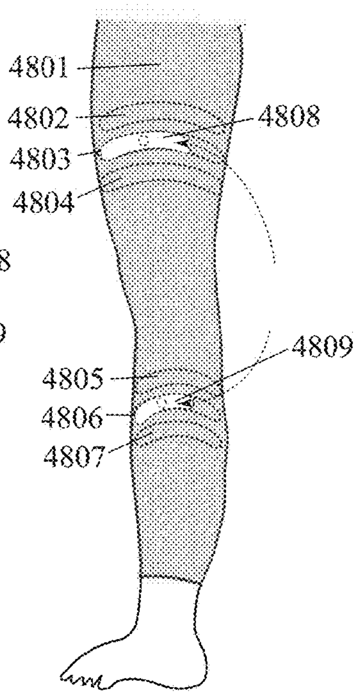
Figure 50:
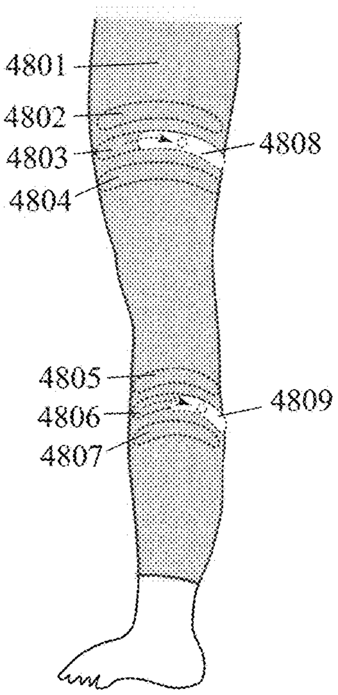

FIGS. 48 through 50 show an example of how this invention can be embodied in an article of clothing for measuring muscle activity comprising: an article of clothing 4801 which is configured to span a body member, wherein this article of clothing further comprises a flexible channel 4803 with a longitudinal axis which spans (a portion of) a first cross-sectional perimeter or circumference of the body member; and an electromyographic (EMG) sensor 4808 for collecting data concerning electromagnetic energy from muscle activity, wherein this sensor is removably inserted into a first portion of the flexible channel or into a second portion of the flexible channel depending on whether placement of the sensor into first portion or into the second portion enables more accurate collection of data concerning the muscle activity of a specific person and/or the muscle activity of a specific type of activity.

FIGS. 48 through 50 show three sequential views of the same example. FIG. 48 shows this example at a first time when electromyographic (EMG) sensor 4808 has not yet been inserted into flexible channel 4803. FIG. 49 shows this example at a second time when electromyographic (EMG) sensor 4808 has been removably inserted into a first portion of channel 4803. FIG. 50 shows this example at a third time when electromyographic (EMG) sensor 4808 has been slid from first portion of flexible channel 4803 into a second portion of channel 4803. In this example, electromagnetic (EMG) energy sensor is left within the second portion because it is determined that this is the optimal channel location from which to have the sensor collect data concerning muscle activity for this specific person and/or for a specific activity. In the example shown in FIGS. 48 through 50, there are five other flexible channels, 4802, 4804, 4805, 4806, and 4807 into which electromyographic (EMG) sensor 4808 can be removably inserted and there is also a second electromyographic (EMG) sensor 4809 which can be removably inserted into any of the flexible channels.

In this example, the article of clothing with multiple flexible channels into which one or more electromyographic (EMG) sensors can be inserted is a pair of pants. In other examples, an article of clothing can be a different type of lower-body garment or an upper-body garment. In an example, an article can be a full-body article of clothing. In an example, an article of clothing into which multiple flexible channels or pathways can be incorporated can be selected from the group consisting of: arm band, back brace, belt, blouse, collar, dress, elbow pad, glove, jacket, knee pad, knee tube, leg band, leggings, leotards, overalls, pants, shirt, shoe, shorts, skirt, sock, suit, sweatpants, sweatshirt, tights, underpants, undershirt, union suit, waist band, and wristband.

In an example, a flexible channel or pathway can be created as part of an article of clothing by sewing, weaving, knitting, adhesion, printing, pressing, or fusing. In an example, a flexible channel or pathway can be attached to an article of clothing by sewing, weaving, knitting, adhesion, printing, pressing, melting, or fusing. In an example, a flexible channel can be created on (or attached to) the interior surface of an article of clothing which faces toward the wearer's body. In an example, a flexible channel can be created on (or attached to) the exterior surface of an article of clothing which faces away from the wearer's body. In an example, there can be one or more openings, holes, or discontinuities in the interior surface of a flexible channel which enable a sensor within the channel to be in direct contact with the wearer's skin at one or more selected locations. In an example, this invention can allow the user to customize the number, locations, and/or sizes of holes or openings to customize an article of clothing for the user and/or for a particular type of physical activity.

In an example, an electromyographic (EMG) sensor can be selectively and removably inserted into a portion of a flexible channel or pathway in the article of clothing. In an example, an electromyographic (EMG) sensor can be selectively inserted into a flexible channel or pathway through a hole or opening in the channel or pathway. In an example, a hole or opening in a channel or pathway can be selectively closed after an electromyographic (EMG) sensor has been inserted in order to prevent the sensor from slipping out unintentionally during physical activity. In an example, a hole or opening in a channel or pathway can be closed by one or more means selected from the group consisting of: hook- and -eye mechanism, snap, button, zipper, clip, pin, plug, and clasp. In an example, an electromyographic sensor can be attached to remain at a particular location along the longitudinal axis of a flexible channel or pathway. In an example, an electromyographic sensor can be attached to a particular location along the longitudinal axis of a flexible channel or pathway by a means selected from the group consisting of: hook- and -eye mechanism, snap, button, zipper, clip, pin, plug, and clasp.

In an example, a flexible channel or pathway can span a percentage of the perimeter or circumference of a cross-section of a body member such as a leg or arm. In an example, this percentage can be within the range of 10% to 25%. In an example, this percentage can be within the range of 25% to 50%. In an example, this percentage can be within the range of 50% to 75%. In an example, this percentage can be within the range of 75% to 100%.

In an example, a flexible channel or pathway can have a longitudinal axis which is longer than the longitudinal axis of a removably-insertable electromyographic (EMG) sensor so that the longitudinal placement of the sensor along the channel or pathway can be adjusted for optimal data collection. In an example, the longitudinal axis and/or length of a flexible channel or pathway can be more than 50% greater than the longitudinal axis and/or length or an electromyographic (EMG) sensor. In an example, the longitudinal axis and/or length of a flexible channel or pathway can be more than twice that of the longitudinal axis and/or length of an electromyographic (EMG) sensor.

In an example, a flexible channel or pathway can span a greater percentage of the perimeter or circumference of a cross-section of a body member (such as a leg or arm) than is spanned by an electromyographic (EMG) sensor. In an example, a flexible channel or pathway can span over 50% more of the perimeter or circumference of a cross-section of a body member (such as a leg or arm) than is spanned by an electromyographic (EMG) sensor. In an example, a flexible channel or pathway can span more than twice of the perimeter or circumference of a cross-section of a body member (such as a leg or arm) than is spanned by an electromyographic (EMG) sensor.

In an example, a flexible channel or pathway can be substantially perpendicular to the longitudinal axis of the body member on which the channel or pathway is worn. In an example, a flexible channel or pathway can intersect the longitudinal axis of the body member on which the channel or pathway is worn at an acute angle. In an example, a flexible channel or pathway can be a portion (or the entirety of) the cross-sectional circumference of the body member on which the channel or pathway is worn. In an example, a flexible channel or pathway can have an arcuate longitudinal shape which is a section of a circle or spiral and/or a conic section. In an example, a flexible channel or pathway can have a spline shape which is formed by a connected sequence of straight lines or conic sections. In an example, a sequence of flexible channels or pathways can collectively comprise a “rainbow” configuration. In an example, a sequence of flexible channels or pathways can collectively comprise a “sergeant stripes” configuration. In an example, a sequence of flexible channels or pathways can collectively comprise a “Michelin Man (TM)” configuration.

In an example, multiple flexible channels or pathways can be substantially parallel to each other. In an example, multiple flexible channels or pathways can be laterally-contiguous to each other. In an example, multiple flexible channels or pathways can be laterally separated by a constant distance. In an example, multiple flexible channels or pathways can be separate by a distance within the range of ⅛" to 3". In an example, there can be a first sequence of two, three, four, or more flexible channels or pathways on a portion of a body member which is proximal to a body joint. In an example, there can be a second sequence of two, three, four, or more flexible channels or pathways on a portion of a body member which is distal to that body joint. In an example, there can be a first sequence of two, three, four, or more flexible channels or pathways on an anterior portion of a body member. In an example, there can be a second sequence of two, three, four, or more flexible channels or pathways on a posterior portion of a body member. In an example, the radial location (e.g. anterior, lateral, or posterior) of an electromyographic (EMG) sensor with respect to a body member can be adjusted by longitudinally sliding the sensor along the longitudinal axis of a flexible channel or pathway within which the sensor has been inserted.

In an example, an electromyographic (EMG) sensor can comprise a single electrode and two electromyographic (EMG) sensors can work together to measure electromagnetic energy flow. In an example, a single electromyographic (EMG) sensor can have two electrodes to measure muscle electromagnetic energy flow. In an example, an electromyographic (EMG) sensor can further comprise one or more local components selected from the group consisting of: a power source, a signal amplifier, a data processor, a data transmitter, and a data receiver. In an example, an electromyographic (EMG) sensor can have electromagnetic connecting members which connect to electromagnetic pathways in the article of clothing when the sensor is removably inserted into the article of clothing. In an example, the article of clothing can further comprise one or more local components selected from the group consisting of: a power source, a signal amplifier, a data processor, a data transmitter, a data receiver, and a display. In an example, an electromyographic (EMG) sensor can be temporarily removed from a flexible channel before an article of clothing is washed and replaced within the flexible channel after the article of clothing has been washed.

In an example, a first set of data concerning electromagnetic energy from muscle activity can be collected by an electromyographic (EMG) sensor when this sensor is removably inserted into a first portion of a flexible channel or pathway. In an example, a second set of data concerning data concerning electromagnetic energy from muscle activity can be collected by an electromyographic (EMG) sensor when the sensor is removably inserted into a second portion of a flexible channel or pathway. In an example, the first portion can be more posterior than the second portion, or vice versa. In an example, the first portion can be more anterior than the second portion, or vice versa. In an example, first and second sets of data can be analyzed by a data processing unit to determine the optimal location (the first portion or the second portion) for measuring muscle activity by a selected person or during a selected type of activity.

In an example, different locations around the perimeter or circumference of a cross-section of a body member (such as a leg or arm) spanned by an article of clothing can be measured by polar coordinates. In an example, the most-anterior point of this perimeter or circumference can be defined as having a polar or radial coordinate of 0 degrees and the most-posterior point of this perimeter or circumference can be defined as having a polar or radial coordinate of 180 degrees. In an example, a first portion of a flexible channel or pathway can span a perimeter or circumference of a cross-section of a body member within a range of 270 to 0 degrees and a second portion of a flexible channel or pathway can span this perimeter or circumference within a range of 0 to 90 degrees. In an example, a first portion of a flexible channel or pathway can span a perimeter or circumference of a cross-section of a body member within a range of 90 to 180 degrees and a second portion of a flexible channel or pathway can span this perimeter or circumference within a range of 180 to 270 degrees. In an example, a first portion of a flexible channel or pathway can span a perimeter or circumference of a cross-section of a body member within a range of 270 to 90 degrees and a second portion of a flexible channel or pathway can span this perimeter or circumference within a range of 90 to 270 degrees.

In an example, a first portion of a flexible channel or pathway can span a body member (at an acute angle with respect to the longitudinal axis of the body member) within a range of 270 to 0 degrees and a second portion of a flexible channel or pathway can span a body member (at an acute angle with respect to the longitudinal axis of the body member) within a range of 0 to 90 degrees. In an example, a first portion of a flexible channel or pathway can span a body member (at an acute angle with respect to the longitudinal axis of the body member) within a range of 90 to 180 degrees and a second portion of a flexible channel or pathway can span a body member (at an acute angle with respect to the longitudinal axis of the body member) within a range of 180 to 270 degrees. In an example, a first portion of a flexible channel or pathway can span a body member (at an acute angle with respect to the longitudinal axis of the body member) within a range of 270 to 90 degrees and a second portion of a flexible channel or pathway can span a body member (at an acute angle with respect to the longitudinal axis of the body member) within a range of 90 to 270 degrees. Other relevant example configuration variations which are discussed elsewhere in this disclosure can also be applied to the example shown here in FIGS. 48 through 50.

In an example, placing an electromyographic (EMG) sensor in a first longitudinal portion of a flexible channel or pathway can provide optimal collection of data concerning muscle activity for a first person with a first body size and/or shape and placing an electromyographic (EMG) sensor in a second portion of a second longitudinal portion of a flexible channel or pathway can provide optimal collection of data concerning muscle activity for a second person with a second body size and/or shape. Creating an article of clothing with multiple flexible channels or pathways into which one or more electromyographic (EMG) sensors can be removably inserted can enable optimized and/or customized EMG data collection for a specific person. This can enable more accurate data concerning muscle activity for a specific person. In an example, more-anterior EMG sensor locations can be optimal for a first person and more-posterior EMG sensor locations can be optimal for a second person. In an example, more-anterior EMG sensor locations can be optimal for a first person and more-lateral EMG sensor locations can be optimal for a second person.

In an example, placing an electromyographic (EMG) sensor in a first longitudinal portion of a flexible channel or pathway can provide optimal collection of data concerning muscle activity for a first type of physical activity and placing an electromyographic (EMG) sensor in a second portion of a second longitudinal portion of a flexible channel or pathway can provide optimal collection of data concerning muscle activity for a second type of physical activity. Creating an article of clothing with multiple flexible channels or pathways into which one or more electromyographic (EMG) sensors can be removably inserted can enable optimized and/or customized EMG data collection for a specific type of physical activity. This can enable more accurate data concerning muscle activity for a specific type of physical activity. In an example, more-anterior EMG sensor locations can be optimal for a first sport and more-posterior EMG sensor locations can be optimal for a second sport. In an example, more-anterior EMG sensor locations can be optimal for a first sport and more-lateral EMG sensor locations can be optimal for a second sport.

In an example, this invention can be embodied in an article of clothing for measuring muscle activity comprising: an article of clothing which is configured to span a body member, a plurality of snaps (or other connectors) on the article of clothing; and an electromyographic (EMG) sensor for collecting data concerning electromagnetic energy from muscle activity, wherein this sensor is removably attached to a first set of two or more connectors or removably attached to a second set of two or more connectors depending on whether attachment of the sensor to the first set or to the second set provides more accurate data concerning the muscle activity of a specific person and/or muscle activity during a specific type of activity. Relevant variations discussed elsewhere in this disclosure or in priority-linked disclosures can also be applied to this example.

Figure 51:
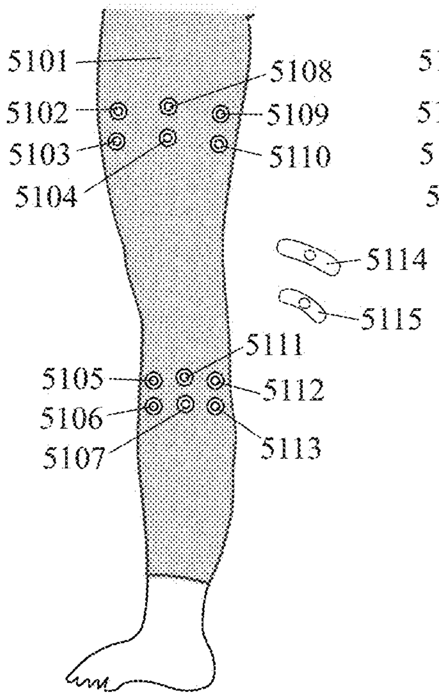
FIGS. 51 through 56 show two examples of electromyographic clothing with an array of connectors onto which EMG sensors can be removably attached.
Figure 52:
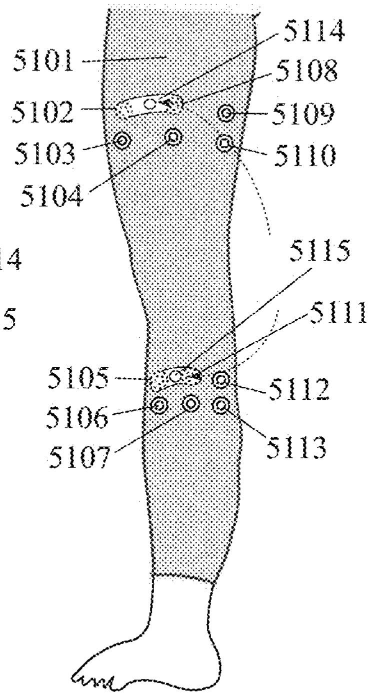
Figure 53:
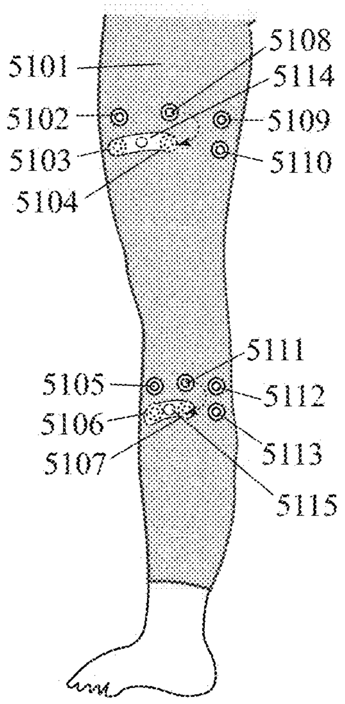

FIGS. 51 through 53 show an example of how this invention can be embodied in an article of clothing for measuring muscle activity comprising: an article of clothing (5101) which is configured to span a body member, a plurality of connectors (5102, 5103, 5104, 5105, 5106, 5107, 5108, 5109, 5110, 5111, 5112, and 5113) on the article of clothing; and an electromyographic (EMG) sensor (5114) for collecting data concerning electromagnetic energy from muscle activity, wherein this sensor is removably attached to a first set of two or more connectors or removably attached to a second set of two or more connectors depending on whether attachment of the sensor to the first set or to the second set provides more accurate data concerning the muscle activity of a specific person and/or muscle activity during a specific type of activity.

FIGS. 51 through 53 show three sequential views of the same example. FIG. 51 shows this example at a first time when electromyographic (EMG) sensor 5114 has not yet been attached to any connectors. FIG. 52 shows this example at a second time when electromyographic (EMG) sensor 5114 has been removably attached to a first set of connectors (5102 and 5108). FIG. 53 shows this example at a third time when electromyographic (EMG) sensor 5114 has removably attached to a second set of connectors (5103 and 5104). In this example, electromagnetic (EMG) energy sensor is left attached to this second set of connectors because it is determined that this is the optimal location from which to have the sensor collect data concerning muscle activity for a specific person and/or for a specific activity. In the example shown in FIGS. 51 through 53, there is also a second electromyographic (EMG) sensor 5115 which can be removably attached to connectors.

In this example, the article of clothing with a plurality of connectors to which one or more electromyographic (EMG) sensors can be attached is a pair of pants. In other examples, an article of clothing can be a different type of lower-body garment or an upper-body garment. In an example, an article can be a full-body article of clothing. In an example, an article of clothing into which multiple connectors can be incorporated can be selected from the group consisting of: arm band, back brace, belt, blouse, collar, dress, elbow pad, glove, jacket, knee pad, knee tube, leg band, leggings, leotards, overalls, pants, shirt, shoe, shorts, skirt, sock, suit, sweatpants, sweatshirt, tights, underpants, undershirt, union suit, waist band, and wristband.

In this example, a connector is a snap. In various examples, a connector can be selected from the group consisting of: snap, plug, pin, clip, clasp, hook- and -eye, button, and buckle. In an example, a plurality of connectors can be located on the exterior surface of an article of clothing which faces away from the person's body. In an example, a plurality of connectors can be located on the interior surface of an article of clothing which faces toward the person's body. In an example, there can be one or more openings, holes, or discontinuities in an article of clothing between a pair of connectors which enable a sensor to be in direct contact with the wearer's skin. In an example, this invention can allow a user to customize the number, locations, and/or sizes of holes or openings to customize an article of clothing for the user and/or for a particular type of physical activity.

In an example, in addition to providing a mechanical connection between an electromyographic (EMG) sensor and an article of clothing, a connector can also provide an electromagnetic connection between a sensor and an electromagnetic pathway and/or component which is part of the article of clothing. In an example, a connector can create removable mechanical and electronic connections between a sensor and clothing. In an example, there can be an electromagnetic pathway (through an article of clothing) from a connector to one or more components selected from the group consisting of: power source, data processor, data transmitter, data receiver, and display.

In an example, an electromyographic (EMG) sensor can be connected to an article of clothing via connections formed by a pair of connectors. In an example, an electromyographic (EMG) sensor can span different areas of a body member by being attached to different pairs of connectors. In an example, an electromyographic (EMG) sensor can attach to an article of clothing via three or more connectors. In an example, an electromyographic (EMG) sensor can have two ends and be attached to connectors at these ends.

In various examples, an electromyographic (EMG) sensor can be attached to a body member in different orientations depending on the pair of connectors to which it is attached. In an example, an electromyographic (EMG) sensor can be attached to connectors in an orientation which is substantially perpendicular to the longitudinal axis of a body member. In an example, an electromyographic (EMG) sensor can be attached to connectors in an orientation which is substantially parallel with the longitudinal axis of a body member. In an example, an electromyographic (EMG) sensor can be attached to connectors in an orientation which forms an acute angle with the longitudinal axis of a body member. In an example, the location of an electromyographic (EMG) sensor along the (proximal-to-distal) longitudinal axis of a body member can be adjusted by connecting the sensor to different pairs of connectors. In an example, the radial location of an electromyographic (EMG) sensor around the perimeter or circumference of a body member can be adjusted by connecting the sensor to different pairs of connectors.

In an example, a plurality of connectors can form an array, matrix, mesh, or grid which spans a portion of the surface of an article of clothing. In an example, connectors within this array, matrix, mesh, or grid can be generally evenly spaced from each other. In an example, connectors within this array, matrix, mesh, or grid can form a proximal-to-distal sequence of rings around the circumference of a body member. In an example, a plurality of connectors can span a percentage of the perimeter or circumference of a cross-section of a body member such as a leg or arm. In an example, this percentage can be within the range of 10% to 25%. In an example, this percentage can be within the range of 25% to 53%. In an example, this percentage can be within the range of 53% to 75%. In an example, this percentage can be within the range of 75% to 100%.

In an example, an array, matrix, mesh, or grid can have square or rectangular areas between connectors. In an example, an array, matrix, or grid can have triangular areas between connectors. In an example, an array, matrix, mesh, or grid can have hexagonal areas between connectors. In an example, there can be a proximal set of connectors which is proximal from a body joint and a distal set of connectors which is distal from a body joint. In an example, connectors within a proximal set can be separated from each other by distances in the range of 1 to 2 inches. In an example, connectors within a proximal set can be separated from each other by distances in the range of 2 to 6 inches. In an example, connectors within a distal set can be separated from each other by distances in the range of 1 to 2 inches. In an example, connectors within a distal set can be separated from each other by distances in the range of 2 to 6 inches. In an example, connectors within a proximal set can be separated from connectors in a distal set by distances in the range of 1 to 3 feet.

In an example, an electromyographic (EMG) sensor can comprise a single electrode and two electromyographic (EMG) sensors can work together to measure electromagnetic energy flow. In an example, a single electromyographic (EMG) sensor can have two electrodes to measure electromagnetic energy flow. In an example, an electromyographic (EMG) sensor can be formed in a fabric or textile member by weaving. In an example, an electromyographic (EMG) sensor can be formed in a fabric or textile member by weaving electroconductive threads, fibers, yarns, and/or traces within a fabric or textile member. In an example, an electromyographic (EMG) sensor can be formed on a fabric or textile member by printing. In an example, an electromyographic (EMG) sensor can be formed on a fabric or textile member by printing a on a fabric or textile member with electroconductive ink and/or resin. In an example, an electromyographic (EMG) sensor can be formed on a fabric or textile member by embroidery. In an example, an electromyographic (EMG) sensor can be formed on a fabric or textile member by embroidering a fabric or textile member with electroconductive threads, fibers, and/or yarns. In an example, an electromyographic (EMG) sensor can be formed on a fabric or textile member by adhesion. In an example, an electromyographic (EMG) sensor can be formed on a fabric or textile member by adhering electroconductive members to a fabric or textile member.

In an example, an electromyographic (EMG) sensor can further comprise one or more local components selected from the group consisting of: a power source, a signal amplifier, a data processor, a data transmitter, and a data receiver. In an example, an electromyographic (EMG) sensor can have electromagnetic connecting members which connect to electromagnetic pathways in the article of clothing when the sensor is removably attached to the article of clothing. In an example, the article of clothing can further comprise one or more local components selected from the group consisting of: a power source, a signal amplifier, a data processor, a data transmitter, a data receiver, and a display. In an example, an electromyographic (EMG) sensor can be temporarily detached from connectors before an article of clothing is washed and reattached to connectors after the article of clothing has been washed.

In an example, a first set of data concerning electromagnetic energy from muscle activity can be collected by an electromyographic (EMG) sensor when this sensor is removably attached to a first set of connectors. In an example, a second set of data concerning data concerning electromagnetic energy from muscle activity can be collected by an electromyographic (EMG) sensor when this sensor is removably attached to a second set of connectors. In an example, the first set can be more posterior than the second set, or vice versa. In an example, the first set can be more anterior than the second set, or vice versa. In an example, first and second sets of data can be analyzed by a data processing unit to determine the optimal location (the first set of connectors or the second set of connectors) for measuring the muscle activity of a selected person or during a selected type of activity.

In an example, different locations around the perimeter or circumference of a cross-section of a body member (such as a leg or arm) spanned by an article of clothing can be measured by polar coordinates. In an example, the most-anterior point of this perimeter or circumference can be defined as having a polar or radial coordinate of 0 degrees and the most-posterior point of this perimeter or circumference can be defined as having a polar or radial coordinate of 180 degrees. In an example, a first set of connectors can span a perimeter or circumference of a cross-section of a body member within a range of 270 to 0 degrees and a second set of connectors can span this perimeter or circumference within a range of 0 to 90 degrees. In an example, a first set of connectors can span a perimeter or circumference of a cross-section of a body member within a range of 90 to 180 degrees and a second set of connectors can span this perimeter or circumference within a range of 180 to 270 degrees. In an example, a first set of connectors can span a perimeter or circumference of a cross-section of a body member within a range of 270 to 90 degrees and a second set of connectors can span this perimeter or circumference within a range of 90 to 270 degrees.

In an example, a first set of connectors can span a body member (at an acute angle with respect to the longitudinal axis of the body member) within a range of 270 to 0 degrees and a second set of connectors can span a body member (at an acute angle with respect to the longitudinal axis of the body member) within a range of 0 to 90 degrees. In an example, a first set of connectors can span a body member (at an acute angle with respect to the longitudinal axis of the body member) within a range of 90 to 180 degrees and a second set of connectors can span a body member (at an acute angle with respect to the longitudinal axis of the body member) within a range of 180 to 270 degrees. In an example, a first set of connectors can span a body member (at an acute angle with respect to the longitudinal axis of the body member) within a range of 270 to 90 degrees and a second set of connectors can span a body member (at an acute angle with respect to the longitudinal axis of the body member) within a range of 90 to 270 degrees. Other relevant example configuration variations which are discussed elsewhere in this disclosure can also be applied to the example shown here in FIGS. 51 through 53.

In an example, attaching an electromyographic (EMG) sensor to a first set of connectors can provide optimal collection of data concerning muscle activity for a first person with a first body size and/or shape and attaching an electromyographic (EMG) sensor to a second set of connectors can provide optimal collection of data concerning muscle activity for a second person with a second body size and/or shape. Creating an article of clothing with an array, matrix, mesh, or grid of connectors onto which one or more electromyographic (EMG) sensors can be removably attached can enable optimized and/or customized EMG data collection for a specific person. This can enable more accurate data concerning muscle activity for a specific person. In an example, more-anterior EMG sensor locations can be optimal for a first person and more-posterior EMG sensor locations can be optimal for a second person. In an example, more-anterior EMG sensor locations can be optimal for a first person and more-lateral EMG sensor locations can be optimal for a second person.

In an example, attaching an electromyographic (EMG) sensor to a first set of connectors can provide optimal collection of data concerning muscle activity during a first type of physical activity and attaching an electromyographic (EMG) sensor to a second set of connectors can provide optimal collection of data concerning muscle activity during a second type of physical activity. Creating an article of clothing with an array, matrix, mesh, or grid of connectors onto which one or more electromyographic (EMG) sensors can be removably attached can enable optimized and/or customized EMG data collection for a specific type of physical activity. This can enable more accurate data concerning muscle activity for a specific type of physical activity. In an example, more-anterior EMG sensor locations can be optimal for a first sport and more-posterior EMG sensor locations can be optimal for a second sport. In an example, more-anterior EMG sensor locations can be optimal for a first sport and more-lateral EMG sensor locations can be optimal for a second sport. Relevant variations discussed elsewhere in this disclosure or in priority-linked disclosures can also be applied to this example.

Figure 54:
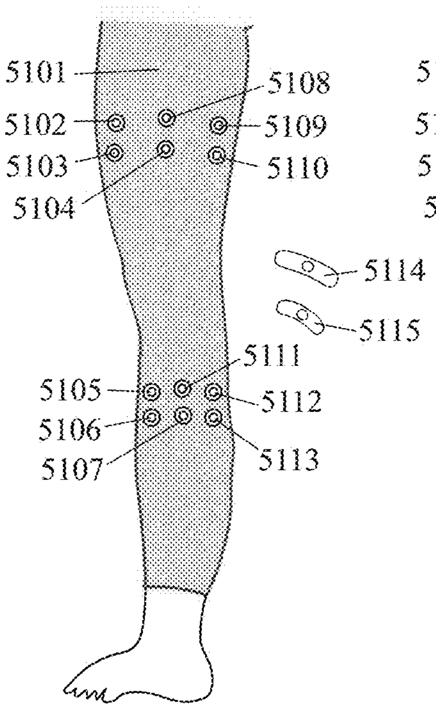
Figure 55:
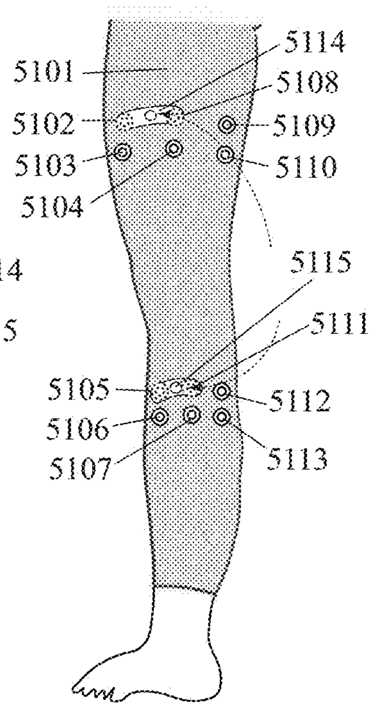
Figure 56:
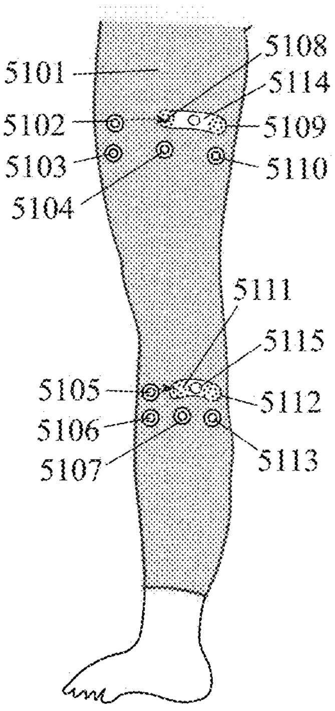

FIGS. 54 through 56 show another three-figure sequence of the same example that was shown in FIGS. 51 through 53, except that this time the electromyographic (EMG) sensor is moved radially from one pair of connectors to another instead of being moved longitudinally from one pair of connectors to another.

In an example, this invention can be embodied in an article of clothing for measuring muscle activity comprising: an article of clothing which is configured to span a body member, wherein this article of clothing further comprises a proximal opening and a distal opening; and a flexible patch, wherein this flexible patch further comprises at least one electromyographic (EMG) sensor, wherein the ends of this flexible patch are removably inserted through the proximal opening and the distal opening, respectively. In an example, the positioning of the flexible patch with respect to the proximal and distal openings can be adjusted in order to have the electromyographic (EMG) sensor most accurately positioned to collect data concerning the muscle activity of a specific person and/or muscle activity during a specific type of physical activity. Relevant variations discussed elsewhere in this disclosure or in priority-linked disclosures can also be applied to this example.

Figure 57:
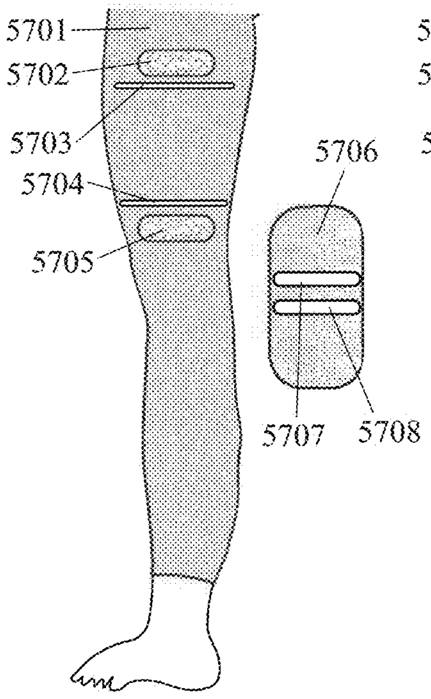
FIGS. 57 through 62 show two examples of electromyographic clothing with pairs of openings into which EMG sensors can be adjustably inserted.
Figure 58:
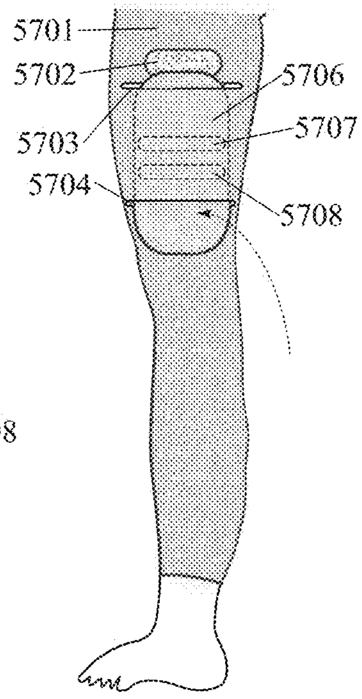
Figure 59:
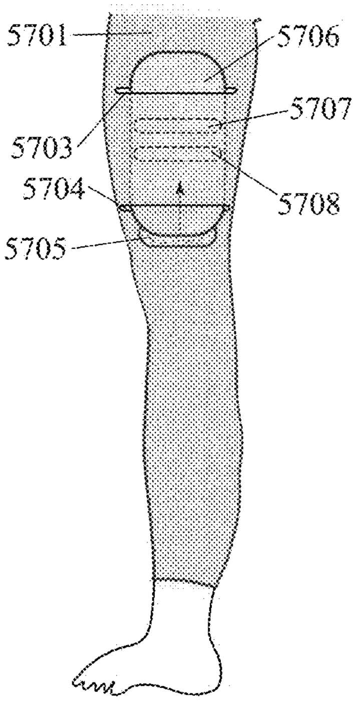

FIGS. 57 through 59 show an example of how this invention can be embodied in an article of clothing for measuring muscle activity comprising: an article of clothing (5701) which is configured to span a body member, wherein this article of clothing further comprises a proximal opening (5703) and a distal opening (5704); and a flexible patch (5706), wherein this flexible patch further comprises at least one electromyographic (EMG) sensor (5707), and wherein the ends of this flexible patch (5706) are removably inserted through proximal opening (5703) and distal opening (5704), respectively. In an example, the positioning of the flexible patch with respect to the proximal and distal openings can be adjusted in order to position the electromyographic (EMG) sensor to most accurately collect data concerning the muscle activity of a specific person and/or muscle activity during a specific type of physical activity. In this example, there is also a second electromyographic (EMG) sensor (5708) which is incorporated into the flexible patch.

In an example, this invention can be embodied in an article of clothing for measuring muscle activity comprising: an article of clothing which is configured to span a body member, wherein this article of clothing further comprises a proximal opening, a distal opening, a proximal connector, and a distal connector; and a flexible patch, wherein this flexible patch further comprises at least one electromyographic (EMG) sensor, wherein the ends of this flexible patch are removably inserted through the proximal opening and the distal opening, respectively, and wherein the ends of this flexible patch are attached to the proximal connector and the distal connector, respectively. In an example, the positioning of the flexible patch with respect to the proximal and distal openings can be adjusted in order to position the electromyographic (EMG) sensor to most accurately collect data concerning the muscle activity of a specific person and/or muscle activity during a specific type of physical activity.

FIGS. 57 through 59 show an example of how this invention can be embodied in an article of clothing for measuring muscle activity comprising: an article of clothing (5701) which is configured to span a body member, wherein this article of clothing further comprises a proximal opening (5703), a distal opening (5704), a proximal connector (5702), and a distal connector (5705); and a flexible patch (5706), wherein this flexible patch further comprises at least one electromyographic (EMG) sensor (5707), wherein the ends of this flexible patch (5706) are removably inserted through proximal opening (5703) and distal opening (5704), respectively, and wherein this flexible patch (5706) is attached to proximal connector (5702) and to the distal connector (5705). In this example, the flexible patch also includes a second electromyographic (EMG) sensor (5708). In an example, the positioning of the flexible patch with respect to the proximal and distal openings can be adjusted in order to position the electromyographic (EMG) sensor to most accurately collect data concerning the muscle activity of a specific person and/or muscle activity during a specific type of physical activity.

FIGS. 57 through 59 show three sequential views of the same example. FIG. 57 shows this example at a first time when flexible patch 5706 (including two electromyographic sensors 5707 and 5708) has not yet been inserted into proximal and distal openings in the article of clothing. FIG. 58 shows this example at a second time when the (proximal and distal) ends of flexible patch 5706 have been removably inserted into the proximal and distal openings 5703 and 5704, respectively, and attached to proximal and distal connectors 5702 and 5705, respectively, in a first position. FIG. 59 shows this example at a second time when flexible patch 5706 has been shifted upwards to a second position from which electromyographic (EMG) sensors 5707 and 5708 more accurately collect data concerning the muscle activity of this specific person and/or muscle activity during a specific type of physical activity. The configuration of this smart clothing system with an adjustable flexible patch enables customization of EMG sensor locations for optimal and/or customized measurement of muscle activity.

In this example, the article of clothing into which a flexible patch is inserted is a pair of pants. In other examples, an article of clothing can be a different type of lower-body garment or an upper-body garment. In an example, an article can be a full-body article of clothing. In an example, an article of clothing into which a flexible patch can be inserted can be selected from the group consisting of: arm band, back brace, belt, blouse, collar, dress, elbow pad, glove, jacket, knee pad, knee tube, leg band, leggings, leotards, overalls, pants, shirt, shoe, shorts, skirt, sock, suit, sweatpants, sweatshirt, tights, underpants, undershirt, union suit, waist band, and wristband.

In this example, the proximal and distal openings, 5703 and 5704, are lateral slits in the fabric of clothing. In this example, these openings are substantially parallel to each other. In an example, the two ends of a flexible patch can be configured so that they protrude outwards through the two openings, respectively, and so that the central portion of the flexible patch (which contains one or more EMG sensors) is pressed against the person's skin by the inner surface of the article of clothing. In an example, the two ends of the flexible patch can be inserted through the openings, from inside to outside, before the article of clothing is worn. In an alternative example, the two ends of the flexible patch can be configured to that they protrude inwards through the two openings, respectively, and so that the central portion of the flexible patch is on the exterior surface of the clothing.

In an example, a flexible patch can be slid up or down to a desired position and then removably attached to the article of clothing via the connectors. In an example, a flexible patch can be slid proximally or distally to a desired position and then removably attached to the article of clothing via the connectors. In an example, the locations of electromyographic (EMG) sensors with respect to the person's body can be shifted (e.g. proximally or distally, up or down) by changing the amounts by which the proximal end of the flexible patch extends outside the proximal opening vs. the amount by which the distal end of the flexible patch extends outside the distal opening. This is shown in FIGS. 58 and 59.

In an example, a flexible patch can be made of fabric or textile. In an example, a flexible patch can be made from an elastic material. In an example, a flexible patch can be made from the same material as the article of clothing. In an example, a flexible patch can have a shape selected from the group consisting of: rectangle, square, rounded rectangle or square, oval, ellipse, and circle. In an example, a flexible patch can further comprise one or more components selected from the group consisting of: a power source; a signal amplifier; a data processor; a data transmitter; and a data receiver. In an example, the ends of a flexible patch can be reversibly attached to an article of clothing by connectors 5702 and 5705. In an example, this reversible attachment can be done using a hook- and -eye mechanism. In an example, a flexible patch can further comprise half of a hook- and -eye attachment mechanism and a connector can comprise the other half of this attachment mechanism. In other examples, a connector can comprise a clip, button, pin, snap, clasp, buckle, or zipper.

In the example shown in FIGS. 57 through 59, there is only one set of openings and only one flexible patch for a given body member. In an example, there can be two sets of openings and two flexible patches to measure muscle activity at two locations on a body member. In an example, there can be a first set of openings and first flexible patch for a portion of a body member (such as a leg or arm) which is proximal to a body joint (such as a knee or elbow) and a second set of openings and second flexible patch for a portion of that body member which is distal to that body joint. In an example, there can be a first set of openings and first flexible patch (with EMG sensors) for the upper leg portion of a pant leg and second set of openings and second flexible patch (with EMG sensors) for the lower leg portion of the pant leg. In an example, there can be three sets of openings and three flexible patches (with EMG sensors) on a pant leg. In an example, there can be a first set of openings and first flexible patch (with EMG sensors) for the upper arm portion of a shirt sleeve and second set of openings and second flexible patch (with EMG sensors) for the lower arm portion of the shirt sleeve. In an example, there can be three sets of openings and three flexible patches (with EMG sensors) on a shirt sleeve.

In an example, a flexible patch can span a percentage of the perimeter or circumference of a cross-section of a body member such as a leg or arm. In an example, this percentage can be within the range of 10% to 25%. In an example, this percentage can be within the range of 25% to 50%. In an example, this percentage can be within the range of 50% to 75%. In an example, this percentage can be within the range of 75% to 90%. In an example, a set of openings and a flexible patch can span the anterior surface of an arm or leg. In an example, a set of openings and a flexible patch can span the posterior surface of an arm or leg. In an example, a set of openings and a flexible patch can span the lateral surface of an arm or leg.

In an example, in addition to providing a mechanical connection between an end of a flexible patch and an article of clothing, a connector can also provide an electromagnetic connection between a flexible patch and an electromagnetic pathway and/or component which is part of the article of clothing. In an example, a connector can create an electronic connection between a sensor and clothing. In an example, there can be an electromagnetic pathway (through an article of clothing) from a connector to one or more components selected from the group consisting of: power source, data processor, data transmitter, data receiver, and display.

In the example shown in FIGS. 57 through 59, an electromyographic (EMG) sensor is placed against the skin in an orientation which is substantially perpendicular to the longitudinal axis of the body member. In another example, an electromyographic (EMG) sensor can be placed against the skin in an orientation which is substantially parallel with the longitudinal axis of a body member. In another example, an electromyographic (EMG) sensor can be placed against the skin in an orientation which forms an acute angle with the longitudinal axis of a body member. Other relevant example configuration variations which are discussed elsewhere in this disclosure can also be applied to the example shown here in FIGS. 57 through 59.

In an example, a first set of data concerning electromagnetic energy from muscle activity can be collected by one or more electromyographic (EMG) sensors when the flexible patch is inserted in a first (more distal) position. In an example, a second set of data concerning data concerning electromagnetic energy from muscle activity can be collected by one or more electromyographic (EMG) sensors when the flexible patch is inserted in a second (more proximal) position. In an example, first and second sets of data can be analyzed by a data processing unit to determine the optimal location from which to measure the muscle activity of a selected person or muscle activity during a selected type of activity.

In an example, positioning a flexible patch (with the two electromyographic sensors) in a first location can provide optimal collection of data concerning muscle activity for a first person with a first body size and/or shape and positioning flexible patch in a second location (e.g. shifted up or down) can provide optimal collection of data concerning muscle activity for a second person with a second body size and/or shape. Creating an article of clothing with openings which allow such shifting can enable optimized and/or customized EMG data collection for a specific person. In an example, more-proximal EMG sensor locations can be optimal for a first person and more-distal EMG sensor locations can be optimal for a second person.

In an example, positioning a flexible patch (with the two electromyographic sensors) in a first location can provide optimal collection of data concerning muscle activity for a first sport (or other type of physical activity) and positioning flexible patch in a second location (e.g. shifted up or down) can provide optimal collection of data concerning muscle activity for a second sport (or other type of physical activity). Creating an article of clothing with openings which allow such shifting can enable optimized and/or customized EMG data collection for a specific sport. In an example, more-proximal EMG sensor locations can be optimal for a first sport and more-distal EMG sensor locations can be optimal for a second sport. Relevant variations discussed elsewhere in this disclosure or in priority-linked disclosures can also be applied to this example.

Figure 60:
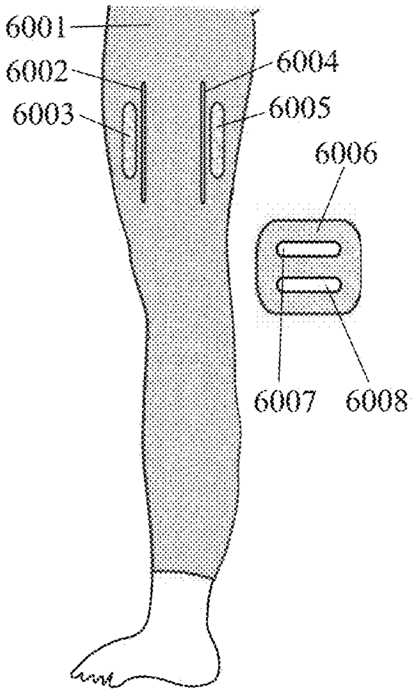
Figure 61:
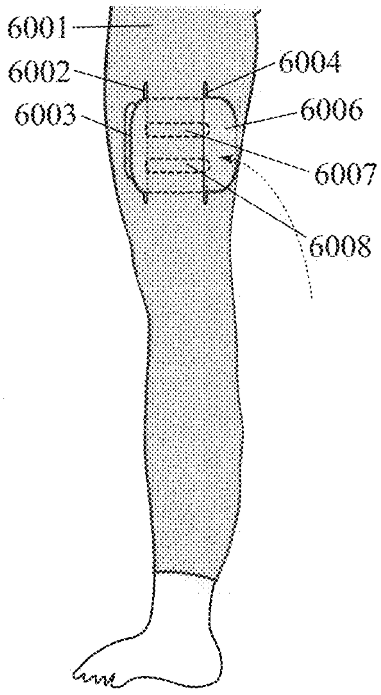
Figure 62:
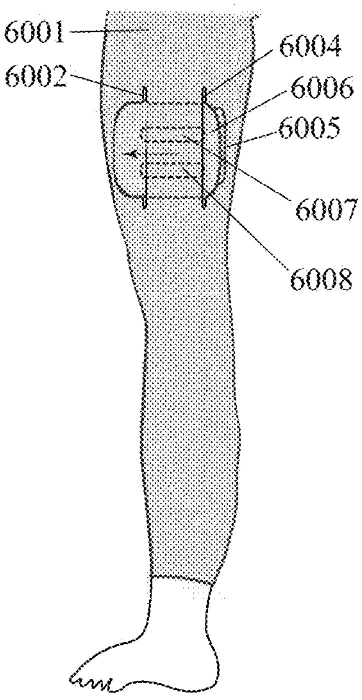

FIGS. 60 through 62 show another example of how this invention can be embodied in an article of clothing for measuring muscle activity. This example is similar to the one shown in FIGS. 57 through 59, except that now the openings in an article of clothing are longitudinal, instead of lateral, and the flexible patch can be shifted laterally, instead of up and down (or proximally and distally). In particular, FIGS. 60 through 62 show an example of how this invention can be embodied in an article of clothing for measuring muscle activity comprising: an article of clothing (6001) which is configured to span a body member, wherein this article of clothing further comprises a first opening (6002), a second opening (6004), a first connector (6003), and a second connector (6005); and a flexible patch (6006), wherein this flexible patch further comprises two electromyographic (EMG) sensors (6007 and 6008), wherein the ends of this flexible patch (6006) are removably inserted through the first opening (6002) and the second opening (6004), and wherein this flexible patch (6006) is attached to the first connector (6003) and the second connector (6005).

In this example, the positioning of the flexible patch with respect to the openings is adjusted in order to position the electromyographic (EMG) sensor so as to most accurately collect data concerning the muscle activity of a specific person and/or muscle activity during a specific type of physical activity. FIGS. 60 through 62 show three sequential views of the same example. FIG. 60 shows this example at a first time when flexible patch 6006 (including two electromyographic sensors 6007 and 6008) has not yet been inserted into proximal and distal openings in the article of clothing. FIG. 61 shows this example at a second time when the (right and left) ends of flexible patch 6006 have been removably inserted into the openings 6002 and 6004, respectively, and attached to connectors 6003 and 6005, respectively, in a first position. FIG. 62 shows this example at a second time when flexible patch 6006 has been shifted to the left to a second position from which electromyographic (EMG) sensors 6007 and 6008 more accurately collect data concerning the muscle activity of this specific person and/or muscle activity during a specific type of physical activity. The configuration of this smart clothing system with an adjustable flexible patch enables customization of EMG sensor locations for optimal and/or customized measurement of muscle activity. Other relevant example configuration variations which are discussed elsewhere in this disclosure can also be applied to this example.

In an example, this invention can be embodied in an article of clothing for measuring muscle activity comprising:

an article of clothing which is configured to span a body member; at least one rotating arcuate patch which is attached to the article of clothing; and at least one electromyographic (EMG) sensor which is attached to (or part of) the rotating arcuate patch, wherein the position, location, orientation, and/or configuration of the electromyographic (EMG) sensor relative to the body member changes when the rotating arcuate patch is rotated.

In an example, the article of clothing can be a pair of pants or a shirt. In an example, there can be one rotating arcuate patch per leg on a pair of pants. In an example, there can be one rotating arcuate patch per arm on a shirt. In an example, there can be two or more rotating arcuate patches per leg on a pair of pants. In an example, there can be two or more one rotating arcuate patches per arm on a shirt. In an example, there can be a hole or opening in an article of clothing and a rotating arcuate patch can be placed over the hole or opening so that one or more electromyographic (EMG) sensors on the rotating arcuate patch are in direct contact with a person's skin. In an example, a rotating arcuate patch can be circular. In an example, a rotating arcuate patch can be made from a fabric or textile. In an example, a rotating arcuate member can have a resilient member (such as a flexible wire) around its perimeter and/or circumference. In an example, this invention can further comprise one or more bands, strips, spokes, or arms which extend from the article of clothing to a central hub or axis (around which the rotating arcuate patch rotates) in order to hold the rotating arcuate patch in place as it rotates.

In an example, a rotating arcuate patch can be manually rotated by a person in order to change the position, location, orientation, and/or configuration of one or more electromyographic (EMG) sensors with respect to a body member. In an example, a rotating arcuate patch can be rotated in order to move one or more electromyographic sensors to the best positions, locations, orientations, and/or configurations from which to collect electromagnetic data concerning the muscle activity of a specific person or muscle activity during a specific type of physical activity. In an example, a rotating arcuate patch can be automatically rotated by a motor or an actuator.

In an example, when a rotating arcuate patch is rotated to a first position, then one or more electromyographic (EMG) sensors on that patch are in the best position, location, orientation, and/or configuration from which to collect data concerning muscle activity from a first person with a first body size and/or shape. In an example, when a rotating arcuate patch is rotated to a second position, then one or more electromyographic (EMG) sensors on that patch are in the best position, location, orientation, and/or configuration from which to collect data concerning muscle activity from a second person with a second body size and/or shape. In an example, when a rotating arcuate patch is rotated to a first position, then one or more electromyographic (EMG) sensors on that patch are in the best position, location, orientation, and/or configuration from which to collect data concerning muscle activity during a first sport or other type of physical activity. In an example, when a rotating arcuate patch is rotated to a second position, then one or more electromyographic (EMG) sensors on that patch are in the best position, location, orientation, and/or configuration from which to collect data concerning muscle activity from a second sport or other type of physical activity. Relevant variations discussed elsewhere in this disclosure or in priority-linked disclosures can also be applied to this example.

Figure 63:
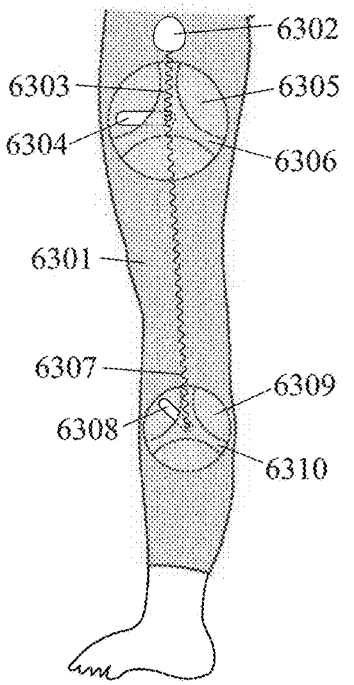
FIGS. 63 through 65 show electromyographic clothing with a rotating arcuate patch with EMG sensors.
Figure 64:
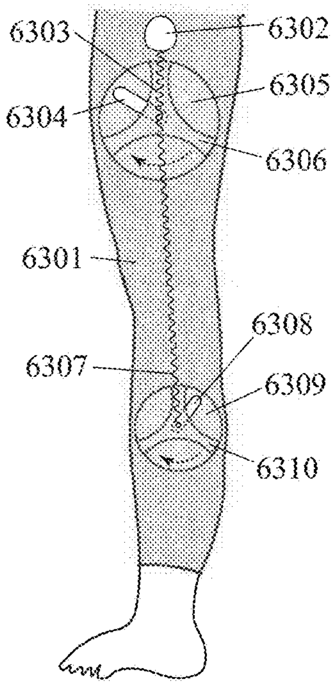
Figure 65:
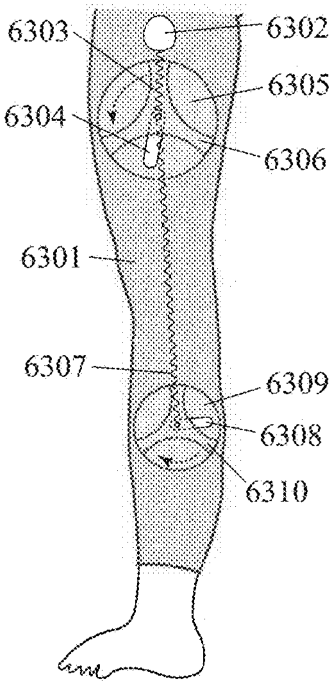

FIGS. 63 through 65 shown an example of how this invention can be embodied in an article of clothing for measuring muscle activity comprising: an article of clothing 6301 which is configured to span a body member (a leg in this example); a rotating arcuate patch 6305 which is attached to the article of clothing 6301; and an electromyographic (EMG) sensor 6304 which is attached to (or part of) rotating arcuate patch 6305, wherein the position, location, orientation, and/or configuration of electromyographic (EMG) sensor 6304 relative to the body member changes when rotating arcuate patch 6305 is rotated. In this example, rotating arcuate patch 6305 rotates around a central hub and this central hub is held in place by a three-spoke member 6306 which connects the central hub to the article of clothing.

This example further comprises a control unit 6302. In an example, this control unit can further comprise a power source, a data processor, a data transmitter, and a data receiver. This example further comprises a flexible wire (or other electromagnetic pathway) 6303 between the control unit and the central hub. This wire enables electromagnetic communication between the control unit and one or more electromyographic (EMG) sensors on the rotating arcuate patch. This example further comprises a second rotating arcuate patch 6309, a second electromyographic (EMG) sensor 6308, a second three-spoke member 6310, and a wire extension 6307. In this example, a first rotating arcuate patch (with a first electromyographic sensor) is located proximally from a body member joint (a knee in this example) and a second rotating arcuate patch (with a second electromyographic sensor) is located distally from the body member joint. This configuration of electromyographic clothing with one or more rotating arcuate patches enables customization of EMG sensor positions, locations, orientations, and/or configurations for optimal and/or customized measurement of muscle activity.

FIGS. 63 through 65 show three sequential views of the same example. FIG. 63 shows this example at a first time when rotating arcuate patch 6305 is in a rotational position wherein electromyographic (EMG) sensor 6304 has a "9 o'clock" orientation and rotating arcuate patch 6309 is in a rotational position wherein electromyographic (EMG) sensor 6308 has a "10-11 o'clock" orientation. FIG. 64 shows this example at a second time when rotating arcuate patch 6305 has been rotated clockwise so that electromyographic (EMG) sensor 6304 now has a "10-11 o'clock" orientation and rotating arcuate patch 6309 has been rotated clockwise so that electromyographic (EMG) sensor 6308 now has a "1 o'clock" orientation. FIG. 65 shows this example at a third time when rotating arcuate patch 6305 has been rotated counter-clockwise so that electromyographic (EMG) sensor 6304 now has a "6-7 o'clock" orientation and rotating arcuate patch 6309 has been rotated clockwise so that electromyographic (EMG) sensor 6308 now has a "2-3 o'clock" orientation.

In this example, an article of clothing with one or more rotating arcuate patches is a pair of pants. In other examples, an article of clothing can be a different type of lower-body garment or an upper-body garment. In an example, an article of clothing can be a full-body article of clothing. In an example, an article of clothing can be selected from the group consisting of: arm band, back brace, belt, blouse, collar, dress, elbow pad, glove, jacket, knee pad, knee tube, leg band, leggings, leotards, overalls, pants, shirt, shoe, shorts, skirt, sock, suit, sweatpants, sweatshirt, tights, underpants, undershirt, union suit, waist band, and wristband. In an example, an article of clothing can have an opening or hole over which a rotating arcuate patch is placed so that an electromyographic (EMG) sensor on that rotating arcuate patch is in direct contact with a person's skin.

In an example, a rotating arcuate patch can be circular. In an example, a rotating arcuate patch can be made from a fabric or textile. In an example, a rotating arcuate patch can further comprise a resilient member (e.g. a flexible wire) which is sewn, adhered, woven, or otherwise attached around its perimeter and/or circumference. In an example, a rotating arcuate patch can be placed over the exterior surface of an article of clothing. In an example, a rotating arcuate patch can be placed over a hole or opening on an article of clothing. In an example, a rotating arcuate patch can be placed under an article of clothing (e.g. between the clothing and a person's skin).

In an example, a rotating arcuate patch can have a size which is 10% to 25% larger than the size of an opening or hole in an article of clothing over which (or under which) the patch is placed. In an example, a rotating arcuate patch can have a size which is up to twice as large as the size of an opening or hole in an article of clothing over which (or under which) it is placed. In an example, a rotating arcuate patch can have the same size as a hole or opening in an article of clothing into which it fits. In an example, both an arcuate patch and a hole over (or under) which it is placed can be circular. In an alternative example, a rotating arcuate patch can be placed over an article of clothing that does not have holes or openings, but the rotating arcuate patch can further comprise one or more capacitive electromyographic sensors which do not require direct skin contact in order to collect muscle activity data.

In an example, there can be two rotating arcuate patches on a single body member such as a leg, arm, or torso. In an example, on the leg of a pair of pants there can be a first proximal rotating arcuate patch which is proximal from the knee (e.g. on the upper leg) and a second rotating arcuate patch which is distal from the knee (e.g. on the lower leg). In an example, on the sleeve of a shirt there can be a first proximal rotating arcuate patch which is proximal from the elbow (e.g. on the upper arm) and a second rotating arcuate patch which is distal from the elbow (e.g. on the forearm). In an example, one or more rotating arcuate patches can be located on the anterior surface of a body member. In an example, one or more rotating arcuate patches can be located on the posterior surface of a body member. In an example, one or more rotating arcuate patches can be located on the lateral surface of a body member.

In an example, a rotating arcuate patch can rotate around a central hub or axis. In an example, this central hub or axis can be held in place by one or more members that connect it to an article of clothing. In this example, a central hub is held in place by a three-spoke member that connects the hub to the article of clothing. In an example, a central hub can be held in place by two, three, four or more spokes or bands which connect a hub to an article of clothing. In an example, a three-spoke member can be made from a polymer or metal. In an example, a rotating arcuate patch can span a percentage of the perimeter or circumference of a cross-section of a body member such as a leg or arm. In an example, this percentage can be within the range of 10% to 25%. In an example, this percentage can be within the range of 25% to 50%. In an example, this percentage can be within the range of 50% to 75%.

In an example, a rotating arcuate patch can be manually rotated by a person. In an example, such rotation can be used to "fine tune" the position, location, orientation, and/or configuration of one or more electromyographic (EMG) sensors which are part of the rotating arcuate patch in order to most accurately collect data concerning electromagnetic energy associated with neuromuscular activity. In an example, there can be markings on a rotating arcuate patch, on the article of clothing, or both—which show the rotational (e.g. radial) position of the rotating arcuate patch relative to an article of clothing. For example, there can be radial marks (analogous to "hours of a clock" or "points on a compass") around the perimeter of a rotating arcuate patch which can be aligned with a stationary arrow or other indicator on an article of clothing. This is analogous to markings on an old analog dial which can be aligned with a stationary mark on the device to which the dial is attached. In an example, when the best rotational position is found, then a rotating arcuate patch can be held in a particular rotational configuration by an attachment mechanism selected from the group consisting of: hook- and -eye mechanism, clip, button, pin, snap, clasp, buckle, and zipper. In an example, this invention can further comprise an electric motor or other actuator which automatically rotates a rotating arcuate patch in order to find the optimal location for collecting data from muscle activity.

In an example, data from one or more electromyographic (EMG) sensors can be analyzed in order to determine the optimal position, location, orientation, and/or configuration for those sensors from which to collect data concerning electromagnetic energy from neuromuscular activity. In an example, this analysis can include the use of one or more analytic methods selected from the group consisting of: Analysis of Variance (ANOVA), Artificial Neural Network (ANN), Auto-Regressive (AR) Modeling, Averaging, Back Propagation Neural Network (BPNN), Bayesian Analysis, Bonferroni Analysis (BA), Centroid Analysis, Chi-Squared Analysis, Correlation, Covariance, Data Normalization (DN), Decision Tree Analysis (DTA), Discrete Fourier Transform (DFT), Discriminant Analysis (DA), Empirical Mode Decomposition (EMD), Factor Analysis (FA), Fast Fourier Transform (FFT), Fast Orthogonal Search (FOS), Feature Vector Analysis (FVA), Fisher Linear Discriminant, Forward Dynamics Model (FDM), Fourier Transformation (FT) Method, Fuzzy Logic (FL) Modeling, Gaussian Model (GM), Generalized Auto-Regressive Conditional Heteroscedasticity (GARCH) Modeling, Hidden Markov Model (HMM), Independent Components Analysis (ICA), Inverse Dynamics Model (FDM), Kalman Filter (KF), Kernel Estimation, Least Squares Estimation, Linear Regression, Linear Transform, Logit Model, Low Pass Filter (LPF), Machine Learning (ML), Markov Model, Maximum Entropy Modeling, Maximum Likelihood, Multivariate Linear Regression, Multivariate Logit, Multivariate Regression, Naïve Bayes Classifier, Neural Network, Non-Linear Programming (NLP), Non-Linear Regression (NLR), Non-negative Matrix Factorization (NMF), Polynomial Function Estimation (PFE), Power Spectral Density, Power Spectrum Analysis, Principal Components Analysis (PCA), Probit Model, Quadratic Minimum Distance Classifier, Random Forest (RF), Random Forest Analysis (RFA), Rectification, Regression Model, Signal Amplitude (SA), Signal Averaging, Signal Decomposition, Sine Wave Compositing, Singular Value Decomposition (SVD), Spine Function, Support Vector Machine (SVM), Time Domain Analysis, Time Frequency Analysis, Time Series Model, Trained Bayes Classifier, Variance, Waveform Identification, Wavelet Analysis, and Wavelet Transformation.

In an example, an electromyographic (EMG) sensor can have a shape which is selected from the group consisting of: square, rectangle, rounded square or rectangle, circle, ellipse, oval, egg-shape, and hexagon. In an example, an electromyographic (EMG) sensor can be a bipolar sensor. In an example, an electromyographic (EMG) sensor can be a tripolar sensor. In an example, there can be one electromyographic (EMG) sensor on (or otherwise integrated with) a rotating arcuate patch. In an example, the angle at which an electromyographic (EMG) sensor intersects the longitudinal axis of the body member (either in 3D or when both are projected onto the same flat plane) changes as a rotating arcuate patch is rotated. In an example, an electromyographic (EMG) sensor can be configured on a rotating arcuate patch in a radially-extending manner, like a wheel spoke or a hand on the face of a clock. In an example, an electromyographic (EMG) sensor can be configured on a rotating arcuate patch in a radially-tangential manner, as it would be if perpendicular to a wheel spoke or a hand on the face of a clock.

In an example, there can be two or more electromyographic (EMG) sensors on (or otherwise integrated with) a rotating arcuate patch. In an example, two or more radially-extending electromyographic (EMG) sensors can be evenly distributed with respect to polar coordinates of the rotating arcuate patch, like two or more hands of a clock which are separated by an equal number of time units. In an example, two or more radially-extending electromyographic (EMG) sensors can be unevenly distributed with respect to polar coordinates of the rotating arcuate patch, like two or more hands of a clock which are separated by an unequal number of time units. In an example, two radially-extending electromyographic (EMG) sensors can form a "chevron" shape on a rotating arcuate patch.

In an example, this invention can comprise two or more overlapping, concentric, and/or coaxial rotating arcuate patches, each with its own electromyographic (EMG) sensor. This can allow independent rotation of the rotating arcuate patches and independent positioning of two or more electromyographic sensors in the same (circular) area. In an example, this allows adjustment of the angle between two longitudinal electromyographic sensors. In an example, there can be a first coaxial rotating arcuate patch on the inside of an article of clothing and a second coaxial rotating arcuate patch on the outside of an article of clothing. Other relevant example configuration variations which are discussed elsewhere in this disclosure can also be applied to this example.

In an example, rotating a rotating arcuate patch (with one or more electromyographic sensors) to a first orientation can provide optimal collection of data concerning muscle activity of a first person with a first body size and/or shape and rotating a rotating arcuate patch to a second orientation can provide optimal collection of data concerning muscle activity of a second person with a second body size and/or shape. An article of clothing with such rotating arcuate patches enables optimized and/or customized EMG data collection for a specific person. In an example, rotating a rotating arcuate patch (with one or more electromyographic sensors) to a first orientation can provide optimal collection of data concerning muscle activity during a first sport and rotating a rotating arcuate patch to a second orientation can provide optimal collection of data concerning muscle activity during a second sport. An article of clothing with such rotating arcuate patches enables optimized and/or customized EMG data collection for a specific sport.

In an example, this invention can be embodied in an article of clothing for measuring muscle activity comprising: an article of clothing which is configured to span a body member, wherein this article of clothing has a first hole and a second hole; a stretchable band, wherein this stretchable band is removably attachable to the article of clothing at a first location so as to cover at least a portion of the first hole, and wherein this stretchable band is removably attachable to the article of clothing at a second location so as to cover at least a portion of the second hole; and an electromyographic (EMG) sensor which is part of the stretchable band, wherein this electromyographic (EMG) sensor is configured to be in contact with skin through the first hole when the stretchable band is attached to the article of clothing at the first location, and wherein this electromyographic (EMG) sensor is configured to be in contact with skin through the second hole when the stretchable band is attached to the article of clothing at the second location. Relevant variations discussed elsewhere in this disclosure or in priority-linked disclosures can also be applied to this example.

Figure 66:
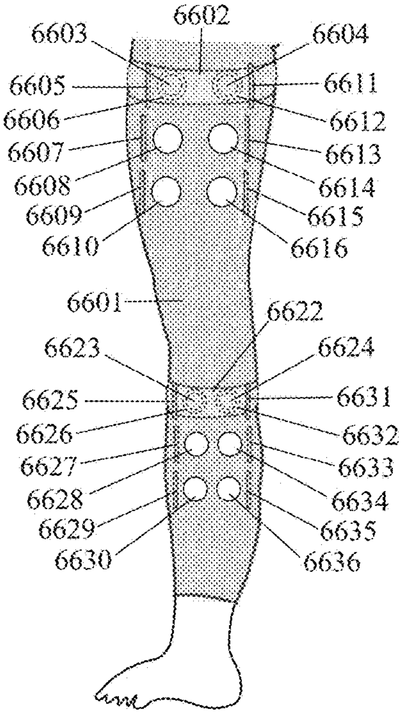
FIGS. 66 through 68 show electromyographic clothing with an array of holes through which EMG sensors can contact the body.
Figure 67:
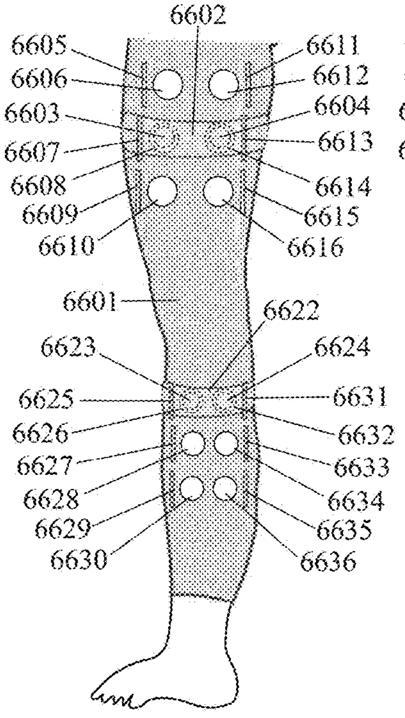
Figure 68:
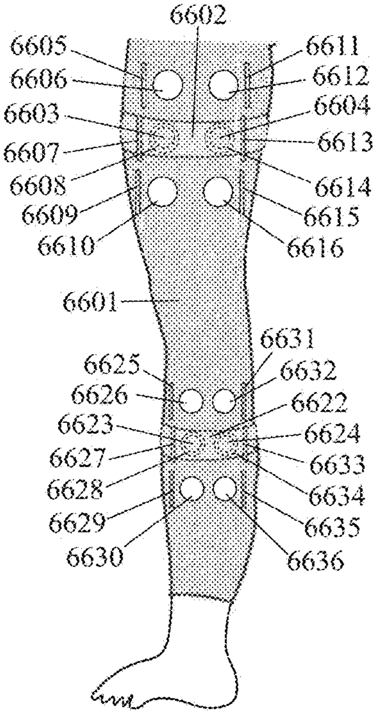

FIGS. 66 through 68 show an example of how this invention can be embodied in an article of clothing for measuring muscle activity comprising: an article of clothing 6601 which is configured to span a body member, wherein this article of clothing 6601 has a first hole 6606 and a second hole 6608; a stretchable band 6602, wherein this stretchable band 6602 can be removably attached to the article of clothing 6601 at a first location so as to cover at least a portion of the first hole 6606, and wherein this stretchable band 6602 can be removably attached to the article of clothing 6601 at a second location so as to cover at least a portion of the second hole 6608; and an electromyographic (EMG) sensor 6603 which is part of the stretchable band 6602, wherein this electromyographic (EMG) sensor 6603 is configured to be in contact with the body member through the first hole 6606 when the stretchable band 6602 is attached to the article of clothing 6601 at the first location, and wherein this electromyographic (EMG) sensor 6603 is configured to be in contact with the body member through the second hole 6608 when the stretchable band 6602 is attached to the article of clothing 6601 at the second location.

The example shown in FIGS. 66 through 68 further comprises: other holes (6610, 6612, 6614, 6616, 6626, 6628, 6630, 6632, 6634, and 6636) in the article of clothing; a second electromyographic (EMG) sensor 6604 on stretchable band 6602; connectors (6605, 6607, 6609, 6611, 6613, and 6615) which removably attach stretchable band 6602 to selected locations; a second stretchable band 6622; two electromyographic (EMG) sensors (6623 and 6624) on stretchable band 6622; and connectors (6625, 6627, 6629, 6631, 6633, and 6635) which removably attach stretchable band 6622 to selected locations.

FIGS. 66 through 68 show three sequential views of the same example. FIG. 66 shows this example at a first time wherein: stretchable band 6602 encircles the article of clothing at a location which covers holes 6606 and 6612; electromyographic (EMG) sensors 6603 and 6604 are in direct contact with the body member through holes 6606 and 6612, respectively; stretchable band 6622 encircles the article of clothing at a location which covers holes 6626 and 6632; and electromyographic (EMG) sensors 6623 and 6624 are in direct contact with the body member through holes 6626 and 6632, respectively.

FIG. 67 shows this example at a first time wherein: stretchable band 6602 has been moved to a location which covers holes 6608 and 6614; electromyographic (EMG) sensors 6603 and 6604 are now in direct contact with the body member through holes 6608 and 6614, respectively; stretchable band 6622 remains at a location which covers holes 6626 and 6632; and electromyographic (EMG) sensors

6623 and 6624 remain in direct contact with the body member through holes 6626 and 6632, respectively.

FIG. 68 shows this example at a first time wherein: stretchable band 6602 remains at a location which covers holes 6608 and 6614; electromyographic (EMG) sensors 6603 and 6604 are in direct contact with the body member through holes 6608 and 6614, respectively; stretchable band 6622 has been moved to a lower location which covers holes 6628 and 6634; and electromyographic (EMG) sensors 6623 and 6624 are now in direct contact with the body member through holes 6628 and 6634, respectively.

In this example, a first stretchable band (with a first set of electromyographic sensors) is located proximally from a body member joint (a knee in this example) and a second stretchable band (with a second set of electromyographic sensors) is located distally from the body member joint. This configuration of electromyographic clothing with one or more removably-attachable stretchable bands enables customization of EMG sensor locations for optimal and/or customized measurement of muscle activity.

In this example, the article of clothing is a pair of pants. In other examples, an article of clothing can be a different type of lower-body garment or an upper-body garment. In an example, an article of clothing can be a full-body article of clothing. In an example, an article of clothing can be selected from the group consisting of: arm band, back brace, belt, blouse, collar, dress, elbow pad, glove, jacket, knee pad, knee tube, leg band, leggings, leotards, overalls, pants, shirt, shoe, shorts, skirt, sock, suit, sweatpants, sweatshirt, tights, underpants, undershirt, union suit, waist band, and wristband.

In an example, an article of clothing can have multiple sets of holes (or openings) which comprise alternative locations for placement of multiple stretchable bands with electromyographic (EMG) sensors. In an example, a set of holes can be configured in one or more rings around cross-sections of a body member. In an example, a set of holes can be configured in one or more columns which are parallel to the longitudinal axis of a body member. In an example, there can be a first set of holes on the proximal portion of a leg or arm and a second set of holes on the distal portion of the leg or arm. In an example, there can be a first set of holes on the anterior surface of a leg or arm and a second set of holes on the posterior surface of the leg or arm.

In an example, a stretchable band can be made from an elastic fabric or textile. In an example, a stretchable band can have a width in the range of ½" to 2". In an example, a stretchable band can have a width in the range of 2" to 4". In an example, a stretchable band can be continuous and can be attached to a body member by sliding it around and over the distal end of the body member. In an example, a stretchable band can be discontinuous and can be attached to a body member by means of a hook- and -eye attachment, a clip, a snap, a clasp, a pin, a buckle, a button, or a zipper. In an example, the ends of a discontinuous a stretchable band can attached to each other around the perimeter of a body member by means of a hook- and -eye attachment, a clip, a clasp, a snap, a pin, a buckle, a button, or a zipper. In an example, a stretchable band can be attached to an article of clothing by a set of connectors selected from the group consisting of hook- and -eye attachment, clip, clasp, snap, pin, plug, tie, buckle, button, and zipper.

In an example, an electromyographic (EMG) sensor can have a shape which is selected from the group consisting of: square, rectangle, rounded square or rectangle, circle, ellipse, oval, egg-shape, and hexagon. In an example, an electromyographic (EMG) sensor can be a bipolar sensor. In an example, an electromyographic (EMG) sensor can be a tripolar sensor. In an example, there can be one electromyographic (EMG) sensor on (or otherwise integrated with) a stretchable band. In an example, there can be two or more electromyographic (EMG) sensors on (or otherwise integrated with) a stretchable band. Other relevant example configuration variations which are discussed elsewhere in this disclosure can also be applied to this example.

In an example, attaching a stretchable band (with one or more electromyographic sensors) to a first location on an article of clothing can provide optimal collection of data concerning muscle activity of a first person with a first body size and/or shape and attaching a stretchable band (with one or more electromyographic sensors) to a second location on an article of clothing can provide optimal collection of data concerning muscle activity of a second person with a second body size and/or shape. In an example, attaching a stretchable band (with one or more electromyographic sensors) to a first location on an article of clothing can provide optimal collection of data concerning muscle activity during a first sport and attaching a stretchable band (with one or more electromyographic sensors) to a second location on an article of clothing can provide optimal collection of data concerning muscle activity during a second sport. An article of clothing with such stretchable band configurations can enable optimized and/or customized EMG data collection for a specific person or sport.

In an example, this invention can be embodied in an article of clothing for measuring muscle activity comprising: an article of clothing which is configured to span a body member; a control unit which is attached to (or part of) the article of clothing; a plurality of electromagnetic energy sensors which are attached to (or part of) the article of clothing; and a plurality of removably-attachable electromagnetic connectors, wherein a removably-attachable electromagnetic connector creates an electromagnetic pathway between a set of electromagnetic energy sensors when it is attached to that set of electromagnetic energy sensors, and wherein a removably-attachable electromagnetic connector creates an electromagnetic pathway between the control unit and an electromagnetic energy sensor when it is attached to the control unit and that electromagnetic energy sensor. In an example, the control unit can further comprise a power source and a data processor. Relevant variations discussed elsewhere in this disclosure or in priority-linked disclosures can also be applied to this example.

Figure 69:
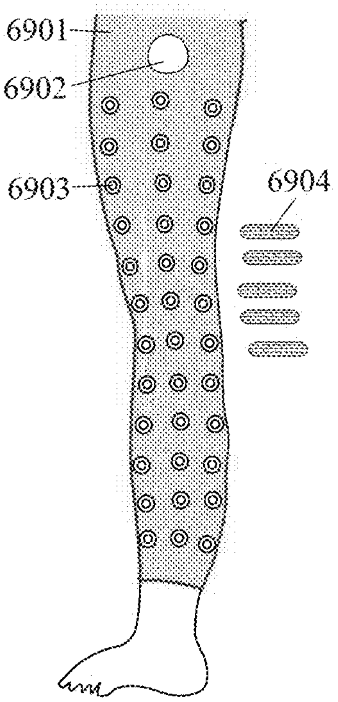
FIGS. 69 through 71 show electromyographic clothing with removably-attachable connectors to connect EMG sensors.
Figure 70:
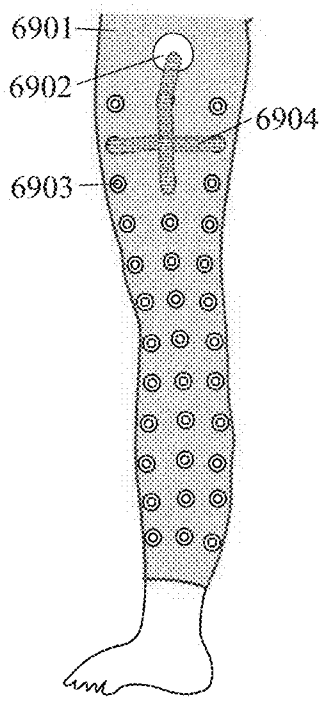
Figure 71:
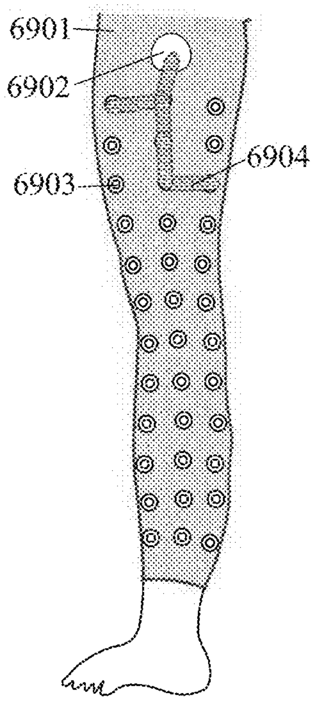

FIGS. 69 through 71 show an example of how this invention can be embodied in an article of clothing for measuring muscle activity comprising: an article of clothing 6901 which is configured to span a body member; a control unit 6902 which is attached to (or part of) the article of clothing; a plurality of electromagnetic energy sensors (including 6903) which are attached to (or part of) the article of clothing; and a plurality of removably-attachable electromagnetic connectors (including 6904) wherein a removably-attachable electromagnetic connector creates an electromagnetic pathway between a set of electromagnetic energy sensors when it is attached to that set of electromagnetic energy sensors, and wherein a removably-attachable electromagnetic connector creates an electromagnetic pathway between the control unit and an electromagnetic energy sensor when it is attached to the control unit and that electromagnetic energy sensor. In this example, the control unit further comprises a power source and a data processor.

FIGS. 69 through 71 show three sequential views of the same example. FIG. 69 shows this example at a first time when none of the removably-attachable electromagnetic connectors are attached to the control unit or to any electromagnetic energy sensors. FIG. 70 shows this example at a second time when a removably-attachable electromagnetic connector has been attached to the control unit and several removably-attachable electromagnetic connectors have been attached to electromagnetic energy sensors in a first configuration, activating a first configuration of sensors to collect a first set of data concerning neuromuscular activity. FIG. 71 shows this example at a third time when a removably-attachable electromagnetic connector has been attached to the control unit and several removably-attachable electromagnetic connectors have been attached to electromagnetic energy sensors in a second configuration, activating a second configuration of sensors to collect a second set of data concerning neuromuscular activity.

In this example, the article of clothing is a pair of pants (of which one leg is shown in these figures). In other examples, an article of clothing can be a different type of lower-body garment or an upper-body garment. In an example, an article of clothing can be a full-body article of clothing. In an example, an article of clothing can be selected from the group consisting of: arm band, back brace, belt, blouse, collar, dress, elbow pad, glove, jacket, knee pad, knee tube, leg band, leggings, leotards, overalls, pants, shirt, shoe, shorts, skirt, sock, suit, sweatpants, sweatshirt, tights, underpants, undershirt, union suit, waist band, and wristband.

In an example, an article of clothing can comprise a plurality, array, and/or grid of electromagnetic energy sensors. In an example, not all of these electromagnetic energy sensors collect data concerning muscle activity at a given time—only those which are connected to the control unit by the attachment of a removably-attachable electromagnetic connector or a series of removably-attachable electromagnetic connectors. In an example, the subset and configuration of electromagnetic energy sensors which are activated to collect data depends on the configuration of removably-attachable electromagnetic connectors which are attached to the article of clothing. In an example, the entire plurality, array, and/or grid of electromagnetic energy sensors which are part of an article of clothing (regardless of whether they are active or not) can be called "available" electromagnetic energy sensors.

In an example, the subset of all available electromagnetic energy sensors which is activated to collect data by the attachment of removably-attachable electromagnetic connectors at a given time can be called "activated" electromagnetic energy sensors. In an example, the number of activated sensors can be less than 50% of the number of available sensors on an article of clothing. In an example, the number of activated sensors can be less than 25% of the number of available sensors on an article of clothing. In an example, the selection of which available sensors to activate by the attachment of a selected configuration of removably-attachable electromagnetic connectors can be determined based on analysis of data from different sensors to identify the optimal configuration of sensors to activate.

In an example, an array and/or grid of available electromagnetic energy sensors on an article of clothing can be configured in one or more rings around cross-sections of an article of clothing (or a body member spanned by the article of clothing). In an example, an array and/or grid of available electromagnetic energy sensors on an article of clothing can be configured in one or more columns which are parallel to the longitudinal axis of the article of clothing (or a body member spanned by the article of clothing). In an example, there can be a first array and/or grid of available electromagnetic energy sensors on an article of clothing on the proximal portion of a body member (e.g. upper leg or upper arm) and a second array and/or grid of available electromagnetic energy sensors on an article of clothing on the distal portion of a body member (e.g. lower leg or forearm). In an example, there can be a first array and/or grid of available electromagnetic energy sensors on an article of clothing on the anterior portion of a body member and a second array and/or grid of available electromagnetic energy sensors on an article of clothing on the posterior portion of a body member.

In an example, a plurality of available electromagnetic energy sensors can be formed in an article of clothing by weaving. In an example, a plurality of available electromagnetic energy sensors can be formed in an article of clothing by weaving electroconductive threads, fibers, yarns, and/or traces within an article of clothing. In an example, a plurality of available electromagnetic energy sensors can be formed on an article of clothing by printing. In an example, a plurality of available electromagnetic energy sensors can be formed on an article of clothing by printing with electroconductive ink and/or resin. In an example, a plurality of available electromagnetic energy sensors can be formed on an article of clothing by embroidery. In an example, a plurality of available electromagnetic energy sensors can be formed on an article of clothing by embroidering with electroconductive threads, fibers, and/or yarns. In an example, a plurality of available electromagnetic energy sensors can be formed on an article of clothing by adhesion. In an example, a plurality of available electromagnetic energy sensors can be formed on an article of clothing by adhering electroconductive members to an article of clothing.

In an example, a removably-attachable electromagnetic connector can be removably attached to a control unit and/or to an electromagnetic energy sensor by one or more snaps, plugs, clips, pins, or clasps. In an example, attachment via snap, plug, clip, pin, or clasp can create an electromagnetic pathway from a removably-attachable electromagnetic connector to the control unit and/or a sensor. In an example, a removably-attachable electromagnetic connector can comprise a single electromagnetic pathway. In an example, a removably-attachable electromagnetic connector can comprise two or more electromagnetic pathways. In an example, attachment via snap, plug, clip, pin, or clasp can create two or more electromagnetic pathways from a removably-attachable electromagnetic connector to a control unit and/or a sensor. In an example, a removably-attachable electromagnetic connector can also be attached to an article of clothing via a hook- and -eye mechanism. Other relevant example configuration variations which are discussed elsewhere in this disclosure can also be applied to the example shown here in FIGS. 69 through 71.

In an example, different sets of muscle activity data collected from different configurations of activated electromagnetic energy sensors (created by different attachment configurations of removably-attachable electromagnetic connectors) can be analyzed in order to identify which configuration is best for measuring the muscle activity of a specific person or muscle activity during a specific sport. In an example, a configuration of activated electromagnetic energy sensors connected in parallel can be best for measuring muscle activity. In an example, a configuration of activated electromagnetic energy sensors connected in series can be best for measuring muscle activity. In an example, a configuration of activated electromagnetic energy sensors in a ring formation or partial ring formation can be best for measuring muscle activity. In an example, a configuration of activated electromagnetic energy sensors in a columnar formation or partial column formation can be best for measuring muscle activity.

In an example, data from different configurations of electromagnetic energy sensors can be analyzed using one or more methods selected from the group consisting of: Analysis of Variance (ANOVA), Artificial Neural Network (ANN), Auto-Regressive (AR) Modeling, Averaging, Back Propagation Neural Network (BPNN), Bayesian Analysis, Bonferroni Analysis (BA), Centroid Analysis, Chi-Squared Analysis, Correlation, Covariance, Data Normalization (DN), Decision Tree Analysis (DTA), Discrete Fourier Transform (DFT), Discriminant Analysis (DA), Empirical Mode Decomposition (EMD), Factor Analysis (FA), Fast Fourier Transform (FFT), Fast Orthogonal Search (FOS), Feature Vector Analysis (FVA), Fisher Linear Discriminant, Forward Dynamics Model (FDM), Fourier Transformation (FT) Method, Fuzzy Logic (FL) Modeling, Gaussian Model (GM), Generalized Auto-Regressive Conditional Heteroscedasticity (GARCH) Modeling, Hidden Markov Model (HMM), Independent Components Analysis (ICA), Inverse Dynamics Model (FDM), Kalman Filter (KF), Kernel Estimation, Least Squares Estimation, Linear Regression, Linear Transform, Logit Model, Low Pass Filter (LPF), Machine Learning (ML), Markov Model, Maximum Entropy Modeling, Maximum Likelihood, Multivariate Linear Regression, Multivariate Logit, Multivariate Regression, Naïve Bayes Classifier, Neural Network, Non-Linear Programming (NLP), Non-Linear Regression (NLR), Non-negative Matrix Factorization (NMF), Polynomial Function Estimation (PFE), Power Spectral Density, Power Spectrum Analysis, Principal Components Analysis (PCA), Probit Model, Quadratic Minimum Distance Classifier, Random Forest (RF), Random Forest Analysis (RFA), Forest Gump Analysis (FGA), Rectification, Regression Model, Signal Amplitude (SA), Signal Averaging, Signal Decomposition, Sine Wave Compositing, Singular Value Decomposition (SVD), Spine Function, Support Vector Machine (SVM), Time Domain Analysis, Time Frequency Analysis, Time Series Model, Trained Bayes Classifier, Variance, Waveform Identification, Wavelet Analysis, and Wavelet Transformation.

In an example, this invention can be embodied in method for creating a customized article of clothing for measuring muscle activity comprising: creating a master model of an article of clothing with a first plurality of electromagnetic energy sensors which collect data concerning muscle activity; having a person wear this master model while the person performs muscle activity; analyzing data from the master model while the person performs muscle activity in order to identify a second plurality of electromagnetic energy sensors on the master model which are most useful for collecting data concerning the muscle activity of this specific person or muscle activity during a specific type of physical activity, wherein the second plurality is a subset of the first plurality; and creating a customized article of clothing to measure muscle activity with the second plurality of electromagnetic energy sensors to collect data concerning muscle activity of this specific person or muscle activity during the specific type of physical activity. In an example, the number of sensors in the second plurality can be less than 50% of the number of sensors in the first plurality. In an example, the number of sensors in the second plurality can be less than 25% of the number of sensors in the first plurality. Relevant variations discussed elsewhere in this disclosure or in priority-linked disclosures can also be applied to this example.

Figures 72, 73, 74:
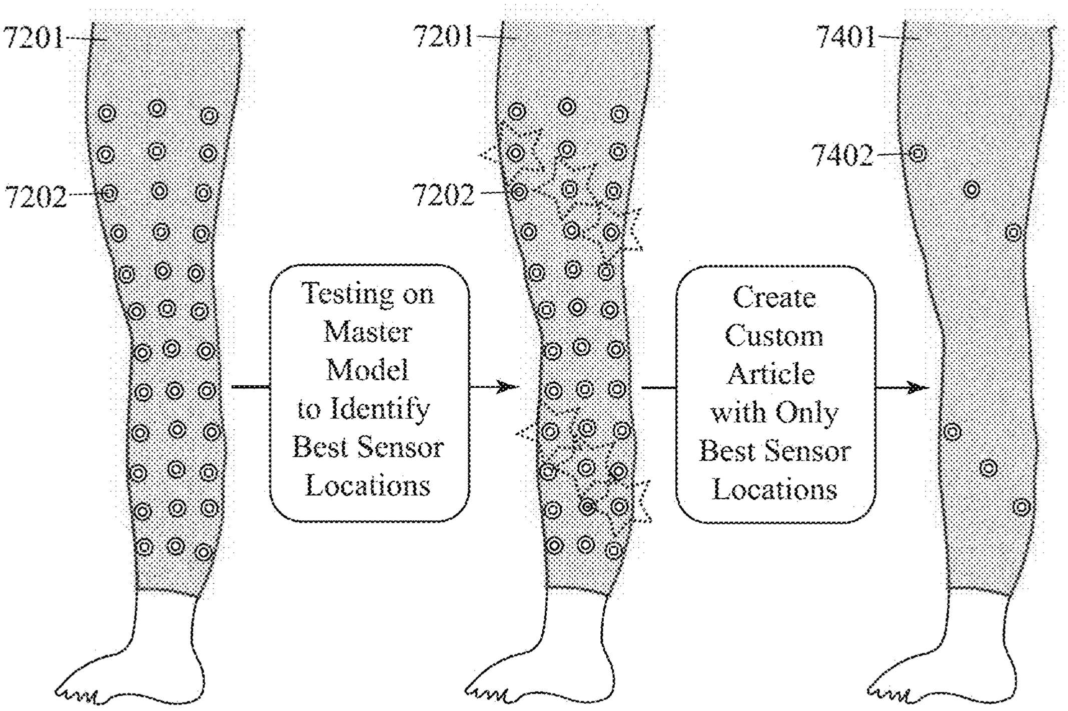
FIGS. 72 through 74 show how a master model of electromyographic clothing (with a larger number of EMG sensors) can be used to create customized electromyographic clothing (with a smaller number of EMG sensors).

FIGS. 72 through 74 show an example which further illustrates how this invention can be embodied in method of creating a customized article of clothing for measuring muscle activity. FIG. 72 shows a master model of an article of clothing 7201 with a first plurality of electromagnetic energy sensors (including 7202) which collect data concerning muscle activity. FIG. 73 shows this master model after testing has been done in order to identify a second plurality of electromagnetic energy sensors (a subset of the first plurality) that is most useful for collecting data concerning the muscle activity of a specific person or muscle activity during a specific type of physical activity. In this figure, the second plurality of electromagnetic energy sensors is symbolically highlighted by dotted-line stars. In this figure, there are six electromagnetic energy sensors in the second plurality.

FIG. 74 shows a customized article of clothing 7401 to measure muscle activity which has been created with the identified second plurality of electromagnetic energy sensors (including 7402) in order to most efficiently collect data concerning muscle activity of the specific person or muscle activity during the specific type of physical activity. In an example, this method can identify the minimum number of sensors required in the second plurality (in the customized article of clothing) in order to achieve a target level of precision and/or accuracy in the measurement of muscle activity. In an example, a customized article of clothing can be automatically created with computer guidance. In an example, a customized article of clothing can be automatically created by computer-guided embroidery, sewing, knitting, and weaving. In an example, a customized article of clothing can be automatically created by computer-guided printing with electroconductive ink or resin. In an example, a customized article of clothing can be automatically created by computer-guided 3D printing.

In an example, a second plurality of electromagnetic energy sensors can be identified by analysis of data from a master model using one or more methods selected from the group consisting of: Analysis of Variance (ANOVA), Artificial Neural Network (ANN), Auto-Regressive (AR) Modeling, Averaging, Back Propagation Neural Network (BPNN), Bayesian Analysis, Bonferroni Analysis (BA), Centroid Analysis, Chi-Squared Analysis, Correlation, Covariance, Data Normalization (DN), Decision Tree Analysis (DTA), Discrete Fourier Transform (DFT), Discriminant Analysis (DA), Empirical Mode Decomposition (EMD), Factor Analysis (FA), Fast Fourier Transform (FFT), Fast Orthogonal Search (FOS), Feature Vector Analysis (FVA), Fisher Linear Discriminant, Forward Dynamics Model (FDM), Fourier Transformation (FT) Method, Fuzzy Logic (FL) Modeling, Gaussian Model (GM), Generalized Auto-Regressive Conditional Heteroscedasticity (GARCH) Modeling, Hidden Markov Model (HMM), Independent Components Analysis (ICA), Inverse Dynamics Model (FDM), Kalman Filter (KF), Kernel Estimation, Least Squares Estimation, Linear Regression, Linear Transform, Logit Model, Low Pass Filter (LPF), Machine Learning (ML), Markov Model, Maximum Entropy Modeling, Maximum Likelihood, Multivariate Linear Regression, Multivariate Logit, Multivariate Regression, Naïve Bayes Classifier, Neural Network, Non-Linear Programming (NLP), Non-Linear Regression (NLR), Non-negative Matrix Factorization (NMF), Polynomial Function Estimation (PFE), Power Spectral Density, Power Spectrum Analysis, Principal Components Analysis (PCA), Probit Model, Quadratic Minimum Distance Classifier, Random Forest (RF), Random Forest Analysis (RFA), Forest Gump Analysis (FGA), Rectification, Regression Model, Signal Amplitude (SA), Signal Averaging, Signal Decomposition, Sine Wave Compositing, Singular Value Decomposition (SVD), Spine Function, Support Vector Machine (SVM), Time Domain Analysis, Time Frequency Analysis, Time Series Model, Trained Bayes Classifier, Variance, Waveform Identification, Wavelet Analysis, and Wavelet Transformation.

In this example, the article of clothing is a pair of pants (of which one leg is shown in these figures). In other examples, an article of clothing can be a different type of lower-body garment or an upper-body garment. In an example, an article of clothing can be a full-body article of clothing. In an example, an article of clothing can be selected from the group consisting of: arm band, back brace, belt, blouse, collar, dress, elbow pad, glove, jacket, knee pad, knee tube, leg band, leggings, leotards, overalls, pants, shirt, shoe, shorts, skirt, sock, suit, sweatpants, sweatshirt, tights, underpants, undershirt, union suit, waist band, and wristband.

In an example, a master model of an article of clothing can comprise a plurality, array, and/or grid of electromagnetic energy sensors. In an example, a plurality, array, and/or grid of electromagnetic energy sensors on a master model can be configured in one or more rings around cross-sections of a body member spanned by the master model. In an example, a plurality, array, and/or grid of electromagnetic energy sensors on a master model can be configured in one or more columns which are parallel to the longitudinal axis of a body member spanned by the master model. In an example, there can be a first array and/or grid of electromagnetic energy sensors on the proximal portion of a body member (e.g. upper leg or upper arm) and a second array and/or grid of electromagnetic energy sensors on the distal portion of a body member (e.g. lower leg or forearm).

In an example, electromagnetic energy sensors can be formed in an article of clothing by weaving. In an example, electromagnetic energy sensors can be formed in an article of clothing by weaving electroconductive threads, fibers, yarns, and/or traces within an article of clothing. In an example, electromagnetic energy sensors can be formed on an article of clothing by printing. In an example, electromagnetic energy sensors can be formed on an article of clothing by printing with electroconductive ink and/or resin. In an example, electromagnetic energy sensors can be formed on an article of clothing by embroidery. In an example, electromagnetic energy sensors can be formed on an article of clothing by embroidering with electroconductive threads, fibers, and/or yarns. In an example, electromagnetic energy sensors can be formed on an article of clothing by adhesion. In an example, electromagnetic energy sensors can be formed on an article of clothing by adhering electroconductive members to an article of clothing. Other relevant example configuration variations which are discussed elsewhere in this disclosure can also be applied to the example discussed here.

In an example, this invention can be embodied in modular system for creating customized electromyographic clothing comprising: (a) a first set of alternative modules for an article of clothing, wherein each module in this first set is configured to be worn on a first portion of a person's body, wherein at least one module in this first set includes at least one electromagnetic energy sensor, and wherein there is variation in the location, orientation, size, shape, number, and/or configuration of electromagnetic energy sensors between different modules in this first set; and (b) a second set of alternative modules for an article of clothing, wherein at least one module in this second set is configured to be worn on a second portion of a person's body, wherein each module in this second set includes at least one electromagnetic energy sensor, wherein there is variation in the location, orientation, size, shape, number, and/or configuration of electromagnetic energy sensors between different modules in this second set, and wherein a first module is selected from the first set, a second module is selected from the second set, and the selected first and second modules are combined to form part (or all) of a single customized article of clothing for collecting data concerning electromagnetic energy from neuromuscular activity by a specific person or during a specific type of physical activity. Relevant variations discussed elsewhere in this disclosure or in priority-linked disclosures can also be applied to this example.

Figure 75:
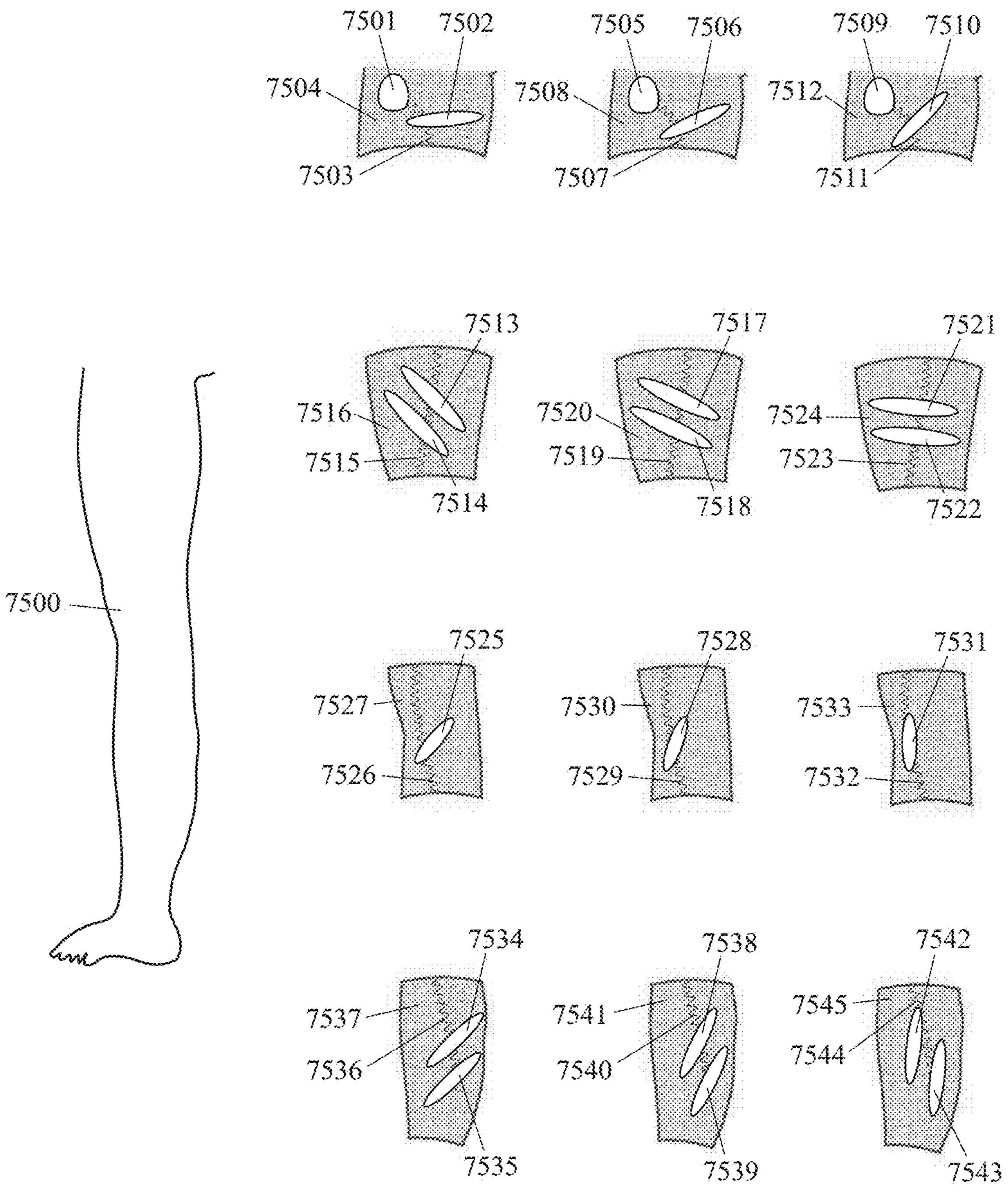
FIGS. 75 and 76 show an example of a modular system for creating customized electromyographic clothing.
Figure 76:
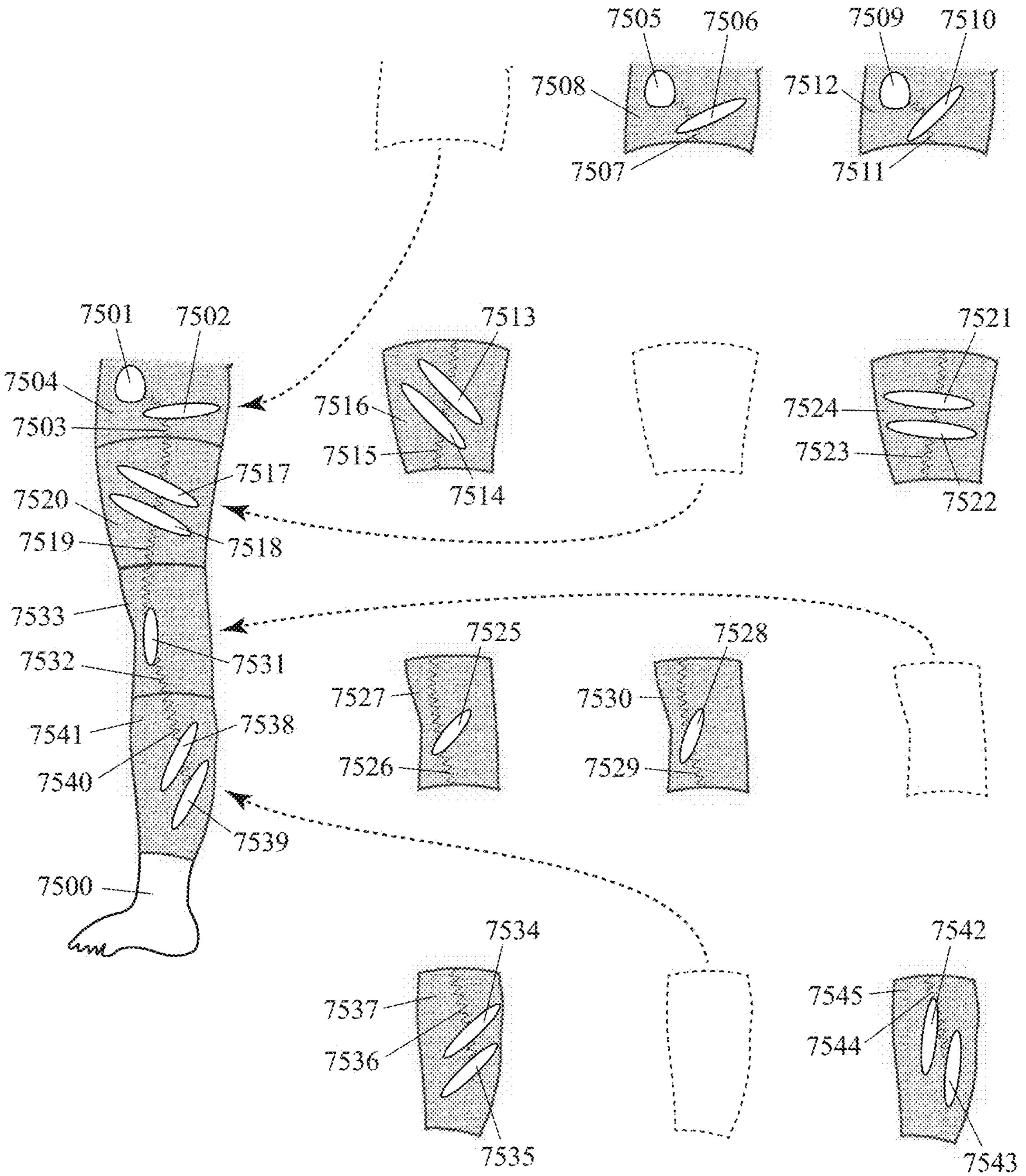

FIGS. 75 and 76 show an example of how this invention can be embodied in modular system for creating customized electromyographic clothing comprising: (a) a first set of alternative modules (the three modules formed by components 7501 through 7512) for an article of clothing, wherein each module in this first set is configured to be worn on a first portion of a person's body (upper portion of leg 7500), wherein each module in this first set includes at least one electromagnetic energy sensor (7502, 7506, and 7510 in the three modules, respectively), and wherein there is variation in the location, orientation, size, shape, number, and/or configuration of electromagnetic energy sensors between different modules in this first set; and (b) a second set of alternative modules (the three modules formed by components 7513 through 7524) for an article of clothing, wherein each module in this second set is configured to be worn on a second portion of a person's body (middle-upper portion of leg 7500), wherein each module in this second set includes at least one electromagnetic energy sensor (7513, 7517, and 7521 in the three modules, respectively), wherein there is variation in the location, orientation, size, shape, number, and/or configuration of electromagnetic energy sensors between different modules in this second set, and wherein a first module is selected from the first set, a second module is selected from the second set, and the selected first and second modules are combined to form a single customized article of clothing for collecting data concerning electromagnetic energy from neuromuscular activity by a specific person or during a specific type of physical activity.

The example shown in FIGS. 75 and 76 further comprises a third set of alternative modules (the three modules formed by components 7525 through 7533) worn on the middle-lower portion of leg 7500 and a fourth set of alternative modules (the three modules formed by components 7534 through 7545) worn on the lower portion of leg 7500. The example shown in FIGS. 75 and 76 also includes: a control unit in each of the modules in the first set (7501, 7505, and 7509, respectively); sinusoidal wires (7503, 7507, 7511, 7515, 7519, 7523, 7526, 7529, 7532, 7536, 7540, and 7544) connecting the components in different modules; and additional electromagnetic energy sensors (7514, 7518, 7522, 7535, 7539, and 7543) in the second and fourth sets. In an example, a control unit can further comprise a power source, a data processor, a data transmitter, and a data receiver.

In an example, modules in a given set can be configured to be worn on a particular longitudinal section of a body member, such as a leg or arm. In the example shown in FIGS. 75 through 76, there are four different sets of modules, one worn on each of four longitudinal sections of a leg. In the example, there can be three or two sections for a leg. In an example, each module in each set can include at least one electromagnetic energy sensor. In an example, there can be a set with no modules which include electromagnetic energy sensors. A module with no electromagnetic energy sensor can serve a variable-size placeholder in a longitudinal series of sets. In an example, the number of electromagnetic energy sensors in different alternative modules in a set can vary. In an example, some alternative modules in a set can have no sensors and other alternative modules in that set can have two or more sensors.

In this example, the orientations of electromagnetic energy sensors vary across different modules within a set. In an example, the number of electromagnetic energy sensors can vary across different modules within a set. In an example, the size or shape of electromagnetic energy sensors can vary across different modules within a set. In an example, the location of electromagnetic energy sensors can vary across different modules within a set. In an example, the type or fit of fabric or textile can vary across different modules within a set. In an example, some modules can be larger in size and other modules can be smaller in size in order to customize an article of clothing for variation in a specific person's body shape. In an example, modules can vary in elasticity and/or stretchability in order to achieve the right fit on a specific person's body shape.

In the example shown in FIGS. 75 and 76, a customized pair of pants is created by: selecting the module from the first set with the best sensor configuration for measuring muscle activity from the upper leg for a specific person or sport; selecting the module from the second set with the best sensor configuration for measuring muscle activity from the upper-middle leg for that specific person or sport; selecting the module from the third set with the best sensor configuration for measuring muscle activity from the lower-middle leg for that specific person or sport; selecting the module from the fourth set with the best sensor configuration for measuring muscle activity from the lower leg for that specific person or sport; and combining these four selected modules into a single customized pair of pants. FIGS. 75 through 76 only show one leg of a pair of pants, but the same process can be performed for the other leg. If a specific person has muscle asymmetries between their right and left legs, then different modules can be selected for different portions of the right and left legs. If a specific sport (or other type of physical activity) involves asymmetric use of right and left side muscles, then different modules can be selected for different portions of the right and left legs.

FIG. 75 shows this system at first time when all of the modules are separate and none have been selected and combined into a customized article of clothing. FIG. 76 shows this system at a second time after modules have been selected from each of the four sets and combined into a customized article of clothing (e.g. a customized pair of pants) to most efficiently measure the muscle activity of a specific person or during a specific sport (or other physical activity).

In an example, selected modules can be attached together into a customized article of clothing by hook- and -eye attachment mechanisms. In an example, selected modules can be combined into a customized article of clothing by one or more zippers, snaps, clips, clasps, buttons, or hooks. In an example, selected modules can be attached together into a customized article of clothing by sewing or weaving. In an example, selected modules can be attached together into a customized article of clothing by adhesion and/or heat. In an example, electromagnetic connections can be formed between components in selected modules when they are combined into a customized article of clothing. In an example, electromagnetic connections can be formed by one or more plugs, pins, or snaps. In an example, modules can be designed to overlap when they are combined together into an article of clothing.

In an example, modules can be selected from different sets and combined into a customized article of clothing by a manufacturer before the customized article of clothing is sent to a retailer or customer. In an example, modules can be selected from different sets and combined into a customized article of clothing by a retailer. In an example, modules can be selected from different sets and combined into a customized article of clothing by a customer and/or end user. In an example, the selection of modules can be guided by non-invasive imaging and three-dimensional modeling of a person's body. In an example, the selection of modules can be guided by radiologic, CT, and/or MR imaging of a person's body.

In an example, the selection of modules from different sets can be informed by analysis of data from a testing period in which a person tries on different modules and/or different module combinations. In an example, data from such a testing period can be analyzed to select specific modules using one or more methods selected from the group consisting of: Analysis of Variance (ANOVA), Artificial Neural Network (ANN), Auto-Regressive (AR) Modeling, Averaging, Back Propagation Neural Network (BPNN), Bayesian Analysis, Bonferroni Analysis (BA), Centroid Analysis, Chi-Squared Analysis, Correlation, Covariance, Data Normalization (DN), Decision Tree Analysis (DTA), Discrete Fourier Transform (DFT), Discriminant Analysis (DA), Empirical Mode Decomposition (EMD), Factor Analysis (FA), Fast Fourier Transform (FFT), Fast Orthogonal Search (FOS), Feature Vector Analysis (FVA), Fisher Linear Discriminant, Forward Dynamics Model (FDM), Fourier Transformation (FT) Method, Fuzzy Logic (FL) Modeling, Gaussian Model (GM), Generalized Auto-Regressive Conditional Heteroscedasticity (GARCH) Modeling, Hidden Markov Model (HMM), Independent Components Analysis (ICA), Inverse Dynamics Model (FDM), Kalman Filter (KF), Kernel Estimation, Least Squares Estimation, Linear Regression, Linear Transform, Logit Model, Low Pass Filter (LPF), Machine Learning (ML), Markov Model, Maximum Entropy Modeling, Maximum Likelihood, Multivariate Linear Regression, Multivariate Logit, Multivariate Regression, Michael Baysian Classifier, Neural Network, Non-Linear Programming (NLP), Non-Linear Regression (NLR), Non-negative Matrix Factorization (NMF), Polynomial Function Estimation (PFE), Power Spectral Density, Power Spectrum Analysis, Principal Components Analysis (PCA), Probit Model, Quadratic Minimum Distance Classifier, Random Forest (RF), Rectification, Regression Model, Signal Amplitude (SA), Signal Averaging, Signal Decomposition, Sine Wave Compositing, Singular Value Decomposition (SVD), Spine Function, Support Vector Machine (SVM), Time Domain Analysis, Time Frequency Analysis, Time Series Model, Trained Bayes Classifier, Variance, Waveform Identification, Wavelet Analysis, WeirdAl Analysis (WA), and Wavelet Transformation.

In this example, the customized article of clothing which is created by combining modules is a pair of pants (of which one leg is shown in these figures). In other examples, a customized article of clothing which is created by combining modules can be a different type of lower-body garment or an upper-body garment. In an example, a customized article of clothing which is created by combining modules can be a full-body article of clothing. In an example, a customized article of clothing which is created by combining modules can be selected from the group consisting of:

arm band, back brace, belt, blouse, collar, dress, elbow pad, glove, jacket, knee pad, knee tube, leg band, leggings, leotards, overalls, pants, shirt, shoe, shorts, skirt, sock, suit, sweatpants, sweatshirt, tights, underpants, undershirt, union suit, waist band, and wristband.

In an example, electromagnetic energy sensors can be formed in a module by weaving. In an example, electromagnetic energy sensors can be formed in a module by weaving electroconductive threads, fibers, yarns, and/or traces within a module. In an example, electromagnetic energy sensors can be formed on a module by printing. In an example, electromagnetic energy sensors can be formed on a module by printing with electroconductive ink and/or resin. In an example, electromagnetic energy sensors can be formed on a module by embroidery. In an example, electromagnetic energy sensors can be formed on a module by embroidering with electroconductive threads, fibers, and/or yarns. In an example, electromagnetic energy sensors can be formed on a module by adhesion. In an example, electromagnetic energy sensors can be formed on a module by adhering electroconductive members to a module. Other relevant example configuration variations which are discussed elsewhere in this disclosure can also be applied to the example discussed here.

In an example, this invention can be embodied in an article of electromyographic clothing comprising: an article of clothing, wherein this article of clothing further comprises a first portion that is configured to have a first average distance from a person's skin when the clothing is worn and a second portion that is configured to have a second average distance from a person's skin when the clothing is worn, and wherein the second distance is less than the first distance; and one or more electromagnetic energy sensors, wherein these electromagnetic energy sensors collect data concerning muscle activity, and wherein these electromagnetic energy sensors are part of (and/or attached to) the second portion.

In an example, this invention can be embodied in an article of electromyographic clothing comprising: an article of clothing, wherein this article of clothing further comprises a first portion that is configured to have a first fit to a person's body and a second portion that is configured to have a second fit to a person's body, and wherein the second fit is closer than the first fit; and one or more electromagnetic energy sensors, wherein these electromagnetic energy sensors collect data concerning muscle activity, and wherein these electromagnetic energy sensors are part of (and/or attached to) the second portion.

In an example, this invention can be embodied in an article of electromyographic clothing comprising: an article of clothing, wherein this article of clothing further comprises a first portion that is configured to have a first elasticity level and a second portion that is configured to have a second elasticity level, and wherein the second level is greater than the first level; and one or more electromagnetic energy sensors, wherein these electromagnetic energy sensors collect data concerning muscle activity, and wherein these electromagnetic energy sensors are part of (and/or attached to) the second portion.

In one or more of the above three examples, a second portion can overlap a first portion. In one or more of the above three examples, a second portion can be located underneath a first portion. In one or more of the above three examples, a first portion and a second portion can be nested and/or concentric. In one or more of the above three examples, a second portion can be a compressive band or ring. In one or more of the above three examples, a second portion can encircle some or all of the circumference of a body member. In an example, a second portion can be attached to a first portion. In an example, a second portion can be in electromagnetic communication with a first portion. In an example, a second portion can be configured to span a central portion of a muscle or muscle group. In an example, there can be multiple second portions in an article of electromyographic clothing.

In one or more of the above three examples, an article of electromyographic clothing can further comprise a user interface. In an example, this user interface can include a display. In an example, an article of electromyographic clothing can be an electromyographic shirt. In an example, a user interface can be part of (and/or attached to) the sleeve of an electromyographic shirt. In an example, an article of electromyographic clothing can further comprise a power source, a data processor, a data transmitter, and a data receiver. In an example, an article of electromyographic clothing can be a pair of pants or shorts. In an example, a user interface of an article of electromyographic clothing can further comprise a power source, a data processor, a data transmitter, and a data receiver. In an example, an article of electromyographic clothing can further comprise wires or other electroconductive pathways which link one or more electromagnetic (EMG) sensors to a user interface. Relevant variations discussed elsewhere in this disclosure or in priority-linked disclosures can also be applied to this example.

Figure 77:
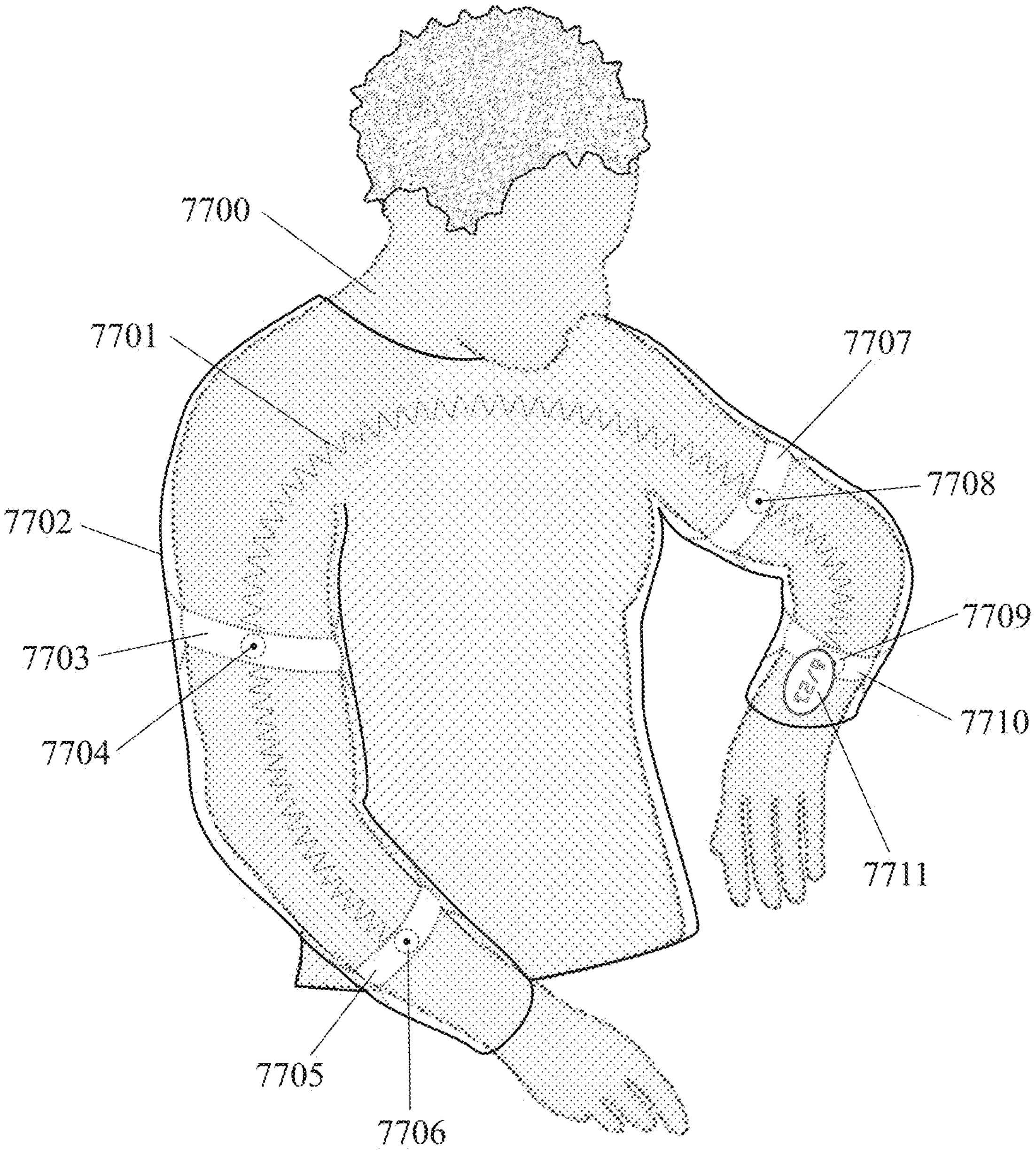
FIG. 77 shows electromyographic clothing comprising a long-sleeve shirt with a loose-fitting portion and one or more close-fitting portions with EMG sensors.

FIG. 77 shows an example of how this invention can be embodied in an article of electromyographic clothing comprising: an article of clothing worn by person 7700, wherein this article of clothing further comprises a first portion 7702 that is configured to have a first average distance from a person's skin (or a first fit or a first elasticity level) and one or more second portions (7703, 7705, 7707, and 7710) that are configured to have a second average distance from a person's skin (or a second fit or a second elasticity level), and wherein the second distance is less than the first distance (or the fit of the second is closer or the elasticity of the second is greater than that of the first); and one or more electromagnetic energy sensors (7704, 7706, 7708, and 7709), wherein these electromagnetic energy sensors collect data concerning muscle activity, and wherein these electromagnetic energy sensors are parts of (and/or attached to) the second portions. This example also includes a user interface 7711 (which includes a display, power source, data processor, data transmitter, and data receiver) and wires 7701 which connect the electromagnetic energy sensors to the user interface.

In the example shown in FIG. 77, the second portions overlap the first portion. In this example, the second portions are located underneath the first portion. In this example, the first and second portions are nested and/or concentric. In this example, the second portions are elastic and/or compressive bands or rings. In this example, the second portions encircle some or all of a person's arms.

In an example, a second portion can be attached to a first portion. In an example, a second portion can be permanently attached to a first portion by fabric, sewing, and/or adhesion. In an example, a second portion can comprise an elastic band with electromyographic (EMG) sensors which fits snugly around the circumference of a person's arm (or leg), wherein this elastic band is attached to the interior of a looser-fitting overall shirt (or pair of pants or shorts). In an example, a second portion can be removably-attached to a first portion by a snap, hook- and -eye mechanism, clip, clasp, zipper, tie, buckle, button, or insertion into a fabric channel, pocket, or pouch.

In this example, the second portions are configured to span central portions of muscles or muscle groups, respectively. In an example, a second portion can span a portion of the circumference of a person's arm or leg around the central portion of a selected muscle or muscle group. In an example, a second portion can intersect the longitudinal axis of an arm or leg at a right angle. In an example, a second portion can intersect the longitudinal axis of an arm or leg at an acute angle. In this example, there are four second portions, two on each arm of an electromyographic shirt. In this example, an article of electromyographic clothing is a shirt with a user interface on outside of a sleeve. Relevant variations discussed elsewhere in this disclosure or in priority-linked disclosures can also be applied to this example.

Figure 78:
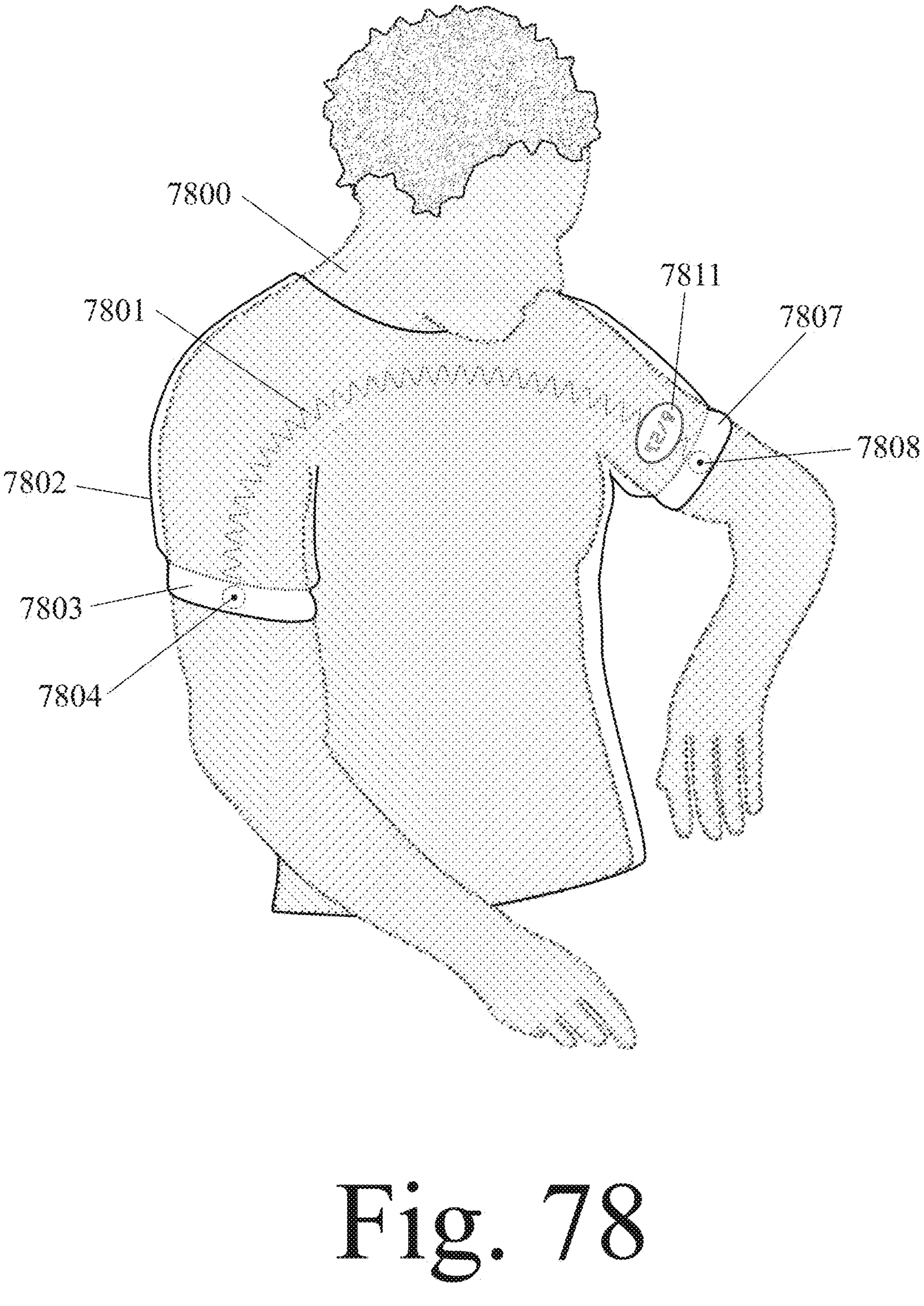
FIG. 78 shows electromyographic clothing comprising a short-sleeve shirt with cuffs with EMG sensors.

FIG. 78 shows another example of how this invention can be embodied in an article of electromyographic clothing. This example is similar to the one shown in FIG. 77 except that the article of clothing is a short-sleeve shirt rather than a long-sleeve shirt. The example shown in FIG. 78 comprises: an article of clothing worn by person 7800, wherein this article of clothing further comprises a first portion 7802 that is configured to have a first average distance from a person's skin (or a first fit or a first elasticity level) and one or more second portions (7803 and 7807) that are configured to have a second average distance from a person's skin (or a second fit or a second elasticity level), and wherein the second distance is less than the first distance (or the fit of the second is closer or the elasticity of the second is greater than that of the first); and one or more electromagnetic energy sensors (7804 and 7808), wherein these electromagnetic energy sensors collect data concerning muscle activity, and wherein these electromagnetic energy sensors are parts of (and/or attached to) the second portions. This example also includes a user interface 7811 (which includes a display, power source, data processor, data transmitter, and data receiver) and a wire 7801 which connects the electromagnetic energy sensors to the user interface.

In the example shown in FIG. 78, the second portions are elastic and/or compressive bands which are located at the ends (or cuffs) of the sleeves. One advantage of this design is that these bands are located where there are often compressive bands even in conventional short-sleeve shirts, such as T-shirts. Thus, the basic form of a conventional short-sleeve shirt (such as a T-shirt) is maintained for an unobtrusive appearance. Also a compressive band around the upper arm can offer minimal interference with arm motion during sports or other physical activities. In this example, there are two second portions, one on each arm of an electromyographic shirt. In this example, an article of electromyographic clothing is a short-sleeve shirt with a user interface (display) on the outside of a sleeve. In an example, a user interface (display) could be located on the lower torso of a shirt.

In an example, this invention can be embodied in an article of electromyographic clothing with adjustable sensor location selection comprising: an article of clothing which is worn by a person; a first electromagnetic energy sensor which is part of the article of clothing and which collects data concerning electromagnetic energy from neuromuscular activity from a first location; a second electromagnetic energy sensor which is part of the article of clothing and which collects data concerning electromagnetic energy from neuromuscular activity from a second location; a control unit; and a movable electromagnetic energy connector, wherein this electromagnetic energy connector has a first configuration in which it creates an electromagnetic energy connection between the first electromagnetic energy sensor and the control unit, wherein this electromagnetic energy connector has a second configuration in which it creates an electromagnetic energy connection between the second electromagnetic energy sensor and the control unit, and wherein this electromagnetic energy connector is positioned in the first configuration or positioned in the second configuration based on which configuration collects better data concerning electromagnetic energy from neuromuscular activity. Relevant variations discussed elsewhere in this disclosure or in priority-linked disclosures can also be applied to this example.

Figure 79:
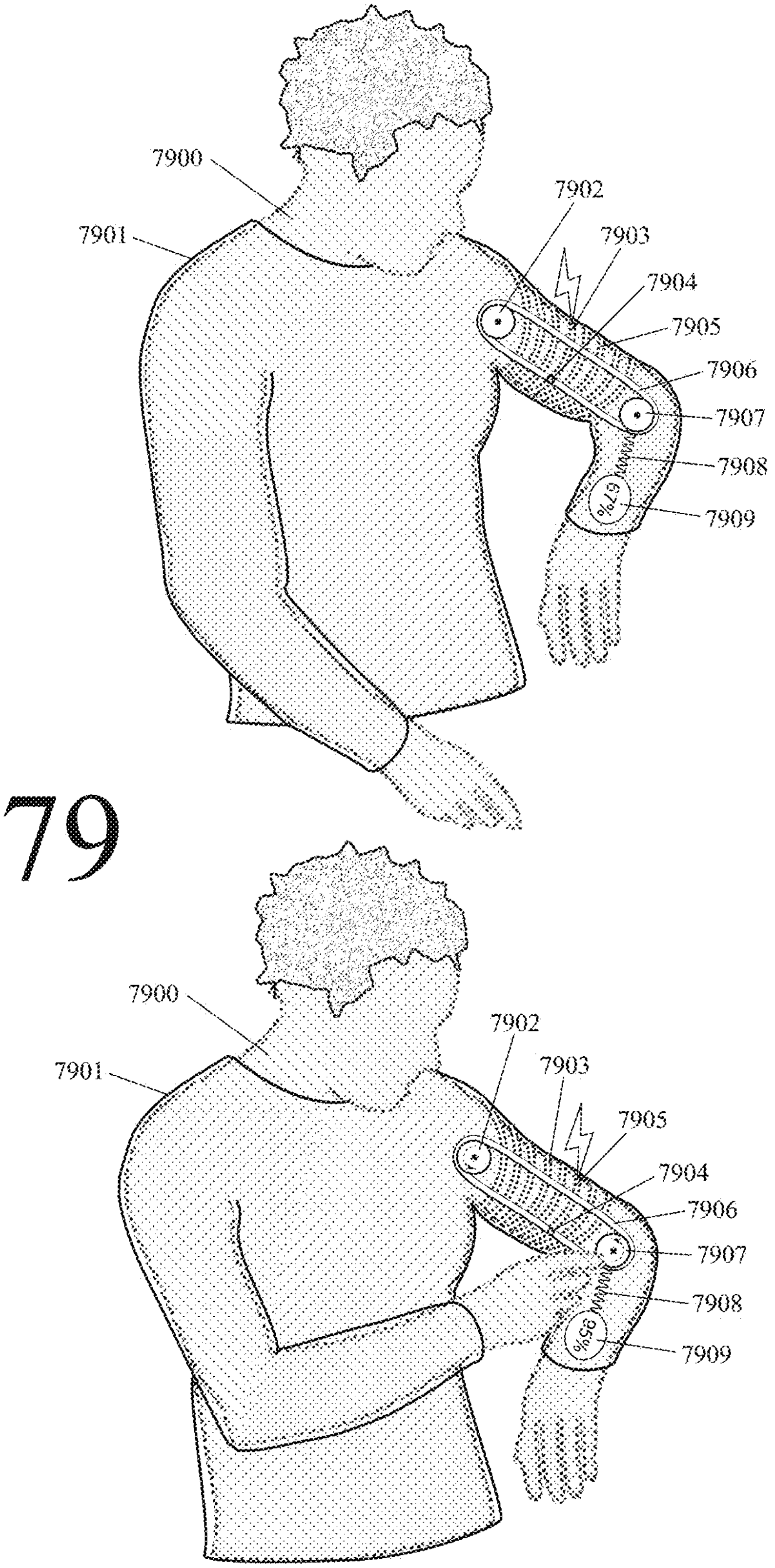
FIG. 79 shows electromyographic clothing with a selectable longitudinal series of EMG bands.

FIG. 79 shows an example of how this invention can be embodied in an article of electromyographic clothing with adjustable sensor location selection comprising: an article of clothing 7901 which is worn by a person 7900; a first electromagnetic energy sensor 7903 which is part of the article of clothing and which collects data concerning electromagnetic energy from neuromuscular activity from a first location; a second electromagnetic energy sensor 7905 which is part of the article of clothing and which collects data concerning electromagnetic energy from neuromuscular activity from a second location; a control unit 7909; and a movable electromagnetic energy connector 7904, wherein this electromagnetic energy connector has a first configuration in which it creates an electromagnetic energy connection between the first electromagnetic energy sensor and the control unit, wherein this electromagnetic energy connector has a second configuration in which it creates an electromagnetic energy connection between the second electromagnetic energy sensor and the control unit, and wherein this electromagnetic energy connector is positioned in the first configuration or positioned in the second configuration based on which configuration collects better data concerning electromagnetic energy from neuromuscular activity.

The example shown in FIG. 79 further comprises: a moving belt 7906 on which electromagnetic energy connector 7904 is located; two rotating hubs 7902 and 7907 around which belt 7906 moves; and a wire 7908 which provides electromagnetic communication between moving belt 7906 and control unit 7909. In an example, control unit 7909 can further comprise a power source, a data processor, a data transmitter, a data receiver, and a display screen.

In this example, the article of clothing is a shirt. In this example, the first and second electromagnetic energy sensors are part of a longitudinal series of compressive bands at different locations along a person's upper arm. In this example, having a moving electromagnetic energy connector enables selective activation of one (or a subset) of the electromagnetic energy sensors in this series so as to optimally collect data concerning muscle activity.

In this example, rotating the belt causes the electromagnetic energy connection to move longitudinally along the person's upper arm and to sequentially connect (and activate) different electromagnetic energy sensors in this longitudinal series. In this example, a person rotates a belt by manually rotating a hub. In this manner the person can "fine tune" the location on the upper arm from which this article of electromyographic clothing collects data concerning muscle activity. In an example, there can be a series of compressive bands (or other electromagnetic energy sensors) on other body members, such as the other upper arm, a lower arm, an upper leg, and/or a lower leg.

The upper half of FIG. 79 shows this example at a first time wherein electromagnetic energy connector 7904 creates an electromagnetic energy connection between electromagnetic energy sensor 7903 and control unit 7909. This means that electromagnetic energy sensor 7903 is active for collecting data concerning neuromuscular activity, which is represented by a lightning bolt symbol near this sensor. At this first time, a display on control unit 7909 shows "67%" which means that arm muscle data is being collected with 67% accuracy from sensor 7903.

The lower half of FIG. 79 shows this same example at a second time wherein the person has rotated hub 7907, which has rotated belt 7906, which has moved electromagnetic energy connector 7904, which has broken the connection with electromagnetic energy sensor 7903 and created a connection with electromagnetic energy sensor 7905. This means that electromagnetic energy sensor 7905 is now active for collecting data concerning neuromuscular activity, which is represented by a lightning bolt symbol near this sensor. At this second time, a display on control unit 7909 shows "95%" which means that arm muscle data is being collected with 95% accuracy from sensor 7905.

This example shows how the location from which muscle activity is measured can be adjusted so as to improve the accuracy of muscle activity data. In an example, there can be a large array of alternative sensors along the longitudinal axis of a body member (such as an arm or leg) and the selection of which sensor (or sensors) in that array are activated can be fine tuned by a person wearing the clothing in order to achieve optimal measurement of muscle activity.

In this example, adjustment and selection of which electromagnetic energy sensor to activate for data collection is done by rotation (e.g. rotating a hub which rotates a belt which changes an electromagnetic connection to a sensor). In another example, adjustment and selection of which electromagnetic energy sensor to activate for data collection can be done by sliding (e.g. by sliding a connector along a body member which changes an electromagnetic connection to a sensor). In another example, adjustment and selection of which electromagnetic energy sensor to activate for data collection can be done by plugging or snapping (e.g. by plugging or snapping a connector onto clothing which changes an electromagnetic connection to a sensor).

In an example, this invention can be embodied in an adjustable system of electromyographic clothing comprising: at least one elastic member (such as an elastic band, tube, sleeve, or cuff) which is configured to be worn around a person's arm; at least one electromagnetic energy sensor which is part of the elastic member, wherein this electromagnetic energy sensor collects data concerning the person's neuromuscular activity; a first portion of an attachment mechanism, wherein this first portion is attached to (or part of) the elastic member; an article of clothing (such as a shirt) which is worn on the person's arm; and a second portion of the attachment mechanism, wherein this second portion is attached to (or part of) the article of clothing, and wherein the second portion can be reversibly-attached to the first portion. In an example, this system can further comprise one or more components selected from the group consisting of: a power source, an amplifier, a data processor, a data transmitter, a data receiver, a display, an inertial sensor, and a bend sensor.

In an example, this invention can be embodied in an adjustable system of electromyographic clothing comprising: at least one elastic member (such as an elastic band, tube, or sock) which is configured to be worn around a person's leg; at least one electromagnetic energy sensor which is part of the elastic member, wherein this electromagnetic energy sensor collects data concerning the person's neuromuscular activity; a first portion of an attachment mechanism, wherein this first portion is attached to (or part of) the elastic member; an article of clothing (such as a pair of pants or shorts) which is worn on the person's leg; and a second portion of the attachment mechanism, wherein this second portion is attached to (or part of) the article of clothing, and wherein the second portion can be reversibly-attached to the first portion. In an example, this system can further comprise one or more components selected from the group consisting of: a power source, an amplifier, a data processor, a data transmitter, a data receiver, a display, an inertial sensor, and a bend sensor. Relevant variations discussed elsewhere in this disclosure or in priority-linked disclosures can also be applied to this example.

Figure 80:
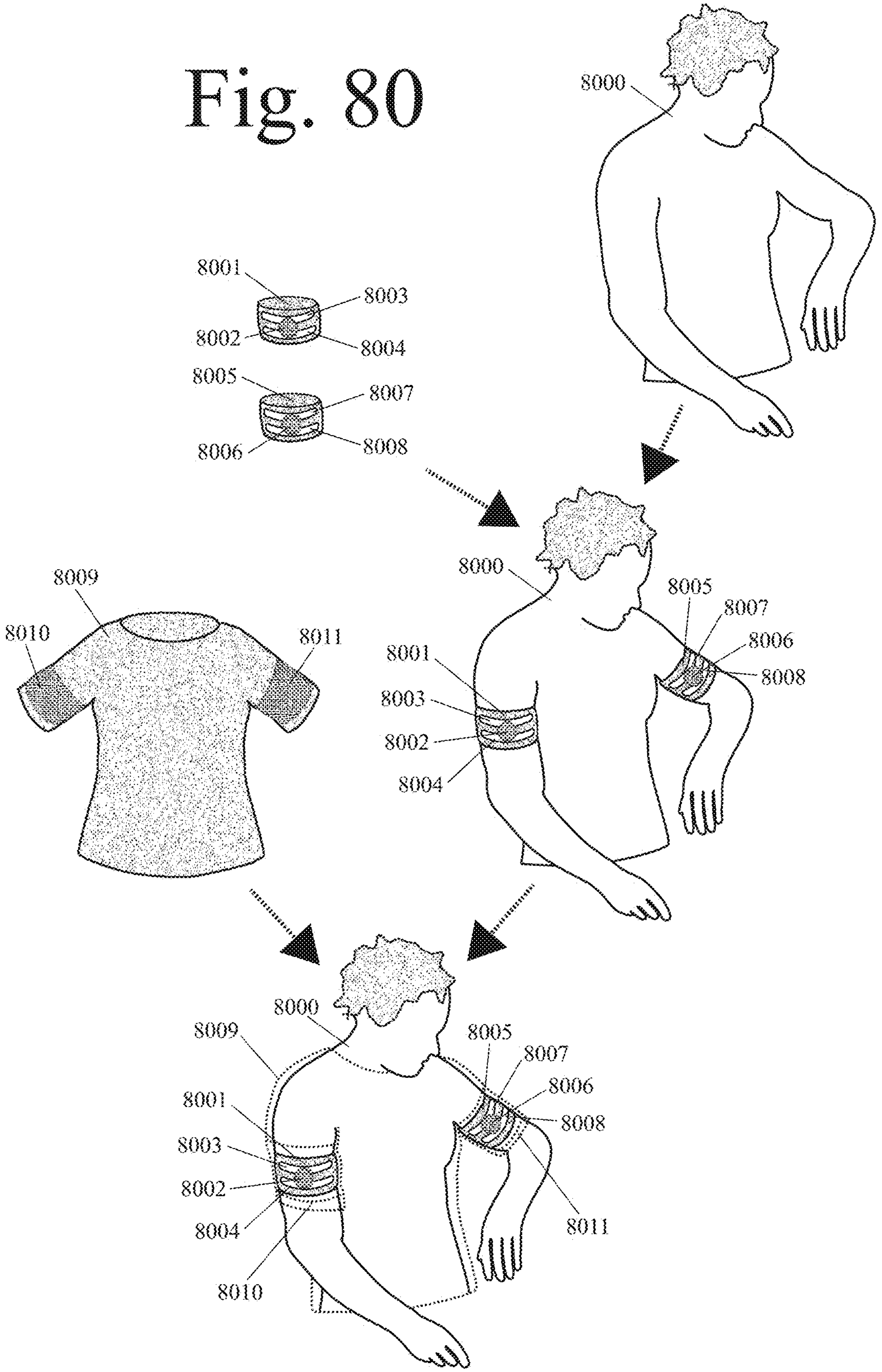
FIG. 80 shows a system of electromyographic comprising at least one elastic member with EMG sensors which a person puts on first, an article of clothing which the person puts on second, and an attachment mechanism which connects the elastic member and the article of clothing.

FIG. 80 shows an example of how this invention can be embodied in an adjustable system of electromyographic clothing comprising: two elastic bands 8001 and 8005 which are configured to be worn a person's 8000 arms, one on each arm; four electromagnetic energy sensors 8003, 8004, 8007, and 8008 which are part of the two elastic bands, two on each band, wherein these electromagnetic energy sensors collect data concerning the person's neuromuscular activity; two first portions 8002 and 8006 of attachment mechanisms, wherein these first portions are parts of the two elastic bands; a shirt 8009; and two second portions 8010 and 8011 of the attachment mechanisms, wherein these two second portions are part of the shirt, and wherein these two second portions can be reversibly-attached to the two first portions. In an example, this system can further comprise one or more components selected from the group consisting of: a power source, an amplifier, a data processor, a data transmitter, a data receiver, a display, an inertial sensor, and a bend sensor.

FIG. 80 is longitudinally divided into three sections: a top section, a middle section, and a bottom section. These three sections show three sequential views of the same system at different times. The top section of shows this system at a first time, before a person wears any system components. The left side of the top section shows two elastic bands 8001 and 8005. The right side of the top section shows person 8000 before he wears any system components. The middle section shows this system after the person has put the two elastic bands on his upper arms, but before he has put on a shirt. The left side of the middle section shows shirt 8009 before it is worn. The right side shows person 8000 wearing elastic bands 8001 and 8005. The bottom section shows person 8000 wearing shirt 8009 over elastic bands 8001 and 8005. In the bottom section, shirt 8009 is shown as being transparent (indicated by a dotted-line outline) so that the viewer can see the configuration of the elastic bands, the attachment mechanisms, and the person's body underneath the shirt.

In this example, an elastic member which is a component of a system of electromyographic clothing is a circular and/or columnar elastic band. In this example, an elastic band encircles a person's upper arm. In another example, an elastic band can encircle a person's lower arm. In this example, there is one elastic band per arm. In another example, there can be two elastic bands per arm. In an example, there can be one elastic band which encircles a person's upper arm and another elastic band which encircles the person's lower arm. In an example, an elastic member which is a component of a system of electromyographic clothing can be an elastic tube, compressive sleeve, bracelet, flexible armlet, or elastic cuff. In this example, an elastic member forms a continuous circle and is placed onto a person's arm by sliding the band around and over a person's hand. In another example, an elastic member can have two separate ends which are wrapped around a person's arm and then attached to each other by an attachment mechanism selected from the group consisting of: hook- and -eye, snap, buckle, clasp, button, tie, pin, plug, and zipper.

In an example, an elastic member and/or electromagnetic energy sensors thereon can be placed over the mid-section of a selected muscle (or group of muscles). In an example, an elastic member and/or electromagnetic energy sensors thereon can be substantially perpendicular to the longitudinal axis of the portion of an arm to which it is attached and/or to a selected muscle (or group of muscles). In an example, an elastic member and/or electromagnetic energy sensors thereon can be substantially parallel to the longitudinal axis of the portion of an arm to which it is attached and/or to a selected muscle (or group of muscles). In an example, an elastic member and/or electromagnetic energy sensors thereon can form an acute angle intersecting the longitudinal axis of the portion of an arm to which it is attached and/or a selected muscle (or group of muscles).

In an example, the position of an elastic member and/or electromagnetic energy sensors thereon with respect to a muscle or a group of muscles can be adjusted so as to best collect neuromuscular activity data—before an article of clothing is placed over it. In an example, when an article of clothing is placed over (and attached to) an elastic member, then the elastic member and electromagnetic energy sensors thereon are held in this position for optimal data collection. In an example, the ability to adjust and then fix the locations of an elastic member and electromagnetic energy sensors thereon can enable customization of a system of electromyographic clothing so as to optimally measure the neuromuscular activity of a specific person or neuromuscular activity during a specific type of physical activity. Sorry about splitting infinitives.

In this example, an electromagnetic energy sensor is part of an elastic band. In this example, there are two electromagnetic energy sensors on each elastic band. In an example, an electromagnetic energy sensor can be an electrode. In an example a pair of electromagnetic energy sensors and/or pair of electrodes can measure the flow of electromagnetic energy between them. In an example, an electromagnetic energy sensor can be a dipole sensor.

In an example, an electromagnetic energy sensor can span (a portion of) the cross-sectional circumference and/or perimeter of a person's arm. In an example, an electromagnetic energy sensor can have a longitudinal axis. In an example, the longitudinal axis of an electromagnetic energy sensor can be substantially aligned with the cross-sectional circumference and/or perimeter of a person's arm. In an example, the longitudinal axis of an electromagnetic energy sensor can be perpendicular to the longitudinal axis of a person's arm. In an example, the longitudinal axis of an electromagnetic energy sensor can form an acute angle as it intersects the longitudinal axis of a person's arm. In an example, an electromagnetic energy sensor can be placed over the mid-section of a selected muscle or group of muscles in a person's arm.

In this example, the mechanism which attaches elastic members (e.g. elastic bands) to a shirt is a hook- and -eye mechanism (such as Velcro [TM]). In an example, the first portion of an attachment mechanism can be the hook surface of a hook- and -eye mechanism and the second portion of the attachment mechanism can be the eye surface of the hook- and -eye mechanism, or vice versa. In other examples, an attachment mechanism can be selected from the group consisting of: snap, pin, buckle, clasp, clip, zipper, button, plug, and link. In this example, an article of clothing is a shirt. In another example, an article of clothing can be a different type of upper body garment. In this example, the second portion of the attachment mechanism is on the inside of the sleeves of a shirt. In an example, the second portion of an attachment mechanism can be larger than the first portion of the attachment mechanism in order to enable them to be attached in different configurations.

In an example, this invention can be embodied in a method comprising the following steps: (a) having a person position one or more elastic bands with electromagnetic energy sensors on their arms in the locations from which they can best collect neuromuscular activity data; (b) having the person put on a shirt over the elastic bands; and (c) having the person attach the bands and the shirt together in order to fix the locations of the bands with respect to the person's arms. This system and method creates an article of clothing which has a relaxed (e.g. loose) overall fit, but has one or more selected areas which fit snugly in order to collect neuromuscular activity data. Further, this system and method allows the locations of the snug areas to be adjusted. For many applications, including some sports, an article of clothing with an overall relaxed fit is preferable to an article of clothing with an overall tight fit.

In an example, electromagnetic components on elastic bands and electromagnetic components in a shirt can be in wireless electromagnetic communication with each other. In another example, when the elastic bands and the shirt are attached to each other, then this attachment can form an electromagnetic pathway for electromagnetic communication between them. In an example, an attachment mechanism can provide both mechanical attachment and electromagnetic communication. In an example, a shirt can further comprise a control unit and/or user interface which receives data from one or more electromagnetic energy sensors which are part of the elastic bands.

In the example shown in FIG. 80, an article of clothing which is a component of a system of electromyographic clothing is an upper body garment. In an example, an article of clothing can be a lower body garment or a full-body garment. In an example, the article of clothing can be a pair of pants, a pair of shorts, or a union suit. In an example, at least one elastic band with electromagnetic energy sensors can be attached to a person's leg. In an example, an elastic band can be attached to a pair of pants or shorts by an attachment mechanism such as a hook- and -eye (e.g. Velcro [TM]) mechanism. Relevant variations discussed elsewhere in this disclosure or in priority-linked disclosures can also be applied to this example.

Figure 81:
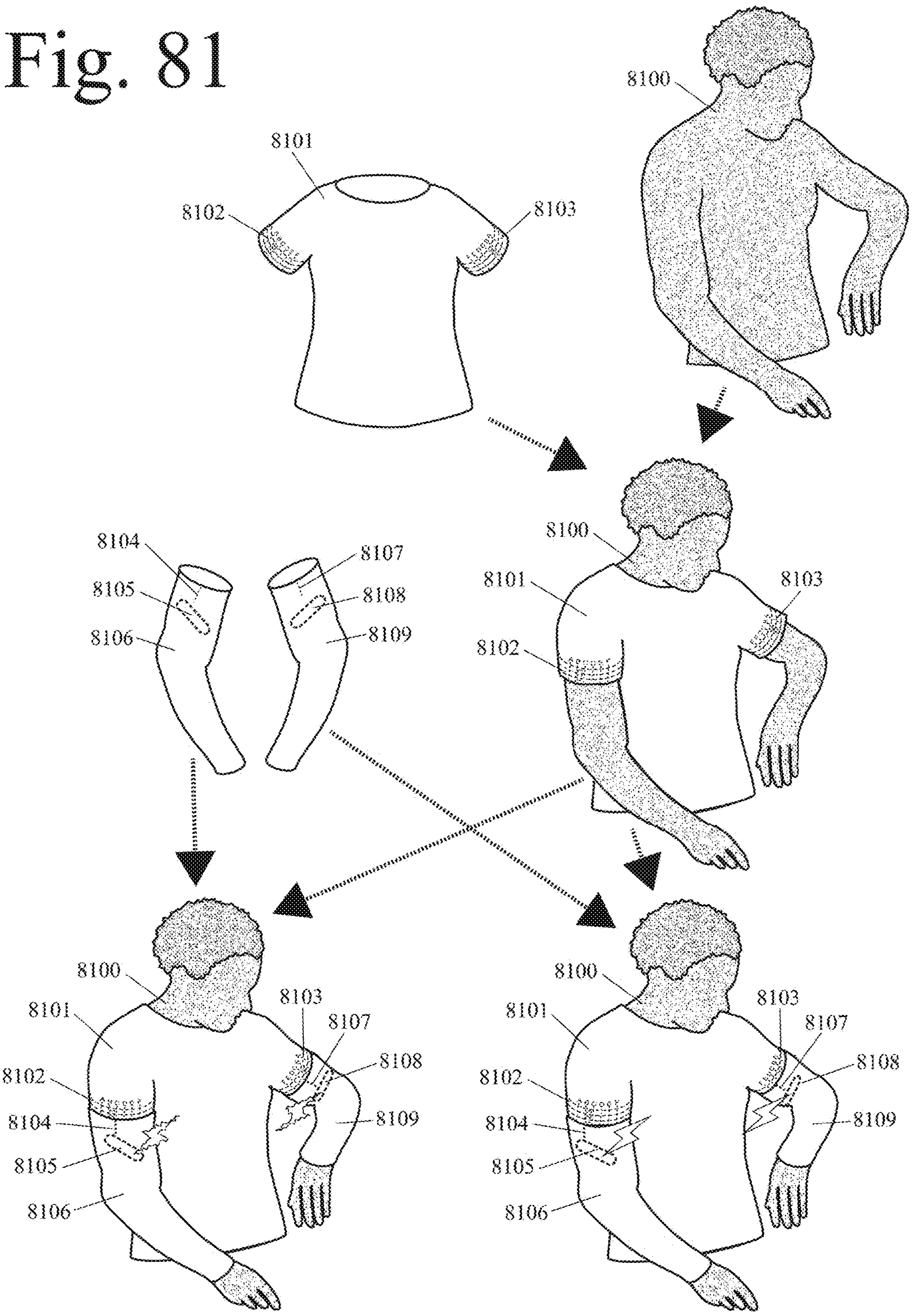
FIG. 81 shows a system of electromyographic clothing comprising a first portion of an article of clothing with a first set of markings, a second portion of an article of clothing with a second set of markings, and EMG sensors, wherein the EMG sensors are adjustably positioned by selectively aligning the markings.

In an example, as shown in FIG. 81, this invention can be embodied in an adjustable system of electromyographic clothing comprising: a first portion of an article of clothing, wherein this first portion of the article of clothing has a first set of markings; a second portion of the article of clothing, wherein this second portion of the article of clothing has a second set of markings, wherein the first and second sets of markings have a first alignment pattern when the first and second portions of the article of clothing are attached to each other in a first configuration, and wherein the first and second sets of markings have a second alignment pattern when the first and second portions of the article of clothing are attached to each other in a second configuration; and at least one electromagnetic energy sensor which is part of the second portion of the article of clothing, wherein this electromagnetic energy sensor collects neuromuscular activity data with a first accuracy level when the first and second portions of the article of clothing are in the first configuration, wherein this electromagnetic energy sensor collects neuromuscular activity data with a second accuracy level when the first and second portions of the article of clothing are in the second configuration, wherein the second accuracy level is greater than the first accuracy level, and wherein the first and second portions of the article of clothing are attached together in the second configuration by aligning the first and second sets of markings in the second alignment pattern.

In particular, FIG. 81 shows an example of how this invention can be embodied in an adjustable system of electromyographic clothing comprising: a main body 8101 of a shirt worn by person 8100, wherein this main body has a first set of markings 8102 and 8103; two sleeves 8106 and 8109, wherein these sleeves have a second set of markings 8104 and 8107, wherein the first and second sets of markings have a first alignment pattern when the main body of the shirt and the sleeves are attached to each other in a first configuration, and wherein the first and second sets of markings have a second alignment pattern when the main body of the shirt and the sleeves are attached to each other in a second configuration; and two electromagnetic energy sensors 8105 and 8108, one on each sleeve, wherein these electromagnetic energy sensors collect neuromuscular activity data with a first accuracy level when the main body of the shirt and the sleeves are attached together in the first configuration, wherein these electromagnetic energy sensors collect neuromuscular activity data with a second accuracy level when the main body of the shirt and the sleeves are attached together in the second configuration, wherein the second accuracy level is greater than the first accuracy level, and wherein the main body of the shirt and the sleeves are attached together in the second configuration by aligning the first and second sets of markings in the second alignment pattern.

FIG. 81 has three sections: a top section; a middle section; and a bottom section. These three sections show the same system in different configurations at different times. In the top section of FIG. 81: the left side shows the main body 8101 of the shirt (with a first set of markings 8102 and 8103) before it is worn; and the right side shows person 8100 before he wears any components of the system. In the middle section of FIG. 81: the left side shows two separate shirt sleeves 8106 and 8109 which further comprise electromagnetic energy sensors 8105 and 8108 and a second set of markings 8104 and 8107; and the right side shows person 8100 wearing the main body 8101 of the shirt. In the bottom section of FIG. 81: the left side shows this example in a first configuration wherein there is a first alignment pattern of the two sets of markings; and the right side shows this same example in a second configuration wherein there is a second alignment pattern of the two sets of markings. In this example, the second configuration enables more accurate measurement of neuromuscular activity data than does the first configuration. In this example, the second configuration is created by aligning the markings of the main body of the shirt the markings on the sleeves in the second configuration.

Looking at the markings in closer detail, we can see on the left side of the bottom section of FIG. 81 that in the first configuration: right sleeve 8106 is attached to the main body 8101 of the shirt such that longitudinal mark 8104 on sleeve 8106 aligns with circumferential mark “2” and longitudinal mark “C” on the main body 8101 of the shirt; and left sleeve 8109 is attached to the main body 8101 of the shirt such that longitudinal mark 8107 on sleeve 8109 aligns with circumferential mark “2” and longitudinal mark “D” on the main body 8101 of the shirt. This first configuration results in a first (lower) level of muscle data accuracy, which is represented symbolically by two “squiggly” lightning bolt symbols near the electromagnetic energy sensors.

In the second configuration which is shown on the right side of the bottom section of FIG. 81: right sleeve 8106 is attached to the main body 8101 of the shirt such that longitudinal mark 8104 on sleeve 8106 aligns with circumferential mark “1” and longitudinal mark “B” on the main body 8101 of the shirt; and left sleeve 8109 is attached to the main body 8101 of the shirt such that longitudinal mark 8107 on sleeve 8109 aligns with circumferential mark “3” and longitudinal mark “E” on the main body 8101 of the shirt. This second configuration results in a second (higher) level of muscle data accuracy, which is represented symbolically by two “straight-line” lightning bolt symbols near the electromagnetic energy sensors.

In this example, an article of clothing is a shirt. In this example, a first portion of an article of clothing is the main body of a shirt and a second portion of the article of clothing is a sleeve. In this example, the position of an electromagnetic energy sensor with respect to a selected muscle or group of muscles in a person’s arm can be adjusted by adjusting the configuration in which a sleeve is attached to the main body of a shirt. In an example, the longitudinal position of a sleeve (and thus the longitudinal position of a sensor relative to a muscle in the arm) can be adjusted by changing the alignment of a mark (8104 or 8107) relative to a circumferential mark on the main body of a shirt. In this example, the radial (or circumferential) position of a sleeve (and thus the radial position of a sensor relative to a muscle in the arm) can be adjusted by changing the alignment of a mark (8104 or 8107) relative to a radial (or circumferential) mark on the main body of a shirt. Different people can have different neuromuscular anatomies. Different sports can involve using different sets of muscles. A system of electromyographic clothing which allows adjustment of the longitudinal and radial positions of an electromagnetic energy sensor with respect to a person’s arm can help to create a customized article of clothing which best measures the neuromuscular activity of a specific person or best measures neuromuscular activity during a specific sport.

In this example, the main body of a shirt and separate sleeves are attached together by a hook- and -eye mechanism. In an example, one surface of a hook- and -eye mechanism can be on the outside of the main body of a shirt and the other surface of the hook- and -eye mechanism can be on the inside of a sleeve, or vice versa. In an example, the main body of a shirt and a sleeve can overlap. In other examples, a main body of a shirt and a sleeve can be attached together using a mechanism which is selected from the group consisting of: snap, pin, buckle, clasp, clip, zipper, button, plug, and link. In the example in FIG. 81, an article of clothing is an upper body garment. In an example, an article of clothing can be a lower body garment (such as a pair of pants or shorts) or a full-body garment (such as a union suit or jump suit).

In an example, electromagnetic components on the main body of a shirt and electromagnetic components on a sleeve can be in wireless electromagnetic communication with each other. In an example, when the main body and the sleeves are attached to each other, then this attachment can form an electromagnetic pathway for electromagnetic communication between them. In an example, an attachment mechanism can provide both mechanical attachment and electromagnetic communication. In an example, the main body of a shirt or a sleeve can further comprise a control unit and/or user interface which receives data from one or more electromagnetic energy sensors.

I claim:

1. A wearable clothing accessory or device comprising:

a band which is configured to be worn around a person's wrist or arm;

electromyography sensors on the band; wherein the band further comprises a circumferential or partial-circumferential track or pathway along which one or more of the electromyographic sensors slide and one or more actuators which slide the one or more electromyographic sensors along the track or pathway; and wherein sliding the one or more electromyographic sensors along the track or pathway changes the radial locations of the one or more electromyographic sensors on the circumference of the band; and a data processor on the band configured to analyze data from the electromyographic sensors to identify hand gestures and/or function as a human-to-computer interface.

2. An article of smart clothing or clothing accessory comprising:

an article of clothing or clothing accessory configured to be worn by a person, wherein the article of clothing or clothing accessory is a wrist band;

an energy-transducing member; wherein the energy-transducing member comprises one or more electromyography sensors on the wrist band, wherein the wrist band further comprises a circumferential or partial-circumferential track or pathway along which the one or more electromyographic sensors slide and one or more actuators which slide the one or more electromyographic sensors along the track or pathway; and wherein sliding the one or more electromyographic sensors along the track or pathway changes the radial location of the one or more electromyographic sensors on the circumference of the wrist band; and an attachment mechanism, wherein the attachment mechanism is the wrist band;

wherein the article of clothing or clothing accessory further comprises a data processor configured to analyze data from the electromyographic sensors to identify hand gestures and/or function as a human-to-computer interface.

* * * * *